(12) United States Patent
Brest et al.

(10) Patent No.: US 8,771,937 B2
(45) Date of Patent: Jul. 8, 2014

(54) METHODS FOR DIAGNOSING AND TREATING A PATHOLOGY ASSOCIATED WITH A SYNONYMOUS MUTATION OCCURING WITHIN A GENE OF INTEREST

(75) Inventors: Patrick Brest, Nice Cedex (FR); Paul Hofman, Nice Cedex (FR); Baharia Mograbi, Nice Cedex (FR)

(73) Assignees: Institut National de la Sante et de la Recherche Medicale (INSERM), Paris (FR); The Nice Sophia Antipolis University, Nice (FR)

( * ) Notice: Subject to any disclaimer, the term of this patent is extended or adjusted under 35 U.S.C. 154(b) by 0 days.

(21) Appl. No.: 13/501,267

(22) PCT Filed: Oct. 13, 2010

(86) PCT No.: PCT/EP2010/065360
§ 371 (c)(1),
(2), (4) Date: Jul. 30, 2012

(87) PCT Pub. No.: WO2011/045349
PCT Pub. Date: Apr. 21, 2011

(65) Prior Publication Data
US 2012/0289582 A1 Nov. 15, 2012

(30) Foreign Application Priority Data

Oct. 13, 2009 (EP) ..................................... 09305973

(51) Int. Cl.
*C12Q 1/68* (2006.01)
*C07H 21/02* (2006.01)
*C07H 21/04* (2006.01)

(52) U.S. Cl.
USPC .............................. 435/6; 536/23.1; 536/24.5

(58) Field of Classification Search
None
See application file for complete search history.

(56) References Cited

PUBLICATIONS

Massey, D.C.O., et al., "Genome-Wide Association Scanning Highlights Two Autophagy Genes, ATG16L1 and IRGM, as Being Significantly Associated," Autophagy3:6, 649-651; Nov./Dec. 2007. Landes Bioscience. XP007916707.
McCarroll, S. A., et al., "Deletion polymorphism upstream of IRGM associated with altered IRGM expression and Crohn's Disease," Nature Genetics . vol. 40. No. 9. Sep. 2008. pp. 1107-1112.
Parks, M., et al., Sequence variants in the autophagy gene IRGM and multiple other replicating loci contribute to Crohn's disease susceptibility. Nature Genetics. vol. 39, No. 7, Jul. 2007.

*Primary Examiner* — Amy Bowman
(74) *Attorney, Agent, or Firm* — Whitham Curtis Christofferson & Cook, PC

(57) ABSTRACT

The present invention relates to a method for diagnosing and/or prognosing a pathology (such as inflammatory disease, especially Crohn disease) associated with a synonymous mutation occurring within a gene of interest (such as IRGM, NOD2 or BSN) in a subject and to a method for treating such pathology in a subject.

Figure 1:
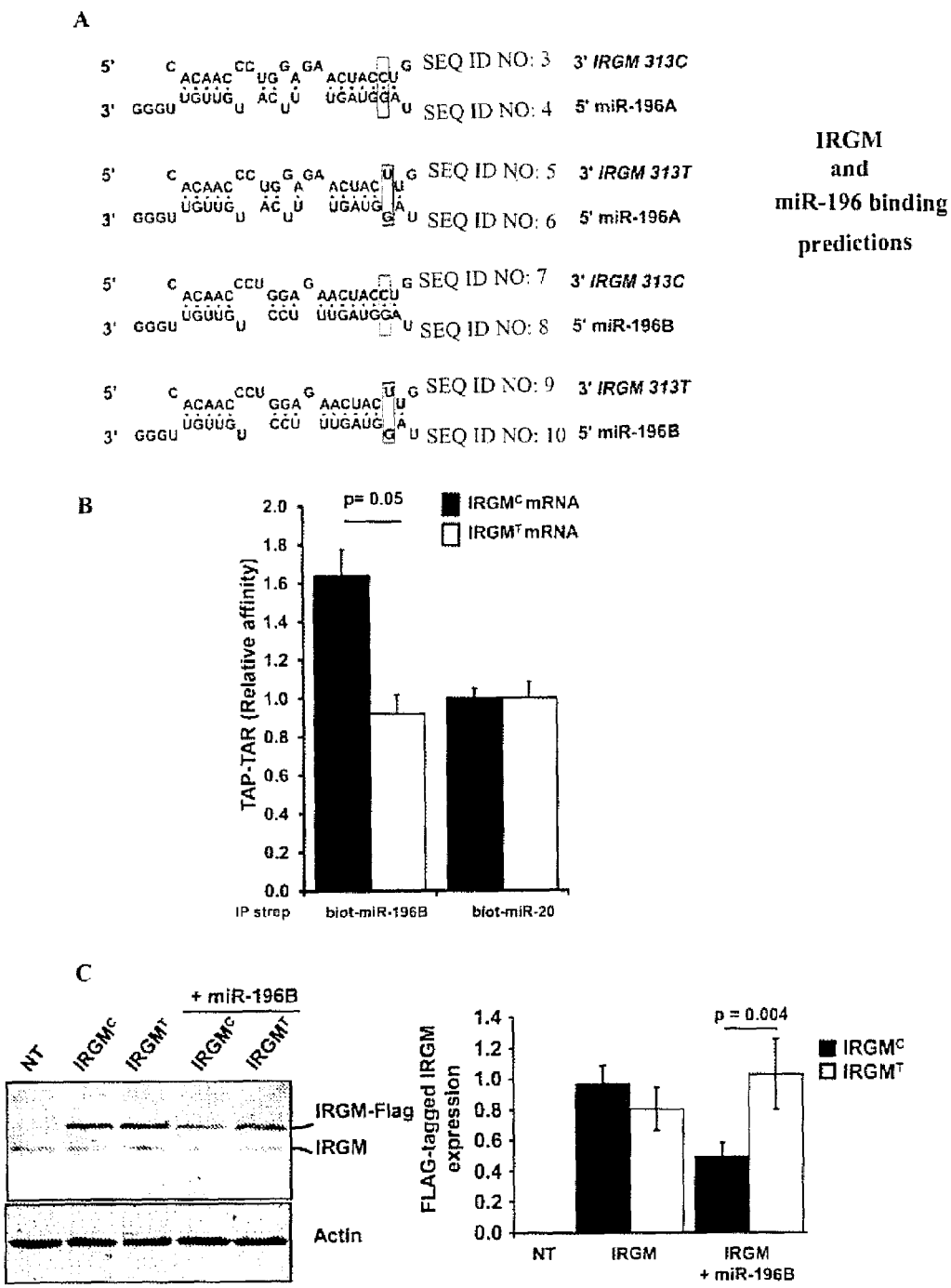

6 Claims, 3 Drawing Sheets

METHODS FOR DIAGNOSING AND TREATING A PATHOLOGY ASSOCIATED WITH A SYNONYMOUS MUTATION OCCURING WITHIN A GENE OF INTEREST

FIELD OF THE INVENTION

The present invention relates to a method for diagnosing and/or prognosing a pathology associated with a synonymous mutation occurring within a gene of interest in a subject and to a method for treating such pathology in a subject.

BACKGROUND OF THE INVENTION

MicroRNA (miRNA), small non-coding RNA, have been involved in regulation of the transcription and the translation of thousands of genes. Recently, it has been shown that Single-Nucleotide Polymorphisms (SNP) frequently alter microRNA-directed repression in mammals including humans but only in 3'-untranslated region[25,26].

For instance, inflammatory bowel disease (IBD) is a group of inflammatory conditions of the colon and small intestine. The major types of IBD are Crohn disease and ulcerative colitis. Immunity Related GTPase, M (IRGM), involved in xerophagy and playing a role in the control of intracellular pathogens (like *Mycobacterium tuberculosis*) was found in genome wild association (GWA) studies as a risk associated locus for IBD, in particular the exonic synonymous mutation C313T (rs10065172; IRGM polymorphism in 313 position induce a nucleic change on the first base of the codon (CTG>TTG) and both codes for leucine amino acid) that is in strong linkage disequilibrium with a large deletion polymorphism upstream of the IRGM locus close to the promotor[1,4].

This observation has led to the proposal that the deletion may be the cause of the difference of expression between the protective and the risk allele. However, until now despite strong computational analysis, no conserved transcription factor binding sequences on IRGM locus has been found within the deleted region that could explain the differences of expression between the risk and the protective allele.

It results thus that such synonymous mutation leading to a silent polymorphism with in the coding region of a gene of interest has never been shown as involved in the physiopathology of mammal diseases including human diseases by impairing the binding of related-miRNA with said gene of interest.

SUMMARY OF THE INVENTION

The present invention relates to an in vitro method for diagnosing and/or prognosing a pathology associated with a synonymous mutation occurring within a gene of interest in a subject, said method comprising the following steps of:
  detecting said synonymous mutation in a biological sample from said subject,
  measuring the level of expression of the miR liable to bind to said wild-type (WT) gene of interest in said biological sample, and
  comparing the level of expression of said miR to a predetermined value, wherein a higher level of expression than the predetermined value is indicative for said subject to be affected with said pathology associated with a synonymous mutation occurring within a gene of interest.

The present invention also relates to a miR liable to bind to a gene of interest comprising a synonymous mutation for use in the treatment of a pathology associated with said synonymous mutation occurring within said gene of interest.

DETAILED DESCRIPTION OF THE INVENTION

By showing for the first time that a synonymous mutation could be responsible for an alternative miRNA binding site, the inventors put in evidence a novel mechanism, based on microRNA alternative binding, whereby such synonymous mutations are implicated in human pathology. More particularly, the inventors showed that the IRGM mRNA is targeted by miR-196A and B in the wild type population (C/C) but not in patients harboring the homozygous (T/T) variant. Differential regulation is due to incorrect binding within the seed region that is crucial for miRNA-RNA interaction. It results that miRNA-196 binding to IRGM is thus the first example of a miRNA regulative motif within the coding sequence in human.

DEFINITIONS

Throughout the specification, several terms are employed and are defined in the following paragraphs.

As used herein, the term "synonymous mutation" refers to a silent DNA mutation occurring within the coding region of a gene of interest (i.e. in one exon of said gene) that does not result in a change to the amino acid sequence of the related protein.

A "coding sequence", "a coding frame sequence", "a coding region" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The term "gene" means a DNA sequence that code for to a particular sequence of amino acids which comprise all or part of one or more proteins, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription. In particular, the term gene may be intended for the genomic sequence encoding a protein, i.e. a sequence comprising regulator, promoter, intron and exon sequences.

As used herein, the terms "miR" or "miRNA" are used interchangeably and have their general meaning in the art. They refer to a microRNA molecule found in eukaryotes that is involved in RNA-based gene regulation. They refer to single-stranded RNA molecules of 21-23 nucleotides in length to the single-stranded RNA molecule processed into a short stem-loop structure called a pre-miRNA and finally into a functional miRNA. Generally, miRNA are defined by their miRNA seed sequence (positions 2-7) corresponding to the minimal 5' sequence complementarity necessary to confer target gene binding and regulation.

As used herein, "measuring" encompasses detecting or quantifying. As used herein, "detecting" means determining if a miR of interest is present or not in a biological sample and "quantifying" means determining the amount of a miR of interest in a biological sample.

A "pathology associated with a synonymous mutation occurring within a gene of interest" according to the invention refers to a disease caused by the impairment of the binding of a miR to a gene of interest (which usually binds in order to regulate its level expression), such impairment being the direct consequence of the appearance of a synonymous mutation in the coding region of a gene of interest. The term refers to any pathology for which a synonymous mutation has been identified as a risk factor of developing said pathology (e.g. 313C>T substitution in the IRGM gene is a risk factor of developing IBD, especially Crohn disease). Such term thus encompasses inflammatory diseases, auto-immune diseases, cancerous disease, neurological disorders including neurodegenerative disorders, metabolic diseases, infectious diseases including bacterial, viral, parasite, or fungal infection, cardiovascular diseases, respiratory diseases, skin diseases and musculoskeletal diseases.

As used herein, the term "subject" denotes a mammal, such as a rodent, a feline, a canine, and a primate. Preferably a subject according to the invention is a human.

Diagnostic Methods of the Invention

The inventors have notably shown that a synonymous mutation (e.g. 313C>T substitution) found in a gene of interest (e.g. IRGM) may be result in a pathology associated with said synonymous mutation occurring within said gene of interest (e.g. inflammatory bowel disease especially Crohn disease). Indeed, they have demonstrated that such synonymous mutation could have a physiopathological impact since said mutation impairs the binding of miR-196 with IRGM in order to down-regulate its level expression.

Therefore, the present invention relates to an in vitro method for diagnosing and/or prognosing a pathology associated with a synonymous mutation occurring within a gene of interest in a subject, said method comprising the following steps of:
  detecting said synonymous mutation in a biological sample from said subject,
  measuring the level of expression of the miR liable to bind to said wild-type (WT) gene of interest in said biological sample, and
  comparing the level of expression of said miR to a predetermined value, wherein a higher level of expression than the predetermined value is indicative for said subject to be affected with said pathology associated with a synonymous mutation occurring within a gene of interest.

In one embodiment, the synonymous mutation is in the coding region of the immunity-related GTPase family, M (IRGM) gene.

In a particular embodiment, the synonymous mutation is a homozygous mutation stricto sensu, wherein both alleles of the IRGM gene present the 313C>T substitution (rs10065172). In another embodiment, the mutation is a composite heterozygous mutation, wherein one allele of the IRGM gene presents the 313C>T substitution.

According to this embodiment, the miR liable to bind WT IRGM gene to is miR-196.

In another embodiment, the synonymous mutation is in the coding region of nucleotide-binding oligomerization domain containing 2 (NOD2) gene.

In a particular embodiment, the synonymous mutation is a homozygous mutation stricto sensu, wherein both alleles of the NOD2 gene present the 639C>G substitution (rs2067085). In another embodiment, the mutation is a composite heterozygous mutation, wherein one allele of the NOD2 gene presents the 639C>G substitution.

According to this embodiment, the miR liable to bind WT NOD2 gene to is miR-92b*.

In still another embodiment, the synonymous mutation is in the coding region of presynaptic cytomatrix protein or bassoon (BSN) gene.

In a particular embodiment, the synonymous mutation is a homozygous mutation stricto sensu, wherein both alleles of the BSN gene present the 11850G>A substitution (rs9858542). In another embodiment, the mutation is a composite heterozygous mutation, wherein one allele of the BSN gene presents the 11850G>A substitution.

Accordingly, the pathology associated with a synonymous mutation occurring within IRGM gene, NOD2 gene or BSN gene is an inflammatory disease.

In a particular embodiment, said inflammatory disease is an inflammatory bowel disease such as Crohn disease and Ulcerative colitis.

These three pertaining to the invention are known per se as well as implicated in Crohn disease, and are listed in the below Table 1 with associated SNP leading to a synonymous mutation and particular miR liable to bind to said WT genes of interest

TABLE 1

Examples of synonymous mutation implicated in Crohn disease with particular miR liable to bind to said wild-type (WT) gene of interest.

| | SNP | | | Crohn | miRNA | | |
|---|---|---|---|---|---|---|---|
| | | | | | Patrocles | | SNPMIR |
| Gene | rs Number | AminoAcid | Mutation | Implicated | (7mer) | RegRNA | (2-7) |
| IRGM | rs10065172 | Leu 105 | synonymous | yes | −196/+26/+1297 | −196 | −196/+26/+1297/+562/+1244 |
| NOD2 | rs2067085 | Ser 178 | synonymous | yes | −92b* | −92b*/−326/−330-5p | −92b*/−326/−330-5p/−1302/−184 |
| BSN | rs9858542 | Thr 3912 | synonymous | yes | +223/+1237 | +223/+1237 | +1237 |

In another embodiment, the synonymous mutation is a homozygous mutation stricto sensu, wherein both alleles of the telomerase reverse transcriptase (TERT) gene present the 973G>A substitution (rs2736098). In another embodiment, the mutation is a composite heterozygous mutation, wherein one allele of the TERT gene presents the 973G>A substitution.

Accordingly, the pathology associated with a synonymous mutation occurring within TERT is a cancerous disease as previously described[24].

In a particular embodiment, said cancerous disease is selected in the group consisting of basal cell carcinoma, lung cancer, bladder cancer, prostate cancer, squamous cell carcinoma of the head and neck, and cervix cancer.

In another particular embodiment, said cancerous disease is lung cancer, According to this embodiment, the miR liable to bind WT TERT gene to is hsa-miR-1471.

Synonymous mutations in a gene of interest (e.g. the 313C>T substitution in the IRGM gene) may be detected by analyzing a nucleic acid molecule of said gene of interest. In the context of the invention, nucleic acid molecules include mRNA, genomic DNA and cDNA derived from mRNA. DNA or RNA can be single stranded or double stranded. These may be utilized for detection by amplification and/or hybridization with a probe, for instance.

The nucleic acid sample may be obtained from any cell source or tissue biopsy. Non-limiting examples of cell sources available include without limitation blood cells, buccal cells, epithelial cells, fibroblasts, or any cells present in a tissue obtained by biopsy. Cells may also be obtained from body fluids, such as blood, plasma, serum, lymph, etc. DNA may be extracted using any methods known in the art, such as described in Sambrook et al., 1989. RNA may also be isolated, for instance from tissue biopsy, using standard methods well known to the one skilled in the art.

Synonymous mutations may be detected in a RNA or DNA sample, preferably after amplification. For instance, the isolated RNA may be subjected to coupled reverse transcription and amplification, such as reverse transcription and amplification by polymerase chain reaction (RT-PCR), using specific oligonucleotide primers that are specific for a mutated site or that enable amplification of a region containing the mutated site. According to a first alternative, conditions for primer annealing may be chosen to ensure specific reverse transcription (where appropriate) and amplification; so that the appearance of an amplification product be a diagnostic of the presence of a particular mutation in a gene of interest. Otherwise, RNA may be reverse-transcribed and amplified, or DNA may be amplified, after which a mutated site may be detected in the amplified sequence by hybridization with a suitable probe or by direct sequencing, or any other appropriate method known in the art. For instance, a cDNA obtained from RNA may be cloned and sequenced to identify a mutation in the sequence of a gene of interest.

Actually numerous strategies for genotype analysis are available (Antonarakis et al., 1989; Cooper et al., 1991; Grompe, 1993). Briefly, the nucleic acid molecule may be tested for the presence or absence of a restriction site. When a base substitution mutation creates or abolishes the recognition site of a restriction enzyme, this allows a simple direct PCR test for the mutation. Further strategies include, but are not limited to, direct sequencing, restriction fragment length polymorphism (RFLP) analysis; hybridization with allele-specific oligonucleotides (ASO) that are short synthetic probes which hybridize only to a perfectly matched sequence under suitably stringent hybridization conditions; allele-specific PCR; PCR using mutagenic primers; ligase-PCR, HOT cleavage; denaturing gradient gel electrophoresis (DGGE), temperature denaturing gradient gel electrophoresis (TGGE), single-stranded conformational polymorphism (SSCP) and denaturing high performance liquid chromatography (Kuklin et al., 1997). Direct sequencing may be accomplished by any method, including without limitation chemical sequencing, using the Maxam-Gilbert method; by enzymatic sequencing, using the Sanger method; mass spectrometry sequencing; sequencing using a chip-based technology; and real-time quantitative PCR. Preferably, DNA from a subject is first subjected to amplification by polymerase chain reaction (PCR) using specific amplification primers. However several other methods are available, allowing DNA to be studied independently of PCR, such as the rolling circle amplification (RCA), the InvaderTMassay, or oligonucleotide ligation assay (OLA). OLA may be used for revealing base substitution mutations. According to this method, two oligonucleotides are constructed that hybridize to adjacent sequences in the target nucleic acid, with the join sited at the position of the mutation. DNA ligase will covalently join the two oligonucleotides only if they are perfectly hybridized.

Therefore, useful nucleic acid molecules, in particular oligonucleotide probes or primers, according to the present invention include those which specifically hybridize the regions where the mutations are located.

Oligonucleotide probes or primers may contain at least 10, 15, 20 or 30 nucleotides. Their length may be shorter than 400, 300, 200 or 100 nucleotides.

Probes or primers of the invention may be labelled with a detectable molecule or substance, such as a fluorescent molecule, a radioactive molecule or any others labels known in the art. Labels are known in the art that generally provide (either directly or indirectly) a signal. The term "labelled", with regard to the probes or primers of the invention, is intended to encompass direct labelling of the probes or primers of the invention by coupling (i.e., physically linking) a detectable substance to the probes or primers of the invention, as well as indirect labeling of the probes or primers of the invention by reactivity with another reagent that is directly labeled. Other examples of detectable substances include but are not limited to radioactive agents or a fluorophore (e.g. fluorescein isothiocyanate (FITC) or phycoerythrin (PE) or Indocyanine (Cy5)). Examples of indirect labeling include detection of a primary antibody using a fluorescently labeled secondary antibody and end-labeling of a DNA probe with biotin such that it can be detected with fluorescently labeled streptavidin.

When a synonymous mutation is detected in a gene of interest, it is possible to determine if said mutation impairs the binding of a particular miR, usually binding the wild type sequence of said gene of interested. For this purpose, this determination may be conducted by a comparative analysis of mRNA sequence of a gene of interest harboring a synonymous mutation such the C313T polymorphism in the IRGM mRNA sequence on several applications (e.g., SNIPMIR, REGRNA, and PATROCLES.

The level of expression of any miR liable to bind to the wild-type gene of interest may be measured by any method familiar to one of skill in the art.

This measurement can be performed by various methods which method which are well known to the person skilled in the art, including in particular quantitative methods involving reverse transcriptase PCR(RT-PCR), such as real-time quantitative RT-PCR (qRT-PCR).

The method for diagnosing and/or prognosing of the invention involves comparing the level of expression of a particular miR (i.e. a miR liable to bind to a particular WT gene of interest) to a predetermined value.

The "predetermined value" according to the invention can be a single value such as a level or a mean level of expression of said particular miR as determined in a reference group of individuals who did not develop a pathology associated with a synonymous mutation occurring within a gene of interest (e.g. an inflammatory disease such as Crohn disease).

More preferably, the predetermined value corresponds essentially to an absence of expression of said particular miR. When a gene is "not expressed", essentially no miR resulting from transcription can be detected. In one embodiment according to the invention, depending on the technique which is used, a gene will be considered as "non-expressed" when the level of expression is below that which can be detected by said technique or when it is below the background level of the technique.

A level of expression of a particular miR higher than the predetermined value indicates that the individual is afflicted with a pathology associated with a synonymous mutation occurring within a gene of interest. In particular, the miR expression measured in the biological sample of the individual may be at least 10%, 20%, 30%, 40%, 50%, 60%, 70%, 80%, 90%, 100%, 150% or 200% higher than the predetermined value.

The present invention also encompasses kits containing means to implement diagnostic methods of the invention.

Therapeutic Methods of the Invention

In another aspect, the present invention relates to use, methods and pharmaceutical compositions for treating a pathology associated with a synonymous mutation occurring within a gene of interest (e.g. an inflammatory disease such as Crohn disease).

In the context of the invention, the term "treating" or "treatment" means reversing, alleviating, inhibiting the progress of, or preventing the disorder or condition to which such term applies, or one or more symptoms of such disorder or condition. In particular, the treatment of the disorder may consist in inhibiting the progress of the pathology associated with a synonymous mutation occurring within a gene of interest (e.g. an inflammatory disease). More preferably, such treatment leads to the total disparition of the pathology.

Therefore, the invention also relates to a miR liable to bind to a gene of interest comprising a synonymous mutation for use in the treatment of a pathology associated with said synonymous mutation occurring within said gene of interest.

Indeed, modifications may be generated in the sequence of wild-type (WT) miR by introducing the compensatory mutation. Said modified miR can thus bind to the gene of interest comprising a synonymous mutation (impairing the binding of the WT miR to said mutated gene) and can therefore regulate the level expression of said mutated gene of interest.

More precisely, the seed sequence of a miR will be designed in order to comprise the compensatory mutation necessary for binding the mutated gene of interest. Since several miR may comprise the same seed sequence comprising compensatory mutation.

For instance, miR-196a having the nucleotide sequence "uagguaguuucauguuguuggg" (SEQ ID NO. 1) and miR-196b having the nucleotide sequence "uagguaguuuccuguuguuggg" (SEQ ID NO. 2) comprise the same seed sequence "agguag" but differ by one sole nucleotide at the twelfth position (a>c).

In one embodiment, said miR liable to bind to a gene of interest is a modified miR-196 which binds to the mutated IRGM presenting the 313C>T substitution (rs10065172). In a particular embodiment, said modified miR-196a is represented by SEQ ID NO: 1. In another particular embodiment, said modified miR-196b is represented by SEQ ID NO: 2.

In certain embodiments, a miR liable to bind to a gene of interest such as modified miR-196 according to the invention, or a segment or a mimetic thereof, will comprise 6, 7, 8, 9, 10, 11, 12, 13, 14, 15, 16, 17, 18, 19, 20, 21, 22, 23, 24, 25, 26, 27, 28, 29 or more nucleotides of the precursor miRNA or its processed sequence, including all ranges and integers there between. In other embodiments, the miR according to the invention contains the full-length processed miRNA sequence.

It must also noted that a modified miR such as the modified miR-196 according to the invention can be administered with 1, 2, 3, 4, 5, 6, 7, 8, 9, 10 or more miRNAs and that such miRNAs can be administered concurrently, in sequence, or in an ordered progression.

The present invention also encompasses pharmaceutical compositions comprising an effective amount of a miR liable to bind to a gene of interest comprising a synonymous mutation according to the invention such as the above-mentioned modified miR-196.

An "effective amount" of the pharmaceutical composition, generally, is defined as that amount sufficient to detectably and repeatedly to achieve the stated desired result, for example, to ameliorate, reduce, minimize or limit the extent of the disease or its symptoms. Other more rigorous definitions may apply, including elimination or cure of disease.

Accordingly, the pathology associated with a synonymous mutation occurring within IRGM gene, NOD2 gene or BSN gene is an inflammatory disease.

In a particular embodiment, said inflammatory disease is an inflammatory bowel disease such as Crohn disease and Ulcerative colitis.

Accordingly, the invention also provides a method for treating a pathology associated with a synonymous mutation occurring within said gene of interest comprising a step of administering a miR liable to bind to a gene of interest comprising said synonymous mutation.

The invention will be further illustrated by the following figures and examples. However, these examples and figures should not be interpreted in any way as limiting the scope of the present invention.

FIGURES

FIG. 1: Allele specific restricted regulation of IRGM by miR-196. A. In silico prediction of miR-196 and IRGM mRNA interactions showed differences in binding within the seed region. B. IRGMC WT mRNA is significantly enriched in miR-196B complexes. Extracts of cells expressing Flag-tagged-AGO1 and transfected with biotinylated miR-196B or control miR-20 as indicated, were submitted to tandem affinity purification (immunoprecipitation with anti-Flag antibodies followed by affinity purification on streptavidin beads). IRGM mRNAs variants were quantified using qRT-PCR; results are presented as the ratio between miR-196BWT and miR-20 (non-relevant miRNA) pull-downs; mean of 3 independent experiments. C. HEK293 cells were transfected with either FLAG-tagged-IRGMC or FLAG-tagged-IRGMT plasmids and co-transfected with miR-196B. Immunoblotting with an anti-IRGM antibody revealed the specificity of the downregulation effect of miRNA-IRGM mRNA interaction. D. Quantification of the immunoblot signals are presented as IRGM expression relative to actin, mean of at least three independent experiments ±SEM.

Figure 2:
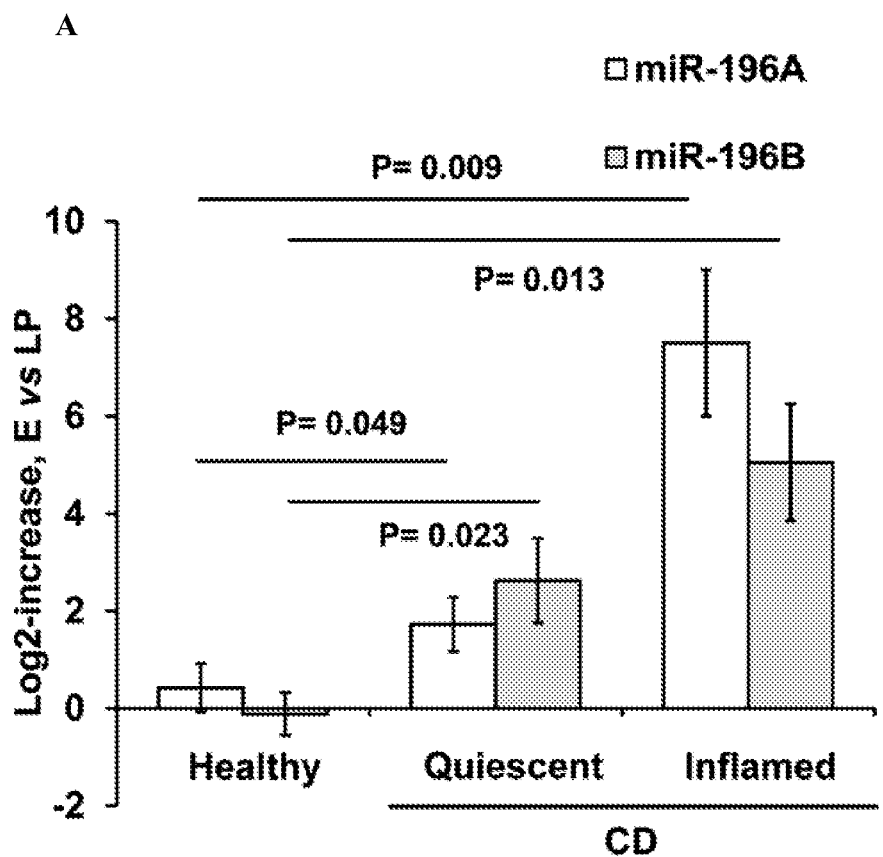
Figure 2:
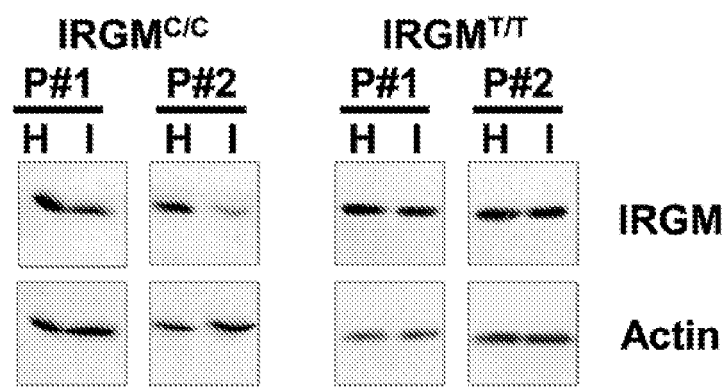

FIG. 2: Mir-196 over-expression in active mucosa correlates with decreased expression of the IRGM 313C variant ex vivo. A. Epithelial or laminal fractions were captured from sections of biopsies of healthy controls or CD patients (both n=8) with no inflammation (n=16), quiescent (defined as low-grade inflammation) (n=8) or acute inflammation (n=8) using laser capture microdissection. After RNA extraction, miR-196A (black bars) and miR-196B (white bars) relative expression was analyzed using RNU19, 44 and U6 and to overcome possible inter-patient bias the lamina propria fraction value was used for relative quantification. Due to high differences in expression between healthy and inflamed tissues, the results are presented as a log 2-fold ratio. B. The expression level of IRGM was confirmed by immunoblotting of samples from patients with different genotypes from non-inflamed and inflamed colons.

Figure 3:
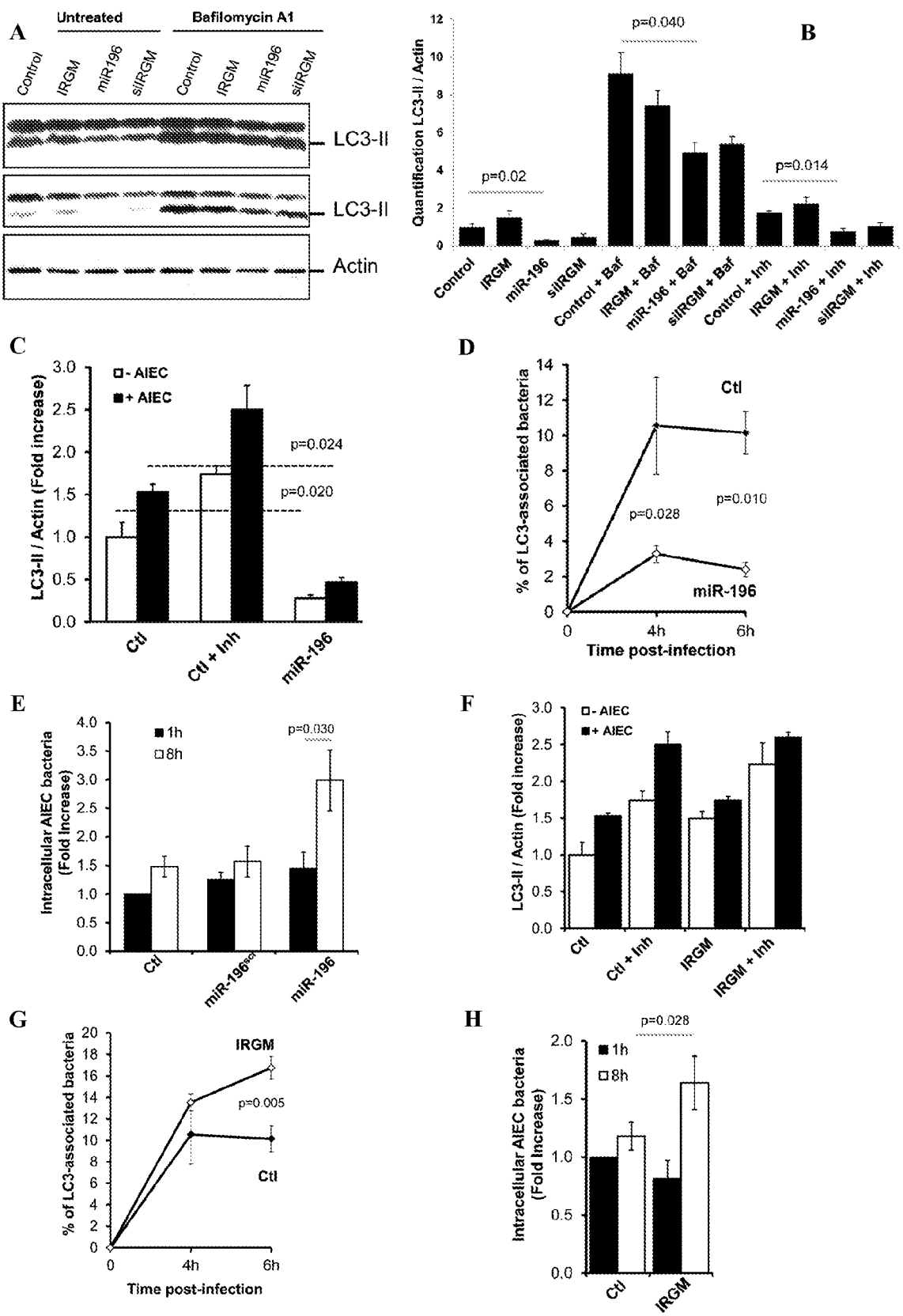

FIG. 3: IRGM expression and miR-196 affect autophagic flux and AIEC-bacteria-mediated autophagy. A. The basal flux of autophagy is affected by the IRGM expression level. HEK293 cells transfected with either an IRGM expressing plasmid, or miR-196b or siIRGM, were treated with bafilomycin A1 for 2 h and processed for immunoblotting with anti-LC3B. B. Quantification of LC3-II relative to actin. C. Downregulation of IRGM expression by miR-196 abrogates AIEC-mediated autophagy in cells treated with autophagic inhibitors (Inh), or transfected with miR-196b, and infected for 4 h with AIEC LF82. D. Confocal microscopic examination of LC3 reveals a significant decrease in the percentage of LC3 (red) associated-LF82 bacteria (green) in miR-196 transfected cells, compared to control cells. E. miR-196 transfection leads to increased intracellular LF82 replication. Results are expressed as a fold increase +/−SEM of intracellular bacteria. F. IRGM overexpression did not inhibit autophagic flux and increased slightly LC3-II accumulation in response to AIEC infection. HEK293 cells were transfected with a IRGM expressing plasmid, treated with autophagic inhibitors, and infected with AIEC bacteria for 4 h. G. Confocal microscopic examination showed a significant increase in the percentage of LC3 associated-AIEC bacteria in IRGM cells, compared to control cells (ct1). H. IRGM overexpression leads to a high rate of intracellular replication of LF82 bacteria and most of the bacteria reside in non acidic vacuoles as shown with lysotracker at 8 h post-infection. All values are means of at least three independent experiments.

EXAMPLE

Regulation of IRGM-Dependent Xenophagy by miR-196 is Lost by Synonymous Variant C313T in Crohn's Disease (CD)

Material & Methods

Patients, Biopsy Specimens and Histology:

All patients included in this study were hospitalized in the Department of Gastroenterology (Archet Hospital, Nice, France). Clinical information regarding associated GI (and non-GI) symptoms were obtained from the hospital information system. All patients gave signed agreement for this study and the protocol was approved by the local ethics committee of the University of Nice. There were 170 French Caucasians patients (120 CD) and 50 controls. For measurement of histological disease activity, the scoring system for histological abnormalities in CD mucosal biopsy specimens was used[18]. For each patient included in this series, seven supplementary intestinal biopsies from each area were taken. Three biopsies were used to set up tissue microarrays (TMAs). The latter biopsies were fixed in 10% buffered formalin then processed, oriented on their edge, embedded in paraffin, cut into sequential 4-μm sections, and stained with haematoxylin-eosin. Other biopsies were immediately snap-frozen in liquid nitrogen for mRNA extraction (3 biopsies). The IRGM genotype was first examined using a TaqMan discrimination assay (rs10065172) and a 7500 fast PCR instrument (Applied Biosystems, Courtaboeuf, France). The genomic DNA of patients was re-analyzed by amplification and sequencing. FLAG tagged-IRGM plasmids were used as controls.

Cell Lines, miRNA and Plasmid Transfection:

HeLa, HEK293, T84 and HCT116 cells were obtained from the European Collection of Cell Cultures (ECACC, Sigma-Aldrich) and grown according to the supplier's recommendations. Pre-miR miRNA precursors of miR-CON1 (Control), and all the other miR-196 were purchased from Ambion (Applied Biosystems, France). SiRNA duplexes directed against human IRGM were purchased from Invitrogen (HSS156156, Stealth siRNA). Control duplexes were purchased from the same supplier and were GC-matched, nontargeting sequences. HEK293 cells were transfected with miR or siRNA using Lipofectamine RNAimax (Invitrogen) for 48 h according to the manufacturer's protocol for this cell line. The empty plasmid pCMV and plasmid pCMV-3× Flag-IRGM have been described previously[1,19]. Site directed mutagenesis of C313T was performed using the Quick-Change II site-directed mutagenesis kit (Stratagene, Agilent technologies, France). Mutagenesis and clone selection was assessed by allelic discrimination of IRGM and re-sequencing was done with specific primers as described above. HEK293 cells were transfected with plasmids using Lipofectamine LTX (Invitrogen) for 20 h according to the manufacturer's protocol for this cell line. Immunoblotting was done using antibodies to actin (Sigma), IRGM NT or IN (ProSci) and the appropriate HRP-conjugated secondary antibody (Santa Cruz Biotechnology, San Diego, Calif.).

Tandem Affinity Purification of miRNA Target mRNAs (TAP-Tar):

HeLa S3 (XLP) cells were cultured with Dulbecco's modified Eagle's medium (Invitrogen) containing 10% foetal calf serum. The HeLa S3 cell lines stably expressing Flag-HA-AGO1 or Flag-HA-AGO2 were obtained using retroviral vectors as previously described[27]. Cells were transfected with synthetic miRNA (15 nM) miR 196B-WT, miR-196B-MOD, and miR-20A biotinylated at the 3'-end with a C1004 spacer (purchased from Sigma-Aldrich) and the pCMV plasmid containing IRGM (250 ng) were transfected into cells using HiPerfect (Qiagen) according to the manufacturer's instructions. After tandem purification, as previously described, total RNA was reverse transcribed and IRGM expression was monitored using allelic discrimination PCR.

miRNA in Situ Hybridization:

To investigate the cell-specific distribution of miRNA in normal and inflamed tissues, in situ hybridization was performed using 5'- and 3' end digoxigenin (DIG)-labeled LNA modified DNA oligonucleotides (LNAs) complementary to the mature miRNA (Exiqon A/S, Denmark) following the manufacturer's instructions. In this study, the global expression of miR-196 (the temperature of annealing may not differentiate both isoforms according to the manufacturer's instructions) was examined in intestinal biopsies (LNA-miR-196 and LNA-scrambled as a negative control).

Tissue Microarray (TMA) Construction and Immunohistochemistry:

Representative intestinal biopsies of each individual were selected from haematoxylin and eosin stained sections for building TMAs. TMAs were set up as previously described[20, 21]. Immunohistochemical methods were performed using anti-IRGM-IN or NT (ProSci Incorporated, Poway, Calif.) or anti-lysozyme (DAKO Envision System, DAKO Corp, Carpinteria, Calif.) antibodies as previously described[20-22]. IRGM antibody specificity was confirmed by immunoblotting.

Laser Capture Microdissection:

Snap-frozen tissue blocks of intestinal biopsies were chosen from the tissue bank of the Human Tissue Biobank Unit, Nice and included in Cryomatrix (Thermo Fisher Scientific, Courtaboeuf, France). Four- to eight-micron serial frozen sections were microdissected using a PixCell laser capture microscope (Arcturus Engineering, Santa Clara, Calif.). After visual control of the completeness of dissection, miRNA from the captured tissue was obtained with the MicroRNA isolation kit (Stratagene, La Jolla, Calif.).

Autophagy Flux Assay:

Autophagy flux was blocked by incubating cells with pharmacological inhibitors: bafilomycin A1 (100 nM, Sigma), or pepstatin+E64d (10 mM, Sigma) 30 min prior to cell infection and kept for the entire duration (4 h) of the experiments. Cells were processed for immunoblotting by loading 25 μg of proteins, separated on a 15% SDS gel by PAGE, and then transferred onto a PVDF membrane. LC3-II accumulation was revealed using anti-LC3-B (Sigma). Anti-actin (Sigma), as loading control, and anti-IRGM (ProSci), as an experimental control, were also used. Quantification was performed by using ImageJ software.

Invasion and Intracellular Survival Assay:

Bacterial invasion of human epithelial HEK293 cells was performed using the gentamycin protection assay[23]. Monolayers were infected for 3 h at a multiplicity of infection (MOI) of 10 bacteria per cell. At 1 and 8 h post-infection the number of intracellular bacteria was determined by counting the number of colony forming units (CFU). Experiments were independently carried out at least three times and one representative data set of three independent experiments was presented where appropriate.

Fluorescence Microscopy:

At indicated times after bacterial infection HEK293 cells were fixed with 4% paraformaldehyde and immunostained with anti-IRGM-NT (Prosci), anti-LC3 (MBL) and with appropriate secondary antibodies (Invitrogen). Staining of acidic compartments was carried out by incubating cells for 1 h prior to fixation in medium containing 100 nM of acidotropic dye LysoTracker Red DND99 (Invitrogen). The slides were examined with a Zeiss LSM 510 Meta confocal microscope. Counting was done at ×63 magnification and at least 100 cells were counted for each experimental condition.

Statistical Analysis:

The results were evaluated for statistical significance with the Student's t-test. Error bars represent the standard deviation (S.D.) of the mean. P values less than 0.05 were regarded as significant.

Results:

IRGM expression is affected by multiple polymorphisms that can create tissue-specific variation in IRGM expression[1-3]. A "silent" variation within the coding region (rs10065172, C313T), in perfect linkage disequilibrium ($r^2$=1.0) with a 20 kb deletion upstream of the IRGM gene, has been strongly associated with CD in Caucasians[1,4,5]. Recent data proposed that the promoter region might be the causal variant involved in CD pathogenesis[1], since the deletion, or other copy number variations, closely juxtaposes the transcription factor binding sites. An alternative hypothesis would be to consider that the exonic (CTG>TTG, Leu) variant might affect protein expression. In this regard, evidence that a polymorphism can alter miRNA-directed repression of mRNA in a 3'-untranslated region[6,7] is of particular interest. Therefore, we investigated whether miRNA binding to IRGM mRNA could be defective and consequently lead to abnormal regulation of IRGM expression in subjects with the T allele.

For this purpose, binding of miRNAs to the different forms of IRGM mRNA was assessed in silico using SNIPMIR, REGRNA and PATROCLES software (SNIPMIR, http://www.microarray.fr:8080/merge/index?action=MISNP, REGRNA, http://regrna.mbc.nctu.edu.tw/, PATROCLES, http://www.patrocles.org/). We observed a loss in binding of two miRNAs, miR-196A and miR-196B, to the risk haplotype carrying the T allele (FIG. 1A). Indeed, the C313T polymorphism of IRGM is located within the "seed" region where mRNA/miRNA forms an affinity complex within RISC(RNA-Induced Silencing Complex), which is important for mRNA regulation. Two pre-miR-196A (A1 and A2) encode the same mature miR-196A while miR-196B is unique within the genome. Both miRNA share the same "seed" region and target specificity. Moreover, tandem affinity purification of miRNA target mRNA (TAP-TAR)[8] showed higher binding of miR-196 to $IRGIVI^C$ than $IRGM^T$ confirming in silico predictions (FIG. 1B). In HEK293 cells, miR-196 transfection decreased expression of the FLAG-tagged $IRGIVI^C$ and endogenous IRGM protein levels while the $IRGM^T$ variant expression remained constant (FIG. 1C). Using a miR-196$^{MOD}$, by introducing the compensatory mutation 3G>A, we observed stronger binding to $IRGM^T$ than to $IRGIVI^C$ and a concomitant decrease in $IRGM^T$ expression. Together, these results indicate that the CD-associated risk (T allele) and protective (C allele) haplotypes confer differences in IRGM expression under the control of miR-196. Interestingly, the miR-196 family and miR-196 binding site within the coding sequence of IRGM family members are conserved in different species, which is highly suggestive of shared critical control of IRGM protein expression by miRNA throughout evolution.

To correlate in silico and in vitro data with CD pathophysiology, the expression of miR-196 was analyzed in human biopsies using both in situ hybridization (ISH) and fractional laser capture microdissection followed by qPCR. MiR-196 increased expression was restricted to intestinal epithelial cells within inflamed ileum and colon in CD patients in comparison with healthy controls, as shown by representative images of global staining for miR-196 by ISH. To confirm these data, expression levels of miR-196A and B were determined on epithelial and lamina propria fractions isolated by laser capture microdissection. Interestingly, the expression of both miR-196A and miR-196B in the epithelium, relative to that in the lamina propria, gradually increased for healthy tissue from control patients or CD patients, quiescent and inflamed tissues from CD patients (FIG. 2A) independently of the $IRGM^{C/T}$ allelic status. We investigated whether the increase in miRNA expression could be consecutive to stimulation by bacterial components or cytokines, as previously reported for various cell lines[9-12]. In vitro experiments indicated no variation in both miR-196A and B under pro-inflammatory cytokine stimulation (IFN-7) or infection of HEK293 cells with CD-associated AIEC bacteria.

The correlation between miR-196 and IRGM expression in epithelial cells within the human intestinal mucosa was analyzed in tissue microarrays of CD patients. In healthy mucosa, IRGM staining was strongly positive in epithelial cells and only weakly positive in the lamina propria. Interestingly, in active mucosa, a decrease in IRGM expression was restricted to epithelial cells of patients with the $IRGM^{C/C}$ genotype, whereas IRGM expression was maintained in patients with the $IRGM^{T/T}$ genotype, independently of the inflammatory status (FIG. 2B). Thus, our findings show that miR-196 expression in inflammatory conditions correlates with down-regulated IRGM expression in human epithelial cells. Of note, IRGM staining was maintained at a high level in Paneth cells, indicating a possible difference in IRGM regulation in these cells. Together with a previous report showing that the levels of autophagy-related proteins ATG16L1 and ATG5 were critical in maintaining normal granule biogenesis[13], we hypothesized that alternative mechanisms regulating autophagy-related events could exist in Paneth cells.

IRGM encodes an autophagic protein that plays an important role in innate immunity against intracellular pathogens like *Mycobacterium tuberculosis, Salmonella typhimurium* and CD-associated adherent invasive *E. coli* (AIEC)[1,14,15]. Compelling evidence indicates that a critical threshold of IRGM can regulate the efficiency of the autophagic process[1,14], but the mechanism of regulation of human IRGM expression remains unknown[3,16]. Thus, we investigated whether miR-196 and subsequent modified IRGM expression may influence the basal autophagic flux by monitoring LC3-II conversion. LC3-II levels decrease during prolonged autophagy due to its degradation after autophagosomal-lysosomal fusion, so the flux through the autophagic system was measured by comparing LC3-II levels in the presence or absence of lysosomal inhibitors that partially (pepstatin+E64D) or completely (bafilomycin) prevent LC3-II degradation. Interestingly, miR-196, which reduced IRGM expression (FIG. 1), induced a significant decrease in LC3-II conversion (FIGS. 3A and B, p=0.02). Moreover, when autophagy was blocked with lysosomal inhibitors, miR-196 inhibited the accumulation of LC3-II (FIGS. 3A and B), which suggests strongly that miR-196 overexpression inhibits the autophagic process at the initiation step.

To determine the impact of the increase in miR-196 expression observed in CD patients, we examined autophagic flux in response to CD-associated AIEC infection. In response to AIEC bacterial infection, increased formation of LC3-II was observed (FIG. 3C). When lysosomal LC3-II degradation was blocked a larger increase in LC3-II was observed in AIEC infected cells, indicating functional autophagic flux. In miR-196 transfected cells, we noted a decrease in autophagic flux (FIGS. 3B and C) associated with decreased numbers of LC3-II-associated bacteria (p=0.01), and a significant (p=0.03) higher number of intracellular AIEC LF82 bacteria (FIG. 3E). Of note, similar results were found for IRGM siRNA infected cells while not observed in cells transfected with miR-196$^{MOD}$ or miR-196$^{SC}$. Thus, miR-196 by controlling IRGM expression may act in endogenous fine-tuning of the initiation of the autophagic pathway and the control of intracellular pathogen degradation in human cells.

According to data shown above (FIG. 2), the absence of regulation of IRGM$^T$ by miR-196 is concomitant with sustained IRGM expression in intestinal epithelial cells. Analysis of IRGM localization and autophagic flux in HEK293 cells overexpressing the IRGM protein indicated unchanged compartmentalization and a normal basal autophagic flux as shown by the LC3-II/actin ratio (FIGS. 3A and 3B). As IRGM over-expression leads to an increase in intracellular *Salmonella* spp. targeted by the autophagic machinery[1], we conducted experiments with AIEC. HEK293 cells overexpressing the IRGM protein exhibited induction of autophagy in response to AIEC infection, as shown by the LC3-II/actin ratio (FIG. 3F). In addition, IRGM overexpression was associated with increased numbers of LC3-II-associated bacteria (p=0.005), which was more pronounced at 6 h post-infection (FIG. 3G), together with an increased number of intracellular AIEC bacteria (FIG. 3H). Irgm1, the murine ortholog, has been described to be associated with the membrane of the phagosome and to be involved in phagosome full maturation[17]. We therefore analyzed whether AIEC bacteria colocalized with acidic vacuoles in cells over-expressing IRGM. Using the lysotracker probe, we observed a significant decrease in the percentage of AIEC LF82 bacteria in acidic compartments in cells overexpressing IRGM compared to non-transfected cells. Taken together our data show that miR-196 controls the IRGM level, which is critical for both the initiation and the maturation of xenophagy.

Taken together the results provide an explanation for the potential consequence of the IRGM C313T polymorphism, among other polymorphisms, which jointly create tissue-specific variation in IRGM expression in predisposition to inflammatory bowel disease in Caucasians. Indeed, by showing for the first time that a synonymous mutation could be responsible for an alternative miRNA binding site, we provide evidence for inflammatory-dependent loss in the regulation of the autophagy-related protein IRGM with the CD risk haplotype. The in vivo relevance of these findings could be that AIEC infection in Caucasian CD patients with miR196-dysregulated IRGM (T313) expression lead to altered antibacterial activity of intestinal epithelial cells and abnormal persistence of CD-associated intracellular bacteria with a significant impact on the outcome of intestinal inflammation.

Finally, our data provide the first example of a miRNA-associated "noisy" silent polymorphism in a human genetic disease and shed light on the possible role in other human pathologies of other potential silent causative polymorphisms that has been "forgotten" due to the lack of possible explanation. So far, More than 4000 synonymous have been associated with increased risk for an human pathology, but due to fact that they had no consequences on the nature of amino acid in the protein, their role was minimized. We are investigating whether the synonymous polymorphisms (Table 2) may affect protein level and have some pathophysiological consequences on human health.

Therefore, other Single-Nucleotide Polymorphisms (SNP) corresponding to synonymous mutations in a gene of interest pertaining to the invention associated with a given pathology (defined by its Online Mendelian Inheritance in Man code (OMIM)) and for which miR liable to bind to WT gene are known per se, are listed in the below Table 2:

TABLE 2

| SNP | OMIM | MUTATION | GENE | MIR |
| --- | --- | --- | --- | --- |
| rs28936082 | 301500 | G/T | GLA | hsa-miR-665 |
| rs28936082 | 301500 | G/T | GLA | hsa-miR-1915 |
| rs28936082 | 301500 | G/T | GLA | hsa-miR-483-3p |
| rs28936082 | 301500 | G/T | GLA | hsa-miR-532-3p, hsa-miR-150 |
| rs28936082 | 301500 | G/T | GLA | hsa-miR-513a-5p, hsa-miR-27b, hsa-miR-27a |
| rs28936082 | 301500 | G/T | GLA | hsa-miR-220c |
| rs28936082 | 301500 | G/T | GLA | hsa-miR-342-3p |
| rs28936083 | 306700 | A/G | F8 | hsa-miR-449b* |

TABLE 2-continued

| SNP | OMIM | MUTATION | GENE | MIR |
|---|---|---|---|---|
| rs28936368 | 600310 | C/T | COMP | hsa-miR-1975 |
| rs28936370 | 600509 | C/G | ABCC8 | hsa-miR-1296 |
| rs28936370 | 600509 | C/G | ABCC8 | hsa-miR-564 |
| rs28936371 | 600509 | C/T | ABCC8 | hsa-miR-1915 |
| rs28936371 | 600509 | C/T | ABCC8 | hsa-miR-1538 |
| rs28936371 | 600509 | C/T | ABCC8 | hsa-miR-1972 |
| rs28936371 | 600509 | C/T | ABCC8 | hsa-miR-15a* |
| rs28936372 | 600528 | A/G | CPT1A | hsa-miR-1913, hsa-miR-324-3p, hsa-miR-18a* |
| rs28936372 | 600528 | A/G | CPT1A | hsa-miR-136 |
| rs28936372 | 600528 | A/G | CPT1A | hsa-miR-767-3p |
| rs28936373 | 600528 | C/T | CPT1A | hsa-miR-138-1* |
| rs28936374 | 600528 | A/G | CPT1A | hsa-miR-639 |
| rs28936374 | 600528 | A/G | CPT1A | hsa-miR-1470 |
| rs28936374 | 600528 | A/G | CPT1A | hsa-miR-572 |
| rs28936375 | 600650 | A/C | CPT2 | hsa-miR-1207-5p |
| rs28936375 | 600650 | A/C | CPT2 | hsa-miR-1254, hsa-miR-661 |
| rs28936375 | 600650 | A/C | CPT2 | hsa-miR-143* |
| rs28936375 | 600650 | A/C | CPT2 | hsa-miR-214* |
| rs28936375 | 600650 | A/C | CPT2 | hsa-miR-1285, hsa-miR-612 |
| rs28936375 | 600650 | A/C | CPT2 | hsa-miR-1914 |
| rs28936376 | 600650 | A/G | CPT2 | hsa-miR-330-3p |
| rs28936376 | 600650 | A/G | CPT2 | hsa-miR-9* |
| rs28936377 | 600726 | A/G | IHH | hsa-miR-1469 |
| rs28936377 | 600726 | A/G | IHH | hsa-miR-92a-1* |
| rs28936378 | 600726 | A/G | IHH | hsa-miR-1247 |
| rs28936379 | 600759 | A/G | PSEN2 | hsa-miR-556-5p |
| rs28936380 | 600759 | C/G | PSEN2 | hsa-miR-20b* |
| rs28936380 | 600759 | C/G | PSEN2 | hsa-miR-486-5p |
| rs28936381 | 600871 | A/G | GFI1 | hsa-miR-377* |
| rs28936381 | 600871 | A/G | GFI1 | hsa-miR-485-5p |
| rs28936381 | 600871 | A/G | GFI1 | hsa-miR-92a-1* |
| rs28936381 | 600871 | A/G | GFI1 | hsa-miR-1287 |
| rs28936382 | 600871 | A/G | GFI1 | hsa-miR-532-3p, hsa-miR-150 |
| rs28936382 | 600871 | A/G | GFI1 | hsa-miR-1470 |
| rs28936383 | 600900 | C/G | SGCB | hsa-miR-578 |
| rs28936384 | 600900 | C/G/T | SGCB | hsa-miR-1300, hsa-miR-580 |
| rs28936385 | 600900 | G/T | SGCB | hsa-miR-1972 |
| rs28936385 | 600900 | G/T | SGCB | hsa-miR-15a* |
| rs28936386 | 600900 | A/T | SGCB | hsa-miR-136 |
| rs28936386 | 600900 | A/T | SGCB | hsa-miR-508-5p |
| rs28936387 | 600968 | C/T | SLC12A3 | hsa-miR-1972 |
| rs28936387 | 600968 | C/T | SLC12A3 | hsa-miR-1205, hsa-miR-1184, hsa-miR-17* |
| rs28936387 | 600968 | C/T | SLC12A3 | hsa-miR-15a* |
| rs28936388 | 600968 | C/T | SLC12A3 | hsa-miR-665 |
| rs28936388 | 600968 | C/T | SLC12A3 | hsa-miR-508-5p |
| rs28936388 | 600968 | C/T | SLC12A3 | hsa-miR-766 |
| rs28936389 | 600968 | G/T | SLC12A3 | hsa-miR-1224-5p |
| rs28936389 | 600968 | G/T | SLC12A3 | hsa-miR-1280, hsa-miR-1224-3p |
| rs28936390 | 600970 | A/T | MYO6 | hsa-miR-335* |
| rs28936390 | 600970 | A/T | MYO6 | hsa-miR-323-3p |
| rs28936391 | 600970 | A/G | MYO6 | hsa-miR-190b, hsa-miR-190 |
| rs28936392 | 600993 | C/G | SMAD4 | hsa-miR-421 |
| rs28936392 | 600993 | C/G | SMAD4 | hsa-miR-433 |
| rs28936393 | 600993 | A/G | SMAD4 | hsa-miR-1228, hsa-miR-220a |
| rs28936395 | 600997 | A/G | EPHB2 | hsa-miR-563, hsa-miR-380* |
| rs28936395 | 600997 | A/G | EPHB2 | hsa-miR-218-2* |
| rs28936399 | 601284 | G/T | ACVRL1 | hsa-miR-486-5p |
| rs28936399 | 601284 | G/T | ACVRL1 | hsa-miR-1274b, hsa-miR-339-5p |
| rs28936399 | 601284 | G/T | ACVRL1 | hsa-miR-1227 |
| rs28936399 | 601284 | G/T | ACVRL1 | hsa-miR-146b-3p |
| rs28936399 | 601284 | G/T | ACVRL1 | hsa-miR-874 |
| rs28936400 | 601284 | A/T | ACVRL1 | hsa-miR-576-3p |
| rs28936400 | 601284 | A/T | ACVRL1 | hsa-miR-488* |
| rs28936401 | 601284 | C/T | ACVRL1 | hsa-miR-890 |
| rs28936402 | 601284 | C/G | ACVRL1 | hsa-miR-143 |
| rs28936402 | 601284 | C/G | ACVRL1 | hsa-miR-488* |
| rs28936403 | 601309 | A/G | PTCH1 | hsa-miR-2052, hsa-miR-19a*, hsa-miR-19b-1*, hsa-miR-19b-2* |
| rs28936404 | 601309 | C/T | PTCH1 | hsa-miR-485-3p |
| rs28936405 | 601309 | C/T | PTCH1 | hsa-miR-198 |
| rs28936407 | 601487 | A/G | PPARG | hsa-miR-122 |
| rs28936408 | 601542 | A/T | PITX2 | hsa-miR-596 |
| rs28936408 | 601542 | A/T | PITX2 | hsa-miR-766 |
| rs28936408 | 601542 | A/T | PITX2 | hsa-miR-1976 |
| rs28936409 | 601542 | C/G | PITX2 | hsa-miR-450a |
| rs28936410 | 601545 | A/G | PAFAH1B1 | hsa-miR-93* |
| rs28936411 | 601545 | C/G | PAFAH1B1 | hsa-miR-126 |
| rs28936412 | 601615 | C/T | ABCA3 | hsa-miR-513b |

TABLE 2-continued

| SNP | OMIM | MUTATION | GENE | MIR |
|---|---|---|---|---|
| rs28936412 | 601615 | C/T | ABCA3 | hsa-miR-125b-2* |
| rs28936412 | 601615 | C/T | ABCA3 | hsa-miR-513a-5p, hsa-miR-27b, hsa-miR-27a |
| rs28936412 | 601615 | C/T | ABCA3 | hsa-miR-520b, hsa-miR-302e, hsa-miR-519a, hsa-miR-519a, hsa-miR-520c-3p, hsa-miR-520d-3p, hsa-miR-520e, hsa-miR-519c-3p, hsa-miR-520a-3p, hsa-miR-519b-3p, hsa-miR-302c, hsa-miR-302d, hsa-miR-372, hsa-miR-373, hsa-miR-302b, hsa-miR-302a |
| rs28936412 | 601615 | C/T | ABCA3 | hsa-miR-220c |
| rs28936412 | 601615 | C/T | ABCA3 | hsa-miR-33b*, hsa-miR-515-3p, hsa-miR-519e, hsa-miR-515-3p, hsa-miR-371-3p |
| rs28936412 | 601615 | C/T | ABCA3 | hsa-miR-125a-3p |
| rs28936412 | 601615 | C/T | ABCA3 | hsa-miR-552 |
| rs28936413 | 601771 | A/G | CYP1B1 | hsa-miR-409-5p |
| rs28936413 | 601771 | A/G | CYP1B1 | hsa-miR-29b-1* |
| rs28936414 | 601771 | A/G | CYP1B1 | hsa-miR-483-5p |
| rs28936415 | 601785 | A/G | PMM2 | hsa-miR-124* |
| rs28936416 | 601802 | C/T | HESX1 | hsa-miR-182* |
| rs28936668 | 600310 | A/G | COMP | hsa-miR-1208 |
| rs28936668 | 600310 | A/G | COMP | hsa-miR-1258 |
| rs28936668 | 600310 | A/G | COMP | hsa-miR-452 |
| rs28936668 | 600310 | A/G | COMP | hsa-miR-645 |
| rs28936670 | 600584 | C/T | NKX2-5 | hsa-miR-191* |
| rs28936671 | 600635 | A/C | NKX2-1 | hsa-miR-876-3p, hsa-miR-323-5p |
| rs28936672 | 600635 | G/T | NKX2-1 | hsa-miR-488* |
| rs28936673 | 600650 | A/C | CPT2 | hsa-miR-149* |
| rs28936673 | 600650 | A/C | CPT2 | hsa-miR-939 |
| rs28936673 | 600650 | A/C | CPT2 | hsa-miR-2110 |
| rs28936673 | 600650 | A/C | CPT2 | hsa-miR-637 |
| rs28936673 | 600650 | A/C | CPT2 | hsa-miR-765 |
| rs28936673 | 600650 | A/C | CPT2 | hsa-miR-1225-5p |
| rs28936674 | 600650 | A/G | CPT2 | hsa-miR-664*, hsa-miR-149 |
| rs28936675 | 600725 | A/G | SHH | hsa-miR-1200, hsa-miR-378* |
| rs28936676 | 600923 | A/C | PPOX | hsa-miR-485-3p |
| rs28936676 | 600923 | A/C | PPOX | hsa-miR-627 |
| rs28936676 | 600923 | A/C | PPOX | hsa-miR-1827 |
| rs28936677 | 600923 | C/T | PPOX | hsa-miR-532-5p |
| rs28936677 | 600923 | C/T | PPOX | hsa-miR-138 |
| rs28936677 | 600923 | C/T | PPOX | hsa-miR-550 |
| rs28936678 | 600937 | C/T | KCNJ11 | hsa-miR-425* |
| rs28936678 | 600937 | C/T | KCNJ11 | hsa-miR-1265 |
| rs28936678 | 600937 | C/T | KCNJ11 | hsa-miR-383 |
| rs28936679 | 600950 | A/G | AANAT | hsa-miR-525-3p, hsa-miR-524-3p |
| rs28936679 | 600950 | A/G | AANAT | hsa-miR-675 |
| rs28936679 | 600950 | A/G | AANAT | hsa-miR-493 |
| rs28936679 | 600950 | A/G | AANAT | hsa-miR-18b, hsa-miR-18a |
| rs28936680 | 601059 | C/T | ADAR | hsa-miR-539 |
| rs28936680 | 601059 | C/T | ADAR | hsa-miR-135b* |
| rs28936681 | 601059 | C/T | ADAR | hsa-miR-302a* |
| rs28936682 | 601097 | C/T | PMP22 | hsa-miR-125b-2* |
| rs28936683 | 601146 | C/T | GDF5 | hsa-miR-1293, hsa-miR-363* |
| rs28936683 | 601146 | C/T | GDF5 | hsa-miR-125a-3p |
| rs28936683 | 601146 | C/T | GDF5 | hsa-miR-766 |
| rs28936684 | 601199 | G/T | CASR | hsa-miR-1251, hsa-miR-517*, hsa-miR-517*, hsa-miR-517* |
| rs28936685 | 601253 | C/T | CAV3 | hsa-miR-1207-5p |
| rs28936685 | 601253 | C/T | CAV3 | hsa-miR-1915 |
| rs28936686 | 601253 | A/G | CAV3 | hsa-miR-125a-3p |
| rs28936686 | 601253 | A/G | CAV3 | hsa-miR-657 |
| rs28936687 | 601284 | A/G | ACVRL1 | hsa-miR-1234 |
| rs28936688 | 601284 | A/G | ACVRL1 | hsa-miR-429, hsa-miR-200c, hsa-miR-200b |
| rs28936688 | 601284 | A/G | ACVRL1 | hsa-miR-106a* |
| rs28936688 | 601284 | A/G | ACVRL1 | hsa-miR-200a, hsa-miR-141 |
| rs28936689 | 601545 | C/G | PAFAH1B1 | hsa-miR-592 |
| rs28936689 | 601545 | C/G | PAFAH1B1 | hsa-miR-581 |
| rs28936689 | 601545 | C/G | PAFAH1B1 | hsa-miR-1231, hsa-miR-632 |
| rs28936689 | 601545 | C/G | PAFAH1B1 | hsa-miR-599 |
| rs28936689 | 601545 | C/G | PAFAH1B1 | hsa-miR-518c*, hsa-miR-330-5p, hsa-miR-326 |
| rs28936689 | 601545 | C/G | PAFAH1B1 | hsa-miR-593 |
| rs28936690 | 601615 | C/T | ABCA3 | hsa-miR-518b, hsa-miR-518a-3p, hsa-miR-518f, hsa-miR-518c, hsa-miR-518a-3p, hsa-miR-518d-3p |
| rs28936691 | 601615 | A/C | ABCA3 | hsa-miR-1913, hsa-miR-324-3p, hsa-miR-18a* |
| rs28936691 | 601615 | A/C | ABCA3 | hsa-miR-337-5p |
| rs28936691 | 601615 | A/C | ABCA3 | hsa-miR-887 |
| rs28936692 | 601618 | C/G | SOX18 | hsa-miR-885-3p |
| rs28936692 | 601618 | C/G | SOX18 | hsa-miR-575 |
| rs28936692 | 601618 | C/G | SOX18 | hsa-miR-1827 |

TABLE 2-continued

| SNP | OMIM | MUTATION | GENE | MIR |
|---|---|---|---|---|
| rs28936692 | 601618 | C/G | SOX18 | hsa-miR-940, hsa-miR-34b* |
| rs28936693 | 601618 | A/T | SOX18 | hsa-miR-1228, hsa-miR-220a |
| rs28936693 | 601618 | A/T | SOX18 | hsa-miR-874 |
| rs28936693 | 601618 | A/T | SOX18 | hsa-miR-197 |
| rs28936694 | 601652 | G/T | MYOC | hsa-miR-891b |
| rs28936694 | 601652 | G/T | MYOC | hsa-miR-593* |
| rs28936694 | 601652 | G/T | MYOC | hsa-miR-196a* |
| rs28936695 | 601687 | C/T | KRT12 | hsa-miR-450a |
| rs28936695 | 601687 | C/T | KRT12 | hsa-miR-448, hsa-miR-153, hsa-miR-153 |
| rs28936695 | 601687 | C/T | KRT12 | hsa-miR-450b-5p, hsa-miR-557, hsa-miR-507 |
| rs28936696 | 601719 | A/G | TBX4 | hsa-miR-1183 |
| rs28936697 | 601758 | C/T | PEX12 | hsa-miR-575 |
| rs28936697 | 601758 | C/T | PEX12 | hsa-miR-18b, hsa-miR-18a |
| rs28936697 | 601758 | C/T | PEX12 | hsa-miR-548m |
| rs28936698 | 601758 | A/T | PEX12 | hsa-miR-429, hsa-miR-200c, hsa-miR-200b |
| rs28936698 | 601758 | A/T | PEX12 | hsa-miR-338-5p |
| rs28936699 | 601762 | C/T | CASP10 | hsa-miR-138-1* |
| rs28936701 | 601771 | C/T | CYP1B1 | hsa-miR-220b |
| rs28936701 | 601771 | C/T | CYP1B1 | hsa-miR-767-5p |
| rs28936702 | 601802 | C/T | HESX1 | hsa-miR-1228, hsa-miR-220a |
| rs28936703 | 601802 | C/T | HESX1 | hsa-miR-2054 |
| rs28936703 | 601802 | C/T | HESX1 | hsa-miR-1183 |
| rs28936703 | 601802 | C/T | HESX1 | hsa-miR-892a |
| rs28936704 | 601802 | A/G | HESX1 | hsa-miR-450a |
| rs28936704 | 601802 | A/G | HESX1 | hsa-miR-599 |
| rs28936704 | 601802 | A/G | HESX1 | hsa-miR-2113 |
| rs28936704 | 601802 | A/G | HESX1 | hsa-miR-653 |
| rs28936968 | 306700 | C/T | F8 | hsa-miR-576-3p |
| rs28936968 | 306700 | C/T | F8 | hsa-miR-379 |
| rs28936969 | 306700 | A/G | F8 | hsa-miR-145* |
| rs28936970 | 306700 | C/T | F8 | hsa-miR-518a-5p, hsa-miR-527 |
| rs28936970 | 306700 | C/T | F8 | hsa-miR-105 |
| rs28936971 | 600163 | A/G | SCN5A | hsa-miR-941 |
| rs28936971 | 600163 | A/G | SCN5A | hsa-miR-221* |
| rs28936971 | 600163 | A/G | SCN5A | hsa-miR-328 |
| rs28936971 | 600163 | A/G | SCN5A | hsa-miR-619 |
| rs28936972 | 600287 | A/G | GARS | hsa-miR-532-3p, hsa-miR-150 |
| rs28936972 | 600287 | A/G | GARS | hsa-miR-587 |
| rs28936972 | 600287 | A/G | GARS | hsa-miR-141* |
| rs28937268 | 306700 | C/T | F8 | hsa-miR-31 |
| rs28937268 | 306700 | C/T | F8 | hsa-miR-1271, hsa-miR-182, hsa-miR-96 |
| rs28937269 | 306700 | A/G | F8 | hsa-miR-646, hsa-miR-503, hsa-miR-497, hsa-miR-424, hsa-miR-195, hsa-miR-15b, hsa-miR-16, hsa-miR-15a, hsa-miR-16 |
| rs28937269 | 306700 | A/G | F8 | hsa-miR-545* |
| rs28937269 | 306700 | A/G | F8 | hsa-miR-545 |
| rs28937269 | 306700 | A/G | F8 | hsa-miR-103, hsa-miR-107 |
| rs28937270 | 306700 | C/T | F8 | hsa-miR-101, hsa-miR-144 |
| rs28937270 | 306700 | C/T | F8 | hsa-miR-936, hsa-miR-199a-3p, hsa-miR-199b-3p, hsa-miR-199a-3p |
| rs28937270 | 306700 | C/T | F8 | hsa-miR-553 |
| rs28937270 | 306700 | C/T | F8 | hsa-miR-424* |
| rs28937270 | 306700 | C/T | F8 | hsa-miR-379 |
| rs28937270 | 306700 | C/T | F8 | hsa-miR-132, hsa-miR-212 |
| rs28937270 | 306700 | C/T | F8 | hsa-miR-411 |
| rs28937271 | 306700 | A/C/G | F8 | hsa-miR-539 |
| rs28937271 | 306700 | A/C/G | F8 | hsa-miR-425 |
| rs28937271 | 306700 | A/C/G | F8 | hsa-miR-548o, hsa-miR-1323 |
| rs28937271 | 306700 | A/C/G | F8 | hsa-miR-570 |
| rs28937271 | 306700 | A/C/G | F8 | hsa-miR-1300, hsa-miR-580 |
| rs28937272 | 306700 | A/G | F8 | hsa-miR-130b* |
| rs28937272 | 306700 | A/G | F8 | hsa-miR-129-5p |
| rs28937273 | 306700 | A/T | F8 | hsa-miR-297, hsa-miR-675* |
| rs28937273 | 306700 | A/T | F8 | hsa-miR-223* |
| rs28937274 | 306700 | C/T | F8 | hsa-miR-299-3p |
| rs28937274 | 306700 | C/T | F8 | hsa-miR-1259 |
| rs28937274 | 306700 | C/T | F8 | hsa-miR-584 |
| rs28937275 | 306700 | A/G | F8 | hsa-miR-1259 |
| rs28937275 | 306700 | A/G | F8 | hsa-miR-584 |
| rs28937276 | 306700 | A/G | F8 | hsa-miR-29a* |
| rs28937276 | 306700 | A/G | F8 | hsa-miR-1290, hsa-miR-876-5p |
| rs28937277 | 306700 | C/T | F8 | hsa-miR-541* |
| rs28937277 | 306700 | C/T | F8 | hsa-miR-611, hsa-miR-151-5p |
| rs28937277 | 306700 | C/T | F8 | hsa-miR-767-5p |
| rs28937277 | 306700 | C/T | F8 | hsa-miR-1185 |
| rs28937278 | 306700 | C/G/T | F8 | hsa-miR-886-3p |
| rs28937278 | 306700 | C/G/T | F8 | hsa-miR-657 |
| rs28937279 | 306700 | A/G | F8 | hsa-miR-886-3p |

TABLE 2-continued

| SNP | OMIM | MUTATION | GENE | MIR |
|---|---|---|---|---|
| rs28937280 | 306700 | A/G | F8 | hsa-miR-497* |
| rs28937280 | 306700 | A/G | F8 | hsa-miR-708* |
| rs28937280 | 306700 | A/G | F8 | hsa-miR-28-3p |
| rs28937282 | 306700 | C/T | F8 | hsa-miR-139-5p |
| rs28937282 | 306700 | C/T | F8 | hsa-miR-1283 |
| rs28937282 | 306700 | C/T | F8 | hsa-miR-10b* |
| rs28937282 | 306700 | C/T | F8 | hsa-miR-524-5p, hsa-miR-520d-5p |
| rs28937282 | 306700 | C/T | F8 | hsa-miR-10a* |
| rs28937283 | 306700 | C/T | F8 | hsa-miR-22* |
| rs28937283 | 306700 | C/T | F8 | hsa-miR-10b* |
| rs28937283 | 306700 | C/T | F8 | hsa-miR-552 |
| rs28937283 | 306700 | C/T | F8 | hsa-miR-182* |
| rs28937285 | 306700 | A/G | F8 | hsa-miR-502-5p |
| rs28937285 | 306700 | A/G | F8 | hsa-miR-643 |
| rs28937285 | 306700 | A/G | F8 | hsa-miR-2054 |
| rs28937287 | 306700 | G/T | F8 | hsa-miR-1979, hsa-miR-1260, hsa-miR-188-3p |
| rs28937287 | 306700 | G/T | F8 | hsa-miR-186* |
| rs28937287 | 306700 | G/T | F8 | hsa-miR-105 |
| rs28937287 | 306700 | G/T | F8 | hsa-miR-409-3p, hsa-miR-33a* |
| rs28937288 | 306700 | C/G | F8 | hsa-miR-186* |
| rs28937288 | 306700 | C/G | F8 | hsa-miR-105 |
| rs28937289 | 306700 | A/G | F8 | hsa-miR-1915 |
| rs28937289 | 306700 | A/G | F8 | hsa-miR-328 |
| rs28937289 | 306700 | A/G | F8 | hsa-miR-135b, hsa-miR-135a, hsa-miR-135a |
| rs28937289 | 306700 | A/G | F8 | hsa-miR-766 |
| rs28937290 | 306700 | A/G | F8 | hsa-miR-92b* |
| rs28937290 | 306700 | A/G | F8 | hsa-miR-1255b, hsa-miR-1255a |
| rs28937291 | 306700 | C/G/T | F8 | hsa-miR-335 |
| rs28937291 | 306700 | C/G/T | F8 | hsa-miR-92b* |
| rs28937292 | 306700 | A/C | F8 | hsa-miR-633 |
| rs28937292 | 306700 | A/C | F8 | hsa-miR-1252 |
| rs28937293 | 306700 | C/T | F8 | hsa-miR-142-5p |
| rs28937293 | 306700 | C/T | F8 | hsa-miR-9* |
| rs28937293 | 306700 | C/T | F8 | hsa-miR-320d, hsa-miR-320c, hsa-miR-320b, hsa-miR-320c, hsa-miR-320b, hsa-miR-320a |
| rs28937294 | 306700 | A/G/T | F8 | hsa-miR-181a* |
| rs28937294 | 306700 | A/G/T | F8 | hsa-miR-181c* |
| rs28937295 | 306700 | A/G | F8 | hsa-miR-1913, hsa-miR-324-3p, hsa-miR-18a* |
| rs28937295 | 306700 | A/G | F8 | hsa-miR-626 |
| rs28937296 | 306700 | G/T | F8 | hsa-miR-493*, hsa-let-7g*, hsa-let-7a-2* |
| rs28937296 | 306700 | G/T | F8 | hsa-miR-181a-2* |
| rs28937298 | 306700 | C/T | F8 | hsa-miR-1280, hsa-miR-1224-3p |
| rs28937299 | 306700 | C/T | F8 | hsa-miR-1208 |
| rs28937299 | 306700 | C/T | F8 | hsa-miR-626 |
| rs28937299 | 306700 | C/T | F8 | hsa-miR-1538 |
| rs28937299 | 306700 | C/T | F8 | hsa-miR-181a-2* |
| rs28937301 | 306700 | A/G | F8 | hsa-miR-1280, hsa-miR-1224-3p |
| rs28937302 | 306700 | A/G/T | F8 | hsa-miR-1257 |
| rs28937302 | 306700 | A/G/T | F8 | hsa-miR-628-5p |
| rs28937302 | 306700 | A/G/T | F8 | hsa-miR-1300, hsa-miR-580 |
| rs28937304 | 306700 | C/T | F8 | hsa-miR-1276, hsa-miR-583 |
| rs28937304 | 306700 | C/T | F8 | hsa-miR-518a-5p, hsa-miR-527 |
| rs28937305 | 306700 | C/G | F8 | hsa-miR-545* |
| rs28937305 | 306700 | C/G | F8 | hsa-miR-127-5p |
| rs28937305 | 306700 | C/G | F8 | hsa-miR-1252 |
| rs28937306 | 306700 | C/G | F8 | hsa-miR-198 |
| rs28937306 | 306700 | C/G | F8 | hsa-miR-27b* |
| rs28937307 | 306700 | G/T | F8 | hsa-miR-1324 |
| rs28937307 | 306700 | G/T | F8 | hsa-miR-449b* |
| rs28937307 | 306700 | G/T | F8 | hsa-miR-1301 |
| rs28937308 | 306700 | A/G | F8 | hsa-miR-1274a |
| rs28937308 | 306700 | A/G | F8 | hsa-miR-125a-5p, hsa-miR-125b, hsa-miR-125b |
| rs28937309 | 308700 | A/G | KAL1 | hsa-miR-544 |
| rs28937309 | 308700 | A/G | KAL1 | hsa-miR-103-2* |
| rs28937310 | 309900 | G/T | IDS | hsa-miR-885-3p |
| rs28937310 | 309900 | G/T | IDS | hsa-miR-486-3p |
| rs28937311 | 309900 | A/G | IDS | hsa-miR-1236 |
| rs28937312 | 314200 | C/T | SERPINA7 | hsa-miR-181a-2* |
| rs28937312 | 314200 | C/T | SERPINA7 | hsa-miR-1262 |
| rs28937313 | 600046 | A/G | ABCA1 | hsa-miR-136 |
| rs28937313 | 600046 | A/G | ABCA1 | hsa-miR-1208 |
| rs28937313 | 600046 | A/G | ABCA1 | hsa-miR-181a-2* |
| rs28937313 | 600046 | A/G | ABCA1 | hsa-miR-892a |
| rs28937315 | 600140 | A/G | CREBBP | hsa-miR-151-3p |
| rs28937315 | 600140 | A/G | CREBBP | hsa-miR-600 |
| rs28937316 | 600163 | A/G | SCN5A | hsa-miR-644 |
| rs28937316 | 600163 | A/G | SCN5A | hsa-miR-127-3p |
| rs28937317 | 600163 | A/G | SCN5A | hsa-miR-1256 |

TABLE 2-continued

| SNP | OMIM | MUTATION | GENE | MIR |
|---|---|---|---|---|
| rs28937317 | 600163 | A/G | SCN5A | hsa-miR-888* |
| rs28937318 | 600163 | A/G | SCN5A | hsa-miR-25* |
| rs28937318 | 600163 | A/G | SCN5A | hsa-miR-125a-3p |
| rs28937319 | 600163 | C/T | SCN5A | hsa-miR-296-5p |
| rs28937320 | 600234 | A/G | HMGCS2 | hsa-miR-662 |
| rs28937321 | 600276 | G/T | NOTCH3 | hsa-miR-1912 |
| rs28937321 | 600276 | G/T | NOTCH3 | hsa-miR-1280, hsa-miR-1224-3p |
| rs28937322 | 600287 | C/G | GARS | hsa-miR-1915 |
| rs28937322 | 600287 | C/G | GARS | hsa-miR-1827 |
| rs28937322 | 600287 | C/G | GARS | hsa-miR-1912 |
| rs28937323 | 600287 | C/G | GARS | hsa-miR-1972 |
| rs28937323 | 600287 | C/G | GARS | hsa-miR-25* |
| rs28937568 | 602195 | C/T | HSPB1 | hsa-miR-432* |
| rs28937568 | 602195 | C/T | HSPB1 | hsa-miR-635 |
| rs28937568 | 602195 | C/T | HSPB1 | hsa-miR-491-5p |
| rs28937568 | 602195 | C/T | HSPB1 | hsa-miR-541, hsa-miR-654-5p, hsa-miR-92a-2* |
| rs28937568 | 602195 | C/T | HSPB1 | hsa-miR-1293, hsa-miR-363* |
| rs28937568 | 602195 | C/T | HSPB1 | hsa-miR-432 |
| rs28937568 | 602195 | C/T | HSPB1 | hsa-miR-1262 |
| rs28937569 | 602195 | C/T | HSPB1 | hsa-miR-943 |
| rs28937569 | 602195 | C/T | HSPB1 | hsa-miR-1265 |
| rs28937569 | 602195 | C/T | HSPB1 | hsa-miR-450b-3p, hsa-miR-769-3p |
| rs28937571 | 602365 | A/G | — | hsa-miR-103-as |
| rs28937572 | 602438 | C/T | HSF4 | hsa-miR-1825, hsa-miR-199a-5p, hsa-miR-199b-5p, hsa-miR-199a-5p |
| rs28937572 | 602438 | C/T | HSF4 | hsa-miR-604 |
| rs28937572 | 602438 | C/T | HSF4 | hsa-miR-936, hsa-miR-199a-3p, hsa-miR-199b-3p, hsa-miR-199a-3p |
| rs28937572 | 602438 | C/T | HSF4 | hsa-miR-770-5p |
| rs28937572 | 602438 | C/T | HSF4 | hsa-miR-647 |
| rs28937572 | 602438 | C/T | HSF4 | hsa-miR-194* |
| rs28937572 | 602438 | C/T | HSF4 | hsa-miR-22 |
| rs28937573 | 602438 | C/T | HSF4 | hsa-miR-500* |
| rs28937574 | 602566 | A/C | P2RX7 | hsa-miR-766 |
| rs28937575 | 602617 | A/G | FOXE1 | hsa-miR-20b* |
| rs28937577 | 602690 | A/G | — | hsa-miR-297, hsa-miR-675* |
| rs28937577 | 602690 | A/G | — | hsa-miR-223* |
| rs28937577 | 602690 | A/G | — | hsa-miR-595 |
| rs28937578 | 602700 | A/C | EP300 | hsa-miR-541, hsa-miR-654-5p, hsa-miR-92a-2* |
| rs28937578 | 602700 | A/C | EP300 | hsa-miR-1267, hsa-miR-367* |
| rs28937579 | 602938 | A/G | BAAT | hsa-miR-662 |
| rs28937579 | 602938 | A/G | BAAT | hsa-miR-660 |
| rs28937579 | 602938 | A/G | BAAT | hsa-miR-1308 |
| rs28937580 | 602991 | C/T | NOG | hsa-miR-25* |
| rs28937580 | 602991 | C/T | NOG | hsa-miR-615-3p |
| rs28937581 | 603009 | G/T | DYSF | hsa-miR-591 |
| rs28937581 | 603009 | G/T | DYSF | hsa-miR-543 |
| rs28937581 | 603009 | G/T | DYSF | hsa-miR-181d, hsa-miR-181b, hsa-miR-181a, hsa-miR-181a, hsa-miR-181b, hsa-miR-181c |
| rs28937582 | 603094 | A/C | B3GALNT1 | hsa-miR-518a-5p, hsa-miR-527 |
| rs28937582 | 603094 | A/C | B3GALNT1 | hsa-miR-607 |
| rs28937582 | 603094 | A/C | B3GALNT1 | hsa-miR-141* |
| rs28937583 | 603324 | C/T | GJB3 | hsa-miR-634 |
| rs28937583 | 603324 | C/T | GJB3 | hsa-miR-338-3p |
| rs28937583 | 603324 | C/T | GJB3 | hsa-miR-593* |
| rs28937583 | 603324 | C/T | GJB3 | hsa-miR-29c, hsa-miR-29b, hsa-miR-29b, hsa-miR-29a |
| rs28937584 | 603372 | C/G | TSHR | hsa-miR-1262 |
| rs28937586 | 603381 | C/T | FLNB | hsa-miR-665 |
| rs28937587 | 603381 | C/G | FLNB | hsa-miR-663b |
| rs28937587 | 603381 | C/G | FLNB | hsa-miR-1228, hsa-miR-220a |
| rs28937587 | 603381 | C/G | FLNB | hsa-miR-221* |
| rs28937587 | 603381 | C/G | FLNB | hsa-miR-619 |
| rs28937587 | 603381 | C/G | FLNB | hsa-miR-1204 |
| rs28937589 | 603537 | C/G | KCNQ4 | hsa-miR-1226 |
| rs28937589 | 603537 | C/G | KCNQ4 | hsa-miR-662 |
| rs28937589 | 603537 | C/G | KCNQ4 | hsa-miR-1280, hsa-miR-1224-3p |
| rs28937591 | 603681 | C/G | OTOF | hsa-miR-638 |
| rs28937591 | 603681 | C/G | OTOF | hsa-miR-744 |
| rs28937591 | 603681 | C/G | OTOF | hsa-miR-542-5p |
| rs28937593 | 603799 | A/G | CHST3 | hsa-miR-1254, hsa-miR-661 |
| rs28937593 | 603799 | A/G | CHST3 | hsa-miR-637 |
| rs28937593 | 603799 | A/G | CHST3 | hsa-miR-1538 |
| rs28937593 | 603799 | A/G | CHST3 | hsa-miR-1275 |
| rs28937593 | 603799 | A/G | CHST3 | hsa-miR-1234 |
| rs28937594 | 603824 | C/T | GNE | hsa-miR-451 |
| rs28937594 | 603824 | C/T | GNE | hsa-miR-1973 |
| rs28937595 | 603941 | A/G | SLC19A2 | hsa-miR-1225-3p, hsa-miR-1233 |

TABLE 2-continued

| SNP | OMIM | MUTATION | GENE | MIR |
|---|---|---|---|---|
| rs28937596 | 603945 | C/T | EIF2B5 | hsa-miR-1972 |
| rs28937596 | 603945 | C/T | EIF2B5 | hsa-miR-766 |
| rs28937597 | 604103 | C/T | MYOT | hsa-miR-222* |
| rs28937597 | 604103 | C/T | MYOT | hsa-miR-653 |
| rs28937597 | 604103 | C/T | MYOT | hsa-miR-16-1* |
| rs28937598 | 604272 | C/T | SCO2 | hsa-miR-423-3p |
| rs28937598 | 604272 | C/T | SCO2 | hsa-miR-1979, hsa-miR-1260, hsa-miR-188-3p |
| rs28937868 | 604272 | A/G | SCO2 | hsa-miR-142-3p |
| rs28937868 | 604272 | A/G | SCO2 | hsa-miR-449b, hsa-miR-449a, hsa-miR-34c-5p, hsa-miR-34a |
| rs28937868 | 604272 | A/G | SCO2 | hsa-miR-921 |
| rs28937869 | 604327 | C/T | B4GALT7 | hsa-miR-501-3p, hsa-miR-502-3p |
| rs28937869 | 604327 | C/T | B4GALT7 | hsa-miR-103-2* |
| rs28937870 | 604395 | C/G | MLH3 | hsa-miR-328 |
| rs28937870 | 604395 | C/G | MLH3 | hsa-miR-181d, hsa-miR-181b, hsa-miR-181a, hsa-miR-181a, hsa-miR-181b, hsa-miR-181c |
| rs28937871 | 604395 | A/G | MLH3 | hsa-miR-1290, hsa-miR-876-5p |
| rs28937872 | 604418 | C/T | GJB6 | hsa-miR-103, hsa-miR-107 |
| rs28937873 | 604485 | A/G | NR2E3 | hsa-miR-875-3p |
| rs28937873 | 604485 | A/G | NR2E3 | hsa-miR-532-5p |
| rs28937873 | 604485 | A/G | NR2E3 | hsa-miR-1254, hsa-miR-661 |
| rs28937874 | 604619 | A/C | LGI1 | hsa-miR-190b, hsa-miR-190 |
| rs28937875 | 604896 | A/G | MKKS | hsa-miR-216b, hsa-miR-216a |
| rs28937875 | 604896 | A/G | MKKS | hsa-miR-515-5p, hsa-miR-519e* |
| rs28937876 | 605086 | G/T | TREM2 | hsa-miR-526b |
| rs28937877 | 605294 | A/G | CHST6 | hsa-miR-502-5p |
| rs28937877 | 605294 | A/G | CHST6 | hsa-miR-1274a |
| rs28937877 | 605294 | A/G | CHST6 | hsa-miR-125a-5p, hsa-miR-125b, hsa-miR-125b |
| rs28937878 | 605294 | A/C | CHST6 | hsa-miR-886-3p |
| rs28937878 | 605294 | A/C | CHST6 | hsa-miR-886-5p |
| rs28937879 | 605294 | G/T | CHST6 | hsa-miR-1226 |
| rs28937879 | 605294 | G/T | CHST6 | hsa-miR-1250 |
| rs28937879 | 605294 | G/T | CHST6 | hsa-miR-941 |
| rs28937879 | 605294 | G/T | CHST6 | hsa-miR-125a-3p |
| rs28937879 | 605294 | G/T | CHST6 | hsa-miR-1911* |
| rs28937879 | 605294 | G/T | CHST6 | hsa-miR-767-5p |
| rs28937880 | 605371 | A/G | ARFGEF2 | hsa-miR-335* |
| rs28937880 | 605371 | A/G | ARFGEF2 | hsa-miR-30e*, hsa-miR-30d*, hsa-miR-30a* |
| rs28937880 | 605371 | A/G | ARFGEF2 | hsa-miR-145 |
| rs28937881 | 605380 | A/G | FGF23 | hsa-miR-132* |
| rs28937882 | 605380 | C/T | FGF23 | hsa-miR-125a-3p |
| rs28937882 | 605380 | C/T | FGF23 | hsa-miR-609 |
| rs28937882 | 605380 | C/T | FGF23 | hsa-miR-766 |
| rs28937883 | 605446 | G/T | RPGRIP1 | hsa-miR-202, hsa-let-7i, hsa-let-7g, hsa-miR-98, hsa-let-7a, hsa-let-7a, hsa-let-7a, hsa-let-7b, hsa-let-7c, hsa-let-7d, hsa-let-7e, hsa-let-7f, hsa-let-7f |
| rs28937884 | 605597 | G/T | FOXL2 | hsa-miR-1322, hsa-miR-1272 |
| rs28937885 | 605597 | A/T | FOXL2 | hsa-miR-124* |
| rs28937886 | 605881 | C/G | SLC35C1 | hsa-miR-1208 |
| rs28937886 | 605881 | C/G | SLC35C1 | hsa-miR-1231, hsa-miR-632 |
| rs28937886 | 605881 | C/G | SLC35C1 | hsa-miR-518c*, hsa-miR-330-5p, hsa-miR-326 |
| rs28937887 | 606075 | A/G | C10orf2 | hsa-miR-29b-1* |
| rs28937887 | 606075 | A/G | C10orf2 | hsa-miR-500* |
| rs28937888 | 606119 | A/C/G | SLURP1 | hsa-miR-1291 |
| rs28937888 | 606119 | A/C/G | SLURP1 | hsa-miR-1538 |
| rs28937888 | 606119 | A/C/G | SLURP1 | hsa-miR-105* |
| rs28937888 | 606119 | A/C/G | SLURP1 | hsa-miR-146b-3p |
| rs28937888 | 606119 | A/C/G | SLURP1 | hsa-miR-125a-5p, hsa-miR-125b, hsa-miR-125b |
| rs28937889 | 606119 | A/C | SLURP1 | hsa-miR-148b, hsa-miR-152, hsa-miR-148a |
| rs28937889 | 606119 | A/C | SLURP1 | hsa-miR-1825, hsa-miR-199a-5p, hsa-miR-199b-5p, hsa-miR-199a-5p |
| rs28937889 | 606119 | A/C | SLURP1 | hsa-miR-512-3p, hsa-miR-520f |
| rs28937890 | 606201 | C/T | WFS1 | hsa-miR-920 |
| rs28937890 | 606201 | C/T | WFS1 | hsa-miR-708, hsa-miR-28-5p |
| rs28937891 | 606201 | G/T | WFS1 | hsa-miR-1291 |
| rs28937891 | 606201 | G/T | WFS1 | hsa-miR-663b |
| rs28937891 | 606201 | G/T | WFS1 | hsa-miR-492 |
| rs28937891 | 606201 | G/T | WFS1 | hsa-miR-1470 |
| rs28937891 | 606201 | G/T | WFS1 | hsa-miR-328 |
| rs28937892 | 606201 | C/T | WFS1 | hsa-miR-92b* |
| rs28937892 | 606201 | C/T | WFS1 | hsa-miR-564 |
| rs28937892 | 606201 | C/T | WFS1 | hsa-miR-220c |
| rs28937893 | 606201 | A/G | WFS1 | hsa-miR-1250 |
| rs28937893 | 606201 | A/G | WFS1 | hsa-miR-1307 |
| rs28937893 | 606201 | A/G | WFS1 | hsa-miR-1469 |
| rs28937895 | 606201 | A/G | WFS1 | hsa-miR-1291 |
| rs28937895 | 606201 | A/G | WFS1 | hsa-miR-1470 |
| rs28937896 | 606416 | C/T | NLRP3 | hsa-miR-515-5p, hsa-miR-519e* |

TABLE 2-continued

| SNP | OMIM | MUTATION | GENE | MIR |
|---|---|---|---|---|
| rs28937896 | 606416 | C/T | NLRP3 | hsa-miR-766 |
| rs28937897 | 606551 | C/T | LZTS1 | hsa-miR-149* |
| rs28937897 | 606551 | C/T | LZTS1 | hsa-miR-365* |
| rs28937897 | 606551 | C/T | LZTS1 | hsa-miR-491-5p |
| rs28937897 | 606551 | C/T | LZTS1 | hsa-miR-625 |
| rs28937897 | 606551 | C/T | LZTS1 | hsa-miR-765 |
| rs28937897 | 606551 | C/T | LZTS1 | hsa-miR-1275 |
| rs28937897 | 606551 | C/T | LZTS1 | hsa-miR-30c-1*, hsa-miR-30b*, hsa-miR-30c-2* |
| rs28937898 | 606580 | A/G | OPA3 | hsa-miR-663b |
| rs28937898 | 606580 | A/G | OPA3 | hsa-miR-328 |
| rs28937898 | 606580 | A/G | OPA3 | hsa-miR-24 |
| rs28937898 | 606580 | A/G | OPA3 | hsa-miR-1280, hsa-miR-1224-3p |
| rs28937899 | 606580 | C/G | OPA3 | hsa-miR-1539 |
| rs28937899 | 606580 | C/G | OPA3 | hsa-miR-191* |
| rs28937900 | 606596 | A/C | FKRP | hsa-miR-25* |
| rs28937900 | 606596 | A/C | FKRP | hsa-miR-645 |
| rs28937901 | 606596 | A/C | FKRP | hsa-miR-541, hsa-miR-654-5p, hsa-miR-92a-2* |
| rs28937901 | 606596 | A/C | FKRP | hsa-miR-1228* |
| rs28937901 | 606596 | A/C | FKRP | hsa-miR-1909 |
| rs28937901 | 606596 | A/C | FKRP | hsa-miR-125a-3p |
| rs28937901 | 606596 | A/C | FKRP | hsa-miR-657 |
| rs28937902 | 606596 | A/C | FKRP | hsa-miR-485-5p |
| rs28937902 | 606596 | A/C | FKRP | hsa-miR-138 |
| rs28937902 | 606596 | A/C | FKRP | hsa-miR-924 |
| rs28937905 | 606596 | C/T | FKRP | hsa-miR-532-3p, hsa-miR-150 |
| rs28937905 | 606596 | C/T | FKRP | hsa-miR-1979, hsa-miR-1260, hsa-miR-188-3p |
| rs28937905 | 606596 | C/T | FKRP | hsa-miR-1228, hsa-miR-220a |
| rs28937905 | 606596 | C/T | FKRP | hsa-miR-767-5p |
| rs28937906 | 606598 | C/T | GDAP1 | hsa-miR-603, hsa-miR-329, hsa-miR-329, hsa-miR-362-3p |
| rs28937906 | 606598 | C/T | GDAP1 | hsa-miR-574-3p |
| rs28937907 | 606702 | C/T | PKHD1 | hsa-miR-539 |
| rs28937907 | 606702 | C/T | PKHD1 | hsa-miR-548c-3p |
| rs28937907 | 606702 | C/T | PKHD1 | hsa-miR-1300, hsa-miR-580 |
| rs28937908 | 606761 | C/T | MLYCD | hsa-miR-663b |
| rs28937908 | 606761 | C/T | MLYCD | hsa-miR-132* |
| rs28937908 | 606761 | C/T | MLYCD | hsa-miR-1204 |
| rs28937909 | 606800 | A/G | GAA | hsa-miR-1291 |
| rs28937909 | 606800 | A/G | GAA | hsa-miR-146b-3p |
| rs28937909 | 606800 | A/G | GAA | hsa-miR-125a-5p, hsa-miR-125b, hsa-miR-125b |
| rs28938168 | 601814 | A/G | FXYD2 | hsa-miR-662 |
| rs28938168 | 601814 | A/G | FXYD2 | hsa-miR-1975 |
| rs28938168 | 601814 | A/G | FXYD2 | hsa-miR-1225-3p, hsa-miR-1233 |
| rs28938169 | 602026 | C/T | PHYH | hsa-miR-613, hsa-miR-1, hsa-miR-206, hsa-miR-1 |
| rs28938169 | 602026 | C/T | PHYH | hsa-miR-450b-3p, hsa-miR-769-3p |
| rs28938169 | 602026 | C/T | PHYH | hsa-miR-1255b, hsa-miR-1255a |
| rs28938170 | 602104 | C/G | SH3BP2 | hsa-miR-1913, hsa-miR-324-3p, hsa-miR-18a* |
| rs28938170 | 602104 | C/G | SH3BP2 | hsa-miR-181a* |
| rs28938171 | 602104 | A/G | SH3BP2 | hsa-miR-1913, hsa-miR-324-3p, hsa-miR-18a* |
| rs28938171 | 602104 | A/G | SH3BP2 | hsa-miR-181a* |
| rs28938171 | 602104 | A/G | SH3BP2 | hsa-miR-767-3p |
| rs28938171 | 602104 | A/G | SH3BP2 | hsa-miR-1178 |
| rs28938172 | 602533 | C/T | — | hsa-miR-518e |
| rs28938173 | 602743 | A/C | PRKAG2 | hsa-miR-555 |
| rs28938173 | 602743 | A/C | PRKAG2 | hsa-miR-1225-5p |
| rs28938174 | 602858 | A/T | DHCR7 | hsa-miR-183 |
| rs28938174 | 602858 | A/T | DHCR7 | hsa-miR-940, hsa-miR-34b* |
| rs28938174 | 602858 | A/T | DHCR7 | hsa-miR-506, hsa-miR-124, hsa-miR-124, hsa-miR-124 |
| rs28938175 | 603196 | C/T | COCH | hsa-miR-1285, hsa-miR-612 |
| rs28938175 | 603196 | C/T | COCH | hsa-miR-125a-5p, hsa-miR-125b, hsa-miR-125b |
| rs28938468 | 600374 | A/C | — | hsa-miR-617 |
| rs28938468 | 600374 | A/C | — | hsa-miR-1288 |
| rs28938468 | 600374 | A/C | — | hsa-miR-103-2* |
| rs28938469 | 600509 | C/T | ABCC8 | hsa-miR-1827 |
| rs28938470 | 600570 | A/G | — | hsa-miR-1274a |
| rs28938470 | 600570 | A/G | — | hsa-miR-1274b, hsa-miR-339-5p |
| rs28938470 | 600570 | A/G | — | hsa-miR-1914 |
| rs28938471 | 600617 | C/G | — | hsa-miR-1249 |
| rs28938471 | 600617 | C/G | — | hsa-miR-146b-3p |
| rs28938471 | 600617 | C/G | — | hsa-miR-125a-5p, hsa-miR-125b, hsa-miR-125b |
| rs28938472 | 601002 | A/G | GSS | hsa-miR-588 |
| rs28938472 | 601002 | A/G | GSS | hsa-miR-138 |
| rs28938473 | 601691 | C/T | ABCA4 | hsa-miR-650 |
| rs28938473 | 601691 | C/T | ABCA4 | hsa-miR-873 |
| rs28938473 | 601691 | C/T | ABCA4 | hsa-miR-671-5p |
| rs28938473 | 601691 | C/T | ABCA4 | hsa-miR-15a* |
| rs28938474 | 601719 | G/T | TBX4 | hsa-miR-188-5p |

TABLE 2-continued

| SNP | OMIM | MUTATION | GENE | MIR |
|---|---|---|---|---|
| rs28938474 | 601719 | G/T | TBX4 | hsa-miR-623, hsa-miR-204, hsa-miR-211 |
| rs28938474 | 601719 | G/T | TBX4 | hsa-miR-875-5p |
| rs28939068 | 604312 | A/T | CST3 | hsa-miR-1291 |
| rs28939068 | 604312 | A/T | CST3 | hsa-miR-767-3p |
| rs28939068 | 604312 | A/T | CST3 | hsa-miR-370 |
| rs28939068 | 604312 | A/T | CST3 | hsa-miR-146b-3p |
| rs28939069 | 604386 | C/T | TRPS1 | hsa-miR-525-3p, hsa-miR-524-3p |
| rs28939069 | 604386 | C/T | TRPS1 | hsa-miR-506, hsa-miR-124, hsa-miR-124, hsa-miR-124 |
| rs28939070 | 604386 | A/G | TRPS1 | hsa-miR-525-3p, hsa-miR-524-3p |
| rs28939070 | 604386 | A/G | TRPS1 | hsa-miR-636 |
| rs28939070 | 604386 | A/G | TRPS1 | hsa-miR-18b, hsa-miR-18a |
| rs28939071 | 604395 | A/G | MLH3 | hsa-miR-513a-5p, hsa-miR-27b, hsa-miR-27a |
| rs28939071 | 604395 | A/G | MLH3 | hsa-miR-220c |
| rs28939071 | 604395 | A/G | MLH3 | hsa-miR-342-3p |
| rs28939071 | 604395 | A/G | MLH3 | hsa-miR-24 |
| rs28939071 | 604395 | A/G | MLH3 | hsa-miR-600 |
| rs28939072 | 604580 | C/T | FBLN5 | hsa-miR-654-3p |
| rs28939073 | 604580 | C/T | FBLN5 | hsa-miR-770-5p |
| rs28939075 | 604619 | G/T | LGI1 | hsa-miR-491-3p |
| rs28939075 | 604619 | G/T | LGI1 | hsa-miR-586 |
| rs28939075 | 604619 | G/T | LGI1 | hsa-miR-33b, hsa-miR-33a |
| rs28939075 | 604619 | G/T | LGI1 | hsa-miR-183* |
| rs28939075 | 604619 | G/T | LGI1 | hsa-miR-32* |
| rs28939076 | 604653 | A/C | SLC40A1 | hsa-miR-135b, hsa-miR-135a, hsa-miR-135a |
| rs28939076 | 604653 | A/C | SLC40A1 | hsa-miR-654-3p |
| rs28939077 | 604780 | A/C | ABHD5 | hsa-miR-29a* |
| rs28939077 | 604780 | A/C | ABHD5 | hsa-miR-191 |
| rs28939077 | 604780 | A/C | ABHD5 | hsa-miR-553 |
| rs28939077 | 604780 | A/C | ABHD5 | hsa-miR-548g |
| rs28939078 | 604780 | A/G | ABHD5 | hsa-miR-220b |
| rs28939078 | 604780 | A/G | ABHD5 | hsa-miR-1229 |
| rs28939078 | 604780 | A/G | ABHD5 | hsa-miR-550*, hsa-miR-200c* |
| rs28939078 | 604780 | A/G | ABHD5 | hsa-miR-511 |
| rs28939078 | 604780 | A/G | ABHD5 | hsa-miR-197 |
| rs28939079 | 605086 | A/G | TREM2 | hsa-miR-1915 |
| rs28939079 | 605086 | A/G | TREM2 | hsa-miR-640 |
| rs28939079 | 605086 | A/G | TREM2 | hsa-miR-1912 |
| rs28939080 | 605145 | A/G | ANKH | hsa-miR-941 |
| rs28939080 | 605145 | A/G | ANKH | hsa-miR-619 |
| rs28939082 | 605290 | A/G | OPA1 | hsa-miR-338-3p |
| rs28939082 | 605290 | A/G | OPA1 | hsa-miR-335* |
| rs28939082 | 605290 | A/G | OPA1 | hsa-miR-30e*, hsa-miR-30d*, hsa-miR-30a* |
| rs28939084 | 605511 | C/T | TMPRSS3 | hsa-miR-665 |
| rs28939084 | 605511 | C/T | TMPRSS3 | hsa-miR-296-5p |
| rs28939084 | 605511 | C/T | TMPRSS3 | hsa-miR-1225-3p, hsa-miR-1233 |
| rs28939084 | 605511 | C/T | TMPRSS3 | hsa-miR-505* |
| rs28939084 | 605511 | C/T | TMPRSS3 | hsa-miR-708, hsa-miR-28-5p |
| rs28939085 | 605573 | C/T | HSD17B3 | hsa-miR-641 |
| rs28939086 | 605646 | A/C | SLC26A4 | hsa-miR-148b, hsa-miR-152, hsa-miR-148a |
| rs28939086 | 605646 | A/C | SLC26A4 | hsa-miR-1825, hsa-miR-199a-5p, hsa-miR-199b-5p, hsa-miR-199a-5p |
| rs28939086 | 605646 | A/C | SLC26A4 | hsa-miR-512-3p, hsa-miR-520f |
| rs28939086 | 605646 | A/C | SLC26A4 | hsa-miR-145 |
| rs28939086 | 605646 | A/C | SLC26A4 | hsa-miR-760 |
| rs28939087 | 605881 | C/T | SLC35C1 | hsa-miR-646, hsa-miR-503, hsa-miR-497, hsa-miR-424, hsa-miR-195, hsa-miR-15b, hsa-miR-16, hsa-miR-15a, hsa-miR-16 |
| rs28939088 | 606157 | C/T | PANK2 | hsa-miR-205* |
| rs28939089 | 606347 | C/G | PSTPIP1 | hsa-miR-379 |
| rs28939089 | 606347 | C/G | PSTPIP1 | hsa-miR-1238 |
| rs28939092 | 606418 | A/C | DHCR24 | hsa-miR-1324 |
| rs28939093 | 606418 | A/G | DHCR24 | hsa-miR-643 |
| rs28939094 | 606439 | A/G | ATL1 | hsa-miR-1248, hsa-miR-1237 |
| rs28939094 | 606439 | A/G | ATL1 | hsa-miR-660 |
| rs28939094 | 606439 | A/G | ATL1 | hsa-miR-1280, hsa-miR-1224-3p |
| rs28939094 | 606439 | A/G | ATL1 | hsa-miR-141* |
| rs28939095 | 606597 | C/G | PAX3 | hsa-miR-1254, hsa-miR-661 |
| rs28939095 | 606597 | C/G | PAX3 | hsa-miR-221* |
| rs28939096 | 606597 | C/T | PAX3 | hsa-miR-1263, hsa-miR-150* |
| rs28939096 | 606597 | C/T | PAX3 | hsa-miR-550 |
| rs28939097 | 606628 | C/T | GNMT | hsa-miR-646, hsa-miR-503, hsa-miR-497, hsa-miR-424, hsa-miR-195, hsa-miR-15b, hsa-miR-16, hsa-miR-15a, hsa-miR-16 |
| rs28939098 | 606639 | A/G | GFM1 | hsa-miR-569 |
| rs28939098 | 606639 | A/G | GFM1 | hsa-miR-2053 |
| rs28939099 | 606702 | A/G | PKHD1 | hsa-miR-668 |
| rs28939099 | 606702 | A/G | PKHD1 | hsa-miR-616 |

TABLE 2-continued

| SNP | OMIM | MUTATION | GENE | MIR |
|---|---|---|---|---|
| rs28939099 | 606702 | A/G | PKHD1 | hsa-miR-93* |
| rs28939100 | 606800 | C/T | GAA | hsa-miR-1972 |
| rs28939100 | 606800 | C/T | GAA | hsa-miR-15a* |
| rs28939368 | 604277 | A/T | SPAST | hsa-miR-181c* |
| rs28939368 | 604277 | A/T | SPAST | hsa-miR-495, hsa-miR-7-1*, hsa-miR-7-2* |
| rs28939369 | 604366 | A/G | DNAI1 | hsa-miR-1178 |
| rs28939369 | 604366 | A/G | DNAI1 | hsa-miR-218 |
| rs28939370 | 604580 | C/T | FBLN5 | hsa-miR-1276, hsa-miR-583 |
| rs28939371 | 604580 | C/G | FBLN5 | hsa-miR-603, hsa-miR-329, hsa-miR-329, hsa-miR-362-3p |
| rs28939371 | 604580 | C/G | FBLN5 | hsa-miR-641 |
| rs28939371 | 604580 | C/G | FBLN5 | hsa-miR-208b, hsa-miR-499-5p, hsa-miR-208a |
| rs28939371 | 604580 | C/G | FBLN5 | hsa-miR-302c* |
| rs28939372 | 604580 | A/G | FBLN5 | hsa-miR-2110 |
| rs28939372 | 604580 | A/G | FBLN5 | hsa-miR-1231, hsa-miR-632 |
| rs28939372 | 604580 | A/G | FBLN5 | hsa-miR-637 |
| rs28939372 | 604580 | A/G | FBLN5 | hsa-miR-542-5p |
| rs28939373 | 604580 | C/T | FBLN5 | hsa-miR-615-5p |
| rs28939373 | 604580 | C/T | FBLN5 | hsa-miR-886-5p |
| rs28939373 | 604580 | C/T | FBLN5 | hsa-miR-431* |
| rs28939374 | 604638 | A/G | ACTN4 | hsa-miR-942 |
| rs28939374 | 604638 | A/G | ACTN4 | hsa-miR-1248, hsa-miR-1237 |
| rs28939375 | 604638 | C/T | ACTN4 | hsa-miR-616 |
| rs28939376 | 604638 | C/T | ACTN4 | hsa-miR-422a, hsa-miR-378 |
| rs28939376 | 604638 | C/T | ACTN4 | hsa-miR-1285, hsa-miR-612 |
| rs28939376 | 604638 | C/T | ACTN4 | hsa-miR-1287 |
| rs28939377 | 605799 | C/T | AMN | hsa-miR-615-5p |
| rs28939377 | 605799 | C/T | AMN | hsa-miR-638 |
| rs28939378 | 605907 | C/T | ALG1 | hsa-miR-15a* |
| rs28939379 | 605978 | A/T | VPS13A | hsa-miR-625* |
| rs28939379 | 605978 | A/T | VPS13A | hsa-miR-302d*, hsa-miR-302b* |
| rs28939380 | 606202 | C/T | SLC45A2 | hsa-miR-539 |
| rs28939380 | 606202 | C/T | SLC45A2 | hsa-miR-1300, hsa-miR-580 |
| rs28939381 | 606347 | A/G | PSTPIP1 | hsa-miR-744* |
| rs28939381 | 606347 | A/G | PSTPIP1 | hsa-miR-1268, hsa-miR-585 |
| rs28939381 | 606347 | A/G | PSTPIP1 | hsa-miR-609 |
| rs28939382 | 606655 | A/C | RXFP2 | hsa-miR-1225-5p |
| rs28939382 | 606655 | A/C | RXFP2 | hsa-miR-29b-1* |
| rs28939383 | 606702 | C/T | PKHD1 | hsa-miR-181d, hsa-miR-181b, hsa-miR-181a, hsa-miR-181a, hsa-miR-181b, hsa-miR-181c |
| rs28939384 | 606725 | A/G | CLN6 | hsa-miR-593* |
| rs28939384 | 606725 | A/G | CLN6 | hsa-miR-324-5p |
| rs28939384 | 606725 | A/G | CLN6 | hsa-miR-660 |
| rs28939668 | 601920 | A/G | JAG1 | hsa-miR-576-3p |
| rs28939668 | 601920 | A/G | JAG1 | hsa-miR-132* |
| rs28939669 | 601928 | C/G | KRT86 | hsa-miR-432* |
| rs28939669 | 601928 | C/G | KRT86 | hsa-miR-1299, hsa-miR-516b, hsa-miR-516b |
| rs28939669 | 601928 | C/G | KRT86 | hsa-miR-516a-5p |
| rs28939671 | 602026 | C/T | PHYH | hsa-miR-525-5p, hsa-miR-520a-5p |
| rs28939671 | 602026 | C/T | PHYH | hsa-miR-1180 |
| rs28939672 | 602026 | A/C | PHYH | hsa-miR-502-5p |
| rs28939672 | 602026 | A/C | PHYH | hsa-miR-581 |
| rs28939673 | 602026 | A/G | PHYH | hsa-miR-1207-3p |
| rs28939673 | 602026 | A/G | PHYH | hsa-miR-1267, hsa-miR-367* |
| rs28939674 | 602026 | A/G | PHYH | hsa-miR-875-3p |
| rs28939674 | 602026 | A/G | PHYH | hsa-miR-1180 |
| rs28939674 | 602026 | A/G | PHYH | hsa-miR-1248, hsa-miR-1237 |
| rs28939674 | 602026 | A/G | PHYH | hsa-miR-1299, hsa-miR-516b, hsa-miR-516b |
| rs28939677 | 602109 | A/C | MATN3 | hsa-miR-499-3p |
| rs28939677 | 602109 | A/C | MATN3 | hsa-miR-487a, hsa-miR-154* |
| rs28939677 | 602109 | A/C | MATN3 | hsa-miR-376a, hsa-miR-376b |
| rs28939678 | 602136 | C/T | PEX1 | hsa-miR-1182 |
| rs28939679 | 602141 | C/T | NDUFS8 | hsa-miR-588 |
| rs28939679 | 602141 | C/T | NDUFS8 | hsa-miR-671-3p |
| rs28939680 | 602195 | C/T | — | hsa-miR-7 |
| rs28939680 | 602195 | C/T | — | hsa-miR-143 |
| rs28939681 | 602195 | C/T | — | hsa-miR-665 |
| rs28939681 | 602195 | C/T | — | hsa-miR-1226 |
| rs28939681 | 602195 | C/T | — | hsa-miR-1911* |
| rs28939681 | 602195 | C/T | — | hsa-miR-767-5p |
| rs28939682 | 602225 | A/C | CRX | hsa-miR-510, hsa-miR-512-5p, hsa-miR-512-5p |
| rs28939682 | 602225 | A/C | CRX | hsa-miR-1269 |
| rs28939682 | 602225 | A/C | CRX | hsa-miR-1266 |
| rs28939683 | 602235 | A/G | KCNQ2 | hsa-miR-486-3p |
| rs28939684 | 602235 | C/T | KCNQ2 | hsa-miR-1975 |
| rs28939684 | 602235 | C/T | KCNQ2 | hsa-miR-1280, hsa-miR-1224-3p |
| rs28939685 | 602397 | G/T | ATP8B1 | hsa-miR-208b, hsa-miR-499-5p, hsa-miR-208a |
| rs28939685 | 602397 | G/T | ATP8B1 | hsa-miR-132* |

TABLE 2-continued

| SNP | OMIM | MUTATION | GENE | MIR |
|---|---|---|---|---|
| rs28939687 | 602403 | A/G | BLMH | hsa-miR-125b-1* |
| rs28939688 | 602432 | A/G | OPTN | hsa-miR-22* |
| rs28939688 | 602432 | A/G | OPTN | hsa-miR-133b, hsa-miR-133a, hsa-miR-133a |
| rs28939688 | 602432 | A/G | OPTN | hsa-miR-578 |
| rs28939689 | 602432 | A/G | OPTN | hsa-miR-1202 |
| rs28939690 | 602574 | A/G | TECTA | hsa-let-7a*, hsa-let-7b*, hsa-let-7f-1*, hsa-let-7f-2* |
| rs28939692 | 602575 | A/G | LMX1B | hsa-miR-637 |
| rs28939693 | 602630 | A/T | TGIF1 | hsa-miR-29a* |
| rs28939693 | 602630 | A/T | TGIF1 | hsa-miR-10b* |
| rs28939694 | 602686 | C/T | MAD1L1 | hsa-miR-191 |
| rs28939694 | 602686 | C/T | MAD1L1 | hsa-miR-127-3p |
| rs28939698 | 602858 | G/T | DHCR7 | hsa-miR-198 |
| rs28939698 | 602858 | G/T | DHCR7 | hsa-miR-1182 |
| rs28939700 | 603009 | A/G | DYSF | hsa-let-7i* |
| rs28939700 | 603009 | A/G | DYSF | hsa-miR-143* |
| rs28939700 | 603009 | A/G | DYSF | hsa-miR-1539 |
| rs28939700 | 603009 | A/G | DYSF | hsa-miR-1914 |
| rs28939700 | 603009 | A/G | DYSF | hsa-miR-191* |
| rs28939702 | 603234 | C/T | ABCC6 | hsa-miR-339-3p |
| rs28939702 | 603234 | C/T | ABCC6 | hsa-miR-128 |
| rs28939704 | 603248 | C/T | BMPR1B | hsa-miR-220c |
| rs28939704 | 603248 | C/T | BMPR1B | hsa-miR-1909 |
| rs28939705 | 603377 | A/G | SLC22A5 | hsa-miR-128 |
| rs28939705 | 603377 | A/G | SLC22A5 | hsa-miR-376c |
| rs28939706 | 603381 | A/G | FLNB | hsa-miR-622 |
| rs28939706 | 603381 | A/G | FLNB | hsa-miR-554 |
| rs28939707 | 603381 | A/G | FLNB | hsa-miR-20a* |
| rs28939707 | 603381 | A/G | FLNB | hsa-miR-135b, hsa-miR-135a, hsa-miR-135a |
| rs28939709 | 603506 | A/G | LRP5 | hsa-miR-27b* |
| rs28939710 | 603537 | A/G | KCNQ4 | hsa-miR-1203 |
| rs28939710 | 603537 | A/G | KCNQ4 | hsa-miR-1287 |
| rs28939710 | 603537 | A/G | KCNQ4 | hsa-miR-320d, hsa-miR-320c, hsa-miR-320b, hsa-miR-320c, hsa-miR-320b, hsa-miR-320a |
| rs28939712 | 603722 | C/T | IKBKAP | hsa-miR-638 |
| rs28939712 | 603722 | C/T | IKBKAP | hsa-miR-450b-3p, hsa-miR-769-3p |
| rs28939712 | 603722 | C/T | IKBKAP | hsa-miR-9 |
| rs28939713 | 603824 | C/T | GNE | hsa-miR-891b |
| rs28939713 | 603824 | C/T | GNE | hsa-miR-890 |
| rs28939714 | 603846 | C/T | NDUFS3 | hsa-miR-135b* |
| rs28939714 | 603846 | C/T | NDUFS3 | hsa-miR-141* |
| rs28939715 | 603851 | G/T | PHOX2B | hsa-let-7i* |
| rs28939715 | 603851 | G/T | PHOX2B | hsa-miR-1207-3p |
| rs28939715 | 603851 | G/T | PHOX2B | hsa-miR-22 |
| rs28939717 | 603945 | A/G | EIF2B5 | hsa-miR-516a-3p, hsa-miR-516b*, hsa-miR-516b* |
| rs28939717 | 603945 | A/G | EIF2B5 | hsa-miR-409-3p, hsa-miR-33a* |
| rs28939718 | 603951 | A/G | KCNMB1 | hsa-miR-1248, hsa-miR-1237 |
| rs28939718 | 603951 | A/G | KCNMB1 | hsa-miR-1976 |
| rs28939719 | 604161 | C/T | KISS1R | hsa-miR-891a |
| rs28939720 | 604210 | C/T | CRB1 | hsa-miR-1179 |
| rs28940268 | 607800 | A/G | ABCA12 | hsa-miR-136 |
| rs28940269 | 607800 | A/G | ABCA12 | hsa-miR-136 |
| rs28940269 | 607800 | A/G | ABCA12 | hsa-miR-1285, hsa-miR-612 |
| rs28940269 | 607800 | A/G | ABCA12 | hsa-miR-181a-2* |
| rs28940270 | 607800 | A/G | ABCA12 | hsa-miR-1469 |
| rs28940270 | 607800 | A/G | ABCA12 | hsa-miR-1300, hsa-miR-580 |
| rs28940272 | 607817 | A/G | VPS13B | hsa-miR-664 |
| rs28940273 | 607854 | C/G | BEST1 | hsa-miR-646, hsa-miR-503, hsa-miR-497, hsa-miR-424, hsa-miR-195, hsa-miR-15b, hsa-miR-16, hsa-miR-15a, hsa-miR-16 |
| rs28940273 | 607854 | C/G | BEST1 | hsa-miR-1226 |
| rs28940273 | 607854 | C/G | BEST1 | hsa-miR-634 |
| rs28940273 | 607854 | C/G | BEST1 | hsa-miR-338-3p |
| rs28940273 | 607854 | C/G | BEST1 | hsa-miR-922, hsa-miR-214 |
| rs28940274 | 607854 | C/T | BEST1 | hsa-miR-1277 |
| rs28940274 | 607854 | C/T | BEST1 | hsa-miR-671-5p |
| rs28940275 | 607854 | A/C | BEST1 | hsa-miR-581 |
| rs28940275 | 607854 | A/C | BEST1 | hsa-miR-635 |
| rs28940275 | 607854 | A/C | BEST1 | hsa-miR-555 |
| rs28940275 | 607854 | A/C | BEST1 | hsa-miR-599 |
| rs28940275 | 607854 | A/C | BEST1 | hsa-miR-1225-5p |
| rs28940276 | 607854 | A/G | BEST1 | hsa-miR-449b* |
| rs28940276 | 607854 | A/G | BEST1 | hsa-miR-890 |
| rs28940278 | 607854 | A/G | BEST1 | hsa-miR-518b, hsa-miR-518a-3p, hsa-miR-518f, hsa-miR-518c, hsa-miR-518a-3p, hsa-miR-518d-3p |
| rs28940278 | 607854 | A/G | BEST1 | hsa-miR-432* |

TABLE 2-continued

| SNP | OMIM | MUTATION | GENE | MIR |
|---|---|---|---|---|
| rs28940278 | 607854 | A/G | BEST1 | hsa-miR-519d, hsa-miR-526b*, hsa-miR-20b, hsa-miR-106b, hsa-miR-106a, hsa-miR-93, hsa-miR-17, hsa-miR-20a |
| rs28940278 | 607854 | A/G | BEST1 | hsa-miR-105* |
| rs28940278 | 607854 | A/G | BEST1 | hsa-miR-9* |
| rs28940279 | 608034 | A/C | ASPA | hsa-miR-1298 |
| rs28940279 | 608034 | A/C | ASPA | hsa-miR-1234 |
| rs28940280 | 608102 | A/G | CLN5 | hsa-miR-135b* |
| rs28940282 | 608160 | C/T | SOX9 | hsa-miR-581 |
| rs28940282 | 608160 | C/T | SOX9 | hsa-miR-643 |
| rs28940282 | 608160 | C/T | SOX9 | hsa-miR-509-3-5p, hsa-miR-509-5p, hsa-miR-509-5p, hsa-miR-217 |
| rs28940282 | 608160 | C/T | SOX9 | hsa-miR-218 |
| rs28940283 | 608307 | A/G | CPS1 | hsa-miR-449b* |
| rs28940284 | 608309 | A/C | PINK1 | hsa-miR-1304 |
| rs28940284 | 608309 | A/C | PINK1 | hsa-miR-608, hsa-miR-342-5p |
| rs28940284 | 608309 | A/C | PINK1 | hsa-miR-563, hsa-miR-380* |
| rs28940284 | 608309 | A/C | PINK1 | hsa-miR-1294 |
| rs28940285 | 608309 | C/T | PINK1 | hsa-miR-646, hsa-miR-503, hsa-miR-497, hsa-miR-424, hsa-miR-195, hsa-miR-15b, hsa-miR-16, hsa-miR-15a, hsa-miR-16 |
| rs28940285 | 608309 | C/T | PINK1 | hsa-miR-885-3p |
| rs28940285 | 608309 | C/T | PINK1 | hsa-miR-1180 |
| rs28940285 | 608309 | C/T | PINK1 | hsa-miR-338-3p |
| rs28940285 | 608309 | C/T | PINK1 | hsa-miR-922, hsa-miR-214 |
| rs28940286 | 608310 | C/T | ASL | hsa-miR-298 |
| rs28940286 | 608310 | C/T | ASL | hsa-miR-613, hsa-miR-1, hsa-miR-206, hsa-miR-1 |
| rs28940286 | 608310 | C/T | ASL | hsa-miR-25* |
| rs28940287 | 608310 | C/T | ASL | hsa-miR-450a |
| rs28940287 | 608310 | C/T | ASL | hsa-miR-450b-5p, hsa-miR-557, hsa-miR-507 |
| rs28940288 | 608348 | A/G | BCKDHA | hsa-miR-642 |
| rs28940288 | 608348 | A/G | BCKDHA | hsa-miR-1229 |
| rs28940291 | 608507 | A/G | MFN2 | hsa-miR-146a* |
| rs28940291 | 608507 | A/G | MFN2 | hsa-miR-615-3p |
| rs28940293 | 608507 | C/T | MFN2 | hsa-miR-525-5p, hsa-miR-520a-5p |
| rs28940293 | 608507 | C/T | MFN2 | hsa-miR-198 |
| rs28940293 | 608507 | C/T | MFN2 | hsa-miR-589* |
| rs28940294 | 608507 | A/G | MFN2 | hsa-miR-574-3p |
| rs28940295 | 608507 | C/G | MFN2 | hsa-miR-1978 |
| rs28940297 | 608537 | C/T | VHL | hsa-miR-650 |
| rs28940297 | 608537 | C/T | VHL | hsa-miR-637 |
| rs28940297 | 608537 | C/T | VHL | hsa-miR-486-3p |
| rs28940297 | 608537 | C/T | VHL | hsa-miR-1827 |
| rs28940297 | 608537 | C/T | VHL | hsa-miR-1275 |
| rs28940298 | 608537 | C/T | VHL | hsa-miR-483-3p |
| rs28940298 | 608537 | C/T | VHL | hsa-miR-508-5p |
| rs28940298 | 608537 | C/T | VHL | hsa-miR-449b* |
| rs28940300 | 608537 | C/T | VHL | hsa-miR-140-5p |
| rs28940300 | 608537 | C/T | VHL | hsa-miR-876-3p, hsa-miR-323-5p |
| rs28940300 | 608537 | C/T | VHL | hsa-miR-1293, hsa-miR-363* |
| rs28940300 | 608537 | C/T | VHL | hsa-miR-1262 |
| rs28940301 | 608537 | C/G | VHL | hsa-miR-876-3p, hsa-miR-323-5p |
| rs28940301 | 608537 | C/G | VHL | hsa-miR-1293, hsa-miR-363* |
| rs28940301 | 608537 | C/G | VHL | hsa-miR-886-5p |
| rs28940301 | 608537 | C/G | VHL | hsa-miR-1262 |
| rs28940302 | 608547 | G/T | VKORC1 | hsa-miR-1297, hsa-miR-26a, hsa-miR-26a, hsa-miR-26b |
| rs28940302 | 608547 | G/T | VKORC1 | hsa-miR-517b |
| rs28940302 | 608547 | G/T | VKORC1 | hsa-miR-301b, hsa-miR-454, hsa-miR-301a, hsa-miR-130b, hsa-miR-130a |
| rs28940302 | 608547 | G/T | VKORC1 | hsa-miR-412 |
| rs28940302 | 608547 | G/T | VKORC1 | hsa-miR-520b, hsa-miR-302e, hsa-miR-519a, hsa-miR-519a, hsa-miR-520c-3p, hsa-miR-520d-3p, hsa-miR-520e, hsa-miR-519c-3p, hsa-miR-520a-3p, hsa-miR-519b-3p, hsa-miR-302c, hsa-miR-302d, hsa-miR-372, hsa-miR-373, hsa-miR-302b, hsa-miR-302a |
| rs28940302 | 608547 | G/T | VKORC1 | hsa-miR-498 |
| rs28940303 | 608547 | C/T | VKORC1 | hsa-miR-662 |
| rs28940303 | 608547 | C/T | VKORC1 | hsa-miR-1471 |
| rs28940304 | 608547 | A/G | VKORC1 | hsa-miR-1203 |
| rs28940304 | 608547 | A/G | VKORC1 | hsa-miR-941 |
| rs28940304 | 608547 | A/G | VKORC1 | hsa-miR-619 |
| rs28940305 | 608547 | G/T | VKORC1 | hsa-miR-103-as |
| rs28940306 | 608568 | C/T | MYH14 | hsa-miR-541, hsa-miR-654-5p, hsa-miR-92a-2* |
| rs28940306 | 608568 | C/T | MYH14 | hsa-miR-519d, hsa-miR-526b*, hsa-miR-20b, hsa-miR-106b, hsa-miR-106a, hsa-miR-93, hsa-miR-17, hsa-miR-20a |

TABLE 2-continued

| SNP | OMIM | MUTATION | GENE | MIR |
|---|---|---|---|---|
| rs28940306 | 608568 | C/T | MYH14 | hsa-miR-520h, hsa-miR-520g |
| rs28940306 | 608568 | C/T | MYH14 | hsa-miR-18b, hsa-miR-18a |
| rs28940306 | 608568 | C/T | MYH14 | hsa-miR-616*, hsa-miR-371-5p, hsa-miR-373* |
| rs28940307 | 608568 | A/C | MYH14 | hsa-miR-628-5p |
| rs28940307 | 608568 | A/C | MYH14 | hsa-miR-105* |
| rs28940308 | 608666 | A/G | PEX26 | hsa-miR-513b |
| rs28940308 | 608666 | A/G | PEX26 | hsa-miR-1975 |
| rs28940308 | 608666 | A/G | PEX26 | hsa-miR-342-3p |
| rs28940309 | 608771 | A/G | MED13L | hsa-miR-629* |
| rs28940310 | 608771 | A/G | MED13L | hsa-miR-517b |
| rs28940310 | 608771 | A/G | MED13L | hsa-miR-455-5p |
| rs28940313 | 608830 | A/G | RDH12 | hsa-let-7i* |
| rs28940313 | 608830 | A/G | RDH12 | hsa-miR-125a-3p |
| rs28940313 | 608830 | A/G | RDH12 | hsa-miR-657 |
| rs28940313 | 608830 | A/G | RDH12 | hsa-miR-191* |
| rs28940315 | 608830 | A/C | RDH12 | hsa-miR-190b, hsa-miR-190 |
| rs28940568 | 607800 | A/G | ABCA12 | hsa-miR-20b* |
| rs28940568 | 607800 | A/G | ABCA12 | hsa-miR-365 |
| rs28940569 | 607837 | C/G | CLN8 | hsa-miR-382 |
| rs28940569 | 607837 | C/G | CLN8 | hsa-miR-148a* |
| rs28940569 | 607837 | C/G | CLN8 | hsa-miR-145 |
| rs28940570 | 607854 | C/T | BEST1 | hsa-miR-140-3p |
| rs28940570 | 607854 | C/T | BEST1 | hsa-miR-220b |
| rs28940571 | 607922 | C/T | A4GALT | hsa-miR-296-5p |
| rs28940571 | 607922 | C/T | A4GALT | hsa-miR-1972 |
| rs28940571 | 607922 | C/T | A4GALT | hsa-miR-1205, hsa-miR-1184, hsa-miR-17* |
| rs28940573 | 607998 | C/T | TPP1 | hsa-miR-127-3p |
| rs28940573 | 607998 | C/T | TPP1 | hsa-miR-600 |
| rs28940574 | 608034 | A/C | ASPA | hsa-miR-129-5p |
| rs28940574 | 608034 | A/C | ASPA | hsa-miR-335* |
| rs28940574 | 608034 | A/C | ASPA | hsa-miR-33b, hsa-miR-33a |
| rs28940574 | 608034 | A/C | ASPA | hsa-miR-450b-5p, hsa-miR-557, hsa-miR-507 |
| rs28940575 | 608072 | A/T | NHLRC1 | hsa-miR-516a-5p |
| rs28940576 | 608072 | C/G | NHLRC1 | hsa-miR-106b* |
| rs28940576 | 608072 | C/G | NHLRC1 | hsa-let-7i* |
| rs28940577 | 608107 | A/G | MEFV | hsa-miR-374a* |
| rs28940577 | 608107 | A/G | MEFV | hsa-miR-34c-3p |
| rs28940578 | 608107 | A/G | MEFV | hsa-miR-374a* |
| rs28940578 | 608107 | A/G | MEFV | hsa-miR-205 |
| rs28940579 | 608107 | C/T | MEFV | hsa-miR-618 |
| rs28940580 | 608107 | A/C/G | MEFV | hsa-miR-101* |
| rs28940580 | 608107 | A/C/G | MEFV | hsa-miR-1245 |
| rs28940580 | 608107 | A/C/G | MEFV | hsa-let-7c* |
| rs28940581 | 608107 | A/G | MEFV | hsa-miR-663b |
| rs28940581 | 608107 | A/G | MEFV | hsa-miR-588 |
| rs28940581 | 608107 | A/G | MEFV | hsa-miR-337-5p |
| rs28940582 | 608272 | G/T | NEU1 | hsa-miR-139-3p |
| rs28940582 | 608272 | G/T | NEU1 | hsa-miR-1253 |
| rs28940583 | 608272 | A/G | NEU1 | hsa-miR-603, hsa-miR-329, hsa-miR-329, hsa-miR-362-3p |
| rs28940583 | 608272 | A/G | NEU1 | hsa-miR-1322, hsa-miR-1272 |
| rs28940585 | 608310 | C/T | ASL | hsa-miR-885-3p |
| rs28940585 | 608310 | C/T | ASL | hsa-miR-940, hsa-miR-34b* |
| rs28940586 | 608374 | C/T | HFE2 | hsa-miR-650 |
| rs28940586 | 608374 | C/T | HFE2 | hsa-miR-196b* |
| rs28940588 | 608750 | A/G | ALG3 | hsa-miR-148b, hsa-miR-152, hsa-miR-148a |
| rs28940588 | 608750 | A/G | ALG3 | hsa-miR-33b*, hsa-miR-515-3p, hsa-miR-519e, hsa-miR-515-3p, hsa-miR-371-3p |
| rs28940588 | 608750 | A/G | ALG3 | hsa-miR-550 |
| rs28940589 | 608786 | A/G | PC | hsa-miR-218-1* |
| rs28940589 | 608786 | A/G | PC | hsa-miR-1238 |
| rs28940589 | 608786 | A/G | PC | hsa-miR-1204 |
| rs28940591 | 608786 | C/T | PC | hsa-miR-103-2* |
| rs28940868 | 606800 | A/C | GAA | hsa-miR-617 |
| rs28940869 | 606822 | C/T | POMGNT1 | hsa-miR-101, hsa-miR-144 |
| rs28940869 | 606822 | C/T | POMGNT1 | hsa-miR-602 |
| rs28940869 | 606822 | C/T | POMGNT1 | hsa-miR-128 |
| rs28940870 | 606860 | A/C | SERPING1 | hsa-miR-675 |
| rs28940870 | 606860 | A/C | SERPING1 | hsa-miR-588 |
| rs28940871 | 606869 | C/G | HEXA | hsa-miR-140-3p |
| rs28940871 | 606869 | C/G | HEXA | hsa-miR-1226 |
| rs28940871 | 606869 | C/G | HEXA | hsa-miR-220b |
| rs28940872 | 606885 | C/T | ACADS | hsa-miR-936, hsa-miR-199a-3p, hsa-miR-199b-3p, hsa-miR-199a-3p |
| rs28940872 | 606885 | C/T | ACADS | hsa-miR-1244 |
| rs28940875 | 606885 | C/T | ACADS | hsa-miR-1227 |
| rs28940876 | 606933 | C/T | TYR | hsa-miR-449b* |
| rs28940876 | 606933 | C/T | TYR | hsa-miR-15a* |

TABLE 2-continued

| SNP | OMIM | MUTATION | GENE | MIR |
|---|---|---|---|---|
| rs28940877 | 606933 | C/T | TYR | hsa-miR-1207-5p |
| rs28940877 | 606933 | C/T | TYR | hsa-miR-1908, hsa-miR-663 |
| rs28940877 | 606933 | C/T | TYR | hsa-miR-886-3p |
| rs28940877 | 606933 | C/T | TYR | hsa-miR-657 |
| rs28940878 | 606933 | A/G | TYR | hsa-miR-1913, hsa-miR-324-3p, hsa-miR-18a* |
| rs28940879 | 606933 | A/G | TYR | hsa-miR-873 |
| rs28940880 | 606933 | A/G | TYR | hsa-miR-382 |
| rs28940880 | 606933 | A/G | TYR | hsa-miR-548n |
| rs28940880 | 606933 | A/G | TYR | hsa-miR-561 |
| rs28940880 | 606933 | A/G | TYR | hsa-miR-138 |
| rs28940880 | 606933 | A/G | TYR | hsa-miR-320d, hsa-miR-320c, hsa-miR-320b, hsa-miR-320c, hsa-miR-320b, hsa-miR-320a |
| rs28940881 | 606933 | A/G | TYR | hsa-miR-1179 |
| rs28940881 | 606933 | A/G | TYR | hsa-miR-1236 |
| rs28940882 | 606953 | A/G | GALE | hsa-miR-1225-3p, hsa-miR-1233 |
| rs28940883 | 606953 | A/G | GALE | hsa-miR-525-5p, hsa-miR-520a-5p |
| rs28940883 | 606953 | A/G | GALE | hsa-miR-1912 |
| rs28940884 | 606953 | A/G | GALE | hsa-miR-516a-3p, hsa-miR-516b*, hsa-miR-516b* |
| rs28940885 | 606953 | A/G | GALE | hsa-miR-483-3p |
| rs28940885 | 606953 | A/G | GALE | hsa-miR-508-5p |
| rs28940885 | 606953 | A/G | GALE | hsa-miR-766 |
| rs28940886 | 606967 | A/G | LCAT | hsa-miR-608, hsa-miR-342-5p |
| rs28940886 | 606967 | A/G | LCAT | hsa-miR-1268, hsa-miR-585 |
| rs28940886 | 606967 | A/G | LCAT | hsa-miR-1306 |
| rs28940886 | 606967 | A/G | LCAT | hsa-miR-609 |
| rs28940887 | 606967 | C/T | LCAT | hsa-miR-1979, hsa-miR-1260, hsa-miR-188-3p |
| rs28940888 | 606967 | C/T | LCAT | hsa-miR-486-3p |
| rs28940888 | 606967 | C/T | LCAT | hsa-miR-1268, hsa-miR-585 |
| rs28940888 | 606967 | C/T | LCAT | hsa-miR-1308 |
| rs28940889 | 607036 | C/T | IVD | hsa-miR-516a-3p, hsa-miR-516b*, hsa-miR-516b* |
| rs28940889 | 607036 | C/T | IVD | hsa-miR-617 |
| rs28940890 | 607108 | A/T | PAX6 | hsa-miR-1910, hsa-miR-455-3p |
| rs28940890 | 607108 | A/T | PAX6 | hsa-miR-582-5p |
| rs28940891 | 607215 | C/T | NPHP4 | hsa-miR-186 |
| rs28940891 | 607215 | C/T | NPHP4 | hsa-miR-510, hsa-miR-512-5p, hsa-miR-512-5p |
| rs28940891 | 607215 | C/T | NPHP4 | hsa-miR-548b-3p |
| rs28940891 | 607215 | C/T | NPHP4 | hsa-miR-589, hsa-miR-146b-5p, hsa-miR-146a |
| rs28940891 | 607215 | C/T | NPHP4 | hsa-miR-888 |
| rs28940891 | 607215 | C/T | NPHP4 | hsa-miR-616*, hsa-miR-371-5p, hsa-miR-373* |
| rs28940892 | 607397 | A/G | MC2R | hsa-miR-1301 |
| rs28940892 | 607397 | A/G | MC2R | hsa-miR-922, hsa-miR-214 |
| rs28940892 | 607397 | A/G | MC2R | hsa-miR-103, hsa-miR-107 |
| rs28940893 | 607574 | C/T | ARSA | hsa-miR-922, hsa-miR-214 |
| rs28940893 | 607574 | C/T | ARSA | hsa-miR-1909 |
| rs28940893 | 607574 | C/T | ARSA | hsa-miR-744 |
| rs28940893 | 607574 | C/T | ARSA | hsa-miR-103, hsa-miR-107 |
| rs28940894 | 607574 | A/C | ARSA | hsa-miR-24 |
| rs28940894 | 607574 | A/C | ARSA | hsa-miR-1308 |
| rs28940895 | 607574 | C/T | ARSA | hsa-miR-140-5p |
| rs28940895 | 607574 | C/T | ARSA | hsa-miR-194* |
| rs28940895 | 607574 | C/T | ARSA | hsa-miR-144* |
| rs28940895 | 607574 | C/T | ARSA | hsa-miR-1245 |
| rs28940896 | 607606 | C/T | KRT9 | hsa-miR-183* |
| rs28940897 | 607623 | A/C | NPC1 | hsa-miR-1207-3p |
| rs28940897 | 607623 | A/C | NPC1 | hsa-miR-22 |
| rs28940897 | 607623 | A/C | NPC1 | hsa-miR-191* |
| rs28940897 | 607623 | A/C | NPC1 | hsa-miR-566 |
| rs28941468 | 607854 | A/G | BEST1 | hsa-miR-515-5p, hsa-miR-519e* |
| rs28941468 | 607854 | A/G | BEST1 | hsa-miR-877* |
| rs28941468 | 607854 | A/G | BEST1 | hsa-miR-607 |
| rs28941468 | 607854 | A/G | BEST1 | hsa-miR-1236 |
| rs28941469 | 607854 | A/T | BEST1 | hsa-miR-1271, hsa-miR-182, hsa-miR-96 |
| rs28941469 | 607854 | A/T | BEST1 | hsa-miR-1306 |
| rs28941470 | 608221 | C/G | MASTL | hsa-miR-504 |
| rs28941470 | 608221 | C/G | MASTL | hsa-miR-616 |
| rs28941471 | 608222 | A/G | ADSL | hsa-miR-432 |
| rs28941472 | 608310 | A/G | ASL | hsa-miR-1180 |
| rs28941472 | 608310 | A/G | ASL | hsa-miR-637 |
| rs28941473 | 608310 | A/G | ASL | hsa-miR-652 |
| rs28941474 | 608313 | C/T | ARG1 | hsa-miR-770-5p |
| rs28941474 | 608313 | C/T | ARG1 | hsa-miR-545* |
| rs28941474 | 608313 | C/T | ARG1 | hsa-miR-145 |
| rs28941474 | 608313 | C/T | ARG1 | hsa-miR-766 |
| rs28941475 | 608465 | C/T | SETX | hsa-miR-455-5p |
| rs28941475 | 608465 | C/T | SETX | hsa-miR-218 |
| rs28941476 | 608508 | A/G | CYBA | hsa-miR-331-3p |
| rs28941768 | 606806 | C/T | FTCD | hsa-miR-1273 |
| rs28941768 | 606806 | C/T | FTCD | hsa-miR-891b |

TABLE 2-continued

| SNP | OMIM | MUTATION | GENE | MIR |
|---|---|---|---|---|
| rs28941768 | 606806 | C/T | FTCD | hsa-miR-196a* |
| rs28941769 | 606847 | A/G | TCOF1 | hsa-miR-568 |
| rs28941769 | 606847 | A/G | TCOF1 | hsa-miR-493*, hsa-let-7g*, hsa-let-7a-2* |
| rs28941769 | 606847 | A/G | TCOF1 | hsa-miR-223* |
| rs28941770 | 606869 | G/T | HEXA | hsa-miR-1270, hsa-miR-620 |
| rs28941770 | 606869 | G/T | HEXA | hsa-miR-652 |
| rs28941770 | 606869 | G/T | HEXA | hsa-miR-185 |
| rs28941771 | 606869 | C/T | HEXA | hsa-miR-125a-3p |
| rs28941772 | 606873 | A/G | HEXB | hsa-miR-101* |
| rs28941772 | 606873 | A/G | HEXB | hsa-miR-935 |
| rs28941772 | 606873 | A/G | HEXB | hsa-miR-1301 |
| rs28941772 | 606873 | A/G | HEXB | hsa-miR-26a-2*, hsa-miR-26a-1* |
| rs28941773 | 606885 | C/T | ACADS | hsa-miR-525-3p, hsa-miR-524-3p |
| rs28941774 | 606938 | C/T | UROS | hsa-miR-767-3p |
| rs28941774 | 606938 | C/T | UROS | hsa-miR-181a-2* |
| rs28941775 | 606938 | A/G | UROS | hsa-miR-138 |
| rs28941776 | 606945 | A/G | LDLR | hsa-miR-499-3p |
| rs28941776 | 606945 | A/G | LDLR | hsa-miR-1228, hsa-miR-220a |
| rs28941776 | 606945 | A/G | LDLR | hsa-miR-1298 |
| rs28941777 | 607102 | C/T | WT1 | hsa-miR-875-3p |
| rs28941777 | 607102 | C/T | WT1 | hsa-miR-122 |
| rs28941777 | 607102 | C/T | WT1 | hsa-miR-140-5p |
| rs28941777 | 607102 | C/T | WT1 | hsa-miR-613, hsa-miR-1, hsa-miR-206, hsa-miR-1 |
| rs28941777 | 607102 | C/T | WT1 | hsa-miR-218-2* |
| rs28941778 | 607102 | A/G | WT1 | hsa-miR-92a-1* |
| rs28941779 | 607102 | C/T | WT1 | hsa-miR-27b* |
| rs28941779 | 607102 | C/T | WT1 | hsa-miR-589, hsa-miR-146b-5p, hsa-miR-146a |
| rs28941779 | 607102 | C/T | WT1 | hsa-miR-185 |
| rs28941780 | 607170 | A/G | CRELD1 | hsa-miR-876-3p, hsa-miR-323-5p |
| rs28941780 | 607170 | A/G | CRELD1 | hsa-miR-125a-3p |
| rs28941780 | 607170 | A/G | CRELD1 | hsa-miR-657 |
| rs28941781 | 607237 | C/T | TMIE | hsa-miR-1911* |
| rs28941781 | 607237 | C/T | TMIE | hsa-miR-27a* |
| rs28941781 | 607237 | C/T | TMIE | hsa-miR-484 |
| rs28941782 | 607423 | A/G | POMT1 | hsa-miR-532-3p, hsa-miR-150 |
| rs28941782 | 607423 | A/G | POMT1 | hsa-miR-513c |
| rs28941783 | 607474 | A/G | HGD | hsa-miR-623, hsa-miR-204, hsa-miR-211 |
| rs28941784 | 607568 | C/T | MMAB | hsa-miR-338-3p |
| rs28941784 | 607568 | C/T | MMAB | hsa-miR-1538 |
| rs28941784 | 607568 | C/T | MMAB | hsa-miR-922, hsa-miR-214 |
| rs28941786 | 607657 | C/G | CTH | hsa-miR-2052, hsa-miR-19a*, hsa-miR-19b-1*, hsa-miR-19b-2* |
| rs28941786 | 607657 | C/G | CTH | hsa-miR-450b-5p, hsa-miR-557, hsa-miR-507 |
| rs28942068 | 606822 | C/G | POMGNT1 | hsa-miR-105* |
| rs28942071 | 606869 | C/T | HEXA | hsa-miR-298 |
| rs28942071 | 606869 | C/T | HEXA | hsa-miR-922, hsa-miR-214 |
| rs28942072 | 606869 | C/T | HEXA | hsa-miR-551b* |
| rs28942074 | 606882 | G/T | ATP7B | hsa-miR-220c |
| rs28942074 | 606882 | G/T | ATP7B | hsa-miR-1972 |
| rs28942075 | 606882 | A/G | ATP7B | hsa-miR-653 |
| rs28942075 | 606882 | A/G | ATP7B | hsa-miR-187 |
| rs28942076 | 606882 | A/G | ATP7B | hsa-miR-29a* |
| rs28942076 | 606882 | A/G | ATP7B | hsa-miR-1537 |
| rs28942076 | 606882 | A/G | ATP7B | hsa-miR-548g |
| rs28942076 | 606882 | A/G | ATP7B | hsa-miR-548f, hsa-miR-548e, hsa-miR-548a-3p, hsa-miR-548a-3p, hsa-miR-548a-3p |
| rs28942077 | 606897 | A/T | LYST | hsa-miR-617 |
| rs28942078 | 606945 | A/G | LDLR | hsa-miR-591 |
| rs28942080 | 606945 | A/G | LDLR | hsa-miR-220b |
| rs28942080 | 606945 | A/G | LDLR | hsa-miR-1322, hsa-miR-1272 |
| rs28942081 | 606945 | A/G | LDLR | hsa-miR-1972 |
| rs28942082 | 606945 | G/T | LDLR | hsa-miR-489 |
| rs28942082 | 606945 | G/T | LDLR | hsa-miR-425 |
| rs28942083 | 606945 | A/G | LDLR | hsa-miR-1226 |
| rs28942083 | 606945 | A/G | LDLR | hsa-miR-485-3p |
| rs28942083 | 606945 | A/G | LDLR | hsa-miR-1229 |
| rs28942083 | 606945 | A/G | LDLR | hsa-miR-1228, hsa-miR-220a |
| rs28942083 | 606945 | A/G | LDLR | hsa-miR-377 |
| rs28942083 | 606945 | A/G | LDLR | hsa-miR-342-3p |
| rs28942084 | 606945 | C/T | LDLR | hsa-miR-486-3p |
| rs28942084 | 606945 | C/T | LDLR | hsa-miR-1909 |
| rs28942084 | 606945 | C/T | LDLR | hsa-miR-744 |
| rs28942084 | 606945 | C/T | LDLR | hsa-miR-1205, hsa-miR-1184, hsa-miR-17* |
| rs28942086 | 606945 | A/C | LDLR | hsa-miR-1308 |
| rs28942087 | 606967 | C/T | LCAT | hsa-miR-665 |
| rs28942087 | 606967 | C/T | LCAT | hsa-miR-335 |
| rs28942087 | 606967 | C/T | LCAT | hsa-miR-1915 |
| rs28942087 | 606967 | C/T | LCAT | hsa-miR-185 |

TABLE 2-continued

| SNP | OMIM | MUTATION | GENE | MIR |
|---|---|---|---|---|
| rs28942088 | 607035 | C/T | SUFU | hsa-miR-339-3p |
| rs28942088 | 607035 | C/T | SUFU | hsa-miR-920 |
| rs28942089 | 607102 | C/T | WT1 | hsa-miR-568 |
| rs28942089 | 607102 | C/T | WT1 | hsa-miR-297, hsa-miR-675* |
| rs28942089 | 607102 | C/T | WT1 | hsa-miR-567 |
| rs28942089 | 607102 | C/T | WT1 | hsa-miR-654-3p |
| rs28942090 | 607144 | G/T | ALG12 | hsa-miR-499-3p |
| rs28942090 | 607144 | G/T | ALG12 | hsa-miR-591 |
| rs28942090 | 607144 | G/T | ALG12 | hsa-miR-181c* |
| rs28942091 | 607170 | C/T | CRELD1 | hsa-miR-545 |
| rs28942091 | 607170 | C/T | CRELD1 | hsa-miR-103, hsa-miR-107 |
| rs28942093 | 607199 | C/T | IRF6 | hsa-miR-591 |
| rs28942093 | 607199 | C/T | IRF6 | hsa-miR-765 |
| rs28942094 | 607199 | C/T | IRF6 | hsa-miR-1909 |
| rs28942094 | 607199 | C/T | IRF6 | hsa-miR-744 |
| rs28942094 | 607199 | C/T | IRF6 | hsa-miR-1205, hsa-miR-1184, hsa-miR-17* |
| rs28942095 | 607199 | C/T | IRF6 | hsa-miR-615-3p |
| rs28942096 | 607237 | C/T | TMIE | hsa-miR-132, hsa-miR-212 |
| rs28942096 | 607237 | C/T | TMIE | hsa-miR-196b* |
| rs28942097 | 607237 | C/T | TMIE | hsa-miR-183 |
| rs28942097 | 607237 | C/T | TMIE | hsa-miR-132* |
| rs28942097 | 607237 | C/T | TMIE | hsa-miR-1204 |
| rs28942098 | 607393 | A/G | CDC73 | hsa-miR-572 |
| rs28942099 | 607444 | A/C | SBDS | hsa-miR-1978 |
| rs28942099 | 607444 | A/C | SBDS | hsa-miR-92a-1* |
| rs28942099 | 607444 | A/C | SBDS | hsa-miR-29b-1* |
| rs28942100 | 607474 | C/T | HGD | hsa-miR-1246 |
| rs28942100 | 607474 | C/T | HGD | hsa-miR-144* |
| rs28942100 | 607474 | C/T | HGD | hsa-miR-1225-5p |
| rs28942100 | 607474 | C/T | HGD | hsa-miR-1261 |
| rs28942101 | 607585 | G/T | ATM | hsa-miR-513a-3p |
| rs28942101 | 607585 | G/T | ATM | hsa-miR-514 |
| rs28942102 | 607585 | A/G | ATM | hsa-miR-130b* |
| rs28942102 | 607585 | A/G | ATM | hsa-miR-1238 |
| rs28942102 | 607585 | A/G | ATM | hsa-miR-877* |
| rs28942103 | 607585 | A/G | ATM | hsa-miR-1279 |
| rs28942103 | 607585 | A/G | ATM | hsa-miR-181d, hsa-miR-181b, hsa-miR-181a, hsa-miR-181a, hsa-miR-181b, hsa-miR-181c |
| rs28942103 | 607585 | A/G | ATM | hsa-miR-587 |
| rs28942104 | 607623 | C/T | NPC1 | hsa-miR-135b, hsa-miR-135a, hsa-miR-135a |
| rs28942104 | 607623 | C/T | NPC1 | hsa-miR-1204 |
| rs28942105 | 607623 | A/G | NPC1 | hsa-miR-563, hsa-miR-380* |
| rs28942105 | 607623 | A/G | NPC1 | hsa-miR-484 |
| rs28942106 | 607623 | A/G | NPC1 | hsa-miR-298 |
| rs28942107 | 607623 | C/T | NPC1 | hsa-miR-134 |
| rs28942107 | 607623 | C/T | NPC1 | hsa-miR-1204 |
| rs28942108 | 607623 | C/T | NPC1 | hsa-miR-548p |
| rs28942108 | 607623 | C/T | NPC1 | hsa-miR-545 |
| rs28942108 | 607623 | C/T | NPC1 | hsa-miR-103, hsa-miR-107 |
| rs28942109 | 607690 | A/G | SAR1B | hsa-miR-1826 |
| rs28942109 | 607690 | A/G | SAR1B | hsa-miR-1267, hsa-miR-367* |
| rs28942109 | 607690 | A/G | SAR1B | hsa-miR-653 |
| rs28942111 | 607786 | A/T | PCSK9 | hsa-miR-1281 |
| rs28942112 | 607786 | C/T | PCSK9 | hsa-miR-650 |
| rs28942112 | 607786 | C/T | PCSK9 | hsa-miR-1908, hsa-miR-663 |
| rs28942112 | 607786 | C/T | PCSK9 | hsa-miR-671-5p |
| rs28942113 | 607788 | C/G | MCFD2 | hsa-miR-942 |
| rs28942113 | 607788 | C/G | MCFD2 | hsa-miR-578 |
| rs28942114 | 607788 | C/T | MCFD2 | hsa-miR-223 |
| rs28942114 | 607788 | C/T | MCFD2 | hsa-miR-223* |
| rs28999110 | 100725 | C/T | CHRNE | hsa-miR-548b-3p |
| rs28999110 | 100725 | C/T | CHRNE | hsa-miR-337-5p |
| rs28999111 | 102560 | C/T | ACTG1 | hsa-miR-644 |
| rs28999111 | 102560 | C/T | ACTG1 | hsa-miR-299-3p |
| rs28999111 | 102560 | C/T | ACTG1 | hsa-miR-576-3p |
| rs28999111 | 102560 | C/T | ACTG1 | hsa-miR-493 |
| rs28999111 | 102560 | C/T | ACTG1 | hsa-miR-18b, hsa-miR-18a |
| rs28999112 | 102560 | C/T | ACTG1 | hsa-miR-493 |
| rs28999112 | 102560 | C/T | ACTG1 | hsa-miR-876-3p, hsa-miR-323-5p |
| rs28999112 | 102560 | C/T | ACTG1 | hsa-miR-18b, hsa-miR-18a |
| rs28999113 | 102600 | C/T | APRT | hsa-miR-218-2* |
| rs28999113 | 102600 | C/T | APRT | hsa-miR-1206 |
| rs28999114 | 103220 | A/G | SLC25A4 | hsa-miR-551a, hsa-miR-551b |
| rs28999969 | 190160 | A/G | THRB | hsa-miR-454* |
| rs28999969 | 190160 | A/G | THRB | hsa-miR-26a-2*, hsa-miR-26a-1* |
| rs28999970 | 190160 | G/T | THRB | hsa-miR-548b-3p |
| rs28999970 | 190160 | G/T | THRB | hsa-miR-361-3p |
| rs29001566 | 180380 | C/G/T | RHO | hsa-miR-1538 |

TABLE 2-continued

| SNP | OMIM | MUTATION | GENE | MIR |
|---|---|---|---|---|
| rs29001566 | 180380 | C/G/T | RHO | hsa-miR-15a* |
| rs29001571 | 602195 | C/T | HSPB1 | hsa-miR-483-3p |
| rs29001584 | 608465 | C/T | SETX | hsa-miR-647 |
| rs29001584 | 608465 | C/T | SETX | hsa-miR-409-3p, hsa-miR-33a* |
| rs29001637 | 180380 | C/T | RHO | hsa-miR-15a* |
| rs29001653 | 180380 | A/G | RHO | hsa-miR-1307 |
| rs29001653 | 180380 | A/G | RHO | hsa-miR-1271, hsa-miR-182, hsa-miR-96 |
| rs29001665 | 608465 | C/T | SETX | hsa-miR-587 |
| rs29001685 | 601105 | C/T | CTSK | hsa-miR-2110 |
| rs29001685 | 601105 | C/T | CTSK | hsa-miR-1224-5p |
| rs29001685 | 601105 | C/T | CTSK | hsa-miR-1185 |
| rs29001685 | 601105 | C/T | CTSK | hsa-miR-1308 |
| rs33910209 | 141900 | A/C/G | HBB | hsa-miR-376a, hsa-miR-376b |
| rs33910377 | 141800 | C/G/T | HBA2 | hsa-miR-149* |
| rs33910377 | 141800 | C/G/T | HBA2 | hsa-miR-939 |
| rs33910377 | 141800 | C/G/T | HBA2 | hsa-miR-1908, hsa-miR-663 |
| rs33910377 | 141800 | C/G/T | HBA2 | hsa-miR-658 |
| rs33910377 | 141800 | C/G/T | HBA2 | hsa-miR-611, hsa-miR-151-5p |
| rs33910377 | 141800 | C/G/T | HBA2 | hsa-miR-744 |
| rs33910377 | 141800 | C/G/T | HBA2 | hsa-miR-542-5p |
| rs33910475 | 141900 | A/G/T | — | hsa-miR-1256 |
| rs33910569 | 141900 | A/C/G | HBB | hsa-miR-106b* |
| rs33910569 | 141900 | A/C/G | HBB | hsa-miR-596 |
| rs33911106 | 141850 | A/C/G/T | HBA2 | hsa-miR-581 |
| rs33911106 | 141850 | A/C/G/T | HBA2 | hsa-miR-214* |
| rs33911106 | 141850 | A/C/G/T | HBA2 | hsa-miR-1914 |
| rs33911106 | 141850 | A/C/G/T | HBA2 | hsa-miR-596 |
| rs33911106 | 141850 | A/C/G/T | HBA2 | hsa-miR-455-5p |
| rs33911106 | 141850 | A/C/G/T | HBA2 | hsa-miR-100* |
| rs33911434 | 141900 | A/C/G | HBB | hsa-miR-125a-5p, hsa-miR-125b, hsa-miR-125b |
| rs33911434 | 141900 | A/C/G | HBB | hsa-miR-10a, hsa-miR-10b |
| rs33912272 | 141900 | C/G/T | HBB | hsa-miR-224 |
| rs33912272 | 141900 | C/G/T | HBB | hsa-miR-1289 |
| rs33912272 | 141900 | C/G/T | HBB | hsa-miR-922, hsa-miR-214 |
| rs33912272 | 141900 | C/G/T | HBB | hsa-miR-1266 |
| rs33913712 | 141900 | A/G/T | HBB | hsa-miR-590-5p, hsa-miR-21 |
| rs33914470 | 141800 | C/G/T | HBA2 | hsa-miR-581 |
| rs33914470 | 141800 | C/G/T | HBA2 | hsa-miR-493 |
| rs33914470 | 141800 | C/G/T | HBA2 | hsa-miR-508-3p, hsa-miR-219-5p, hsa-miR-219-5p |
| rs33914470 | 141800 | C/G/T | HBA2 | hsa-miR-1974, hsa-miR-453 |
| rs33914470 | 141800 | C/G/T | HBA2 | hsa-miR-100* |
| rs33914944 | 141900 | C/G/T | HBB | hsa-miR-377 |
| rs33914944 | 141900 | C/G/T | HBB | hsa-miR-342-3p |
| rs33914944 | 141900 | C/G/T | HBB | hsa-miR-125a-5p, hsa-miR-125b, hsa-miR-125b |
| rs33914944 | 141900 | C/G/T | HBB | hsa-miR-10a, hsa-miR-10b |
| rs33915112 | 141900 | A/C/G/T | — | hsa-miR-1975 |
| rs33915112 | 141900 | A/C/G/T | — | hsa-miR-296-5p |
| rs33915112 | 141900 | A/C/G/T | — | hsa-miR-1228, hsa-miR-220a |
| rs33915112 | 141900 | A/C/G/T | — | hsa-miR-197 |
| rs33915112 | 141900 | A/C/G/T | — | hsa-miR-1280, hsa-miR-1224-3p |
| rs33915112 | 141900 | A/C/G/T | — | hsa-miR-767-5p |
| rs33915947 | 141800 | A/G/T | HBA2 | hsa-miR-196b, hsa-miR-196a, hsa-miR-196a |
| rs33915947 | 141800 | A/G/T | HBA2 | hsa-miR-1178 |
| rs33915947 | 141800 | A/G/T | HBA2 | hsa-miR-431* |
| rs33916412 | 141900 | A/C/G/T | HBB | hsa-miR-1915 |
| rs33916412 | 141900 | A/C/G/T | HBB | hsa-miR-1285, hsa-miR-612 |
| rs33916412 | 141900 | A/C/G/T | HBB | hsa-miR-146b-3p |
| rs33916412 | 141900 | A/C/G/T | HBB | hsa-miR-874 |
| rs33917394 | 141900 | A/C | HBB | hsa-miR-338-3p |
| rs33917394 | 141900 | A/C | HBB | hsa-miR-377 |
| rs33917628 | 141900 | A/C/G | HBB | hsa-miR-223 |
| rs33917628 | 141900 | A/C/G | HBB | hsa-miR-510, hsa-miR-512-5p, hsa-miR-512-5p |
| rs33917628 | 141900 | A/C/G | HBB | hsa-miR-1298 |
| rs33917785 | 141900 | C/G/T | HBB | hsa-miR-301b, hsa-miR-454, hsa-miR-301a, hsa-miR-130b, hsa-miR-130a |
| rs33917785 | 141900 | C/G/T | HBB | hsa-miR-143* |
| rs33917785 | 141900 | C/G/T | HBB | hsa-miR-1301 |
| rs33917785 | 141900 | C/G/T | HBB | hsa-miR-33b*, hsa-miR-515-3p, hsa-miR-519e, hsa-miR-515-3p, hsa-miR-371-3p |
| rs33917785 | 141900 | C/G/T | HBB | hsa-miR-24 |
| rs33918131 | 141900 | A/C/G | HBB | hsa-miR-617 |
| rs33918343 | 141900 | A/C/G/T | — | hsa-miR-938 |
| rs33918343 | 141900 | A/C/G/T | — | hsa-miR-130b* |
| rs33918343 | 141900 | A/C/G/T | — | hsa-miR-129-3p, hsa-miR-129* |
| rs33918343 | 141900 | A/C/G/T | — | hsa-miR-339-3p |
| rs33918343 | 141900 | A/C/G/T | — | hsa-miR-1225-3p, hsa-miR-1233 |
| rs33919821 | 141900 | A/C/G | HBB | hsa-miR-1977 |
| rs33919821 | 141900 | A/C/G | HBB | hsa-miR-449b* |

TABLE 2-continued

| SNP | OMIM | MUTATION | GENE | MIR |
|---|---|---|---|---|
| rs33919821 | 141900 | A/C/G | HBB | hsa-miR-377 |
| rs33919924 | 141900 | A/C/G/T | HBB | hsa-miR-665 |
| rs33919924 | 141900 | A/C/G/T | HBB | hsa-miR-646, hsa-miR-503, hsa-miR-497, hsa-miR-424, hsa-miR-195, hsa-miR-15b, hsa-miR-16, hsa-miR-15a, hsa-miR-16 |
| rs33919924 | 141900 | A/C/G/T | HBB | hsa-miR-1226 |
| rs33919924 | 141900 | A/C/G/T | HBB | hsa-miR-1286 |
| rs33919924 | 141900 | A/C/G/T | HBB | hsa-miR-545 |
| rs33919924 | 141900 | A/C/G/T | HBB | hsa-miR-29c, hsa-miR-29b, hsa-miR-29b, hsa-miR-29a |
| rs33919924 | 141900 | A/C/G/T | HBB | hsa-miR-922, hsa-miR-214 |
| rs33919924 | 141900 | A/C/G/T | HBB | hsa-miR-1911* |
| rs33919924 | 141900 | A/C/G/T | HBB | hsa-miR-767-5p |
| rs33919924 | 141900 | A/C/G/T | HBB | hsa-miR-103, hsa-miR-107 |
| rs33920173 | 141900 | C/G/T | HBB | hsa-miR-646, hsa-miR-503, hsa-miR-497, hsa-miR-424, hsa-miR-195, hsa-miR-15b, hsa-miR-16, hsa-miR-15a, hsa-miR-16 |
| rs33920173 | 141900 | C/G/T | HBB | hsa-miR-338-3p |
| rs33920173 | 141900 | C/G/T | HBB | hsa-miR-922, hsa-miR-214 |
| rs33920173 | 141900 | C/G/T | HBB | hsa-miR-1234 |
| rs33921047 | 141800 | A/C/G | HBA2 | hsa-miR-662 |
| rs33921589 | 141900 | A/G/T | HBB | hsa-miR-573 |
| rs33921589 | 141900 | A/G/T | HBB | hsa-miR-148a* |
| rs33921589 | 141900 | A/G/T | HBB | hsa-miR-148b* |
| rs33921821 | 141900 | A/C/T | HBB | hsa-miR-198 |
| rs33921821 | 141900 | A/C/T | HBB | hsa-miR-1911* |
| rs33922018 | 141900 | A/C/G | HBB | hsa-miR-1271, hsa-miR-182, hsa-miR-96 |
| rs33922018 | 141900 | A/C/G | HBB | hsa-miR-433 |
| rs33922842 | 141900 | A/C/G/T | — | hsa-miR-302a* |
| rs33922842 | 141900 | A/C/G/T | — | hsa-miR-1288 |
| rs33922842 | 141900 | A/C/G/T | — | hsa-miR-888 |
| rs33922842 | 141900 | A/C/G/T | — | hsa-miR-616*, hsa-miR-371-5p, hsa-miR-373* |
| rs33922842 | 141900 | A/C/G/T | — | hsa-miR-488 |
| rs33922873 | 141900 | A/C/T | HBB | hsa-miR-885-5p |
| rs33922873 | 141900 | A/C/T | HBB | hsa-miR-556-5p |
| rs33923844 | 141800 | C/G/T | HBA2 | hsa-miR-323-3p |
| rs33924134 | 141900 | A/C/G | HBB | hsa-miR-588 |
| rs33924134 | 141900 | A/C/G | HBB | hsa-miR-192* |
| rs33924134 | 141900 | A/C/G | HBB | hsa-miR-578 |
| rs33924146 | 141900 | C/G/T | — | hsa-miR-186 |
| rs33924146 | 141900 | C/G/T | — | hsa-miR-548b-3p |
| rs33924146 | 141900 | C/G/T | — | hsa-miR-95 |
| rs33924146 | 141900 | C/G/T | — | hsa-miR-616*, hsa-miR-371-5p, hsa-miR-373* |
| rs33924775 | 141900 | A/C/G/T | HBB | hsa-miR-148b, hsa-miR-152, hsa-miR-148a |
| rs33924775 | 141900 | A/C/G/T | HBB | hsa-miR-101, hsa-miR-144 |
| rs33924775 | 141900 | A/C/G/T | HBB | hsa-miR-301b, hsa-miR-454, hsa-miR-301a, hsa-miR-130b, hsa-miR-130a |
| rs33924775 | 141900 | A/C/G/T | HBB | hsa-miR-1910, hsa-miR-455-3p |
| rs33924775 | 141900 | A/C/G/T | HBB | hsa-miR-143* |
| rs33924775 | 141900 | A/C/G/T | HBB | hsa-miR-198 |
| rs33924775 | 141900 | A/C/G/T | HBB | hsa-miR-1301 |
| rs33924825 | 142200 | A/C/G | HBG1 | hsa-miR-942 |
| rs33924825 | 142200 | A/C/G | HBG1 | hsa-miR-767-3p |
| rs33924825 | 142200 | A/C/G | HBG1 | hsa-miR-1248, hsa-miR-1237 |
| rs33924825 | 142200 | A/C/G | HBG1 | hsa-miR-370 |
| rs33926206 | 141800 | A/C/G | HBA2 | hsa-miR-1915 |
| rs33926206 | 141800 | A/C/G | HBA2 | hsa-miR-1909 |
| rs33926206 | 141800 | A/C/G | HBA2 | hsa-miR-1266 |
| rs33926764 | 141900 | A/C/G | HBB | hsa-miR-942 |
| rs33926764 | 141900 | A/C/G | HBB | hsa-miR-767-3p |
| rs33926764 | 141900 | A/C/G | HBB | hsa-miR-617 |
| rs33926764 | 141900 | A/C/G | HBB | hsa-miR-629* |
| rs33926796 | 141900 | A/C/G/T | HBB | hsa-miR-330-3p |
| rs33926796 | 141900 | A/C/G/T | HBB | hsa-miR-186 |
| rs33926796 | 141900 | A/C/G/T | HBB | hsa-miR-548b-3p |
| rs33926796 | 141900 | A/C/G/T | HBB | hsa-miR-492 |
| rs33926796 | 141900 | A/C/G/T | HBB | hsa-miR-548h, hsa-miR-548i, hsa-miR-548i, hsa-miR-548i, hsa-miR-548i, hsa-miR-548j, hsa-miR-548k, hsa-miR-548l, hsa-miR-548d-5p, hsa-miR-548d-5p, hsa-miR-548a-5p, hsa-miR-548c-5p, hsa-miR-548b-5p, hsa-miR-559 |
| rs33926796 | 141900 | A/C/G/T | HBB | hsa-miR-624* |
| rs33926796 | 141900 | A/C/G/T | HBB | hsa-miR-29c, hsa-miR-29b, hsa-miR-29b, hsa-miR-29a |
| rs33926796 | 141900 | A/C/G/T | HBB | hsa-miR-520h, hsa-miR-520g |
| rs33927093 | 141900 | A/C/T | HBB | hsa-miR-665 |
| rs33927093 | 141900 | A/C/T | HBB | hsa-miR-1256 |
| rs33927093 | 141900 | A/C/T | HBB | hsa-miR-1197 |

TABLE 2-continued

| SNP | OMIM | MUTATION | GENE | MIR |
|---|---|---|---|---|
| rs33927093 | 141900 | A/C/T | HBB | hsa-miR-616 |
| rs33927093 | 141900 | A/C/T | HBB | hsa-miR-323-3p |
| rs33927739 | 141900 | A/C/T | HBB | hsa-miR-510, hsa-miR-512-5p, hsa-miR-512-5p |
| rs33927739 | 141900 | A/C/T | HBB | hsa-miR-1178 |
| rs33927739 | 141900 | A/C/T | HBB | hsa-miR-148a* |
| rs33927739 | 141900 | A/C/T | HBB | hsa-miR-148b* |
| rs33927739 | 141900 | A/C/T | HBB | hsa-miR-520b, hsa-miR-302e, hsa-miR-519a, hsa-miR-519a, hsa-miR-520c-3p, hsa-miR-520d-3p, hsa-miR-520e, hsa-miR-519c-3p, hsa-miR-520a-3p, hsa-miR-519b-3p, hsa-miR-302c, hsa-miR-302d, hsa-miR-372, hsa-miR-373, hsa-miR-302b, hsa-miR-302a |
| rs33927739 | 141900 | A/C/T | HBB | hsa-miR-512-3p, hsa-miR-520f |
| rs33927739 | 141900 | A/C/T | HBB | hsa-miR-1278 |
| rs33928092 | 141900 | A/G/T | HBB | hsa-miR-128 |
| rs33928092 | 141900 | A/G/T | HBB | hsa-miR-519d, hsa-miR-526b*, hsa-miR-20b, hsa-miR-106b, hsa-miR-106a, hsa-miR-93, hsa-miR-17, hsa-miR-20a |
| rs33928092 | 141900 | A/G/T | HBB | hsa-miR-192* |
| rs33928092 | 141900 | A/G/T | HBB | hsa-miR-520h, hsa-miR-520g |
| rs33928092 | 141900 | A/G/T | HBB | hsa-miR-921 |
| rs33929415 | 141900 | A/C/G/T | HBB | hsa-miR-1295 |
| rs33929415 | 141900 | A/C/G/T | HBB | hsa-miR-581 |
| rs33929415 | 141900 | A/C/G/T | HBB | hsa-miR-135b* |
| rs33929415 | 141900 | A/C/G/T | HBB | hsa-miR-643 |
| rs33929415 | 141900 | A/C/G/T | HBB | hsa-miR-588 |
| rs33929415 | 141900 | A/C/G/T | HBB | hsa-miR-15a* |
| rs33929459 | 141900 | A/G/T | HBB | hsa-miR-664 |
| rs33929459 | 141900 | A/G/T | HBB | hsa-miR-10a* |
| rs33929459 | 141900 | A/G/T | HBB | hsa-miR-205* |
| rs33930165 | 141900 | A/C/G | HBB | hsa-miR-1224-5p |
| rs33930165 | 141900 | A/C/G | HBB | hsa-miR-1266 |
| rs33930165 | 141900 | A/C/G | HBB | hsa-miR-1200, hsa-miR-378* |
| rs33930165 | 141900 | A/C/G | HBB | hsa-miR-651 |
| rs33930165 | 141900 | A/C/G | HBB | hsa-miR-1976 |
| rs33930702 | 141900 | A/C/G/T | HBB | hsa-miR-584 |
| rs33930702 | 141900 | A/C/G/T | HBB | hsa-miR-500* |
| rs33930702 | 141900 | A/C/G/T | HBB | hsa-miR-767-5p |
| rs33931314 | 141800 | A/C/G/T | HBA2 | hsa-miR-631 |
| rs33931314 | 141800 | A/C/G/T | HBA2 | hsa-miR-941 |
| rs33931314 | 141800 | A/C/G/T | HBA2 | hsa-miR-215, hsa-miR-192 |
| rs33931314 | 141800 | A/C/G/T | HBA2 | hsa-miR-619 |
| rs33931314 | 141800 | A/C/G/T | HBA2 | hsa-miR-1911* |
| rs33931779 | 141900 | A/C/T | HBB | hsa-miR-942 |
| rs33931779 | 141900 | A/C/T | HBB | hsa-miR-412 |
| rs33931779 | 141900 | A/C/T | HBB | hsa-miR-1248, hsa-miR-1237 |
| rs33931779 | 141900 | A/C/T | HBB | hsa-miR-629* |
| rs33931779 | 141900 | A/C/T | HBB | hsa-miR-205 |
| rs33931806 | 141900 | A/C/G | HBB | hsa-miR-1207-5p |
| rs33931806 | 141900 | A/C/G | HBB | hsa-miR-491-5p |
| rs33931806 | 141900 | A/C/G | HBB | hsa-miR-486-3p |
| rs33931806 | 141900 | A/C/G | HBB | hsa-miR-1909 |
| rs33931984 | 141800 | C/G/T | HBA2 | hsa-miR-520b, hsa-miR-302e, hsa-miR-519a, hsa-miR-519a, hsa-miR-520c-3p, hsa-miR-520d-3p, hsa-miR-520e, hsa-miR-519c-3p, hsa-miR-520a-3p, hsa-miR-519b-3p, hsa-miR-302c, hsa-miR-302d, hsa-miR-372, hsa-miR-373, hsa-miR-302b, hsa-miR-302a |
| rs33932070 | 141900 | A/C/G/T | HBB | hsa-miR-10b* |
| rs33932070 | 141900 | A/C/G/T | HBB | hsa-miR-145* |
| rs33932548 | 141900 | A/T | HBB | hsa-miR-578 |
| rs33932908 | 141900 | A/G/T | HBB | hsa-miR-376c |
| rs33932981 | 141900 | A/C/G/T | — | hsa-miR-942 |
| rs33932981 | 141900 | A/C/G/T | — | hsa-miR-1324 |
| rs33932981 | 141900 | A/C/G/T | — | hsa-miR-617 |
| rs33932981 | 141900 | A/C/G/T | — | hsa-miR-629* |
| rs33933481 | 141850 | A/C/G/T | HBA2 | hsa-miR-581 |
| rs33933481 | 141850 | A/C/G/T | HBA2 | hsa-miR-143* |
| rs33933481 | 141850 | A/C/G/T | HBA2 | hsa-miR-198 |
| rs33933481 | 141850 | A/C/G/T | HBA2 | hsa-miR-643 |
| rs33933481 | 141850 | A/C/G/T | HBA2 | hsa-miR-1909 |
| rs33933481 | 141850 | A/C/G/T | HBA2 | hsa-miR-493*, hsa-let-7g*, hsa-let-7a-2* |
| rs33933481 | 141850 | A/C/G/T | HBA2 | hsa-miR-375 |
| rs33935328 | 141800 | A/C/G/T | HBA1 | hsa-miR-302a* |
| rs33935328 | 141800 | A/C/G/T | HBA1 | hsa-miR-548m |
| rs33935383 | 141900 | A/C/T | HBB | hsa-miR-1257 |
| rs33935383 | 141900 | A/C/T | HBB | hsa-miR-491-5p |
| rs33935383 | 141900 | A/C/T | HBB | hsa-miR-608, hsa-miR-342-5p |

TABLE 2-continued

| SNP | OMIM | MUTATION | GENE | MIR |
|---|---|---|---|---|
| rs33935383 | 141900 | A/C/T | HBB | hsa-miR-563, hsa-miR-380* |
| rs33935383 | 141900 | A/C/T | HBB | hsa-miR-450b-3p, hsa-miR-769-3p |
| rs33935383 | 141900 | A/C/T | HBB | hsa-miR-1255b, hsa-miR-1255a |
| rs33935445 | 141900 | C/G/T | HBB | hsa-miR-662 |
| rs33935445 | 141900 | C/G/T | HBB | hsa-miR-220c |
| rs33935445 | 141900 | C/G/T | HBB | hsa-miR-486-3p |
| rs33935445 | 141900 | C/G/T | HBB | hsa-miR-1280, hsa-miR-1224-3p |
| rs33935527 | 141900 | A/C/T | HBB | hsa-miR-101* |
| rs33935527 | 141900 | A/C/T | HBB | hsa-miR-561 |
| rs33935527 | 141900 | A/C/T | HBB | hsa-miR-548h, hsa-miR-548i, hsa-miR-548i, hsa-miR-548i, hsa-miR-548i, hsa-miR-548j, hsa-miR-548k, hsa-miR-548l, hsa-miR-548d-5p, hsa-miR-548d-5p, hsa-miR-548a-5p, hsa-miR-548c-5p, hsa-miR-548b-5p, hsa-miR-559 |
| rs33935527 | 141900 | A/C/T | HBB | hsa-miR-519d, hsa-miR-526b*, hsa-miR-20b, hsa-miR-106b, hsa-miR-106a, hsa-miR-93, hsa-miR-17, hsa-miR-20a |
| rs33935527 | 141900 | A/C/T | HBB | hsa-miR-1245 |
| rs33935673 | 141900 | A/C/G | HBB | hsa-miR-518b, hsa-miR-518a-3p, hsa-miR-518f, hsa-miR-518c, hsa-miR-518a-3p, hsa-miR-518d-3p |
| rs33935673 | 141900 | A/C/G | HBB | hsa-miR-330-3p |
| rs33935673 | 141900 | A/C/G | HBB | hsa-miR-519d, hsa-miR-526b*, hsa-miR-20b, hsa-miR-106b, hsa-miR-106a, hsa-miR-93, hsa-miR-17, hsa-miR-20a |
| rs33935673 | 141900 | A/C/G | HBB | hsa-miR-1245 |
| rs33935673 | 141900 | A/C/G | HBB | hsa-miR-520h, hsa-miR-520g |
| rs33935983 | 141900 | C/G | HBB | hsa-let-7i* |
| rs33936254 | 141900 | A/C/G/T | HBB | hsa-miR-136 |
| rs33936254 | 141900 | A/C/G/T | HBB | hsa-miR-606 |
| rs33936254 | 141900 | A/C/G/T | HBB | hsa-miR-508-5p |
| rs33936254 | 141900 | A/C/G/T | HBB | hsa-miR-20a* |
| rs33936254 | 141900 | A/C/G/T | HBB | hsa-miR-509-3-5p, hsa-miR-509-5p, hsa-miR-509-5p, hsa-miR-217 |
| rs33936254 | 141900 | A/C/G/T | HBB | hsa-miR-324-5p |
| rs33936967 | 141900 | A/G/T | HBB | hsa-miR-377* |
| rs33936967 | 141900 | A/G/T | HBB | hsa-miR-581 |
| rs33936967 | 141900 | A/G/T | HBB | hsa-miR-1304 |
| rs33936967 | 141900 | A/G/T | HBB | hsa-miR-1915* |
| rs33937393 | 141900 | A/C/G | HBB | hsa-miR-665 |
| rs33937393 | 141900 | A/C/G | HBB | hsa-miR-1915 |
| rs33937393 | 141900 | A/C/G | HBB | hsa-miR-1286 |
| rs33937393 | 141900 | A/C/G | HBB | hsa-miR-148b* |
| rs33937393 | 141900 | A/C/G | HBB | hsa-miR-1266 |
| rs33937535 | 141900 | A/C/G | HBB | hsa-miR-1827 |
| rs33938574 | 141800 | A/C/G | HBA2 | hsa-miR-422a, hsa-miR-378 |
| rs33938574 | 141800 | A/C/G | HBA2 | hsa-miR-1254, hsa-miR-661 |
| rs33939421 | 141800 | A/G/T | HBA2 | hsa-miR-122* |
| rs33939620 | 141850 | A/C/G/T | HBA2 | hsa-miR-575 |
| rs33939620 | 141850 | A/C/G/T | HBA2 | hsa-miR-892b, hsa-miR-193b, hsa-miR-193a-3p |
| rs33939620 | 141850 | A/C/G/T | HBA2 | hsa-miR-588 |
| rs33939620 | 141850 | A/C/G/T | HBA2 | hsa-miR-1202 |
| rs33940051 | 141900 | A/C/G | HBB | hsa-miR-938 |
| rs33940051 | 141900 | A/C/G | HBB | hsa-miR-1304 |
| rs33940051 | 141900 | A/C/G | HBB | hsa-miR-146b-3p |
| rs33940204 | 141900 | C/G/T | HBB | hsa-miR-483-3p |
| rs33940204 | 141900 | C/G/T | HBB | hsa-miR-510, hsa-miR-512-5p, hsa-miR-512-5p |
| rs33940204 | 141900 | C/G/T | HBB | hsa-miR-648 |
| rs33941844 | 141900 | A/C/G/T | HBB | hsa-miR-665 |
| rs33941844 | 141900 | A/C/G/T | HBB | hsa-miR-1915 |
| rs33941844 | 141900 | A/C/G/T | HBB | hsa-miR-1203 |
| rs33941844 | 141900 | A/C/G/T | HBB | hsa-miR-146b-3p |
| rs33941844 | 141900 | A/C/G/T | HBB | hsa-miR-874 |
| rs33941844 | 141900 | A/C/G/T | HBB | hsa-miR-920 |
| rs33941844 | 141900 | A/C/G/T | HBB | hsa-miR-708, hsa-miR-28-5p |
| rs33941849 | 141900 | C/G/T | HBB | hsa-miR-10a, hsa-miR-10b |
| rs33941849 | 141900 | C/G/T | HBB | hsa-miR-767-5p |
| rs33941849 | 141900 | C/G/T | HBB | hsa-miR-132* |
| rs33943087 | 141800 | A/C/G | HBA2 | hsa-miR-933 |
| rs33944368 | 141800 | A/C/G | HBA2 | hsa-miR-1972 |
| rs33944368 | 141800 | A/C/G | HBA2 | hsa-miR-431* |
| rs33944813 | 141800 | A/C/G/T | HBA2 | hsa-miR-933 |
| rs33944813 | 141800 | A/C/G/T | HBA2 | hsa-miR-147b, hsa-miR-210 |
| rs33944813 | 141800 | A/C/G/T | HBA2 | hsa-miR-581 |
| rs33944813 | 141800 | A/C/G/T | HBA2 | hsa-miR-635 |
| rs33944813 | 141800 | A/C/G/T | HBA2 | hsa-miR-339-3p |
| rs33944813 | 141800 | A/C/G/T | HBA2 | hsa-miR-1228* |
| rs33945546 | 141900 | A/C/G/T | HBB | hsa-miR-1226 |

TABLE 2-continued

| SNP | OMIM | MUTATION | GENE | MIR |
|---|---|---|---|---|
| rs33945546 | 141900 | A/C/G/T | HBB | hsa-miR-181c* |
| rs33945546 | 141900 | A/C/G/T | HBB | hsa-miR-220b |
| rs33945546 | 141900 | A/C/G/T | HBB | hsa-miR-634 |
| rs33945546 | 141900 | A/C/G/T | HBB | hsa-miR-205 |
| rs33945546 | 141900 | A/C/G/T | HBB | hsa-miR-141* |
| rs33945705 | 141900 | A/G/T | HBB | hsa-miR-885-5p |
| rs33945705 | 141900 | A/G/T | HBB | hsa-miR-34c-3p |
| rs33946267 | 141900 | A/C/G/T | — | hsa-miR-944 |
| rs33946267 | 141900 | A/C/G/T | — | hsa-miR-129-5p |
| rs33946267 | 141900 | A/C/G/T | — | hsa-miR-126* |
| rs33946267 | 141900 | A/C/G/T | — | hsa-miR-219-2-3p |
| rs33946267 | 141900 | A/C/G/T | — | hsa-miR-590-3p |
| rs33946401 | 141900 | A/C/G | HBB | hsa-miR-224 |
| rs33946401 | 141900 | A/C/G | HBB | hsa-miR-449b* |
| rs33946401 | 141900 | A/C/G | HBB | hsa-miR-593* |
| rs33946401 | 141900 | A/C/G | HBB | hsa-miR-9* |
| rs33946401 | 141900 | A/C/G | HBB | hsa-miR-506, hsa-miR-124, hsa-miR-124, hsa-miR-124 |
| rs33946775 | 141900 | A/C/T | HBB | hsa-miR-140-3p |
| rs33946775 | 141900 | A/C/T | HBB | hsa-miR-181d, hsa-miR-181b, hsa-miR-181a, hsa-miR-181a, hsa-miR-181b, hsa-miR-181c |
| rs33947020 | 141900 | A/C/G/T | HBB | hsa-miR-514 |
| rs33947020 | 141900 | A/C/G/T | HBB | hsa-miR-1271, hsa-miR-182, hsa-miR-96 |
| rs33947020 | 141900 | A/C/G/T | HBB | hsa-miR-192* |
| rs33947020 | 141900 | A/C/G/T | HBB | hsa-miR-9 |
| rs33947112 | 142200 | A/G/T | HBG1 | hsa-miR-577 |
| rs33947112 | 142200 | A/G/T | HBG1 | hsa-miR-136* |
| rs33947415 | 141900 | A/C/G | HBB | hsa-miR-564 |
| rs33947415 | 141900 | A/C/G | HBB | hsa-miR-593* |
| rs33947415 | 141900 | A/C/G | HBB | hsa-miR-615-3p |
| rs33947457 | 141900 | A/C/T | HBB | hsa-miR-337-5p |
| rs33947457 | 141900 | A/C/T | HBB | hsa-miR-598 |
| rs33947457 | 141900 | A/C/T | HBB | hsa-miR-196b* |
| rs33948057 | 141900 | A/C/G | HBB | hsa-miR-573 |
| rs33948057 | 141900 | A/C/G | HBB | hsa-miR-99b*, hsa-miR-99a* |
| rs33948057 | 141900 | A/C/G | HBB | hsa-miR-493 |
| rs33948057 | 141900 | A/C/G | HBB | hsa-miR-148a* |
| rs33948057 | 141900 | A/C/G | HBB | hsa-miR-148b* |
| rs33948057 | 141900 | A/C/G | HBB | hsa-miR-127-5p |
| rs33948578 | 141900 | A/C/G/T | HBB | hsa-miR-646, hsa-miR-503, hsa-miR-497, hsa-miR-424, hsa-miR-195, hsa-miR-15b, hsa-miR-16, hsa-miR-15a, hsa-miR-16 |
| rs33948578 | 141900 | A/C/G/T | HBB | hsa-miR-1226 |
| rs33948578 | 141900 | A/C/G/T | HBB | hsa-miR-634 |
| rs33948578 | 141900 | A/C/G/T | HBB | hsa-miR-885-3p |
| rs33948578 | 141900 | A/C/G/T | HBB | hsa-miR-338-3p |
| rs33948578 | 141900 | A/C/G/T | HBB | hsa-miR-1301 |
| rs33948578 | 141900 | A/C/G/T | HBB | hsa-miR-922, hsa-miR-214 |
| rs33948578 | 141900 | A/C/G/T | HBB | hsa-miR-1205, hsa-miR-1184, hsa-miR-17* |
| rs33948615 | 141900 | A/C/G/T | HBB | hsa-miR-335 |
| rs33948615 | 141900 | A/C/G/T | HBB | hsa-miR-379 |
| rs33948615 | 141900 | A/C/G/T | HBB | hsa-miR-411 |
| rs33948615 | 141900 | A/C/G/T | HBB | hsa-miR-595 |
| rs33949106 | 141800 | A/C/G | HBA2 | hsa-miR-938 |
| rs33949106 | 141800 | A/C/G | HBA2 | hsa-miR-1291 |
| rs33949106 | 141800 | A/C/G | HBA2 | hsa-miR-1538 |
| rs33949486 | 141900 | A/C/G | HBB | hsa-miR-499-3p |
| rs33949486 | 141900 | A/C/G | HBB | hsa-miR-646, hsa-miR-503, hsa-miR-497, hsa-miR-424, hsa-miR-195, hsa-miR-15b, hsa-miR-16, hsa-miR-15a, hsa-miR-16 |
| rs33949486 | 141900 | A/C/G | HBB | hsa-miR-1226 |
| rs33949486 | 141900 | A/C/G | HBB | hsa-miR-634 |
| rs33949486 | 141900 | A/C/G | HBB | hsa-miR-1228, hsa-miR-220a |
| rs33949486 | 141900 | A/C/G | HBB | hsa-miR-922, hsa-miR-214 |
| rs33949869 | 141900 | A/C/G/T | HBB | hsa-miR-502-5p |
| rs33949869 | 141900 | A/C/G/T | HBB | hsa-miR-501-5p, hsa-miR-362-5p |
| rs33949869 | 141900 | A/C/G/T | HBB | hsa-miR-640 |
| rs33949869 | 141900 | A/C/G/T | HBB | hsa-miR-578 |
| rs33950093 | 141900 | A/C/G/T | HBB | hsa-miR-485-3p |
| rs33950093 | 141900 | A/C/G/T | HBB | hsa-miR-1298 |
| rs33950093 | 141900 | A/C/G/T | HBB | hsa-miR-501-3p, hsa-miR-502-3p |
| rs33950507 | 141900 | A/G/T | — | hsa-miR-220b |
| rs33950507 | 141900 | A/G/T | — | hsa-miR-197 |
| rs33950542 | 141900 | C/G/T | HBB | hsa-miR-575 |
| rs33950542 | 141900 | C/G/T | HBB | hsa-miR-1225-3p, hsa-miR-1233 |
| rs33950542 | 141900 | C/G/T | HBB | hsa-miR-1972 |
| rs33950542 | 141900 | C/G/T | HBB | hsa-miR-15a* |
| rs33950993 | 141900 | A/C/T | HBB | hsa-miR-517b |

TABLE 2-continued

| SNP | OMIM | MUTATION | GENE | MIR |
|---|---|---|---|---|
| rs33950993 | 141900 | A/C/T | HBB | hsa-miR-143* |
| rs33950993 | 141900 | A/C/T | HBB | hsa-miR-1301 |
| rs33951978 | 141900 | A/C/T | HBB | hsa-miR-646, hsa-miR-503, hsa-miR-497, hsa-miR-424, hsa-miR-195, hsa-miR-15b, hsa-miR-16, hsa-miR-15a, hsa-miR-16 |
| rs33951978 | 141900 | A/C/T | HBB | hsa-miR-517b |
| rs33951978 | 141900 | A/C/T | HBB | hsa-miR-885-3p |
| rs33951978 | 141900 | A/C/T | HBB | hsa-miR-143* |
| rs33951978 | 141900 | A/C/T | HBB | hsa-miR-1301 |
| rs33952543 | 0 | A/C/G/T | HBB | hsa-miR-665 |
| rs33952543 | 0 | A/C/G/T | HBB | hsa-miR-939 |
| rs33952543 | 0 | A/C/G/T | HBB | hsa-miR-125a-3p |
| rs33952543 | 0 | A/C/G/T | HBB | hsa-miR-505* |
| rs33952543 | 0 | A/C/G/T | HBB | hsa-miR-920 |
| rs33952543 | 0 | A/C/G/T | HBB | hsa-miR-185 |
| rs33952850 | 141900 | C/G/T | HBB | hsa-miR-29c* |
| rs33952850 | 141900 | C/G/T | HBB | hsa-miR-184 |
| rs33952850 | 141900 | C/G/T | HBB | hsa-miR-127-3p |
| rs33953406 | 141900 | A/C/G | — | hsa-miR-628-5p |
| rs33953406 | 141900 | A/C/G | — | hsa-miR-1200, hsa-miR-378* |
| rs33954264 | 141900 | A/C/G/T | HBB | hsa-miR-1303 |
| rs33954264 | 141900 | A/C/G/T | HBB | hsa-miR-1245 |
| rs33954264 | 141900 | A/C/G/T | HBB | hsa-miR-921 |
| rs33954595 | 141900 | A/C/G/T | HBB | hsa-miR-1265 |
| rs33954595 | 141900 | A/C/G/T | HBB | hsa-miR-501-3p, hsa-miR-502-3p |
| rs33954632 | 141900 | A/C/G/T | HBB | hsa-miR-665 |
| rs33954632 | 141900 | A/C/G/T | HBB | hsa-miR-1291 |
| rs33954632 | 141900 | A/C/G/T | HBB | hsa-miR-492 |
| rs33954632 | 141900 | A/C/G/T | HBB | hsa-miR-1972 |
| rs33955330 | 142250 | A/C/G | HBG1 | hsa-miR-23b, hsa-miR-130a*, hsa-miR-23a |
| rs33955330 | 142250 | A/C/G | HBG1 | hsa-miR-141* |
| rs33956485 | 142000 | C/T | HBD | hsa-miR-575 |
| rs33956485 | 142000 | C/T | HBD | hsa-miR-486-3p |
| rs33957286 | 141900 | A/C/T | HBB | hsa-miR-885-3p |
| rs33957286 | 141900 | A/C/T | HBB | hsa-miR-196a* |
| rs33957286 | 141900 | A/C/T | HBB | hsa-miR-596 |
| rs33957286 | 141900 | A/C/T | HBB | hsa-miR-940, hsa-miR-34b* |
| rs33957286 | 141900 | A/C/T | HBB | hsa-miR-324-5p |
| rs33957286 | 141900 | A/C/T | HBB | hsa-miR-649, hsa-miR-490-3p |
| rs33957766 | 141800 | A/G/T | HBA2 | hsa-miR-1915 |
| rs33957766 | 141800 | A/G/T | HBA2 | hsa-miR-198 |
| rs33957766 | 141800 | A/G/T | HBA2 | hsa-miR-1911* |
| rs33957964 | 141900 | C/G/T | HBB | hsa-miR-646, hsa-miR-503, hsa-miR-497, hsa-miR-424, hsa-miR-195, hsa-miR-15b, hsa-miR-16, hsa-miR-15a, hsa-miR-16 |
| rs33957964 | 141900 | C/G/T | HBB | hsa-miR-634 |
| rs33957964 | 141900 | C/G/T | HBB | hsa-miR-338-3p |
| rs33957964 | 141900 | C/G/T | HBB | hsa-miR-589* |
| rs33957964 | 141900 | C/G/T | HBB | hsa-miR-103, hsa-miR-107 |
| rs33958358 | 141900 | A/G/T | HBB | hsa-miR-96* |
| rs33958358 | 141900 | A/G/T | HBB | hsa-miR-586 |
| rs33958358 | 141900 | A/G/T | HBB | hsa-miR-500* |
| rs33958358 | 141900 | A/G/T | HBB | hsa-miR-767-5p |
| rs33958358 | 141900 | A/G/T | HBB | hsa-miR-501-3p, hsa-miR-502-3p |
| rs33958637 | 141900 | A/C/G | HBB | hsa-miR-663b |
| rs33958637 | 141900 | A/C/G | HBB | hsa-miR-1181 |
| rs33958637 | 141900 | A/C/G | HBB | hsa-miR-328 |
| rs33958637 | 141900 | A/C/G | HBB | hsa-miR-1204 |
| rs33959340 | 141900 | A/C/G/T | HBB | hsa-miR-581 |
| rs33959340 | 141900 | A/C/G/T | HBB | hsa-miR-513a-5p, hsa-miR-27b, hsa-miR-27a |
| rs33959340 | 141900 | A/C/G/T | HBB | hsa-miR-128 |
| rs33959340 | 141900 | A/C/G/T | HBB | hsa-miR-643 |
| rs33959340 | 141900 | A/C/G/T | HBB | hsa-miR-758 |
| rs33959340 | 141900 | A/C/G/T | HBB | hsa-miR-542-3p |
| rs33959340 | 141900 | A/C/G/T | HBB | hsa-miR-194 |
| rs33959340 | 141900 | A/C/G/T | HBB | hsa-miR-132, hsa-miR-212 |
| rs33959340 | 141900 | A/C/G/T | HBB | hsa-miR-582-5p |
| rs33959483 | 141800 | C/G/T | HBA2 | hsa-miR-938 |
| rs33959483 | 141800 | C/G/T | HBA2 | hsa-miR-1291 |
| rs33959483 | 141800 | C/G/T | HBA2 | hsa-miR-885-5p |
| rs33959483 | 141800 | C/G/T | HBA2 | hsa-miR-588 |
| rs33959483 | 141800 | C/G/T | HBA2 | hsa-miR-328 |
| rs33959855 | 141900 | A/C/G/T | HBB | hsa-miR-1826 |
| rs33959855 | 141900 | A/C/G/T | HBB | hsa-miR-640 |
| rs33960103 | 141900 | A/C/G | HBB | hsa-miR-1913, hsa-miR-324-3p, hsa-miR-18a* |
| rs33960103 | 141900 | A/C/G | HBB | hsa-miR-649, hsa-miR-490-3p |
| rs33960522 | 141800 | A/C/G | — | hsa-miR-558 |
| rs33960522 | 141800 | A/C/G | — | hsa-miR-132* |

TABLE 2-continued

| SNP | OMIM | MUTATION | GENE | MIR |
|---|---|---|---|---|
| rs33960522 | 141800 | A/C/G | — | hsa-miR-1204 |
| rs33960790 | 141850 | A/C/G | HBA2 | hsa-miR-933 |
| rs33960790 | 141850 | A/C/G | HBA2 | hsa-let-7i* |
| rs33960790 | 141850 | A/C/G | HBA2 | hsa-miR-675 |
| rs33960790 | 141850 | A/C/G | HBA2 | hsa-miR-1178 |
| rs33960790 | 141850 | A/C/G | HBA2 | hsa-miR-513a-5p, hsa-miR-27b, hsa-miR-27a |
| rs33960790 | 141850 | A/C/G | HBA2 | hsa-miR-342-3p |
| rs33960931 | 141900 | C/G/T | HBB | hsa-miR-301b, hsa-miR-454, hsa-miR-301a, hsa-miR-130b, hsa-miR-130a |
| rs33960931 | 141900 | C/G/T | HBB | hsa-miR-1909* |
| rs33961444 | 141900 | C/G/T | HBB | hsa-miR-429, hsa-miR-200c, hsa-miR-200b |
| rs33961444 | 141900 | C/G/T | HBB | hsa-miR-655 |
| rs33961444 | 141900 | C/G/T | HBB | hsa-miR-485-3p |
| rs33961444 | 141900 | C/G/T | HBB | hsa-miR-1245 |
| rs33961444 | 141900 | C/G/T | HBB | hsa-miR-921 |
| rs33961459 | 141900 | C/T | HBB | hsa-miR-615-3p |
| rs33961459 | 141900 | C/T | HBB | hsa-miR-200a, hsa-miR-141 |
| rs33961886 | 141900 | A/C/G | HBB | hsa-miR-1977 |
| rs33961886 | 141900 | A/C/G | HBB | hsa-miR-1179 |
| rs33961886 | 141900 | A/C/G | HBB | hsa-miR-1224-5p |
| rs33961886 | 141900 | A/C/G | HBB | hsa-miR-651 |
| rs33961916 | 141800 | A/G/T | — | hsa-miR-135b* |
| rs33961916 | 141800 | A/G/T | — | hsa-miR-1271, hsa-miR-182, hsa-miR-96 |
| rs33961916 | 141800 | A/G/T | — | hsa-miR-643 |
| rs33961916 | 141800 | A/G/T | — | hsa-miR-940, hsa-miR-34b* |
| rs33962676 | 141900 | A/C/G | HBB | hsa-miR-1975 |
| rs33962676 | 141900 | A/C/G | HBB | hsa-miR-1979, hsa-miR-1260, hsa-miR-188-3p |
| rs33962676 | 141900 | A/C/G | HBB | hsa-miR-328 |
| rs33962676 | 141900 | A/C/G | HBB | hsa-miR-1915* |
| rs33964317 | 141800 | A/C/T | HBA2 | hsa-miR-1915 |
| rs33964317 | 141800 | A/C/T | HBA2 | hsa-miR-331-3p |
| rs33964317 | 141800 | A/C/T | HBA2 | hsa-miR-221* |
| rs33964352 | 141900 | A/G/T | — | hsa-miR-581 |
| rs33964507 | 141850 | A/C/G/T | HBA2 | hsa-miR-296-5p |
| rs33964623 | 141850 | A/C/G | HBA2 | hsa-miR-491-5p |
| rs33964623 | 141850 | A/C/G | HBA2 | hsa-miR-486-3p |
| rs33964623 | 141850 | A/C/G | HBA2 | hsa-miR-1306 |
| rs33965000 | 141900 | C/G/T | HBB | hsa-miR-1229 |
| rs33965000 | 141900 | C/G/T | HBB | hsa-miR-513c |
| rs33965000 | 141900 | C/G/T | HBB | hsa-miR-1266 |
| rs33965337 | 142200 | A/C/G | HBG1 | hsa-miR-1256 |
| rs33965337 | 142200 | A/C/G | HBG1 | hsa-miR-532-3p, hsa-miR-150 |
| rs33966487 | 141900 | A/C/G | HBB | hsa-miR-22* |
| rs33966487 | 141900 | A/C/G | HBB | hsa-miR-1224-5p |
| rs33966487 | 141900 | A/C/G | HBB | hsa-miR-1266 |
| rs33966487 | 141900 | A/C/G | HBB | hsa-miR-1185 |
| rs33966487 | 141900 | A/C/G | HBB | hsa-miR-651 |
| rs33966761 | 141900 | A/C/T | HBB | hsa-miR-220b |
| rs33966761 | 141900 | A/C/T | HBB | hsa-miR-449b* |
| rs33967561 | 141800 | A/G/T | HBA2 | hsa-miR-485-5p |
| rs33967561 | 141800 | A/G/T | HBA2 | hsa-miR-132* |
| rs33967561 | 141800 | A/G/T | HBA2 | hsa-miR-1204 |
| rs33967755 | 141900 | A/G/T | — | hsa-miR-220b |
| rs33967755 | 141900 | A/G/T | — | hsa-miR-34c-3p |
| rs33967755 | 141900 | A/G/T | — | hsa-miR-200a, hsa-miR-141 |
| rs33968721 | 141900 | A/C/G | — | hsa-miR-181c* |
| rs33968721 | 141900 | A/C/G | — | hsa-miR-220b |
| rs33969727 | 141900 | A/C/G | HBB | hsa-miR-96* |
| rs33969727 | 141900 | A/C/G | HBB | hsa-miR-122 |
| rs33969727 | 141900 | A/C/G | HBB | hsa-miR-433 |
| rs33969953 | 141800 | A/C/G/T | HBA2 | hsa-miR-214* |
| rs33969953 | 141800 | A/C/G/T | HBA2 | hsa-miR-1228* |
| rs33969953 | 141800 | A/C/G/T | HBA2 | hsa-miR-1268, hsa-miR-585 |
| rs33969953 | 141800 | A/C/G/T | HBA2 | hsa-miR-187 |
| rs33969953 | 141800 | A/C/G/T | HBA2 | hsa-miR-27a* |
| rs33970907 | 142250 | A/G/T | HBG1 | hsa-miR-891b |
| rs33970907 | 142250 | A/G/T | HBG1 | hsa-miR-545 |
| rs33970907 | 142250 | A/G/T | HBG1 | hsa-miR-29c, hsa-miR-29b, hsa-miR-29a |
| rs33970907 | 142250 | A/G/T | HBG1 | hsa-miR-141* |
| rs33971048 | 141900 | A/C/G/T | HBB | hsa-miR-662 |
| rs33971048 | 141900 | A/C/G/T | HBB | hsa-miR-873 |
| rs33971048 | 141900 | A/C/G/T | HBB | hsa-miR-449b* |
| rs33971048 | 141900 | A/C/G/T | HBB | hsa-miR-505* |
| rs33971048 | 141900 | A/C/G/T | HBB | hsa-miR-708, hsa-miR-28-5p |
| rs33971270 | 142000 | C/T | HBD | hsa-miR-1972 |
| rs33971270 | 142000 | C/T | HBD | hsa-miR-15a* |
| rs33971634 | 141900 | A/C/G/T | HBB | hsa-miR-24-1*, hsa-miR-24-2* |

TABLE 2-continued

| SNP | OMIM | MUTATION | GENE | MIR |
|---|---|---|---|---|
| rs33971634 | 141900 | A/C/G/T | HBB | hsa-miR-412 |
| rs33971634 | 141900 | A/C/G/T | HBB | hsa-miR-596 |
| rs33971634 | 141900 | A/C/G/T | HBB | hsa-miR-181a-2* |
| rs33971634 | 141900 | A/C/G/T | HBB | hsa-miR-205 |
| rs33971848 | 141900 | A/C/G/T | HBB | hsa-miR-1257 |
| rs33971848 | 141900 | A/C/G/T | HBB | hsa-miR-22* |
| rs33971848 | 141900 | A/C/G/T | HBB | hsa-miR-183* |
| rs33971848 | 141900 | A/C/G/T | HBB | hsa-miR-617 |
| rs33971848 | 141900 | A/C/G/T | HBB | hsa-miR-148b* |
| rs33971848 | 141900 | A/C/G/T | HBB | hsa-miR-134 |
| rs33972047 | 141900 | A/C/G | HBB | hsa-miR-574-3p |
| rs33972593 | 141900 | A/C/T | HBB | hsa-miR-517b |
| rs33972593 | 141900 | A/C/T | HBB | hsa-miR-615-3p |
| rs33972593 | 141900 | A/C/T | HBB | hsa-miR-1973 |
| rs33972894 | 141800 | C/G/T | HBA2 | hsa-miR-382 |
| rs33972927 | 141900 | C/T | HBB | hsa-miR-148b, hsa-miR-152, hsa-miR-148a |
| rs33972927 | 141900 | C/T | HBB | hsa-miR-301b, hsa-miR-454, hsa-miR-301a, hsa-miR-130b, hsa-miR-130a |
| rs33972927 | 141900 | C/T | HBB | hsa-miR-1250 |
| rs33972927 | 141900 | C/T | HBB | hsa-miR-513a-5p, hsa-miR-27b, hsa-miR-27a |
| rs33972927 | 141900 | C/T | HBB | hsa-miR-128 |
| rs33973589 | 141900 | A/C/G/T | HBB | hsa-miR-615-5p |
| rs33973589 | 141900 | A/C/G/T | HBB | hsa-miR-1257 |
| rs33973589 | 141900 | A/C/G/T | HBB | hsa-miR-193b* |
| rs33973589 | 141900 | A/C/G/T | HBB | hsa-miR-183* |
| rs33973589 | 141900 | A/C/G/T | HBB | hsa-miR-555 |
| rs33973589 | 141900 | A/C/G/T | HBB | hsa-miR-608, hsa-miR-342-5p |
| rs33973589 | 141900 | A/C/G/T | HBB | hsa-miR-10a* |
| rs33973589 | 141900 | A/C/G/T | HBB | hsa-miR-569 |
| rs33974228 | 141900 | A/G/T | HBB | hsa-miR-183 |
| rs33974228 | 141900 | A/G/T | HBB | hsa-miR-802 |
| rs33974228 | 141900 | A/G/T | HBB | hsa-miR-337-5p |
| rs33974228 | 141900 | A/G/T | HBB | hsa-miR-940, hsa-miR-34b* |
| rs33974228 | 141900 | A/G/T | HBB | hsa-miR-506, hsa-miR-124, hsa-miR-124, hsa-miR-124 |
| rs33974325 | 141900 | A/C/G | HBB | hsa-miR-148b, hsa-miR-152, hsa-miR-148a |
| rs33974325 | 141900 | A/C/G | HBB | hsa-miR-885-3p |
| rs33974325 | 141900 | A/C/G | HBB | hsa-miR-301b, hsa-miR-454, hsa-miR-301a, hsa-miR-130b, hsa-miR-130a |
| rs33974325 | 141900 | A/C/G | HBB | hsa-miR-143* |
| rs33974325 | 141900 | A/C/G | HBB | hsa-miR-220c |
| rs33974325 | 141900 | A/C/G | HBB | hsa-miR-128 |
| rs33974325 | 141900 | A/C/G | HBG1 | hsa-miR-1301 |
| rs33974602 | 142250 | A/G | HBG1 | hsa-miR-518c*, hsa-miR-330-5p, hsa-miR-326 |
| rs33976006 | 141900 | A/G/T | HBB | hsa-miR-665 |
| rs33976006 | 141900 | A/G/T | HBB | hsa-miR-499-3p |
| rs33976006 | 141900 | A/G/T | HBB | hsa-miR-1197 |
| rs33976006 | 141900 | A/G/T | HBB | hsa-miR-1972 |
| rs33976006 | 141900 | A/G/T | HBB | hsa-miR-15a* |
| rs33976776 | 141800 | A/C/G | HBA2 | hsa-miR-1207-5p |
| rs33976776 | 141800 | A/C/G | HBA2 | hsa-miR-517b |
| rs33976776 | 141800 | A/C/G | HBA2 | hsa-miR-143* |
| rs33977363 | 141800 | A/C/G/T | — | hsa-miR-299-3p |
| rs33977479 | 141850 | C/G/T | HBA2 | hsa-miR-1539 |
| rs33977536 | 141900 | A/G/T | HBB | hsa-miR-662 |
| rs33977536 | 141900 | A/G/T | HBB | hsa-miR-412 |
| rs33978134 | 141800 | C/G/T | HBA2 | hsa-miR-301b, hsa-miR-454, hsa-miR-301a, hsa-miR-130b, hsa-miR-130a |
| rs33978134 | 141800 | C/G/T | HBA2 | hsa-miR-873 |
| rs33978134 | 141800 | C/G/T | HBA2 | hsa-miR-143* |
| rs33978134 | 141800 | C/G/T | HBA2 | hsa-miR-1286 |
| rs33978134 | 141800 | C/G/T | HBA2 | hsa-miR-33b*, hsa-miR-515-3p, hsa-miR-519e, hsa-miR-515-3p, hsa-miR-371-3p |
| rs33978338 | 141900 | C/G/T | HBB | hsa-miR-1975 |
| rs33978338 | 141900 | C/G/T | HBB | hsa-miR-220c |
| rs33978338 | 141900 | C/G/T | HBB | hsa-miR-186* |
| rs33980484 | 141900 | A/C/G/T | HBB | hsa-miR-1225-3p, hsa-miR-1233 |
| rs33980484 | 141900 | A/C/G/T | HBB | hsa-miR-361-3p |
| rs33980484 | 141900 | A/C/G/T | HBB | hsa-miR-589* |
| rs33983205 | 141900 | A/C/G/T | HBB | hsa-miR-521 |
| rs33983205 | 141900 | A/C/G/T | HBB | hsa-miR-593* |
| rs33983205 | 141900 | A/C/G/T | HBB | hsa-miR-29c, hsa-miR-29b, hsa-miR-29b, hsa-miR-29a |
| rs33983205 | 141900 | A/C/G/T | HBB | hsa-miR-1827 |
| rs33983205 | 141900 | A/C/G/T | HBB | hsa-miR-500* |
| rs33983205 | 141900 | A/C/G/T | HBB | hsa-miR-501-3p, hsa-miR-502-3p |
| rs33983276 | 141900 | A/C/G/T | HBB | hsa-miR-491-5p |
| rs33983276 | 141900 | A/C/G/T | HBB | hsa-miR-541, hsa-miR-654-5p, hsa-miR-92a-2* |

TABLE 2-continued

| SNP | OMIM | MUTATION | GENE | MIR |
|---|---|---|---|---|
| rs33983276 | 141900 | A/C/G/T | HBB | hsa-miR-608, hsa-miR-342-5p |
| rs33983276 | 141900 | A/C/G/T | HBB | hsa-miR-92a-1* |
| rs33983276 | 141900 | A/C/G/T | HBB | hsa-miR-29b-1* |
| rs33983276 | 141900 | A/C/G/T | HBB | hsa-miR-1262 |
| rs33983416 | 141850 | C/G/T | HBA2 | hsa-miR-933 |
| rs33983416 | 141850 | C/G/T | HBA2 | hsa-miR-147b, hsa-miR-210 |
| rs33983416 | 141850 | C/G/T | HBA2 | hsa-miR-1973 |
| rs33984024 | 141800 | A/C/G/T | HBA2 | hsa-miR-1295 |
| rs33984024 | 141800 | A/C/G/T | HBA2 | hsa-miR-588 |
| rs33984024 | 141800 | A/C/G/T | HBA2 | hsa-miR-1306 |
| rs33984024 | 141800 | A/C/G/T | HBA2 | hsa-miR-15a* |
| rs33984621 | 141850 | A/C/G/T | HBA2 | hsa-miR-29c* |
| rs33984621 | 141850 | A/C/G/T | HBA2 | hsa-miR-187 |
| rs33984863 | 141900 | A/C/G/T | HBB | hsa-miR-125b-2* |
| rs33984863 | 141900 | A/C/G/T | HBB | hsa-miR-1226 |
| rs33984863 | 141900 | A/C/G/T | HBB | hsa-miR-634 |
| rs33984863 | 141900 | A/C/G/T | HBB | hsa-miR-1228, hsa-miR-220a |
| rs33985510 | 141900 | A/C/G/T | HBB | hsa-miR-937 |
| rs33985510 | 141900 | A/C/G/T | HBB | hsa-miR-517c, hsa-miR-517a |
| rs33985510 | 141900 | A/C/G/T | HBB | hsa-miR-1973 |
| rs33985544 | 141900 | A/C/G | HBB | hsa-miR-665 |
| rs33985544 | 141900 | A/C/G | HBB | hsa-miR-556-5p |
| rs33985544 | 141900 | A/C/G | HBB | hsa-miR-505* |
| rs33985544 | 141900 | A/C/G | HBB | hsa-miR-1202 |
| rs33985544 | 141900 | A/C/G | HBB | hsa-miR-708, hsa-miR-28-5p |
| rs33985574 | 141850 | C/G/T | HBA2 | hsa-miR-1248, hsa-miR-1237 |
| rs33985574 | 141850 | C/G/T | HBA2 | hsa-miR-22* |
| rs33985574 | 141850 | C/G/T | HBA2 | hsa-miR-181d, hsa-miR-181b, hsa-miR-181a, hsa-miR-181a, hsa-miR-181b, hsa-miR-181c |
| rs33985739 | 141900 | A/C/G | HBB | hsa-miR-1245 |
| rs33985739 | 141900 | A/C/G | HBB | hsa-miR-921 |
| rs33986902 | 141800 | A/C/G/T | HBA2 | hsa-miR-526b |
| rs33987053 | 141850 | A/C/G/T | HBA2 | hsa-miR-582-3p |
| rs33987053 | 141850 | A/C/G/T | HBA2 | hsa-miR-1307 |
| rs33987053 | 141850 | A/C/G/T | HBA2 | hsa-miR-1469 |
| rs33987053 | 141850 | A/C/G/T | HBA2 | hsa-miR-1228* |
| rs33987053 | 141850 | A/C/G/T | HBA2 | hsa-miR-1285, hsa-miR-612 |
| rs33987053 | 141850 | A/C/G/T | HBA2 | hsa-miR-708* |
| rs33987053 | 141850 | A/C/G/T | HBA2 | hsa-miR-645 |
| rs33987053 | 141850 | A/C/G/T | HBA2 | hsa-miR-890 |
| rs33987903 | 141900 | A/C/G/T | HBB | hsa-miR-938 |
| rs33987903 | 141900 | A/C/G/T | HBB | hsa-miR-1304 |
| rs33987903 | 141900 | A/C/G/T | HBB | hsa-miR-331-3p |
| rs33987903 | 141900 | A/C/G/T | HBB | hsa-miR-874 |
| rs33987903 | 141900 | A/C/G/T | HBB | hsa-miR-125a-5p, hsa-miR-125b, hsa-miR-125b |
| rs33987903 | 141900 | A/C/G/T | HBB | hsa-miR-1294 |
| rs33987957 | 141900 | A/C/G/T | HBB | hsa-miR-429, hsa-miR-200c, hsa-miR-200b |
| rs33987957 | 141900 | A/C/G/T | HBB | hsa-miR-501-5p, hsa-miR-362-5p |
| rs33987957 | 141900 | A/C/G/T | HBB | hsa-miR-500 |
| rs33987957 | 141900 | A/C/G/T | HBB | hsa-miR-183* |
| rs33988732 | 141900 | A/C/G | HBB | hsa-miR-296-3p |
| rs33988732 | 141900 | A/C/G | HBB | hsa-miR-663b |
| rs33988732 | 141900 | A/C/G | HBB | hsa-miR-1182 |
| rs33988732 | 141900 | A/C/G | HBB | hsa-miR-1293, hsa-miR-363* |
| rs33988732 | 141900 | A/C/G | HBB | hsa-miR-886-5p |
| rs33988732 | 141900 | A/C/G | HBB | hsa-miR-328 |
| rs33990858 | 141900 | A/C/G/T | HBB | hsa-miR-143* |
| rs33990858 | 141900 | A/C/G/T | HBB | hsa-miR-198 |
| rs33990858 | 141900 | A/C/G/T | HBB | hsa-miR-493*, hsa-let-7g*, hsa-let-7a-2* |
| rs33990858 | 141900 | A/C/G/T | HBB | hsa-miR-657 |
| rs33990858 | 141900 | A/C/G/T | HBB | hsa-miR-552 |
| rs33990858 | 141900 | A/C/G/T | HBB | hsa-miR-375 |
| rs33991223 | 141800 | A/C/G | HBA2 | hsa-miR-652 |
| rs33991294 | 141900 | C/G/T | HBB | hsa-miR-125a-3p |
| rs33991472 | 141900 | C/G | HBB | hsa-miR-296-3p |
| rs33991779 | 141800 | A/C/G/T | HBA2 | hsa-miR-1226 |
| rs33991779 | 141800 | A/C/G/T | HBA2 | hsa-miR-671-5p |
| rs33991779 | 141800 | A/C/G/T | HBA2 | hsa-miR-127-5p |
| rs33991910 | 141800 | A/C/G/T | HBA1 | hsa-miR-101, hsa-miR-144 |
| rs33991910 | 141800 | A/C/G/T | HBA1 | hsa-miR-302c* |
| rs33991910 | 141800 | A/C/G/T | HBA1 | hsa-miR-451 |
| rs33991910 | 141800 | A/C/G/T | HBA1 | hsa-miR-1183 |
| rs33991910 | 141800 | A/C/G/T | HBA1 | hsa-miR-132, hsa-miR-212 |
| rs33991910 | 141800 | A/C/G/T | HBA1 | hsa-miR-16-1* |
| rs33991993 | 141900 | C/G/T | HBB | hsa-miR-938 |
| rs33991993 | 141900 | C/G/T | HBB | hsa-miR-1227 |
| rs33991993 | 141900 | C/G/T | HBB | hsa-miR-874 |
| rs33992775 | 142250 | A/C/G | HBG1 | hsa-miR-581 |

TABLE 2-continued

| SNP | OMIM | MUTATION | GENE | MIR |
|---|---|---|---|---|
| rs33992775 | 142250 | A/C/G | HBG1 | hsa-miR-758 |
| rs33992775 | 142250 | A/C/G | HBG1 | hsa-miR-103-2* |
| rs33993166 | 141850 | C/G | HBA2 | hsa-miR-515-5p, hsa-miR-519e* |
| rs33993166 | 141850 | C/G | HBA2 | hsa-miR-1909 |
| rs33993166 | 141850 | C/G | HBA2 | hsa-miR-1205, hsa-miR-1184, hsa-miR-17* |
| rs33993166 | 141850 | C/G | HBA2 | hsa-miR-766 |
| rs33993568 | 141900 | A/C/T | HBB | hsa-miR-644 |
| rs33993568 | 141900 | A/C/T | HBB | hsa-miR-1978 |
| rs33993568 | 141900 | A/C/T | HBB | hsa-miR-183 |
| rs33993568 | 141900 | A/C/T | HBB | hsa-miR-222* |
| rs33993568 | 141900 | A/C/T | HBB | hsa-miR-648 |
| rs33993568 | 141900 | A/C/T | HBB | hsa-miR-1271, hsa-miR-182, hsa-miR-96 |
| rs33993568 | 141900 | A/C/T | HBB | hsa-miR-16-1* |
| rs33995148 | 141900 | A/C/G/T | HBB | hsa-miR-24-1*, hsa-miR-24-2* |
| rs33995148 | 141900 | A/C/G/T | HBB | hsa-miR-412 |
| rs33995148 | 141900 | A/C/G/T | HBB | hsa-miR-596 |
| rs33995148 | 141900 | A/C/G/T | HBB | hsa-miR-500* |
| rs33995148 | 141900 | A/C/G/T | HBB | hsa-miR-205 |
| rs33996798 | 141800 | A/C/G | HBA2 | hsa-miR-642 |
| rs33996798 | 141800 | A/C/G | HBA2 | hsa-miR-431* |
| rs33996798 | 141800 | A/C/G | HBA2 | hsa-miR-593 |
| rs33996902 | 141800 | C/G/T | HBA2 | hsa-miR-1256 |
| rs33996902 | 141800 | C/G/T | HBA2 | hsa-miR-1234 |
| rs34011123 | 141800 | C/T | HBA1 | hsa-miR-615-5p |
| rs34011123 | 141800 | C/T | HBA1 | hsa-miR-1275 |
| rs34012042 | 191100 | A/G | TSC2 | hsa-miR-370 |
| rs34012042 | 191100 | A/G | TSC2 | hsa-miR-622 |
| rs34012042 | 191100 | A/G | TSC2 | hsa-miR-596 |
| rs34012042 | 191100 | A/G | TSC2 | hsa-miR-346 |
| rs34012042 | 191100 | A/G | TSC2 | hsa-miR-132, hsa-miR-212 |
| rs34012192 | 142000 | C/G | HBD | hsa-miR-1975 |
| rs34012192 | 142000 | C/G | HBD | hsa-miR-450a |
| rs34013622 | 141900 | A/G/T | HBB | hsa-miR-484 |
| rs34017450 | 142250 | A/C | HBG2 | hsa-miR-518b, hsa-miR-518a-3p, hsa-miR-518f, hsa-miR-518c, hsa-miR-518a-3p, hsa-miR-518d-3p |
| rs34017450 | 142250 | A/C | HBG2 | hsa-miR-626 |
| rs34017450 | 142250 | A/C | HBG2 | hsa-miR-320d, hsa-miR-320c, hsa-miR-320b, hsa-miR-320c, hsa-miR-320b, hsa-miR-320a |
| rs34018799 | 142250 | A/G/T | HBG1 | hsa-miR-412 |
| rs34018799 | 142250 | A/G/T | HBG1 | hsa-miR-181d, hsa-miR-181b, hsa-miR-181a, hsa-miR-181a, hsa-miR-181b, hsa-miR-181c |
| rs34018799 | 142250 | A/G/T | HBG1 | hsa-miR-205 |
| rs34019158 | 141850 | A/C/G | HBA2 | hsa-let-7i* |
| rs34019158 | 141850 | A/C/G | HBA2 | hsa-miR-1306 |
| rs34019507 | 142250 | C/G/T | HBG2 | hsa-miR-744* |
| rs34019507 | 142250 | C/G/T | HBG2 | hsa-miR-137 |
| rs34019507 | 142250 | C/G/T | HBG2 | hsa-miR-1248, hsa-miR-1237 |
| rs34019507 | 142250 | C/G/T | HBG2 | hsa-miR-578 |
| rs34022507 | 141900 | C/T | HBB | hsa-miR-873 |
| rs34022507 | 141900 | C/T | HBB | hsa-miR-558 |
| rs34022507 | 141900 | C/T | HBB | hsa-miR-708, hsa-miR-28-5p |
| rs34022507 | 141900 | C/T | HBB | hsa-miR-892a |
| rs34037627 | 141900 | A/T | HBB | hsa-miR-361-5p |
| rs34049764 | 0 | C/T | HBB | hsa-miR-1295 |
| rs34049764 | 0 | C/T | HBB | hsa-miR-15a* |
| rs34049890 | 142250 | C/G | HBG2 | hsa-miR-532-3p, hsa-miR-150 |
| rs34068598 | 141800 | C/G | HBA2 | hsa-miR-619 |
| rs34068598 | 141800 | C/G | HBA2 | hsa-miR-649, hsa-miR-490-3p |
| rs34083951 | 141900 | A/C/G | HBB | hsa-miR-148b, hsa-miR-152, hsa-miR-148a |
| rs34083951 | 141900 | A/C/G | HBB | hsa-miR-301b, hsa-miR-454, hsa-miR-301a, hsa-miR-130b, hsa-miR-130a |
| rs34083951 | 141900 | A/C/G | HBB | hsa-miR-143* |
| rs34083951 | 141900 | A/C/G | HBB | hsa-miR-513a-5p, hsa-miR-27b, hsa-miR-27a |
| rs34083951 | 141900 | A/C/G | HBB | hsa-miR-92b, hsa-miR-367, hsa-miR-363, hsa-miR-25, hsa-miR-32, hsa-miR-92a, hsa-miR-92a |
| rs34083951 | 141900 | A/C/G | HBB | hsa-miR-377 |
| rs34083951 | 141900 | A/C/G | HBB | hsa-miR-128 |
| rs34083951 | 141900 | A/C/G | HBB | hsa-miR-23b, hsa-miR-130a*, hsa-miR-23a |
| rs34083951 | 141900 | A/C/G | HBB | hsa-miR-509-3-5p, hsa-miR-509-5p, hsa-miR-509-5p, hsa-miR-217 |
| rs34083951 | 141900 | A/C/G | HBB | hsa-miR-1205, hsa-miR-1184, hsa-miR-17* |
| rs34090856 | 141800 | A/C | HBA2 | hsa-miR-1207-5p |
| rs34090856 | 141800 | A/C | HBA2 | hsa-miR-1286 |
| rs34095019 | 141900 | C/G | HBB | hsa-miR-1226 |
| rs34095019 | 141900 | C/G | HBB | hsa-miR-220b |
| rs34098449 | 141850 | A/C | HBA2 | hsa-miR-194* |
| rs34098449 | 141850 | A/C | HBA2 | hsa-miR-550*, hsa-miR-200c* |

TABLE 2-continued

| SNP | OMIM | MUTATION | GENE | MIR |
|---|---|---|---|---|
| rs34098449 | 141850 | A/C | HBA2 | hsa-miR-511 |
| rs34102339 | 141800 | A/C/G/T | HBA2 | hsa-miR-125b-1* |
| rs34102339 | 141800 | A/C/G/T | HBA2 | hsa-miR-500* |
| rs34102339 | 141800 | A/C/G/T | HBA2 | hsa-miR-23b*, hsa-miR-23a* |
| rs34127117 | 142200 | A/G | HBG1 | hsa-miR-1301 |
| rs34139813 | 141900 | C/G | — | hsa-miR-1207-5p |
| rs34139813 | 141900 | C/G | — | hsa-miR-604 |
| rs34139813 | 141900 | C/G | — | hsa-miR-885-3p |
| rs34139813 | 141900 | C/G | — | hsa-miR-596 |
| rs34139813 | 141900 | C/G | — | hsa-miR-484 |
| rs34149886 | 142000 | A/G | HBD | hsa-miR-1263, hsa-miR-150* |
| rs34149886 | 142000 | A/G | HBD | hsa-miR-95 |
| rs34150306 | 142250 | A/G | HBG2 | hsa-miR-636 |
| rs34150306 | 142250 | A/G | HBG2 | hsa-miR-125a-3p |
| rs34151786 | 141900 | A/C | HBB | hsa-miR-501-5p, hsa-miR-362-5p |
| rs34151786 | 141900 | A/C | HBB | hsa-miR-556-5p |
| rs34151786 | 141900 | A/C | HBB | hsa-miR-640 |
| rs34165323 | 141900 | A/G | HBB | hsa-miR-502-5p |
| rs34165323 | 141900 | A/G | HBB | hsa-miR-1915* |
| rs34165323 | 141900 | A/G | HBB | hsa-miR-578 |
| rs34173382 | 141900 | A/G | HBB | hsa-miR-1915 |
| rs34173382 | 141900 | A/G | HBB | hsa-miR-198 |
| rs34173382 | 141900 | A/G | HBB | hsa-miR-1974, hsa-miR-453 |
| rs34182019 | 141800 | A/G | HBA2 | hsa-miR-938 |
| rs34188626 | 141900 | C/G | — | hsa-miR-758 |
| rs34188626 | 141900 | C/G | — | hsa-miR-2113 |
| rs34204059 | 141800 | A/C | HBA2 | hsa-miR-1307 |
| rs34204059 | 141800 | A/C | HBA2 | hsa-miR-1908, hsa-miR-663 |
| rs34204059 | 141800 | A/C | HBA2 | hsa-miR-1469 |
| rs34204059 | 141800 | A/C | HBA2 | hsa-miR-744 |
| rs34220980 | 141850 | A/G | HBA2 | hsa-miR-220b |
| rs34227486 | 141900 | A/C/G | HBB | hsa-miR-942 |
| rs34227486 | 141900 | A/C/G | HBB | hsa-miR-573 |
| rs34227486 | 141900 | A/C/G | HBB | hsa-miR-183* |
| rs34227486 | 141900 | A/C/G | HBB | hsa-miR-148a* |
| rs34227486 | 141900 | A/C/G | HBB | hsa-miR-148b* |
| rs34240441 | 141900 | A/C/T | HBB | hsa-miR-1256 |
| rs34240441 | 141900 | A/C/T | HBB | hsa-miR-1268, hsa-miR-585 |
| rs34240441 | 141900 | A/C/T | HBB | hsa-miR-27a* |
| rs34259907 | 141800 | A/G | HBA2 | hsa-miR-942 |
| rs34259907 | 141800 | A/G | HBA2 | hsa-miR-578 |
| rs34263826 | 142250 | A/G | HBG1 | hsa-miR-1274b, hsa-miR-339-5p |
| rs34263826 | 142250 | A/G | HBG1 | hsa-miR-331-3p |
| rs34263826 | 142250 | A/G | HBG1 | hsa-miR-1914 |
| rs34264694 | 142250 | A/C | HBG2 | hsa-miR-1248, hsa-miR-1237 |
| rs34264694 | 142250 | A/C | HBG2 | hsa-miR-370 |
| rs34264694 | 142250 | A/C | HBG2 | hsa-miR-578 |
| rs34269448 | 141850 | A/C/G/T | HBA2 | hsa-miR-196b, hsa-miR-196a, hsa-miR-196a |
| rs34269448 | 141850 | A/C/G/T | HBA2 | hsa-miR-573 |
| rs34269448 | 141850 | A/C/G/T | HBA2 | hsa-miR-379 |
| rs34269448 | 141850 | A/C/G/T | HBA2 | hsa-miR-125a-3p |
| rs34269448 | 141850 | A/C/G/T | HBA2 | hsa-miR-563, hsa-miR-380* |
| rs34269448 | 141850 | A/C/G/T | HBA2 | hsa-miR-431* |
| rs34273731 | 141800 | G/T | HBA2 | hsa-miR-23b, hsa-miR-130a*, hsa-miR-23a |
| rs34273731 | 141800 | G/T | HBA2 | hsa-miR-342-3p |
| rs34289459 | 142000 | C/G | HBD | hsa-miR-1268, hsa-miR-585 |
| rs34305195 | 141900 | A/C | HBB | hsa-miR-411*, hsa-miR-379*, hsa-miR-380 |
| rs34305195 | 141900 | A/C | HBB | hsa-miR-522, hsa-miR-224* |
| rs34305195 | 141900 | A/C | HBB | hsa-miR-671-5p |
| rs34313675 | 142000 | A/T | HBD | hsa-miR-1256 |
| rs34313675 | 142000 | A/T | HBD | hsa-miR-27a* |
| rs34314652 | 141900 | C/G | HBB | hsa-miR-646, hsa-miR-503, hsa-miR-497, hsa-miR-424, hsa-miR-195, hsa-miR-15b, hsa-miR-16, hsa-miR-15a, hsa-miR-16 |
| rs34314652 | 141900 | C/G | HBB | hsa-miR-1226 |
| rs34314652 | 141900 | C/G | HBB | hsa-miR-1226 |
| rs34314652 | 141900 | C/G | HBB | hsa-miR-220b |
| rs34314652 | 141900 | C/G | HBB | hsa-miR-634 |
| rs34314652 | 141900 | C/G | HBB | hsa-miR-634 |
| rs34314652 | 141900 | C/G | HBB | hsa-miR-338-3p |
| rs34314652 | 141900 | C/G | HBB | hsa-miR-922, hsa-miR-214 |
| rs34324664 | 141800 | C/G | HBA2 | hsa-miR-675 |
| rs34362537 | 141900 | C/T | HBB | hsa-miR-28-3p |
| rs34362537 | 141900 | C/T | HBB | hsa-miR-1827 |
| rs34362537 | 141900 | C/T | HBB | hsa-miR-506, hsa-miR-124, hsa-miR-124, hsa-miR-124 |
| rs34362537 | 141900 | C/T | HBB | hsa-miR-877 |
| rs34378160 | 141900 | C/T | HBB | hsa-miR-186 |

TABLE 2-continued

| SNP | OMIM | MUTATION | GENE | MIR |
|---|---|---|---|---|
| rs34378160 | 141900 | C/T | HBB | hsa-miR-510, hsa-miR-512-5p, hsa-miR-512-5p |
| rs34378160 | 141900 | C/T | HBB | hsa-miR-548b-3p |
| rs34378160 | 141900 | C/T | HBB | hsa-miR-589, hsa-miR-146b-5p, hsa-miR-146a |
| rs34378160 | 141900 | C/T | HBB | hsa-miR-888 |
| rs34378160 | 141900 | C/T | HBB | hsa-miR-616*, hsa-miR-371-5p, hsa-miR-373* |
| rs34387455 | 141900 | A/G | HBB | hsa-miR-942 |
| rs34387455 | 141900 | A/G | HBB | hsa-miR-629* |
| rs34389944 | 142000 | A/G | HBD | hsa-miR-220b |
| rs34389944 | 142000 | A/G | HBD | hsa-miR-197 |
| rs34389944 | 142000 | A/G | HBD | hsa-miR-197 |
| rs34390965 | 142000 | G/T | HBD | hsa-miR-377 |
| rs34390965 | 142000 | G/T | HBD | hsa-miR-342-3p |
| rs34390965 | 142000 | G/T | HBD | hsa-miR-125a-5p, hsa-miR-125b, hsa-miR-125b |
| rs34390965 | 142000 | G/T | HBD | hsa-miR-10a, hsa-miR-10b |
| rs34404985 | 141900 | C/G | HBB | hsa-miR-220b |
| rs34404985 | 141900 | C/G | HBB | hsa-miR-197 |
| rs34407387 | 141900 | A/C | HBB | hsa-miR-1256 |
| rs34407387 | 141900 | A/C | HBB | hsa-miR-936, hsa-miR-199a-3p, hsa-miR-199b-3p, hsa-miR-199a-3p |
| rs34407387 | 141900 | A/C | HBB | hsa-miR-449b, hsa-miR-449a, hsa-miR-34c-5p, hsa-miR-34a |
| rs34410516 | 141800 | C/G | HBA2 | hsa-miR-133b, hsa-miR-133a, hsa-miR-133a |
| rs34410516 | 141800 | C/G | HBA2 | hsa-miR-431 |
| rs34420481 | 142000 | A/T | HBD | hsa-miR-103, hsa-miR-107 |
| rs34427034 | 142200 | A/G | HBG1 | hsa-miR-758 |
| rs34427034 | 142200 | A/G | HBG1 | hsa-miR-2113 |
| rs34430836 | 142000 | C/G | HBD | hsa-miR-575 |
| rs34430836 | 142000 | C/G | HBD | hsa-miR-449b* |
| rs34430836 | 142000 | C/G | HBD | hsa-miR-122* |
| rs34430836 | 142000 | C/G | HBD | hsa-miR-1972 |
| rs34430836 | 142000 | C/G | HBD | hsa-miR-15a* |
| rs34435255 | 142200 | A/G | HBG1 | hsa-miR-136* |
| rs34435255 | 142200 | A/G | HBG1 | hsa-miR-1298 |
| rs34438981 | 142250 | C/T | HBG1 | hsa-miR-1975 |
| rs34438981 | 142250 | C/T | HBG1 | hsa-miR-220c |
| rs34439278 | 141900 | A/G | HBB | hsa-miR-1974, hsa-miR-453 |
| rs34440919 | 141800 | C/G | HBA2 | hsa-miR-635 |
| rs34440919 | 141800 | C/G | HBA2 | hsa-miR-1306 |
| rs34446260 | 141900 | C/G/T | HBB | hsa-miR-412 |
| rs34446260 | 141900 | C/G/T | HBB | hsa-miR-1179 |
| rs34446260 | 141900 | C/G/T | HBB | hsa-miR-205 |
| rs34460332 | 142000 | A/G | HBD | hsa-miR-181c* |
| rs34460332 | 142000 | A/G | HBD | hsa-miR-220b |
| rs34462388 | 141800 | C/G | HBA2 | hsa-miR-431 |
| rs34472107 | 141800 | C/T | HBA2 | hsa-miR-149* |
| rs34472107 | 141800 | C/T | HBA2 | hsa-miR-939 |
| rs34472107 | 141800 | C/T | HBA2 | hsa-miR-1908, hsa-miR-663 |
| rs34472107 | 141800 | C/T | HBA2 | hsa-miR-658 |
| rs34472107 | 141800 | C/T | HBA2 | hsa-miR-25* |
| rs34472107 | 141800 | C/T | HBA2 | hsa-miR-744 |
| rs34472107 | 141800 | C/T | HBA2 | hsa-miR-542-5p |
| rs34472107 | 141800 | C/T | HBA2 | hsa-miR-185 |
| rs34474104 | 142250 | C/T | HBG2 | hsa-miR-532-5p |
| rs34474104 | 142250 | C/T | HBG2 | hsa-miR-550 |
| rs34474104 | 142250 | C/T | HBG2 | hsa-miR-455-5p |
| rs34484056 | 141900 | A/T | HBB | hsa-miR-338-3p |
| rs34484056 | 141900 | A/T | HBB | hsa-miR-513a-5p, hsa-miR-27b, hsa-miR-27a |
| rs34484056 | 141900 | A/T | HBB | hsa-miR-342-3p |
| rs34489183 | 142000 | C/G | HBD | hsa-miR-185 |
| rs34492931 | 141800 | A/G | HBA2 | hsa-miR-431 |
| rs34501593 | 142250 | A/G | HBG1 | hsa-miR-629* |
| rs34501593 | 142250 | A/G | HBG1 | hsa-miR-375 |
| rs34504387 | 141800 | C/G | HBA2 | hsa-miR-492 |
| rs34515413 | 141900 | A/C/G | HBB | hsa-miR-517b |
| rs34515413 | 141900 | A/C/G | HBB | hsa-miR-143* |
| rs34515413 | 141900 | A/C/G | HBB | hsa-miR-1205, hsa-miR-1184, hsa-miR-17* |
| rs34532478 | 142250 | A/G | HBG1 | hsa-miR-331-3p |
| rs34532478 | 142250 | A/G | HBG1 | hsa-miR-518c*, hsa-miR-330-5p, hsa-miR-326 |
| rs34563000 | 0 | A/G | HBB | hsa-miR-220b |
| rs34571024 | 141900 | A/C | HBB | hsa-miR-637 |
| rs34574239 | 141800 | A/C | HBA2 | hsa-miR-1285, hsa-miR-612 |
| rs34579351 | 141900 | A/G | — | hsa-miR-513a-5p, hsa-miR-27b, hsa-miR-27a |
| rs34586189 | 141800 | A/G | HBA2 | hsa-miR-1306 |
| rs34621955 | 141900 | C/G/T | HBB | hsa-miR-1977 |
| rs34621955 | 141900 | C/G/T | HBB | hsa-miR-1258 |
| rs34621955 | 141900 | C/G/T | HBB | hsa-miR-23b, hsa-miR-130a*, hsa-miR-23a |
| rs34621955 | 141900 | C/G/T | HBB | hsa-miR-323-3p |
| rs34647752 | 142200 | A/G | HBG1 | hsa-miR-129-5p |

TABLE 2-continued

| SNP | OMIM | MUTATION | GENE | MIR |
|---|---|---|---|---|
| rs34647752 | 142200 | A/G | HBG1 | hsa-miR-590-3p |
| rs34665886 | 141900 | C/G | HBB | hsa-miR-143* |
| rs34665886 | 141900 | C/G | HBB | hsa-miR-1301 |
| rs34665886 | 141900 | C/G | HBB | hsa-miR-500* |
| rs34684963 | 141800 | C/T | HBA2 | hsa-miR-485-5p |
| rs34684963 | 141800 | C/T | HBA2 | hsa-miR-100* |
| rs34703519 | 142250 | A/C | HBG2 | hsa-miR-578 |
| rs34708054 | 141850 | C/G/T | HBA2 | hsa-miR-933 |
| rs34708054 | 141850 | C/G/T | HBA2 | hsa-miR-937 |
| rs34713708 | 141800 | A/G | HBA2 | hsa-miR-650 |
| rs34713708 | 141800 | A/G | HBA2 | hsa-miR-1908, hsa-miR-663 |
| rs34713708 | 141800 | A/G | HBA2 | hsa-miR-541, hsa-miR-654-5p, hsa-miR-92a-2* |
| rs34713708 | 141800 | A/G | HBA2 | hsa-miR-1228* |
| rs34718174 | 141900 | A/G | HBB | hsa-miR-593* |
| rs34718174 | 141900 | A/G | HBB | hsa-miR-615-3p |
| rs34743882 | 141900 | A/G | HBB | hsa-miR-188-5p |
| rs34743882 | 141900 | A/G | HBB | hsa-miR-186* |
| rs34751764 | 141800 | C/G | HBA2 | hsa-miR-425* |
| rs34751764 | 141800 | C/G | HBA2 | hsa-miR-149* |
| rs34751764 | 141800 | C/G | HBA2 | hsa-miR-1207-5p |
| rs34751764 | 141800 | C/G | HBA2 | hsa-miR-1286 |
| rs34751764 | 141800 | C/G | HBA2 | hsa-miR-765 |
| rs34769005 | 141900 | C/G | HBB | hsa-miR-1289 |
| rs34769005 | 141900 | C/G | HBB | hsa-miR-1266 |
| rs34802738 | 142000 | C/T | HBD | hsa-miR-220b |
| rs34806456 | 141800 | A/G | HBA2 | hsa-miR-573 |
| rs34807671 | 142250 | C/T | HBG2 | hsa-miR-936, hsa-miR-199a-3p, hsa-miR-199b-3p, hsa-miR-199a-3p |
| rs34807671 | 142250 | C/T | HBG2 | hsa-miR-222* |
| rs34807671 | 142250 | C/T | HBG2 | hsa-miR-140-5p |
| rs34807671 | 142250 | C/T | HBG2 | hsa-miR-194* |
| rs34807671 | 142250 | C/T | HBG2 | hsa-miR-1244 |
| rs34817956 | 141850 | A/G | HBA2 | hsa-miR-431 |
| rs34823698 | 141800 | A/G | HBA2 | hsa-miR-133b, hsa-miR-133a, hsa-miR-133a |
| rs34823698 | 141800 | A/G | HBA2 | hsa-miR-1306 |
| rs34830032 | 141800 | C/G | HBA2 | hsa-miR-541, hsa-miR-654-5p, hsa-miR-92a-2* |
| rs34830032 | 141800 | C/G | HBA2 | hsa-miR-1469 |
| rs34830032 | 141800 | C/G | HBA2 | hsa-miR-1228* |
| rs34830032 | 141800 | C/G | HBA2 | hsa-miR-431* |
| rs34831026 | 141900 | A/G | HBB | hsa-miR-518c*, hsa-miR-330-5p, hsa-miR-326 |
| rs34849179 | 141800 | A/C | HBA1 | hsa-miR-299-3p |
| rs34849179 | 141800 | A/C | HBA1 | hsa-miR-567 |
| rs34863047 | 141800 | A/G | HBA2 | hsa-miR-663b |
| rs34863047 | 141800 | A/G | HBA2 | hsa-miR-1228* |
| rs34863047 | 141800 | A/G | HBA2 | hsa-miR-1293, hsa-miR-363* |
| rs34863047 | 141800 | A/G | HBA2 | hsa-miR-588 |
| rs34863047 | 141800 | A/G | HBA2 | hsa-miR-1262 |
| rs34868036 | 141800 | C/T | HBA2 | hsa-miR-330-3p |
| rs34868036 | 141800 | C/T | HBA2 | hsa-miR-186* |
| rs34868036 | 141800 | C/T | HBA2 | hsa-miR-320d, hsa-miR-320c, hsa-miR-320b, hsa-miR-320c, hsa-miR-320b, hsa-miR-320a |
| rs34868397 | 141900 | C/G | HBB | hsa-miR-330-3p |
| rs34870172 | 141900 | G/T | HBB | hsa-miR-198 |
| rs34870172 | 141900 | G/T | HBB | hsa-miR-125a-3p |
| rs34870424 | 191100 | A/G | TSC2 | hsa-miR-1249 |
| rs34870424 | 191100 | A/G | TSC2 | hsa-miR-146b-3p |
| rs34870424 | 191100 | A/G | TSC2 | hsa-miR-566 |
| rs34876238 | 142250 | A/G | HBG2 | hsa-miR-22* |
| rs34876238 | 142250 | A/G | HBG2 | hsa-miR-1266 |
| rs34876238 | 142250 | A/G | HBG2 | hsa-miR-651 |
| rs34878913 | 142250 | C/T | HBG1 | hsa-miR-186 |
| rs34878913 | 142250 | C/T | HBG1 | hsa-miR-548b-3p |
| rs34878913 | 142250 | C/T | HBG1 | hsa-miR-492 |
| rs34879587 | 141800 | A/C | HBA2 | hsa-miR-25* |
| rs34879587 | 141800 | A/C | HBA2 | hsa-miR-431* |
| rs34890875 | 141800 | A/T | HBA2 | hsa-miR-431 |
| rs34890875 | 141800 | A/T | HBA2 | hsa-miR-890 |
| rs34907654 | 142250 | C/G | HBG1 | hsa-miR-1975 |
| rs34915311 | 142250 | G/T | HBG2 | hsa-miR-1322, hsa-miR-1272 |
| rs34915311 | 142250 | G/T | HBG2 | hsa-miR-331-3p |
| rs34915311 | 142250 | G/T | HBG2 | hsa-miR-125a-5p, hsa-miR-125b, hsa-miR-125b |
| rs34933313 | 142000 | C/G | HBD | hsa-miR-510, hsa-miR-512-5p, hsa-miR-512-5p |
| rs34933313 | 142000 | C/G | HBD | hsa-miR-1207-3p |
| rs34933455 | 141900 | C/G | HBB | hsa-miR-485-5p |
| rs34933455 | 141900 | C/G | HBB | hsa-miR-556-5p |
| rs34933455 | 141900 | C/G | HBB | hsa-miR-205 |
| rs34933751 | 141900 | A/C/G | HBB | hsa-miR-29c, hsa-miR-29b, hsa-miR-29b, hsa-miR-29a |

TABLE 2-continued

| SNP | OMIM | MUTATION | GENE | MIR |
|---|---|---|---|---|
| rs34933751 | 141900 | A/C/G | HBB | hsa-miR-1915* |
| rs34936612 | 141800 | C/G | HBA2 | hsa-miR-25* |
| rs34945623 | 141900 | C/G | HBB | hsa-miR-885-3p |
| rs34945623 | 141900 | C/G | HBB | hsa-miR-338-3p |
| rs34945623 | 141900 | C/G | HBB | hsa-miR-486-3p |
| rs34945623 | 141900 | C/G | HBB | hsa-miR-103, hsa-miR-107 |
| rs34974709 | 141900 | A/T | HBB | hsa-miR-412 |
| rs34974709 | 141900 | A/T | HBB | hsa-miR-205 |
| rs34975911 | 142000 | C/T | HBD | hsa-miR-577 |
| rs34975911 | 142000 | C/T | HBD | hsa-miR-556-5p |
| rs34977235 | 142000 | A/T | HBD | hsa-miR-589* |
| rs34980264 | 141900 | A/G | HBB | hsa-miR-1256 |
| rs34988734 | 141800 | C/T | — | hsa-miR-933 |
| rs34988734 | 141800 | C/T | — | hsa-miR-147b, hsa-miR-210 |
| rs34988734 | 141800 | C/T | — | hsa-miR-581 |
| rs34988734 | 141800 | C/T | — | hsa-miR-643 |
| rs34991152 | 142000 | C/T | HBD | hsa-miR-500* |
| rs34991152 | 142000 | C/T | HBD | hsa-miR-767-5p |
| rs34991152 | 142000 | C/T | HBD | hsa-miR-501-3p, hsa-miR-502-3p |
| rs34997902 | 142250 | A/C | HBG2 | hsa-miR-1909 |
| rs34997902 | 142250 | A/C | HBG2 | hsa-miR-1266 |
| rs35002698 | 141900 | C/G/T | HBB | hsa-miR-668 |
| rs35002698 | 141900 | C/G/T | HBB | hsa-miR-1301 |
| rs35002698 | 141900 | C/G/T | HBB | hsa-miR-657 |
| rs35002698 | 141900 | C/G/T | HBB | hsa-miR-34c-3p |
| rs35017910 | 141900 | C/G | — | hsa-miR-665 |
| rs35017910 | 141900 | C/G | — | hsa-miR-1915 |
| rs35017910 | 141900 | C/G | — | hsa-let-7i* |
| rs35017910 | 141900 | C/G | — | hsa-miR-1286 |
| rs35020253 | 142250 | C/T | HBG2 | hsa-miR-143 |
| rs35020253 | 142250 | C/T | HBG2 | hsa-miR-522, hsa-miR-224* |
| rs35020585 | 141900 | C/G/T | HBB | hsa-miR-581 |
| rs35059618 | 141800 | A/T | HBA2 | hsa-miR-194* |
| rs35059618 | 141800 | A/T | HBA2 | hsa-miR-449b, hsa-miR-449a, hsa-miR-34c-5p, hsa-miR-34a |
| rs35059618 | 141800 | A/T | HBA2 | hsa-miR-940, hsa-miR-34b* |
| rs35059618 | 141800 | A/T | HBA2 | hsa-miR-484 |
| rs35067717 | 141900 | C/G | HBB | hsa-miR-1297, hsa-miR-26a, hsa-miR-26a, hsa-miR-26b |
| rs35067717 | 141900 | C/G | HBB | hsa-miR-573 |
| rs35067717 | 141900 | C/G | HBB | hsa-miR-125a-5p, hsa-miR-125b, hsa-miR-125b |
| rs35067717 | 141900 | C/G | HBB | hsa-miR-10a, hsa-miR-10b |
| rs35077384 | 610244 | A/C | ZFYVE27 | hsa-miR-513a-5p, hsa-miR-27b, hsa-miR-27a |
| rs35077384 | 610244 | A/C | ZFYVE27 | hsa-miR-1285, hsa-miR-612 |
| rs35094013 | 141900 | A/T | HBB | hsa-miR-938 |
| rs35094013 | 141900 | A/T | HBB | hsa-miR-302c* |
| rs35094013 | 141900 | A/T | HBB | hsa-miR-874 |
| rs35103459 | 142250 | C/T | HBG2 | hsa-miR-148b, hsa-miR-152, hsa-miR-148a |
| rs35103459 | 142250 | C/T | HBG2 | hsa-miR-101, hsa-miR-144 |
| rs35103459 | 142250 | C/T | HBG2 | hsa-miR-301b, hsa-miR-454, hsa-miR-301a, hsa-miR-130b, hsa-miR-130a |
| rs35103459 | 142250 | C/T | HBG2 | hsa-miR-143* |
| rs35103459 | 142250 | C/T | HBG2 | hsa-miR-582-5p |
| rs35117167 | 141900 | A/G | — | hsa-miR-1245 |
| rs35117167 | 141900 | A/G | — | hsa-miR-542-3p |
| rs35118875 | 191100 | C/T | TSC2 | hsa-miR-1975 |
| rs35118875 | 191100 | C/T | TSC2 | hsa-miR-1243 |
| rs35118875 | 191100 | C/T | TSC2 | hsa-miR-1287 |
| rs35118875 | 191100 | C/T | TSC2 | hsa-miR-181a-2* |
| rs35140348 | 141900 | A/T | HBB | hsa-miR-802 |
| rs35140348 | 141900 | A/T | HBB | hsa-miR-545* |
| rs35140348 | 141900 | A/T | HBB | hsa-miR-337-5p |
| rs35140348 | 141900 | A/T | HBB | hsa-miR-16-1* |
| rs35152987 | 142000 | G/T | HBD | hsa-miR-365* |
| rs35166721 | 142000 | A/G | HBD | hsa-miR-302a* |
| rs35166721 | 142000 | A/G | HBD | hsa-miR-888 |
| rs35166721 | 142000 | A/G | HBD | hsa-miR-616*, hsa-miR-371-5p, hsa-miR-373* |
| rs35166834 | 141800 | G/T | HBA1 | hsa-miR-532-3p, hsa-miR-150 |
| rs35166834 | 141800 | G/T | HBA1 | hsa-miR-1178 |
| rs35166834 | 141800 | G/T | HBA1 | hsa-miR-513a-5p, hsa-miR-27b, hsa-miR-27a |
| rs35166834 | 141800 | G/T | HBA1 | hsa-miR-342-3p |
| rs35187567 | 141800 | A/G | HBA2 | hsa-miR-500* |
| rs35198910 | 141900 | C/G | HBB | hsa-miR-942 |
| rs35198910 | 141900 | C/G | HBB | hsa-miR-617 |
| rs35198910 | 141900 | C/G | HBB | hsa-miR-148b* |
| rs35198910 | 141900 | C/G | HBB | hsa-let-7c* |
| rs35203445 | 141800 | G/T | HBA2 | hsa-miR-1197 |
| rs35203445 | 141800 | G/T | HBA2 | hsa-miR-873 |

TABLE 2-continued

| SNP | OMIM | MUTATION | GENE | MIR |
|---|---|---|---|---|
| rs35203747 | 141900 | A/C | HBB | hsa-miR-223 |
| rs35203747 | 141900 | A/C | HBB | hsa-miR-222* |
| rs35203747 | 141900 | A/C | HBB | hsa-miR-449b, hsa-miR-449a, hsa-miR-34c-5p, hsa-miR-34a |
| rs35203747 | 141900 | A/C | HBB | hsa-miR-552 |
| rs35204496 | 141900 | A/T | HBB | hsa-miR-103, hsa-miR-107 |
| rs35209591 | 141900 | C/G/T | HBB | hsa-miR-101* |
| rs35209591 | 141900 | C/G/T | HBB | hsa-miR-382 |
| rs35209591 | 141900 | C/G/T | HBB | hsa-miR-374a* |
| rs35209591 | 141900 | C/G/T | HBB | hsa-miR-148a* |
| rs35209591 | 141900 | C/G/T | HBB | hsa-miR-148b* |
| rs35209591 | 141900 | C/G/T | HBB | hsa-miR-361-5p |
| rs35209591 | 141900 | C/G/T | HBB | hsa-miR-1266 |
| rs35209776 | 141900 | A/G/T | HBB | hsa-miR-1285, hsa-miR-612 |
| rs35209776 | 141900 | A/G/T | HBB | hsa-miR-520b, hsa-miR-302e, hsa-miR-519a, hsa-miR-519a, hsa-miR-520c-3p, hsa-miR-520d-3p, hsa-miR-520e, hsa-miR-519c-3p, hsa-miR-520a-3p, hsa-miR-519b-3p, hsa-miR-302c, hsa-miR-302d, hsa-miR-372, hsa-miR-373, hsa-miR-302b, hsa-miR-302a |
| rs35209776 | 141900 | A/G/T | HBB | hsa-miR-512-3p, hsa-miR-520f |
| rs35209776 | 141900 | A/G/T | HBB | hsa-miR-1245 |
| rs35209776 | 141900 | A/G/T | HBB | hsa-miR-595 |
| rs35210126 | 141800 | A/C/T | HBA2 | hsa-miR-591 |
| rs35210126 | 141800 | A/C/T | HBA2 | hsa-miR-126 |
| rs35213748 | 141800 | C/T | HBA2 | hsa-miR-1291 |
| rs35213748 | 141800 | C/T | HBA2 | hsa-miR-129-3p, hsa-miR-129* |
| rs35213748 | 141800 | C/T | HBA2 | hsa-miR-663b |
| rs35213748 | 141800 | C/T | HBA2 | hsa-miR-328 |
| rs35213748 | 141800 | C/T | HBA2 | hsa-miR-132* |
| rs35213748 | 141800 | C/T | HBA2 | hsa-miR-1204 |
| rs35239527 | 141800 | G/T | HBA2 | hsa-miR-933 |
| rs35239527 | 141800 | G/T | HBA2 | hsa-miR-517b |
| rs35239527 | 141800 | G/T | HBA2 | hsa-miR-301b, hsa-miR-454, hsa-miR-301a, hsa-miR-130b, hsa-miR-130a |
| rs35239527 | 141800 | G/T | HBA2 | hsa-miR-1909* |
| rs35252931 | 141800 | C/G | HBA2 | hsa-miR-938 |
| rs35252931 | 141800 | C/G | HBA2 | hsa-miR-1291 |
| rs35252931 | 141800 | C/G | HBA2 | hsa-miR-663b |
| rs35252931 | 141800 | C/G | HBA2 | hsa-miR-328 |
| rs35256489 | 141900 | C/T | HBB | hsa-miR-634 |
| rs35256489 | 141900 | C/T | HBB | hsa-miR-338-3p |
| rs35256489 | 141900 | C/T | HBB | hsa-miR-564 |
| rs35262412 | 141900 | A/C | HBB | hsa-miR-888 |
| rs35262412 | 141900 | A/C | HBB | hsa-miR-616*, hsa-miR-371-5p, hsa-miR-373* |
| rs35264875 | 612267 | A/T | TPCN2 | hsa-miR-508-5p |
| rs35264875 | 612267 | A/T | TPCN2 | hsa-miR-891b |
| rs35264875 | 612267 | A/T | TPCN2 | hsa-miR-545 |
| rs35264875 | 612267 | A/T | TPCN2 | hsa-miR-515-5p, hsa-miR-519e* |
| rs35278874 | 141900 | A/C/G | HBB | hsa-miR-296-3p |
| rs35282988 | 191100 | C/T | TSC2 | hsa-miR-518b, hsa-miR-518a-3p, hsa-miR-518f, hsa-miR-518c, hsa-miR-518a-3p, hsa-miR-518d-3p |
| rs35286210 | 141900 | C/G | HBB | hsa-miR-1207-5p |
| rs35286210 | 141900 | C/G | HBB | hsa-miR-575 |
| rs35286210 | 141900 | C/G | HBB | hsa-miR-1827 |
| rs35286210 | 141900 | C/G | HBB | hsa-miR-940, hsa-miR-34b* |
| rs35286210 | 141900 | C/G | HBB | hsa-miR-1294 |
| rs35291591 | 141900 | A/T | HBB | hsa-miR-1245 |
| rs35291591 | 141900 | A/T | HBB | hsa-miR-921 |
| rs35303218 | 141900 | A/G | HBB | hsa-miR-186* |
| rs35303218 | 141900 | A/G | HBB | hsa-miR-616*, hsa-miR-371-5p, hsa-miR-373* |
| rs35315638 | 142200 | G/T | HBG1 | hsa-miR-888* |
| rs35315638 | 142200 | G/T | HBG1 | hsa-miR-203 |
| rs35317336 | 141800 | C/G | HBA2 | hsa-miR-1307 |
| rs35317336 | 141800 | C/G | HBA2 | hsa-miR-1285, hsa-miR-612 |
| rs35317336 | 141800 | C/G | HBA2 | hsa-miR-619 |
| rs35317336 | 141800 | C/G | HBA2 | hsa-miR-649, hsa-miR-490-3p |
| rs35329201 | 141800 | A/G | HBA2 | hsa-miR-885-3p |
| rs35329201 | 141800 | A/G | HBA2 | hsa-miR-194* |
| rs35329201 | 141800 | A/G | HBA2 | hsa-miR-449b, hsa-miR-449a, hsa-miR-34c-5p, hsa-miR-34a |
| rs35351128 | 141900 | A/C | HBB | hsa-miR-510, hsa-miR-512-5p, hsa-miR-512-5p |
| rs35353749 | 141900 | A/C | HBB | hsa-miR-588 |
| rs35353749 | 141900 | A/C | HBB | hsa-miR-578 |
| rs35395083 | 142000 | A/C | HBD | hsa-miR-20a* |
| rs35395083 | 142000 | A/C | HBD | hsa-miR-509-3-5p, hsa-miR-509-5p, hsa-miR-509-5p, hsa-miR-217 |

TABLE 2-continued

| SNP | OMIM | MUTATION | GENE | MIR |
|---|---|---|---|---|
| rs35395083 | 142000 | A/C | HBD | hsa-miR-324-5p |
| rs35424040 | 141900 | A/G/T | HBB | hsa-miR-365* |
| rs35424040 | 141900 | A/G/T | HBB | hsa-miR-1229 |
| rs35424040 | 141900 | A/G/T | HBB | hsa-miR-1182 |
| rs35424040 | 141900 | A/G/T | HBB | hsa-miR-193a-5p |
| rs35431217 | 141800 | A/C | HBA2 | hsa-miR-187 |
| rs35433207 | 142000 | A/G | HBD | hsa-miR-521 |
| rs35433207 | 142000 | A/G | HBD | hsa-miR-500* |
| rs35433207 | 142000 | A/G | HBD | hsa-miR-501-3p, hsa-miR-502-3p |
| rs35461710 | 141900 | C/T | HBB | hsa-miR-491-5p |
| rs35461710 | 141900 | C/T | HBB | hsa-miR-541, hsa-miR-654-5p, hsa-miR-92a-2* |
| rs35461710 | 141900 | C/T | HBB | hsa-miR-608, hsa-miR-342-5p |
| rs35461710 | 141900 | C/T | HBB | hsa-miR-1294 |
| rs35474880 | 141900 | A/G | HBB | hsa-miR-220b |
| rs35474880 | 141900 | A/G | HBB | hsa-miR-197 |
| rs35474880 | 141900 | A/G | HBB | hsa-miR-197 |
| rs35477770 | 141850 | A/C/T | HBA2 | hsa-miR-1228, hsa-miR-220a |
| rs35477770 | 141850 | A/C/T | HBA2 | hsa-miR-197 |
| rs35477770 | 141850 | A/C/T | HBA2 | hsa-miR-767-5p |
| rs35481866 | 142250 | A/G | HBG2 | hsa-miR-1248, hsa-miR-1237 |
| rs35481866 | 142250 | A/G | HBG2 | hsa-miR-877* |
| rs35481866 | 142250 | A/G | HBG2 | hsa-miR-578 |
| rs35485099 | 141900 | A/C | HBB | hsa-miR-198 |
| rs35492035 | 141900 | C/G | HBB | hsa-miR-634 |
| rs35492035 | 141900 | C/G | HBB | hsa-miR-449b* |
| rs35492035 | 141900 | C/G | HBB | hsa-miR-593* |
| rs35492035 | 141900 | C/G | HBB | hsa-miR-1911* |
| rs35492035 | 141900 | C/G | HBB | hsa-miR-767-5p |
| rs35511459 | 141800 | G/T | HBA2 | hsa-miR-92b* |
| rs35511459 | 141800 | G/T | HBA2 | hsa-miR-562 |
| rs35511459 | 141800 | G/T | HBA2 | hsa-miR-1277 |
| rs35518301 | 142000 | A/G | HBD | hsa-miR-491-3p |
| rs35521813 | 142250 | A/C/G | HBG1 | hsa-miR-1254, hsa-miR-661 |
| rs35521813 | 142250 | A/C/G | HBG1 | hsa-miR-596 |
| rs35534817 | 191100 | A/G | TSC2 | hsa-miR-181c* |
| rs35534817 | 191100 | A/G | TSC2 | hsa-miR-593* |
| rs35534817 | 191100 | A/G | TSC2 | hsa-miR-767-5p |
| rs35548338 | 141800 | G/T | HBA2 | hsa-miR-517b |
| rs35548338 | 141800 | G/T | HBA2 | hsa-miR-143* |
| rs35548338 | 141800 | G/T | HBA2 | hsa-miR-657 |
| rs35548338 | 141800 | G/T | HBA2 | hsa-miR-431* |
| rs35615982 | 141800 | A/C | HBA2 | hsa-miR-502-5p |
| rs35615982 | 141800 | A/C | HBA2 | hsa-miR-1234 |
| rs35621390 | 142250 | C/G/T | HBG1 | hsa-miR-23b, hsa-miR-130a*, hsa-miR-23a |
| rs35621390 | 142250 | C/G/T | HBG1 | hsa-miR-1915* |
| rs35628685 | 141800 | A/C | HBA2 | hsa-miR-933 |
| rs35654328 | 142250 | A/G | HBG1 | hsa-miR-629* |
| rs35654328 | 142250 | A/G | HBG1 | hsa-miR-1238 |
| rs35654345 | 141850 | A/G/T | HBA2 | hsa-miR-149* |
| rs35654345 | 141850 | A/G/T | HBA2 | hsa-miR-939 |
| rs35654345 | 141850 | A/G/T | HBA2 | hsa-miR-876-3p, hsa-miR-323-5p |
| rs35654345 | 141850 | A/G/T | HBA2 | hsa-miR-1293, hsa-miR-363* |
| rs35654345 | 141850 | A/G/T | HBA2 | hsa-miR-608, hsa-miR-342-5p |
| rs35654345 | 141850 | A/G/T | HBA2 | hsa-miR-542-5p |
| rs35654785 | 142000 | C/G | HBD | hsa-miR-1913, hsa-miR-324-3p, hsa-miR-18a* |
| rs35654785 | 142000 | C/G | HBD | hsa-miR-649, hsa-miR-490-3p |
| rs35658323 | 141900 | C/G | — | hsa-miR-140-5p |
| rs35658323 | 141900 | C/G | — | hsa-miR-194* |
| rs35658323 | 141900 | C/G | — | hsa-miR-1205, hsa-miR-1184, hsa-miR-17* |
| rs35660529 | 191100 | A/G | TSC2 | hsa-miR-525-3p, hsa-miR-524-3p |
| rs35660529 | 191100 | A/G | TSC2 | hsa-miR-493 |
| rs35660529 | 191100 | A/G | TSC2 | hsa-miR-876-3p, hsa-miR-323-5p |
| rs35660529 | 191100 | A/G | TSC2 | hsa-miR-18b, hsa-miR-18a |
| rs35661168 | 142000 | A/T | HBD | hsa-miR-577 |
| rs35666685 | 142000 | A/C | HBD | hsa-miR-296-3p |
| rs35669628 | 141900 | A/C | HBB | hsa-miR-1226 |
| rs35669628 | 141900 | A/C | HBB | hsa-miR-181c* |
| rs35669628 | 141900 | A/C | HBB | hsa-miR-634 |
| rs35669628 | 141900 | A/C | HBB | hsa-miR-449b* |
| rs35685286 | 141900 | A/G | HBB | hsa-miR-1913, hsa-miR-324-3p, hsa-miR-18a* |
| rs35685286 | 141900 | A/G | HBB | hsa-miR-1915 |
| rs35685286 | 141900 | A/G | HBB | hsa-miR-198 |
| rs35687396 | 142250 | A/G | HBG1 | hsa-miR-942 |
| rs35687396 | 142250 | A/G | HBG1 | hsa-miR-629* |
| rs35687396 | 142250 | A/G | HBG1 | hsa-miR-629* |
| rs35687396 | 142250 | A/G | HBG1 | hsa-miR-515-5p, hsa-miR-519e* |
| rs35687532 | 141800 | C/G | HBA2 | hsa-miR-520b, hsa-miR-302e, hsa-miR-519a, hsa-miR-519a, hsa-miR-520c-3p, hsa-miR-520d-3p, hsa- |

TABLE 2-continued

| SNP | OMIM | MUTATION | GENE | MIR |
|---|---|---|---|---|
| | | | | miR-520e, hsa-miR-519c-3p, hsa-miR-520a-3p, hsa-miR-519b-3p, hsa-miR-302c, hsa-miR-302d, hsa-miR-372, hsa-miR-373, hsa-miR-302b, hsa-miR-302a |
| rs35693898 | 141900 | C/T | HBB | hsa-miR-18b, hsa-miR-18a |
| rs35693898 | 141900 | C/T | HBB | hsa-miR-548m |
| rs35700518 | 142200 | G/T | HBG1 | hsa-miR-1274a |
| rs35700518 | 142200 | G/T | HBG1 | hsa-miR-1308 |
| rs35723200 | 141800 | C/T | HBA1 | hsa-miR-1978 |
| rs35746147 | 142200 | A/C | HBG1 | hsa-miR-183 |
| rs35747961 | 141900 | C/G/T | HBB | hsa-miR-744* |
| rs35747961 | 141900 | C/G/T | HBB | hsa-miR-137 |
| rs35747961 | 141900 | C/G/T | HBB | hsa-miR-578 |
| rs35776155 | 141850 | C/G/T | HBA2 | hsa-miR-675 |
| rs35776155 | 141850 | C/G/T | HBA2 | hsa-miR-2110 |
| rs35776155 | 141850 | C/G/T | HBA2 | hsa-miR-491-5p |
| rs35776155 | 141850 | C/G/T | HBA2 | hsa-miR-541, hsa-miR-654-5p, hsa-miR-92a-2* |
| rs35776155 | 141850 | C/G/T | HBA2 | hsa-miR-1224-5p |
| rs35776155 | 141850 | C/G/T | HBA2 | hsa-miR-1294 |
| rs35790721 | 142000 | A/T | HBD | hsa-miR-502-5p |
| rs35790721 | 142000 | A/T | HBD | hsa-miR-183* |
| rs35790721 | 142000 | A/T | HBD | hsa-miR-875-5p |
| rs35802118 | 141900 | A/G | HBB | hsa-miR-1915* |
| rs35802118 | 141900 | A/G | HBB | hsa-miR-1206 |
| rs35802118 | 141900 | A/G | HBB | hsa-miR-452* |
| rs35812514 | 142250 | A/G | HBG2 | hsa-miR-513a-5p, hsa-miR-27b, hsa-miR-27a |
| rs35812514 | 142250 | A/G | HBG2 | hsa-miR-128 |
| rs35812514 | 142250 | A/G | HBG2 | hsa-miR-582-5p |
| rs35816645 | 141800 | C/G | HBA2 | hsa-miR-1915 |
| rs35816645 | 141800 | C/G | HBA2 | hsa-miR-122* |
| rs35819837 | 141900 | A/C | HBB | hsa-miR-592 |
| rs35819837 | 141900 | A/C | HBB | hsa-miR-644 |
| rs35819837 | 141900 | A/C | HBB | hsa-miR-597 |
| rs35825479 | 141900 | C/T | HBB | hsa-miR-220b |
| rs35826780 | 142250 | G/T | HBG2 | hsa-miR-665 |
| rs35826780 | 142250 | G/T | HBG2 | hsa-miR-1913, hsa-miR-324-3p, hsa-miR-18a* |
| rs35826780 | 142250 | G/T | HBG2 | hsa-miR-873 |
| rs35826780 | 142250 | G/T | HBG2 | hsa-miR-1202 |
| rs35834416 | 141900 | G/T | HBB | hsa-miR-940, hsa-miR-34b* |
| rs35848600 | 142000 | A/C | HBD | hsa-miR-575 |
| rs35848600 | 142000 | A/C | HBD | hsa-miR-640 |
| rs35849199 | 141900 | C/T | — | hsa-miR-602 |
| rs35849348 | 142000 | A/G | HBD | hsa-miR-499-3p |
| rs35849348 | 142000 | A/G | HBD | hsa-miR-1226 |
| rs35849348 | 142000 | A/G | HBD | hsa-miR-634 |
| rs35849348 | 142000 | A/G | HBD | hsa-miR-1228, hsa-miR-220a |
| rs35849660 | 142200 | A/G | HBG1 | hsa-miR-181c* |
| rs35849660 | 142200 | A/G | HBG1 | hsa-miR-136* |
| rs35849660 | 142200 | A/G | HBG1 | hsa-miR-197 |
| rs35849660 | 142200 | A/G | HBG1 | hsa-miR-452* |
| rs35850071 | 141800 | C/T | HBA2 | hsa-miR-873 |
| rs35850071 | 141800 | C/T | HBA2 | hsa-miR-494 |
| rs35854892 | 141900 | G/T | HBB | hsa-miR-296-5p |
| rs35854892 | 141900 | G/T | HBB | hsa-miR-1538 |
| rs35857380 | 141900 | A/T | HBB | hsa-miR-7 |
| rs35857380 | 141900 | A/T | HBB | hsa-miR-379 |
| rs35859529 | 141800 | A/G | HBA2 | hsa-miR-933 |
| rs35871407 | 141900 | C/T | HBB | hsa-miR-634 |
| rs35871407 | 141900 | C/T | HBB | hsa-miR-220c |
| rs35871407 | 141900 | C/T | HBB | hsa-miR-1972 |
| rs35871407 | 141900 | C/T | HBB | hsa-miR-15a* |
| rs35885783 | 142250 | A/G | HBG1 | hsa-miR-549 |
| rs35885783 | 142250 | A/G | HBG1 | hsa-miR-577 |
| rs35887507 | 142000 | A/G | HBD | hsa-miR-193a-5p |
| rs35887507 | 142000 | A/G | HBD | hsa-miR-601 |
| rs35890380 | 141900 | A/C/G | HBB | hsa-miR-377* |
| rs35890380 | 141900 | A/C/G | HBB | hsa-miR-1304 |
| rs35890380 | 141900 | A/C/G | HBB | hsa-miR-27b* |
| rs35890380 | 141900 | A/C/G | HBB | hsa-miR-1974, hsa-miR-453 |
| rs35906307 | 141900 | C/T | HBB | hsa-miR-500* |
| rs35906307 | 141900 | C/T | HBB | hsa-miR-767-5p |
| rs35906307 | 141900 | C/T | HBB | hsa-miR-501-3p, hsa-miR-502-3p |
| rs35913713 | 142000 | C/G | HBD | hsa-miR-564 |
| rs35913713 | 142000 | C/G | HBD | hsa-miR-1277 |
| rs35913713 | 142000 | C/G | HBD | hsa-miR-593* |
| rs35914488 | 141900 | C/T | HBB | hsa-miR-18b, hsa-miR-18a |
| rs35914488 | 141900 | C/T | HBB | hsa-miR-548m |
| rs35932809 | 141800 | A/C | HBA2 | hsa-miR-1307 |

TABLE 2-continued

| SNP | OMIM | MUTATION | GENE | MIR |
|---|---|---|---|---|
| rs35932809 | 141800 | A/C | HBA2 | hsa-miR-1469 |
| rs35932809 | 141800 | A/C | HBA2 | hsa-miR-887 |
| rs35932809 | 141800 | A/C | HBA2 | hsa-miR-523 |
| rs35934411 | 141800 | A/G | — | hsa-miR-132* |
| rs35939430 | 141900 | C/G | — | hsa-miR-885-3p |
| rs35939430 | 141900 | C/G | — | hsa-miR-1321 |
| rs35939430 | 141900 | C/G | — | hsa-miR-505* |
| rs35939430 | 141900 | C/G | — | hsa-miR-940, hsa-miR-34b* |
| rs35939430 | 141900 | C/G | — | hsa-miR-135a* |
| rs35939430 | 141900 | C/G | — | hsa-miR-920 |
| rs35939489 | 141900 | A/C | HBB | hsa-miR-1208 |
| rs35939489 | 141900 | A/C | HBB | hsa-miR-511 |
| rs35939489 | 141900 | A/C | HBB | hsa-miR-431 |
| rs35939489 | 141900 | A/C | HBB | hsa-miR-578 |
| rs35957832 | 142200 | C/G | HBG1 | hsa-miR-198 |
| rs35957832 | 142200 | C/G | HBG1 | hsa-miR-629* |
| rs35957832 | 142200 | C/G | HBG1 | hsa-miR-766 |
| rs35960772 | 141900 | A/G | — | hsa-miR-525-3p, hsa-miR-524-3p |
| rs35960772 | 141900 | A/G | — | hsa-miR-1249 |
| rs35960772 | 141900 | A/G | — | hsa-miR-874 |
| rs35960772 | 141900 | A/G | — | hsa-miR-18b, hsa-miR-18a |
| rs35960772 | 141900 | A/G | — | hsa-miR-548m |
| rs35960772 | 141900 | A/G | — | hsa-miR-566 |
| rs35973315 | 141900 | A/G | HBB | hsa-miR-518c*, hsa-miR-330-5p, hsa-miR-326 |
| rs35974739 | 141800 | C/T | HBA1 | hsa-miR-220c |
| rs35974739 | 141800 | C/T | HBA1 | hsa-miR-505* |
| rs35974739 | 141800 | C/T | HBA1 | hsa-miR-708, hsa-miR-28-5p |
| rs35977759 | 142200 | A/G | HBG1 | hsa-miR-518c*, hsa-miR-330-5p, hsa-miR-326 |
| rs35986575 | 191100 | A/G | TSC2 | hsa-miR-1273 |
| rs35986575 | 191100 | A/G | TSC2 | hsa-miR-627 |
| rs35993655 | 141800 | C/T | HBA1 | hsa-miR-665 |
| rs35993655 | 141800 | C/T | HBA1 | hsa-miR-575 |
| rs35993655 | 141800 | C/T | HBA1 | hsa-miR-873 |
| rs35993655 | 141800 | C/T | HBA1 | hsa-miR-1292 |
| rs35994191 | 141800 | C/T | HBA1 | hsa-miR-423-3p |
| rs36006195 | 142250 | G/T | HBG1 | hsa-miR-425 |
| rs36006195 | 142250 | G/T | HBG1 | hsa-miR-660 |
| rs36006214 | 141900 | C/G/T | HBB | hsa-miR-23b, hsa-miR-130a*, hsa-miR-23a |
| rs36006214 | 141900 | C/G/T | HBB | hsa-miR-1915* |
| rs36008922 | 141900 | A/G | HBB | hsa-miR-1179 |
| rs36015961 | 141900 | C/T | — | hsa-miR-338-3p |
| rs36020563 | 141900 | A/C/G | HBB | hsa-miR-581 |
| rs36020563 | 141900 | A/C/G | HBB | hsa-miR-1285, hsa-miR-612 |
| rs36024711 | 141800 | A/G | HBA2 | hsa-miR-941 |
| rs36024711 | 141800 | A/G | HBA2 | hsa-miR-1285, hsa-miR-612 |
| rs36024711 | 141800 | A/G | HBA2 | hsa-miR-619 |
| rs36024711 | 141800 | A/G | HBA2 | hsa-miR-649, hsa-miR-490-3p |
| rs36038739 | 141900 | C/G/T | — | hsa-miR-508-3p, hsa-miR-219-5p, hsa-miR-219-5p |
| rs36038739 | 141900 | C/G/T | — | hsa-miR-10b* |
| rs36038739 | 141900 | C/G/T | — | hsa-miR-1301 |
| rs36038739 | 141900 | C/G/T | — | hsa-miR-657 |
| rs36038739 | 141900 | C/G/T | — | hsa-miR-1974, hsa-miR-453 |
| rs36049074 | 142250 | A/G | HBG2 | hsa-miR-191 |
| rs36049074 | 142250 | A/G | HBG2 | hsa-miR-1246 |
| rs36049074 | 142250 | A/G | HBG2 | hsa-miR-553 |
| rs36049074 | 142250 | A/G | HBG2 | hsa-miR-522, hsa-miR-224* |
| rs36062788 | 141800 | A/G | HBA2 | hsa-miR-938 |
| rs36062788 | 141800 | A/G | HBA2 | hsa-miR-1291 |
| rs36062788 | 141800 | A/G | HBA2 | hsa-miR-663b |
| rs36062788 | 141800 | A/G | HBA2 | hsa-miR-328 |
| rs36062788 | 141800 | A/G | HBA2 | hsa-miR-1204 |
| rs36075744 | 141800 | A/C | HBA2 | hsa-miR-1909 |
| rs36075744 | 141800 | A/C | HBA2 | hsa-miR-1266 |
| rs36078782 | 191100 | C/G | TSC2 | hsa-miR-335 |
| rs36078803 | 142000 | C/G | HBD | hsa-miR-491-5p |
| rs36078803 | 142000 | C/G | HBD | hsa-miR-637 |
| rs36078803 | 142000 | C/G | HBD | hsa-miR-2113 |
| rs36081208 | 141900 | C/T | HBB | hsa-miR-517b |
| rs36081208 | 141900 | C/T | HBB | hsa-miR-143* |
| rs36081208 | 141900 | C/T | HBB | hsa-miR-1301 |
| rs36084266 | 142000 | A/G | HBD | hsa-miR-186* |
| rs36084266 | 142000 | A/G | HBD | hsa-miR-888 |
| rs36084266 | 142000 | A/G | HBD | hsa-miR-616*, hsa-miR-371-5p, hsa-miR-373* |
| rs36104787 | 141850 | C/G/T | HBA2 | hsa-miR-933 |
| rs36104787 | 141850 | C/G/T | HBA2 | hsa-miR-122* |
| rs41278174 | 264800 | A/G | ABCC6 | hsa-miR-618 |
| rs41278174 | 264800 | A/G | ABCC6 | hsa-miR-518c*, hsa-miR-330-5p, hsa-miR-326 |
| rs41321345 | 141850 | A/C | HBA2 | hsa-miR-1207-3p |

TABLE 2-continued

| SNP | OMIM | MUTATION | GENE | MIR |
|---|---|---|---|---|
| rs41321345 | 141850 | A/C | HBA2 | hsa-miR-590-5p, hsa-miR-21 |
| rs41321345 | 141850 | A/C | HBA2 | hsa-miR-887 |
| rs41322954 | 141800 | A/C | HBA2 | hsa-miR-382 |
| rs41323248 | 141850 | C/T | HBA2 | hsa-miR-1469 |
| rs41328049 | 141850 | C/G | HBA2 | hsa-miR-132* |
| rs41328049 | 141850 | C/G | HBA2 | hsa-miR-1204 |
| rs41330850 | 142200 | A/G | HBG1 | hsa-miR-1264 |
| rs41330850 | 142200 | A/G | HBG1 | hsa-miR-596 |
| rs41330850 | 142200 | A/G | HBG1 | hsa-miR-671-5p |
| rs41330850 | 142200 | A/G | HBG1 | hsa-miR-346 |
| rs41331747 | 141850 | A/T | HBA2 | hsa-miR-1286 |
| rs41331747 | 141850 | A/T | HBA2 | hsa-miR-657 |
| rs41331747 | 141850 | A/T | HBA2 | hsa-miR-431* |
| rs41331747 | 141850 | A/T | HBA2 | hsa-miR-574-3p |
| rs41338947 | 141800 | A/C | HBA2 | hsa-miR-382 |
| rs41338947 | 141800 | A/C | HBA2 | hsa-miR-573 |
| rs41338947 | 141800 | A/C | HBA2 | hsa-miR-183* |
| rs41341344 | 141850 | C/T | HBA2 | hsa-miR-515-5p, hsa-miR-519e* |
| rs41341344 | 141850 | C/T | HBA2 | hsa-miR-766 |
| rs41361546 | 141850 | A/G | HBA2 | hsa-miR-630 |
| rs41378349 | 141850 | A/C | HBA2 | hsa-miR-663b |
| rs41378349 | 141850 | A/C | HBA2 | hsa-miR-132* |
| rs41378349 | 141850 | A/C | HBA2 | hsa-miR-1204 |
| rs41381645 | 141800 | A/C | HBA2 | hsa-miR-1248, hsa-miR-1237 |
| rs41381645 | 141800 | A/C | HBA2 | hsa-miR-431 |
| rs41381645 | 141800 | A/C | HBA2 | hsa-miR-340* |
| rs41381645 | 141800 | A/C | HBA2 | hsa-miR-578 |
| rs41392146 | 141850 | G/T | HBA2 | hsa-miR-24 |
| rs41392146 | 141850 | G/T | HBA2 | hsa-miR-1266 |
| rs41392146 | 141850 | G/T | HBA2 | hsa-miR-431* |
| rs41397847 | 141850 | C/G/T | HBA2 | hsa-miR-939 |
| rs41397847 | 141850 | C/G/T | HBA2 | hsa-miR-1321 |
| rs41397847 | 141850 | C/G/T | HBA2 | hsa-miR-198 |
| rs41397847 | 141850 | C/G/T | HBA2 | hsa-miR-542-5p |
| rs41404150 | 142200 | C/G | HBG1 | hsa-miR-181a* |
| rs41404150 | 142200 | C/G | HBG1 | hsa-miR-1225-5p |
| rs41404150 | 142200 | C/G | HBG1 | hsa-miR-1308 |
| rs41412046 | 141850 | A/T | HBA2 | hsa-miR-338-3p |
| rs41412046 | 141850 | A/T | HBA2 | hsa-miR-590-5p, hsa-miR-21 |
| rs41416747 | 141800 | A/T | HBA2 | hsa-miR-431 |
| rs41417548 | 141850 | A/G | HBA2 | hsa-miR-196b, hsa-miR-196a, hsa-miR-196a |
| rs41417548 | 141850 | A/G | HBA2 | hsa-miR-142-3p |
| rs41417548 | 141850 | A/G | HBA2 | hsa-miR-194* |
| rs41417548 | 141850 | A/G | HBA2 | hsa-miR-449b, hsa-miR-449a, hsa-miR-34c-5p, hsa-miR-34a |
| rs41417548 | 141850 | A/G | HBA2 | hsa-miR-657 |
| rs41417548 | 141850 | A/G | HBA2 | hsa-miR-940, hsa-miR-34b* |
| rs41430445 | 141850 | C/T | HBA2 | hsa-miR-873 |
| rs41457351 | 141850 | C/T | HBA2 | hsa-miR-541, hsa-miR-654-5p, hsa-miR-92a-2* |
| rs41457351 | 141850 | C/T | HBA2 | hsa-miR-1228* |
| rs41457351 | 141850 | C/T | HBA2 | hsa-miR-184 |
| rs41461652 | 141850 | C/G | HBA2 | hsa-miR-1181 |
| rs41461652 | 141850 | C/G | HBA2 | hsa-miR-24 |
| rs41461652 | 141850 | C/G | HBA2 | hsa-miR-132* |
| rs41461652 | 141850 | C/G | HBA2 | hsa-miR-1204 |
| rs41464951 | 141850 | C/G/T | — | hsa-miR-412 |
| rs41464951 | 141850 | C/G/T | — | hsa-miR-590-5p, hsa-miR-21 |
| rs41469945 | 141850 | C/T | HBA2 | hsa-miR-564 |
| rs41469945 | 141850 | C/T | HBA2 | hsa-miR-431* |
| rs41475844 | 142200 | A/G | HBG1 | hsa-miR-626 |
| rs41475844 | 142200 | A/G | HBG1 | hsa-miR-2053 |
| rs41479347 | 141800 | C/G | HBA2 | hsa-miR-517b |
| rs41479844 | 141850 | G/T | HBA2 | hsa-miR-1182 |
| rs41479844 | 141850 | G/T | HBA2 | hsa-miR-1538 |
| rs41484451 | 141850 | C/T | HBA2 | hsa-miR-885-3p |
| rs41484451 | 141850 | C/T | HBA2 | hsa-miR-1908, hsa-miR-663 |
| rs41484451 | 141850 | C/T | HBA2 | hsa-miR-25* |
| rs41491146 | 141800 | C/G | HBA2 | hsa-miR-31 |
| rs41510746 | 141850 | A/G | HBA2 | hsa-miR-187 |
| rs41514946 | 141850 | A/C | HBA2 | hsa-miR-1250 |
| rs41514946 | 141850 | A/C | HBA2 | hsa-miR-1178 |
| rs41514946 | 141850 | A/C | HBA2 | hsa-miR-1229 |
| rs41514946 | 141850 | A/C | HBA2 | hsa-miR-182* |
| rs41515649 | 141850 | A/G | — | hsa-miR-1248, hsa-miR-1237 |
| rs41515649 | 141850 | A/G | — | hsa-miR-141* |
| rs41518249 | 141800 | A/C | HBA2 | hsa-miR-24 |
| rs41518249 | 141800 | A/C | HBA2 | hsa-miR-187 |
| rs41518249 | 141800 | A/C | HBA2 | hsa-miR-132* |

TABLE 2-continued

| SNP | OMIM | MUTATION | GENE | MIR |
| --- | --- | --- | --- | --- |
| rs41518249 | 141800 | A/C | HBA2 | hsa-miR-1204 |
| rs41525149 | 141800 | A/C | HBA2 | hsa-miR-933 |
| rs41528545 | 141800 | A/C | HBA2 | hsa-miR-575 |
| rs41529844 | 141850 | C/G | HBA2 | hsa-miR-665 |
| rs41529844 | 141850 | C/G | HBA2 | hsa-miR-1207-5p |
| rs41529844 | 141850 | C/G | HBA2 | hsa-miR-575 |
| rs41529844 | 141850 | C/G | HBA2 | hsa-miR-1286 |
| rs41529844 | 141850 | C/G | HBA2 | hsa-miR-940, hsa-miR-34b* |
| rs41529844 | 141850 | C/G | HBA2 | hsa-miR-506, hsa-miR-124, hsa-miR-124, hsa-miR-124 |
| rs41530750 | 141800 | C/G | HBA2 | hsa-miR-1268, hsa-miR-585 |
| rs45437192 | 191100 | C/T | TSC2 | hsa-miR-1247 |
| rs45437192 | 191100 | C/T | TSC2 | hsa-miR-1538 |
| rs45437193 | 191100 | C/T | TSC2 | hsa-miR-943 |
| rs45437193 | 191100 | C/T | TSC2 | hsa-miR-892a |
| rs45437797 | 191100 | C/G | TSC2 | hsa-miR-517b |
| rs45437797 | 191100 | C/G | TSC2 | hsa-miR-1250 |
| rs45437797 | 191100 | C/G | TSC2 | hsa-miR-1972 |
| rs45437797 | 191100 | C/G | TSC2 | hsa-miR-1973 |
| rs45438093 | 191100 | C/G | TSC2 | hsa-miR-1301 |
| rs45438093 | 191100 | C/G | TSC2 | hsa-miR-657 |
| rs45438192 | 191100 | C/T | TSC2 | hsa-miR-525-5p, hsa-miR-520a-5p |
| rs45438192 | 191100 | C/T | TSC2 | hsa-miR-1324 |
| rs45438192 | 191100 | C/T | TSC2 | hsa-miR-198 |
| rs45438205 | 191100 | C/T | TSC2 | hsa-miR-525-5p, hsa-miR-520a-5p |
| rs45438205 | 191100 | C/T | TSC2 | hsa-miR-766 |
| rs45438898 | 191100 | A/G | TSC2 | hsa-miR-198 |
| rs45438898 | 191100 | A/G | TSC2 | hsa-miR-340* |
| rs45443091 | 191100 | C/G | TSC2 | hsa-miR-136 |
| rs45443091 | 191100 | C/G | TSC2 | hsa-miR-515-5p, hsa-miR-519e* |
| rs45443091 | 191100 | C/G | TSC2 | hsa-miR-516a-5p |
| rs45443091 | 191100 | C/G | TSC2 | hsa-miR-383 |
| rs45443205 | 191100 | C/T | TSC2 | hsa-miR-194 |
| rs45444196 | 191100 | C/G | TSC2 | hsa-miR-562 |
| rs45444196 | 191100 | C/G | TSC2 | hsa-miR-708* |
| rs45446594 | 191100 | A/T | TSC2 | hsa-miR-525-3p, hsa-miR-524-3p |
| rs45446594 | 191100 | A/T | TSC2 | hsa-miR-302d*, hsa-miR-302b* |
| rs45446700 | 191100 | A/G | TSC2 | hsa-miR-422a, hsa-miR-378 |
| rs45446700 | 191100 | A/G | TSC2 | hsa-miR-1207-3p |
| rs45446700 | 191100 | A/G | TSC2 | hsa-miR-1269 |
| rs45446700 | 191100 | A/G | TSC2 | hsa-miR-1287 |
| rs45446901 | 191100 | C/T | TSC2 | hsa-miR-299-3p |
| rs45446901 | 191100 | C/T | TSC2 | hsa-miR-7 |
| rs45448101 | 191100 | C/T | TSC2 | hsa-miR-1291 |
| rs45448101 | 191100 | C/T | TSC2 | hsa-miR-129-3p, hsa-miR-129* |
| rs45448101 | 191100 | C/T | TSC2 | hsa-miR-582-3p |
| rs45448101 | 191100 | C/T | TSC2 | hsa-miR-892b, hsa-miR-193b, hsa-miR-193a-3p |
| rs45448101 | 191100 | C/T | TSC2 | hsa-miR-708* |
| rs45448101 | 191100 | C/T | TSC2 | hsa-miR-328 |
| rs45448791 | 191100 | A/G | TSC2 | hsa-miR-345 |
| rs45448791 | 191100 | A/G | TSC2 | hsa-miR-1291 |
| rs45448791 | 191100 | A/G | TSC2 | hsa-miR-943 |
| rs45448791 | 191100 | A/G | TSC2 | hsa-miR-146b-3p |
| rs45448791 | 191100 | A/G | TSC2 | hsa-miR-125a-5p, hsa-miR-125b, hsa-miR-125b |
| rs45449094 | 191100 | G/T | TSC2 | hsa-miR-99b, hsa-miR-99a, hsa-miR-100 |
| rs45451295 | 191100 | G/T | TSC2 | hsa-miR-596 |
| rs45451295 | 191100 | G/T | TSC2 | hsa-miR-556-5p |
| rs45451497 | 191100 | C/T | TSC2 | hsa-miR-888 |
| rs45451497 | 191100 | C/T | TSC2 | hsa-miR-616*, hsa-miR-371-5p, hsa-miR-373* |
| rs45452994 | 191100 | C/T | TSC2 | hsa-miR-617 |
| rs45454398 | 191100 | A/C | TSC2 | hsa-miR-214* |
| rs45454398 | 191100 | A/C | TSC2 | hsa-miR-520h, hsa-miR-520g |
| rs45455296 | 191100 | C/T | TSC2 | hsa-miR-1915* |
| rs45455296 | 191100 | C/T | TSC2 | hsa-miR-600 |
| rs45455398 | 191100 | A/C | TSC2 | hsa-miR-1322, hsa-miR-1272 |
| rs45455897 | 191100 | A/C/G | TSC2 | hsa-miR-202*, hsa-miR-337-3p |
| rs45455897 | 191100 | A/C/G | TSC2 | hsa-miR-550*, hsa-miR-200c* |
| rs45455897 | 191100 | A/C/G | TSC2 | hsa-miR-511 |
| rs45457694 | 191100 | A/G | TSC2 | hsa-miR-604 |
| rs45457694 | 191100 | A/G | TSC2 | hsa-miR-628-5p |
| rs45457694 | 191100 | A/G | TSC2 | hsa-miR-93* |
| rs45457694 | 191100 | A/G | TSC2 | hsa-miR-1267, hsa-miR-367* |
| rs45457694 | 191100 | A/G | TSC2 | hsa-miR-653 |
| rs45457701 | 191100 | C/T | TSC2 | hsa-miR-208b, hsa-miR-499-5p, hsa-miR-208a |
| rs45457701 | 191100 | C/T | TSC2 | hsa-miR-769-5p |
| rs45457701 | 191100 | C/T | TSC2 | hsa-miR-1200, hsa-miR-378* |
| rs45457701 | 191100 | C/T | TSC2 | hsa-miR-1976 |
| rs45458592 | 191100 | G/T | TSC2 | hsa-miR-1301 |

TABLE 2-continued

| SNP | OMIM | MUTATION | GENE | MIR |
|---|---|---|---|---|
| rs45458592 | 191100 | G/T | TSC2 | hsa-miR-922, hsa-miR-214 |
| rs45458592 | 191100 | G/T | TSC2 | hsa-miR-509-3-5p, hsa-miR-509-5p, hsa-miR-509-5p, hsa-miR-217 |
| rs45458592 | 191100 | G/T | TSC2 | hsa-miR-127-5p |
| rs45458592 | 191100 | G/T | TSC2 | hsa-miR-1205, hsa-miR-1184, hsa-miR-17* |
| rs45458592 | 191100 | G/T | TSC2 | hsa-miR-103, hsa-miR-107 |
| rs45458694 | 191100 | C/T | TSC2 | hsa-miR-619 |
| rs45459299 | 191100 | C/T | TSC2 | hsa-miR-658 |
| rs45459299 | 191100 | C/T | TSC2 | hsa-miR-505* |
| rs45460096 | 191100 | C/T | TSC2 | hsa-miR-891b |
| rs45460096 | 191100 | C/T | TSC2 | hsa-miR-617 |
| rs45460096 | 191100 | C/T | TSC2 | hsa-miR-450a |
| rs45460096 | 191100 | C/T | TSC2 | hsa-miR-450b-5p, hsa-miR-557, hsa-miR-507 |
| rs45462192 | 191100 | A/G | TSC2 | hsa-miR-30e*, hsa-miR-30d*, hsa-miR-30a* |
| rs45462192 | 191100 | A/G | TSC2 | hsa-miR-145 |
| rs45462194 | 191100 | A/G | TSC2 | hsa-miR-1274a |
| rs45462194 | 191100 | A/G | TSC2 | hsa-miR-1539 |
| rs45462593 | 191100 | A/C | TSC2 | hsa-miR-664*, hsa-miR-149 |
| rs45462593 | 191100 | A/C | TSC2 | hsa-miR-647 |
| rs45462593 | 191100 | A/C | TSC2 | hsa-miR-1231, hsa-miR-632 |
| rs45462593 | 191100 | A/C | TSC2 | hsa-miR-1299, hsa-miR-516b, hsa-miR-516b |
| rs45462593 | 191100 | A/C | TSC2 | hsa-miR-221* |
| rs45462593 | 191100 | A/C | TSC2 | hsa-miR-1287 |
| rs45463498 | 191100 | C/T | TSC2 | hsa-miR-596 |
| rs45463498 | 191100 | C/T | TSC2 | hsa-miR-1201 |
| rs45463498 | 191100 | C/T | TSC2 | hsa-miR-649, hsa-miR-490-3p |
| rs45464093 | 191100 | C/T | TSC2 | hsa-miR-1321 |
| rs45464093 | 191100 | C/T | TSC2 | hsa-miR-1909 |
| rs45464093 | 191100 | C/T | TSC2 | hsa-miR-920 |
| rs45465395 | 191100 | A/G | TSC2 | hsa-miR-431 |
| rs45465395 | 191100 | A/G | TSC2 | hsa-miR-526b |
| rs45465395 | 191100 | A/G | TSC2 | hsa-miR-1200, hsa-miR-378* |
| rs45466399 | 191100 | A/G | TSC2 | hsa-miR-1274a |
| rs45466399 | 191100 | A/G | TSC2 | hsa-miR-611, hsa-miR-151-5p |
| rs45466399 | 191100 | A/G | TSC2 | hsa-miR-1224-5p |
| rs45466399 | 191100 | A/G | TSC2 | hsa-miR-125a-5p, hsa-miR-125b, hsa-miR-125b |
| rs45466493 | 191100 | C/T | TSC2 | hsa-miR-604 |
| rs45466493 | 191100 | C/T | TSC2 | hsa-miR-647 |
| rs45467993 | 191100 | A/C/G | TSC2 | hsa-miR-483-3p |
| rs45467993 | 191100 | A/C/G | TSC2 | hsa-miR-554 |
| rs45468201 | 191100 | C/T | TSC2 | hsa-miR-1254, hsa-miR-661 |
| rs45468201 | 191100 | C/T | TSC2 | hsa-miR-596 |
| rs45468201 | 191100 | C/T | TSC2 | hsa-miR-1245 |
| rs45468201 | 191100 | C/T | TSC2 | hsa-miR-921 |
| rs45468491 | 191100 | A/G | TSC2 | hsa-miR-937 |
| rs45469099 | 191100 | C/T | TSC2 | hsa-miR-628-5p |
| rs45469099 | 191100 | C/T | TSC2 | hsa-miR-558 |
| rs45469099 | 191100 | C/T | TSC2 | hsa-miR-93* |
| rs45469099 | 191100 | C/T | TSC2 | hsa-miR-22 |
| rs45469099 | 191100 | C/T | TSC2 | hsa-miR-610 |
| rs45469298 | 191100 | C/G/T | TSC2 | hsa-miR-575 |
| rs45469298 | 191100 | C/G/T | TSC2 | hsa-miR-105* |
| rs45469298 | 191100 | C/G/T | TSC2 | hsa-miR-488* |
| rs45469392 | 191100 | A/G | TSC2 | hsa-miR-635 |
| rs45469702 | 191100 | C/T | TSC2 | hsa-miR-1321 |
| rs45469702 | 191100 | C/T | TSC2 | hsa-miR-1292 |
| rs45469702 | 191100 | C/T | TSC2 | hsa-miR-920 |
| rs45469896 | 191100 | C/T | TSC2 | hsa-miR-619 |
| rs45470502 | 191100 | A/T | TSC2 | hsa-miR-148a* |
| rs45470502 | 191100 | A/T | TSC2 | hsa-miR-215, hsa-miR-192 |
| rs45470695 | 191100 | A/G | TSC2 | hsa-miR-602 |
| rs45470695 | 191100 | A/G | TSC2 | hsa-miR-135b, hsa-miR-135a, hsa-miR-135a |
| rs45471596 | 191100 | A/C | TSC2 | hsa-miR-496 |
| rs45471596 | 191100 | A/C | TSC2 | hsa-miR-628-3p, hsa-miR-325 |
| rs45471697 | 191100 | C/T | TSC2 | hsa-miR-148b* |
| rs45471791 | 191100 | A/C | TSC2 | hsa-miR-1303 |
| rs45471791 | 191100 | A/C | TSC2 | hsa-miR-379 |
| rs45471791 | 191100 | A/C | TSC2 | hsa-miR-409-3p, hsa-miR-33a* |
| rs45471896 | 191100 | C/T | TSC2 | hsa-miR-194* |
| rs45472701 | 191100 | C/T | TSC2 | hsa-miR-1914 |
| rs45472701 | 191100 | C/T | TSC2 | hsa-miR-1294 |
| rs45473098 | 191100 | A/G/T | TSC2 | hsa-miR-223 |
| rs45473098 | 191100 | A/G/T | TSC2 | hsa-miR-1910, hsa-miR-455-3p |
| rs45473098 | 191100 | A/G/T | TSC2 | hsa-miR-140-5p |
| rs45473098 | 191100 | A/G/T | TSC2 | hsa-miR-194* |
| rs45473098 | 191100 | A/G/T | TSC2 | hsa-miR-622 |
| rs45473098 | 191100 | A/G/T | TSC2 | hsa-miR-132* |
| rs45473296 | 191100 | A/C | TSC2 | hsa-miR-221* |

TABLE 2-continued

| SNP | OMIM | MUTATION | GENE | MIR |
|---|---|---|---|---|
| rs45473296 | 191100 | A/C | TSC2 | hsa-miR-619 |
| rs45473598 | 191100 | C/T | TSC2 | hsa-miR-224 |
| rs45473598 | 191100 | C/T | TSC2 | hsa-miR-34a* |
| rs45473598 | 191100 | C/T | TSC2 | hsa-miR-551b* |
| rs45473598 | 191100 | C/T | TSC2 | hsa-miR-520h, hsa-miR-520g |
| rs45473698 | 191100 | C/G | TSC2 | hsa-miR-220c |
| rs45473698 | 191100 | C/G | TSC2 | hsa-miR-196b* |
| rs45474691 | 191100 | A/T | TSC2 | hsa-miR-223 |
| rs45474691 | 191100 | A/T | TSC2 | hsa-miR-1324 |
| rs45474795 | 191100 | G/T | TSC2 | hsa-miR-665 |
| rs45474795 | 191100 | G/T | TSC2 | hsa-miR-885-3p |
| rs45474795 | 191100 | G/T | TSC2 | hsa-miR-873 |
| rs45474795 | 191100 | G/T | TSC2 | hsa-miR-671-5p |
| rs45474795 | 191100 | G/T | TSC2 | hsa-miR-940, hsa-miR-34b* |
| rs45474795 | 191100 | G/T | TSC2 | hsa-miR-103, hsa-miR-107 |
| rs45475501 | 191100 | A/G | TSC2 | hsa-miR-198 |
| rs45475594 | 191100 | A/T | TSC2 | hsa-miR-603, hsa-miR-329, hsa-miR-329, hsa-miR-362-3p |
| rs45475594 | 191100 | A/T | TSC2 | hsa-miR-1324 |
| rs45475594 | 191100 | A/T | TSC2 | hsa-miR-377 |
| rs45476100 | 191100 | C/T | TSC2 | hsa-miR-29a* |
| rs45476793 | 191100 | C/G | TSC2 | hsa-miR-634 |
| rs45476793 | 191100 | C/G | TSC2 | hsa-miR-1911* |
| rs45477298 | 191100 | A/C | TSC2 | hsa-miR-1244 |
| rs45477491 | 191100 | C/T | TSC2 | hsa-miR-149* |
| rs45477491 | 191100 | C/T | TSC2 | hsa-miR-582-3p |
| rs45477491 | 191100 | C/T | TSC2 | hsa-miR-708* |
| rs45477491 | 191100 | C/T | TSC2 | hsa-miR-30c-1*, hsa-miR-30b*, hsa-miR-30c-2* |
| rs45478393 | 191100 | A/G | TSC2 | hsa-miR-647 |
| rs45478593 | 191100 | C/T | TSC2 | hsa-miR-1297, hsa-miR-26a, hsa-miR-26a, hsa-miR-26b |
| rs45478593 | 191100 | C/T | TSC2 | hsa-miR-148a* |
| rs45478593 | 191100 | C/T | TSC2 | hsa-miR-383 |
| rs45478595 | 191100 | C/T | TSC2 | hsa-miR-149* |
| rs45478595 | 191100 | C/T | TSC2 | hsa-miR-539 |
| rs45478595 | 191100 | C/T | TSC2 | hsa-miR-765 |
| rs45478595 | 191100 | C/T | TSC2 | hsa-miR-1253 |
| rs45478892 | 191100 | A/C | TSC2 | hsa-miR-144* |
| rs45478892 | 191100 | A/C | TSC2 | hsa-miR-361-5p |
| rs45478892 | 191100 | A/C | TSC2 | hsa-miR-383 |
| rs45478894 | 191100 | A/G | TSC2 | hsa-miR-517b |
| rs45478894 | 191100 | A/G | TSC2 | hsa-miR-500* |
| rs45478894 | 191100 | A/G | TSC2 | hsa-miR-1973 |
| rs45479192 | 191100 | C/T | TSC2 | hsa-miR-621 |
| rs45479192 | 191100 | C/T | TSC2 | hsa-miR-449b, hsa-miR-449a, hsa-miR-34c-5p, hsa-miR-34a |
| rs45480292 | 191100 | C/T | TSC2 | hsa-miR-139-5p |
| rs45480292 | 191100 | C/T | TSC2 | hsa-miR-1301 |
| rs45480292 | 191100 | C/T | TSC2 | hsa-miR-1205, hsa-miR-1184, hsa-miR-17* |
| rs45481199 | 191100 | G/T | TSC2 | hsa-miR-338-3p |
| rs45481199 | 191100 | G/T | TSC2 | hsa-miR-198 |
| rs45481199 | 191100 | G/T | TSC2 | hsa-miR-29c, hsa-miR-29b, hsa-miR-29b, hsa-miR-29a |
| rs45481496 | 191100 | C/T | TSC2 | hsa-miR-505 |
| rs45481496 | 191100 | C/T | TSC2 | hsa-miR-582-3p |
| rs45481496 | 191100 | C/T | TSC2 | hsa-miR-1207-3p |
| rs45482398 | 191100 | A/G | TSC2 | hsa-miR-744* |
| rs45482398 | 191100 | A/G | TSC2 | hsa-miR-1301 |
| rs45482604 | 191100 | C/T | TSC2 | hsa-miR-1909 |
| rs45482691 | 191100 | C/T | TSC2 | hsa-miR-604 |
| rs45482691 | 191100 | C/T | TSC2 | hsa-miR-1207-3p |
| rs45482691 | 191100 | C/T | TSC2 | hsa-miR-22 |
| rs45482691 | 191100 | C/T | TSC2 | hsa-miR-766 |
| rs45482795 | 191100 | G/T | TSC2 | hsa-miR-575 |
| rs45482795 | 191100 | G/T | TSC2 | hsa-miR-1207-3p |
| rs45483301 | 191100 | C/T | TSC2 | hsa-miR-518e |
| rs45483301 | 191100 | C/T | TSC2 | hsa-miR-509-3-5p, hsa-miR-509-5p, hsa-miR-509-5p, hsa-miR-217 |
| rs45483391 | 191100 | G/T | TSC2 | hsa-miR-942 |
| rs45483391 | 191100 | G/T | TSC2 | hsa-miR-629* |
| rs45483391 | 191100 | G/T | TSC2 | hsa-miR-509-3-5p, hsa-miR-509-5p, hsa-miR-509-5p, hsa-miR-217 |
| rs45483391 | 191100 | G/T | TSC2 | hsa-miR-1976 |
| rs45483392 | 191100 | C/T | TSC2 | hsa-miR-338-3p |
| rs45483392 | 191100 | C/T | TSC2 | hsa-miR-608, hsa-miR-342-5p |
| rs45483392 | 191100 | C/T | TSC2 | hsa-miR-922, hsa-miR-214 |
| rs45483392 | 191100 | C/T | TSC2 | hsa-miR-1909 |
| rs45483392 | 191100 | C/T | TSC2 | hsa-miR-744 |

TABLE 2-continued

| SNP | OMIM | MUTATION | GENE | MIR |
| --- | --- | --- | --- | --- |
| rs45484298 | 191100 | A/G | TSC2 | hsa-miR-1207-3p |
| rs45484298 | 191100 | A/G | TSC2 | hsa-miR-626 |
| rs45484892 | 191100 | G/T | TSC2 | hsa-miR-1975 |
| rs45484892 | 191100 | G/T | TSC2 | hsa-miR-1197 |
| rs45484892 | 191100 | G/T | TSC2 | hsa-miR-220b |
| rs45484892 | 191100 | G/T | TSC2 | hsa-miR-1280, hsa-miR-1224-3p |
| rs45485092 | 191100 | C/T | TSC2 | hsa-miR-196b, hsa-miR-196a, hsa-miR-196a |
| rs45485092 | 191100 | C/T | TSC2 | hsa-miR-125a-3p |
| rs45485395 | 191100 | A/G | TSC2 | hsa-miR-412 |
| rs45485395 | 191100 | A/G | TSC2 | hsa-miR-515-5p, hsa-miR-519e* |
| rs45485395 | 191100 | A/G | TSC2 | hsa-miR-141* |
| rs45485591 | 191100 | C/G | TSC2 | hsa-miR-1226 |
| rs45485591 | 191100 | C/G | TSC2 | hsa-miR-220b |
| rs45485591 | 191100 | C/G | TSC2 | hsa-miR-634 |
| rs45485591 | 191100 | C/G | TSC2 | hsa-miR-338-3p |
| rs45485591 | 191100 | C/G | TSC2 | hsa-miR-29c, hsa-miR-29b, hsa-miR-29b, hsa-miR-29a |
| rs45485591 | 191100 | C/G | TSC2 | hsa-miR-767-5p |
| rs45485599 | 191100 | G/T | TSC2 | hsa-miR-591 |
| rs45485599 | 191100 | G/T | TSC2 | hsa-miR-504 |
| rs45485599 | 191100 | G/T | TSC2 | hsa-miR-181c* |
| rs45485999 | 191100 | C/T | TSC2 | hsa-miR-605 |
| rs45485999 | 191100 | C/T | TSC2 | hsa-miR-495, hsa-miR-7-1*, hsa-miR-7-2* |
| rs45486193 | 191100 | C/T | TSC2 | hsa-miR-518b, hsa-miR-518a-3p, hsa-miR-518f, hsa-miR-518c, hsa-miR-518a-3p, hsa-miR-518d-3p |
| rs45486193 | 191100 | C/T | TSC2 | hsa-miR-302a* |
| rs45486193 | 191100 | C/T | TSC2 | hsa-miR-502-5p |
| rs45486193 | 191100 | C/T | TSC2 | hsa-miR-9* |
| rs45486193 | 191100 | C/T | TSC2 | hsa-miR-127-5p |
| rs45486196 | 191100 | A/G | TSC2 | hsa-miR-1297, hsa-miR-26a, hsa-miR-26a, hsa-miR-26b |
| rs45486196 | 191100 | A/G | TSC2 | hsa-miR-1278 |
| rs45486402 | 191100 | G/T | TSC2 | hsa-miR-513b |
| rs45486402 | 191100 | G/T | TSC2 | hsa-miR-377 |
| rs45486402 | 191100 | G/T | TSC2 | hsa-miR-548d-3p |
| rs45486402 | 191100 | G/T | TSC2 | hsa-miR-548f, hsa-miR-548e, hsa-miR-548a-3p, hsa-miR-548a-3p, hsa-miR-548a-3p |
| rs45486591 | 191100 | C/T | TSC2 | hsa-miR-29c, hsa-miR-29b, hsa-miR-29b, hsa-miR-29a |
| rs45486599 | 191100 | A/T | TSC2 | hsa-miR-577 |
| rs45486599 | 191100 | A/T | TSC2 | hsa-miR-569 |
| rs45487497 | 191100 | A/G | TSC2 | hsa-miR-942 |
| rs45487497 | 191100 | A/G | TSC2 | hsa-miR-103-2* |
| rs45487691 | 191100 | C/T | TSC2 | hsa-miR-564 |
| rs45487691 | 191100 | C/T | TSC2 | hsa-miR-198 |
| rs45487992 | 191100 | A/G | TSC2 | hsa-miR-485-5p |
| rs45488191 | 191100 | C/T | TSC2 | hsa-miR-92b* |
| rs45488191 | 191100 | C/T | TSC2 | hsa-miR-1286 |
| rs45488191 | 191100 | C/T | TSC2 | hsa-miR-922, hsa-miR-214 |
| rs45488191 | 191100 | C/T | TSC2 | hsa-miR-103, hsa-miR-107 |
| rs45488199 | 191100 | A/T | TSC2 | hsa-miR-942 |
| rs45488199 | 191100 | A/T | TSC2 | hsa-miR-510, hsa-miR-512-5p, hsa-miR-512-5p |
| rs45488595 | 191100 | A/T | TSC2 | hsa-miR-543 |
| rs45488595 | 191100 | A/T | TSC2 | hsa-miR-181d, hsa-miR-181b, hsa-miR-181a, hsa-miR-181a, hsa-miR-181b, hsa-miR-181c |
| rs45489791 | 191100 | C/T | TSC2 | hsa-miR-624 |
| rs45490993 | 191100 | C/G | TSC2 | hsa-miR-1224-5p |
| rs45490993 | 191100 | C/G | TSC2 | hsa-miR-1185 |
| rs45490993 | 191100 | C/G | TSC2 | hsa-miR-1294 |
| rs45491095 | 191100 | G/T | TSC2 | hsa-miR-499-3p |
| rs45491095 | 191100 | G/T | TSC2 | hsa-miR-136 |
| rs45491095 | 191100 | G/T | TSC2 | hsa-miR-515-5p, hsa-miR-519e* |
| rs45491698 | 191100 | C/G | TSC2 | hsa-miR-505* |
| rs45492397 | 191100 | A/G | TSC2 | hsa-miR-646, hsa-miR-503, hsa-miR-497, hsa-miR-424, hsa-miR-195, hsa-miR-15b, hsa-miR-16, hsa-miR-15a, hsa-miR-16 |
| rs45492397 | 191100 | A/G | TSC2 | hsa-miR-936, hsa-miR-199a-3p, hsa-miR-199b-3p, hsa-miR-199a-3p |
| rs45492397 | 191100 | A/G | TSC2 | hsa-miR-545 |
| rs45492397 | 191100 | A/G | TSC2 | hsa-miR-922, hsa-miR-214 |
| rs45492397 | 191100 | A/G | TSC2 | hsa-miR-103, hsa-miR-107 |
| rs45493394 | 191100 | G/T | TSC2 | hsa-miR-1251, hsa-miR-517*, hsa-miR-517*, hsa-miR-517* |
| rs45494392 | 191100 | A/G | TSC2 | hsa-let-7i* |
| rs45494392 | 191100 | A/G | TSC2 | hsa-miR-455-5p |
| rs45495796 | 191100 | C/T | TSC2 | hsa-miR-554 |
| rs45496291 | 191100 | C/T | TSC2 | hsa-miR-1913, hsa-miR-324-3p, hsa-miR-18a* |

TABLE 2-continued

| SNP | OMIM | MUTATION | GENE | MIR |
|---|---|---|---|---|
| rs45496291 | 191100 | C/T | TSC2 | hsa-miR-93* |
| rs45496291 | 191100 | C/T | TSC2 | hsa-miR-1912 |
| rs45496402 | 191100 | A/G | TSC2 | hsa-miR-544 |
| rs45496402 | 191100 | A/G | TSC2 | hsa-miR-1539 |
| rs45496402 | 191100 | A/G | TSC2 | hsa-miR-617 |
| rs45496402 | 191100 | A/G | TSC2 | hsa-miR-1976 |
| rs45497997 | 191100 | C/G | TSC2 | hsa-miR-193b* |
| rs45497997 | 191100 | C/G | TSC2 | hsa-miR-1539 |
| rs45497997 | 191100 | C/G | TSC2 | hsa-miR-637 |
| rs45497997 | 191100 | C/G | TSC2 | hsa-miR-619 |
| rs45498401 | 191100 | G/T | TSC2 | hsa-miR-1324 |
| rs45498496 | 191100 | A/C | TSC2 | hsa-miR-513a-5p, hsa-miR-27b, hsa-miR-27a |
| rs45498496 | 191100 | A/C | TSC2 | hsa-miR-521 |
| rs45498496 | 191100 | A/C | TSC2 | hsa-miR-342-3p |
| rs45498892 | 191100 | C/G | TSC2 | hsa-miR-942 |
| rs45498892 | 191100 | C/G | TSC2 | hsa-miR-103-2* |
| rs45498900 | 191100 | A/C | TSC2 | hsa-miR-615-5p |
| rs45498900 | 191100 | A/C | TSC2 | hsa-miR-597 |
| rs45498900 | 191100 | A/C | TSC2 | hsa-miR-637 |
| rs45499191 | 191100 | A/T | TSC2 | hsa-miR-1243 |
| rs45499191 | 191100 | A/T | TSC2 | hsa-miR-1299, hsa-miR-516b, hsa-miR-516b |
| rs45499191 | 191100 | A/T | TSC2 | hsa-miR-518c*, hsa-miR-330-5p, hsa-miR-326 |
| rs45500595 | 191100 | A/C | TSC2 | hsa-miR-92b* |
| rs45500595 | 191100 | A/C | TSC2 | hsa-miR-625 |
| rs45500595 | 191100 | A/C | TSC2 | hsa-miR-608, hsa-miR-342-5p |
| rs45501091 | 191100 | A/G | TSC2 | hsa-miR-1324 |
| rs45501091 | 191100 | A/G | TSC2 | hsa-miR-92b, hsa-miR-367, hsa-miR-363, hsa-miR-25, hsa-miR-32, hsa-miR-92a, hsa-miR-92a |
| rs45501793 | 191100 | A/T | TSC2 | hsa-miR-142-3p |
| rs45501793 | 191100 | A/T | TSC2 | hsa-miR-558 |
| rs45501793 | 191100 | A/T | TSC2 | hsa-miR-22 |
| rs45501793 | 191100 | A/T | TSC2 | hsa-miR-379 |
| rs45501793 | 191100 | A/T | TSC2 | hsa-miR-512-3p, hsa-miR-520f |
| rs45503995 | 191100 | A/G | TSC2 | hsa-miR-1915 |
| rs45503995 | 191100 | A/G | TSC2 | hsa-miR-24 |
| rs45503995 | 191100 | A/G | TSC2 | hsa-miR-1266 |
| rs45505895 | 191100 | A/G | TSC2 | hsa-miR-1227 |
| rs45505895 | 191100 | A/G | TSC2 | hsa-miR-192* |
| rs45505895 | 191100 | A/G | TSC2 | hsa-miR-566 |
| rs45506197 | 191100 | C/G | TSC2 | hsa-miR-136* |
| rs45506197 | 191100 | C/G | TSC2 | hsa-miR-640 |
| rs45506695 | 191100 | A/G | TSC2 | hsa-miR-516a-3p, hsa-miR-516b*, hsa-miR-516b* |
| rs45506695 | 191100 | A/G | TSC2 | hsa-miR-544 |
| rs45506695 | 191100 | A/G | TSC2 | hsa-miR-93* |
| rs45506695 | 191100 | A/G | TSC2 | hsa-miR-572 |
| rs45506695 | 191100 | A/G | TSC2 | hsa-miR-103-2* |
| rs45507198 | 191100 | A/G | TSC2 | hsa-miR-1911* |
| rs45507198 | 191100 | A/G | TSC2 | hsa-miR-645 |
| rs45507199 | 191100 | A/C/G | TSC2 | hsa-miR-1285, hsa-miR-612 |
| rs45507199 | 191100 | A/C/G | TSC2 | hsa-miR-558 |
| rs45507199 | 191100 | A/C/G | TSC2 | hsa-miR-486-3p |
| rs45507199 | 191100 | A/C/G | TSC2 | hsa-miR-505* |
| rs45507199 | 191100 | A/C/G | TSC2 | hsa-miR-744 |
| rs45508504 | 191100 | C/T | TSC2 | hsa-miR-425* |
| rs45508504 | 191100 | C/T | TSC2 | hsa-miR-423-3p |
| rs45508504 | 191100 | C/T | TSC2 | hsa-miR-1266 |
| rs45509000 | 191100 | A/T | TSC2 | hsa-miR-873 |
| rs45509000 | 191100 | A/T | TSC2 | hsa-miR-552 |
| rs45509094 | 191100 | C/G | TSC2 | hsa-miR-142-3p |
| rs45509094 | 191100 | C/G | TSC2 | hsa-miR-643 |
| rs45509094 | 191100 | C/G | TSC2 | hsa-miR-103-2* |
| rs45509500 | 191100 | C/T | TSC2 | hsa-miR-140-3p |
| rs45509500 | 191100 | C/T | TSC2 | hsa-miR-575 |
| rs45509791 | 191100 | A/G | TSC2 | hsa-miR-142-3p |
| rs45509791 | 191100 | A/G | TSC2 | hsa-miR-194* |
| rs45509791 | 191100 | A/G | TSC2 | hsa-miR-643 |
| rs45511204 | 191100 | A/C | TSC2 | hsa-miR-1915 |
| rs45511204 | 191100 | A/C | TSC2 | hsa-miR-493*, hsa-let-7g*, hsa-let-7a-2* |
| rs45511393 | 191100 | A/G | TSC2 | hsa-miR-100* |
| rs45512398 | 191100 | C/T | TSC2 | hsa-miR-1197 |
| rs45512398 | 191100 | C/T | TSC2 | hsa-miR-602 |
| rs45512692 | 191100 | A/T | TSC2 | hsa-miR-1283 |
| rs45512692 | 191100 | A/T | TSC2 | hsa-miR-155* |
| rs45512692 | 191100 | A/T | TSC2 | hsa-miR-498 |
| rs45512692 | 191100 | A/T | TSC2 | hsa-miR-205 |
| rs45514100 | 191100 | C/T | TSC2 | hsa-miR-1295 |
| rs45514100 | 191100 | C/T | TSC2 | hsa-miR-1254, hsa-miR-661 |
| rs45514100 | 191100 | C/T | TSC2 | hsa-miR-1285, hsa-miR-612 |

TABLE 2-continued

| SNP | OMIM | MUTATION | GENE | MIR |
|---|---|---|---|---|
| rs45514100 | 191100 | C/T | TSC2 | hsa-miR-596 |
| rs45514100 | 191100 | C/T | TSC2 | hsa-miR-15a* |
| rs45514100 | 191100 | C/T | TSC2 | hsa-miR-645 |
| rs45514196 | 191100 | A/C | TSC2 | hsa-miR-138 |
| rs45514196 | 191100 | A/C | TSC2 | hsa-miR-518c*, hsa-miR-330-5p, hsa-miR-326 |
| rs45514391 | 191100 | C/T | TSC2 | hsa-miR-365* |
| rs45514391 | 191100 | C/T | TSC2 | hsa-miR-616*, hsa-miR-371-5p, hsa-miR-373* |
| rs45514794 | 191100 | G/T | TSC2 | hsa-miR-376a, hsa-miR-376b |
| rs45514993 | 191100 | C/T | TSC2 | hsa-miR-7 |
| rs45514993 | 191100 | C/T | TSC2 | hsa-miR-139-3p |
| rs45514993 | 191100 | C/T | TSC2 | hsa-miR-30c-1*, hsa-miR-30b*, hsa-miR-30c-2* |
| rs45516293 | 191100 | A/C | TSC2 | hsa-miR-1207-5p |
| rs45516293 | 191100 | A/C | TSC2 | hsa-miR-558 |
| rs45516293 | 191100 | A/C | TSC2 | hsa-miR-22 |
| rs45516293 | 191100 | A/C | TSC2 | hsa-miR-1205, hsa-miR-1184, hsa-miR-17* |
| rs45517093 | 191100 | A/G | TSC2 | hsa-miR-659 |
| rs45517093 | 191100 | A/G | TSC2 | hsa-miR-138 |
| rs45517093 | 191100 | A/G | TSC2 | hsa-miR-29b-1* |
| rs45517094 | 191100 | G/T | TSC2 | hsa-miR-513b |
| rs45517094 | 191100 | G/T | TSC2 | hsa-miR-412 |
| rs45517094 | 191100 | G/T | TSC2 | hsa-miR-302c* |
| rs45517094 | 191100 | G/T | TSC2 | hsa-miR-617 |
| rs45517094 | 191100 | G/T | TSC2 | hsa-miR-495, hsa-miR-7-1*, hsa-miR-7-2* |
| rs45517095 | 191100 | A/T | TSC2 | hsa-miR-299-5p |
| rs45517095 | 191100 | A/T | TSC2 | hsa-miR-491-3p |
| rs45517095 | 191100 | A/T | TSC2 | hsa-miR-129-5p |
| rs45517095 | 191100 | A/T | TSC2 | hsa-miR-450a |
| rs45517097 | 191100 | C/T | TSC2 | hsa-miR-20a* |
| rs45517097 | 191100 | C/T | TSC2 | hsa-miR-509-3-5p, hsa-miR-509-5p, hsa-miR-509-5p, hsa-miR-217 |
| rs45517098 | 191100 | C/T | TSC2 | hsa-miR-937 |
| rs45517099 | 191100 | C/T | TSC2 | hsa-miR-221, hsa-miR-222, hsa-miR-187* |
| rs45517099 | 191100 | C/T | TSC2 | hsa-miR-604 |
| rs45517099 | 191100 | C/T | TSC2 | hsa-miR-1283 |
| rs45517100 | 191100 | A/G | TSC2 | hsa-miR-29c, hsa-miR-29b, hsa-miR-29b, hsa-miR-29a |
| rs45517101 | 191100 | G/T | TSC2 | hsa-miR-646, hsa-miR-503, hsa-miR-497, hsa-miR-424, hsa-miR-195, hsa-miR-15b, hsa-miR-16, hsa-miR-15a, hsa-miR-16 |
| rs45517101 | 191100 | G/T | TSC2 | hsa-miR-575 |
| rs45517106 | 191100 | C/T | TSC2 | hsa-miR-760 |
| rs45517108 | 191100 | G/T | TSC2 | hsa-miR-384 |
| rs45517108 | 191100 | G/T | TSC2 | hsa-miR-1283 |
| rs45517108 | 191100 | G/T | TSC2 | hsa-miR-1238 |
| rs45517108 | 191100 | G/T | TSC2 | hsa-miR-155* |
| rs45517109 | 191100 | C/G | TSC2 | hsa-miR-877* |
| rs45517109 | 191100 | C/G | TSC2 | hsa-miR-1912 |
| rs45517109 | 191100 | C/G | TSC2 | hsa-miR-1280, hsa-miR-1224-3p |
| rs45517111 | 191100 | C/T | TSC2 | hsa-miR-139-5p |
| rs45517111 | 191100 | C/T | TSC2 | hsa-miR-1286 |
| rs45517111 | 191100 | C/T | TSC2 | hsa-miR-181a-2* |
| rs45517111 | 191100 | C/T | TSC2 | hsa-miR-509-3-5p, hsa-miR-509-5p, hsa-miR-509-5p, hsa-miR-217 |
| rs45517111 | 191100 | C/T | TSC2 | hsa-miR-1205, hsa-miR-1184, hsa-miR-17* |
| rs45517112 | 191100 | G/T | TSC2 | hsa-miR-554 |
| rs45517113 | 191100 | A/G | TSC2 | hsa-miR-581 |
| rs45517113 | 191100 | A/G | TSC2 | hsa-miR-1915* |
| rs45517113 | 191100 | A/G | TSC2 | hsa-miR-758 |
| rs45517114 | 191100 | C/T | TSC2 | hsa-miR-181c* |
| rs45517114 | 191100 | C/T | TSC2 | hsa-miR-501-5p, hsa-miR-362-5p |
| rs45517114 | 191100 | C/T | TSC2 | hsa-miR-451 |
| rs45517115 | 191100 | C/T | TSC2 | hsa-miR-497* |
| rs45517118 | 191100 | A/G/T | TSC2 | hsa-miR-1259 |
| rs45517119 | 191100 | C/T | TSC2 | hsa-miR-139-5p |
| rs45517119 | 191100 | C/T | TSC2 | hsa-miR-1909 |
| rs45517119 | 191100 | C/T | TSC2 | hsa-miR-1205, hsa-miR-1184, hsa-miR-17* |
| rs45517120 | 191100 | C/T | TSC2 | hsa-miR-338-3p |
| rs45517120 | 191100 | C/T | TSC2 | hsa-miR-198 |
| rs45517120 | 191100 | C/T | TSC2 | hsa-miR-593* |
| rs45517120 | 191100 | C/T | TSC2 | hsa-miR-29c, hsa-miR-29b, hsa-miR-29b, hsa-miR-29a |
| rs45517121 | 191100 | G/T | TSC2 | hsa-miR-338-3p |
| rs45517121 | 191100 | G/T | TSC2 | hsa-miR-198 |
| rs45517122 | 191100 | A/G | TSC2 | hsa-miR-411 |
| rs45517123 | 191100 | C/T | TSC2 | hsa-miR-194 |
| rs45517124 | 191100 | A/G | TSC2 | hsa-miR-196b* |
| rs45517124 | 191100 | A/G | TSC2 | hsa-miR-877 |
| rs45517125 | 191100 | A/C | TSC2 | hsa-miR-760 |

TABLE 2-continued

| SNP | OMIM | MUTATION | GENE | MIR |
|---|---|---|---|---|
| rs45517126 | 191100 | G/T | TSC2 | hsa-miR-621 |
| rs45517127 | 191100 | A/C | TSC2 | hsa-miR-338-3p |
| rs45517127 | 191100 | A/C | TSC2 | hsa-miR-545 |
| rs45517127 | 191100 | A/C | TSC2 | hsa-miR-587 |
| rs45517130 | 191100 | C/T | TSC2 | hsa-miR-499-3p |
| rs45517131 | 191100 | C/T | TSC2 | hsa-miR-149* |
| rs45517131 | 191100 | C/T | TSC2 | hsa-miR-1321 |
| rs45517131 | 191100 | C/T | TSC2 | hsa-miR-192* |
| rs45517131 | 191100 | C/T | TSC2 | hsa-miR-1202 |
| rs45517136 | 191100 | C/T | TSC2 | hsa-miR-136 |
| rs45517137 | 191100 | C/T | TSC2 | hsa-miR-545 |
| rs45517137 | 191100 | C/T | TSC2 | hsa-miR-922, hsa-miR-214 |
| rs45517137 | 191100 | C/T | TSC2 | hsa-miR-1909 |
| rs45517138 | 191100 | C/T | TSC2 | hsa-miR-1207-5p |
| rs45517138 | 191100 | C/T | TSC2 | hsa-miR-1307 |
| rs45517138 | 191100 | C/T | TSC2 | hsa-miR-922, hsa-miR-214 |
| rs45517139 | 191100 | A/G | TSC2 | hsa-miR-942 |
| rs45517139 | 191100 | A/G | TSC2 | hsa-miR-760 |
| rs45517139 | 191100 | A/G | TSC2 | hsa-miR-1236 |
| rs45517141 | 191100 | A/G | TSC2 | hsa-miR-1469 |
| rs45517143 | 191100 | A/C/G | TSC2 | hsa-miR-370 |
| rs45517143 | 191100 | A/C/G | TSC2 | hsa-miR-619 |
| rs45517143 | 191100 | A/C/G | TSC2 | hsa-miR-2053 |
| rs45517144 | 191100 | C/G | TSC2 | hsa-miR-1197 |
| rs45517144 | 191100 | C/G | TSC2 | hsa-miR-103-as |
| rs45517144 | 191100 | C/G | TSC2 | hsa-miR-1228, hsa-miR-220a |
| rs45517145 | 191100 | A/G | TSC2 | hsa-miR-376a, hsa-miR-376b |
| rs45517145 | 191100 | A/G | TSC2 | hsa-miR-200a*, hsa-miR-200b* |
| rs45517146 | 191100 | A/T | TSC2 | hsa-miR-526b |
| rs45517146 | 191100 | A/T | TSC2 | hsa-miR-578 |
| rs45517146 | 191100 | A/T | TSC2 | hsa-miR-138-1* |
| rs45517147 | 191100 | C/T | TSC2 | hsa-miR-298 |
| rs45517147 | 191100 | C/T | TSC2 | hsa-miR-613, hsa-miR-1, hsa-miR-206, hsa-miR-1 |
| rs45517147 | 191100 | C/T | TSC2 | hsa-miR-922, hsa-miR-214 |
| rs45517149 | 191100 | A/G | TSC2 | hsa-miR-1289 |
| rs45517149 | 191100 | A/G | TSC2 | hsa-miR-505* |
| rs45517149 | 191100 | A/G | TSC2 | hsa-miR-708, hsa-miR-28-5p |
| rs45517152 | 191100 | C/G | TSC2 | hsa-miR-183 |
| rs45517153 | 191100 | A/C/T | TSC2 | hsa-miR-130b* |
| rs45517153 | 191100 | A/C/T | TSC2 | hsa-miR-877* |
| rs45517153 | 191100 | A/C/T | TSC2 | hsa-miR-1298 |
| rs45517154 | 191100 | C/T | TSC2 | hsa-miR-766 |
| rs45517154 | 191100 | C/T | TSC2 | hsa-miR-484 |
| rs45517155 | 191100 | A/G | TSC2 | hsa-miR-218-1* |
| rs45517155 | 191100 | A/G | TSC2 | hsa-miR-182* |
| rs45517155 | 191100 | A/G | TSC2 | hsa-miR-218-2* |
| rs45517155 | 191100 | A/G | TSC2 | hsa-miR-1200, hsa-miR-378* |
| rs45517156 | 191100 | G/T | TSC2 | hsa-miR-548h, hsa-miR-548i, hsa-miR-548i, hsa-miR-548i, hsa-miR-548i, hsa-miR-548j, hsa-miR-548k, hsa-miR-548l, hsa-miR-548d-5p, hsa-miR-548d-5p, hsa-miR-548a-5p, hsa-miR-548c-5p, hsa-miR-548b-5p, hsa-miR-559 |
| rs45517156 | 191100 | G/T | TSC2 | hsa-miR-1264 |
| rs45517156 | 191100 | G/T | TSC2 | hsa-miR-593 |
| rs45517157 | 191100 | G/T | TSC2 | hsa-miR-521 |
| rs45517157 | 191100 | G/T | TSC2 | hsa-miR-1263, hsa-miR-150* |
| rs45517158 | 191100 | C/T | TSC2 | hsa-miR-1251, hsa-miR-517*, hsa-miR-517*, hsa-miR-517* |
| rs45517158 | 191100 | C/T | TSC2 | hsa-miR-554 |
| rs45517158 | 191100 | C/T | TSC2 | hsa-miR-518c*, hsa-miR-330-5p, hsa-miR-326 |
| rs45517159 | 191100 | C/T | TSC2 | hsa-miR-220c |
| rs45517159 | 191100 | C/T | TSC2 | hsa-miR-1972 |
| rs45517162 | 191100 | A/G | TSC2 | hsa-miR-191* |
| rs45517162 | 191100 | A/G | TSC2 | hsa-miR-218 |
| rs45517162 | 191100 | A/G | TSC2 | hsa-miR-892a |
| rs45517163 | 191100 | C/T | TSC2 | hsa-miR-24-1*, hsa-miR-24-2* |
| rs45517163 | 191100 | C/T | TSC2 | hsa-miR-139-5p |
| rs45517163 | 191100 | C/T | TSC2 | hsa-miR-657 |
| rs45517163 | 191100 | C/T | TSC2 | hsa-miR-552 |
| rs45517163 | 191100 | C/T | TSC2 | hsa-miR-1205, hsa-miR-1184, hsa-miR-17* |
| rs45517169 | 191100 | C/T | TSC2 | hsa-miR-425* |
| rs45517169 | 191100 | C/T | TSC2 | hsa-miR-365* |
| rs45517169 | 191100 | C/T | TSC2 | hsa-miR-1266 |
| rs45517170 | 191100 | C/T | TSC2 | hsa-miR-1281 |
| rs45517170 | 191100 | C/T | TSC2 | hsa-miR-593* |
| rs45517170 | 191100 | C/T | TSC2 | hsa-miR-566 |
| rs45517171 | 191100 | A/G | TSC2 | hsa-let-7i* |
| rs45517175 | 191100 | A/G | TSC2 | hsa-miR-143 |

TABLE 2-continued

| SNP | OMIM | MUTATION | GENE | MIR |
|---|---|---|---|---|
| rs45517175 | 191100 | A/G | TSC2 | hsa-miR-139-3p |
| rs45517176 | 191100 | A/C | TSC2 | hsa-miR-143 |
| rs45517177 | 191100 | C/G | TSC2 | hsa-miR-631 |
| rs45517177 | 191100 | C/G | TSC2 | hsa-miR-1539 |
| rs45517177 | 191100 | C/G | TSC2 | hsa-miR-558 |
| rs45517177 | 191100 | C/G | TSC2 | hsa-miR-22 |
| rs45517177 | 191100 | C/G | TSC2 | hsa-miR-769-5p |
| rs45517177 | 191100 | C/G | TSC2 | hsa-miR-185 |
| rs45517178 | 191100 | G/T | TSC2 | hsa-miR-542-5p |
| rs45517179 | 191100 | C/T | TSC2 | hsa-miR-30e*, hsa-miR-30d*, hsa-miR-30a* |
| rs45517179 | 191100 | C/T | TSC2 | hsa-miR-492 |
| rs45517180 | 191100 | C/T | TSC2 | hsa-miR-513c |
| rs45517180 | 191100 | C/T | TSC2 | hsa-miR-516a-5p |
| rs45517187 | 191100 | C/T | TSC2 | hsa-miR-591 |
| rs45517187 | 191100 | C/T | TSC2 | hsa-miR-181c* |
| rs45517188 | 191100 | C/T | TSC2 | hsa-miR-766 |
| rs45517196 | 191100 | C/G | TSC2 | hsa-miR-1207-5p |
| rs45517196 | 191100 | C/G | TSC2 | hsa-miR-575 |
| rs45517196 | 191100 | C/G | TSC2 | hsa-miR-1301 |
| rs45517196 | 191100 | C/G | TSC2 | hsa-miR-1909 |
| rs45517196 | 191100 | C/G | TSC2 | hsa-miR-940, hsa-miR-34b* |
| rs45517197 | 191100 | A/G | TSC2 | hsa-miR-29b-2* |
| rs45517197 | 191100 | A/G | TSC2 | hsa-miR-450b-5p, hsa-miR-557, hsa-miR-507 |
| rs45517197 | 191100 | A/G | TSC2 | hsa-miR-1204 |
| rs45517198 | 191100 | A/G | TSC2 | hsa-miR-299-3p |
| rs45517198 | 191100 | A/G | TSC2 | hsa-miR-647 |
| rs45517199 | 191100 | C/T | TSC2 | hsa-miR-558 |
| rs45517199 | 191100 | C/T | TSC2 | hsa-miR-610 |
| rs45517200 | 191100 | C/T | TSC2 | hsa-miR-185* |
| rs45517200 | 191100 | C/T | TSC2 | hsa-miR-491-5p |
| rs45517200 | 191100 | C/T | TSC2 | hsa-miR-558 |
| rs45517201 | 191100 | C/T | TSC2 | hsa-miR-142-3p |
| rs45517201 | 191100 | C/T | TSC2 | hsa-miR-581 |
| rs45517201 | 191100 | C/T | TSC2 | hsa-miR-643 |
| rs45517202 | 191100 | A/T | TSC2 | hsa-miR-636 |
| rs45517202 | 191100 | A/T | TSC2 | hsa-miR-643 |
| rs45517202 | 191100 | A/T | TSC2 | hsa-miR-218 |
| rs45517206 | 191100 | A/C/G | TSC2 | hsa-miR-885-3p |
| rs45517206 | 191100 | A/C/G | TSC2 | hsa-miR-1538 |
| rs45517206 | 191100 | A/C/G | TSC2 | hsa-miR-1301 |
| rs45517206 | 191100 | A/C/G | TSC2 | hsa-miR-1205, hsa-miR-1184, hsa-miR-17* |
| rs45517206 | 191100 | A/C/G | TSC2 | hsa-miR-1234 |
| rs45517208 | 191100 | C/T | TSC2 | hsa-miR-1207-5p |
| rs45517208 | 191100 | C/T | TSC2 | hsa-miR-1908, hsa-miR-663 |
| rs45517208 | 191100 | C/T | TSC2 | hsa-miR-1909 |
| rs45517208 | 191100 | C/T | TSC2 | hsa-miR-744 |
| rs45517209 | 191100 | C/T | TSC2 | hsa-miR-139-5p |
| rs45517209 | 191100 | C/T | TSC2 | hsa-miR-1301 |
| rs45517209 | 191100 | C/T | TSC2 | hsa-miR-509-3-5p, hsa-miR-509-5p, hsa-miR-509-5p, hsa-miR-217 |
| rs45517209 | 191100 | C/T | TSC2 | hsa-miR-1205, hsa-miR-1184, hsa-miR-17* |
| rs45517209 | 191100 | C/T | TSC2 | hsa-miR-103, hsa-miR-107 |
| rs45517210 | 191100 | C/T | TSC2 | hsa-miR-370 |
| rs45517210 | 191100 | C/T | TSC2 | hsa-miR-138-1* |
| rs45517213 | 191100 | A/G | TSC2 | hsa-miR-1248, hsa-miR-1237 |
| rs45517213 | 191100 | A/G | TSC2 | hsa-miR-145 |
| rs45517213 | 191100 | A/G | TSC2 | hsa-miR-554 |
| rs45517214 | 191100 | G/T | TSC2 | hsa-miR-1909 |
| rs45517215 | 191100 | C/G | TSC2 | hsa-miR-1207-5p |
| rs45517215 | 191100 | C/G | TSC2 | hsa-miR-1296 |
| rs45517215 | 191100 | C/G | TSC2 | hsa-miR-135a* |
| rs45517216 | 191100 | C/T | TSC2 | hsa-miR-1207-3p |
| rs45517216 | 191100 | C/T | TSC2 | hsa-miR-138 |
| rs45517216 | 191100 | C/T | TSC2 | hsa-miR-554 |
| rs45517217 | 191100 | C/T | TSC2 | hsa-miR-1207-3p |
| rs45517220 | 191100 | C/G | TSC2 | hsa-miR-330-3p |
| rs45517220 | 191100 | C/G | TSC2 | hsa-miR-1201 |
| rs45517220 | 191100 | C/G | TSC2 | hsa-miR-616*, hsa-miR-371-5p, hsa-miR-373* |
| rs45517220 | 191100 | C/G | TSC2 | hsa-miR-488 |
| rs45517221 | 191100 | C/T | TSC2 | hsa-miR-1825, hsa-miR-199a-5p, hsa-miR-199b-5p, hsa-miR-199a-5p |
| rs45517221 | 191100 | C/T | TSC2 | hsa-miR-145 |
| rs45517221 | 191100 | C/T | TSC2 | hsa-miR-766 |
| rs45517221 | 191100 | C/T | TSC2 | hsa-miR-654-3p |
| rs45517222 | 191100 | C/T | TSC2 | hsa-miR-505* |
| rs45517223 | 191100 | C/T | TSC2 | hsa-miR-1270, hsa-miR-620 |
| rs45517223 | 191100 | C/T | TSC2 | hsa-miR-1299, hsa-miR-516b, hsa-miR-516b |
| rs45517223 | 191100 | C/T | TSC2 | hsa-miR-1253 |

TABLE 2-continued

| SNP | OMIM | MUTATION | GENE | MIR |
|---|---|---|---|---|
| rs45517224 | 191100 | A/G | TSC2 | hsa-miR-1910, hsa-miR-455-3p |
| rs45517224 | 191100 | A/G | TSC2 | hsa-miR-148b* |
| rs45517224 | 191100 | A/G | TSC2 | hsa-miR-1299, hsa-miR-516b, hsa-miR-516b |
| rs45517225 | 191100 | A/C | TSC2 | hsa-miR-584 |
| rs45517225 | 191100 | A/C | TSC2 | hsa-miR-2053 |
| rs45517226 | 191100 | C/T | TSC2 | hsa-miR-1978 |
| rs45517226 | 191100 | C/T | TSC2 | hsa-miR-138-2* |
| rs45517232 | 191100 | C/G | TSC2 | hsa-miR-936, hsa-miR-199a-3p, hsa-miR-199b-3p, hsa-miR-199a-3p |
| rs45517232 | 191100 | C/G | TSC2 | hsa-miR-449b, hsa-miR-449a, hsa-miR-34c-5p, hsa-miR-34a |
| rs45517232 | 191100 | C/G | TSC2 | hsa-miR-28-3p |
| rs45517232 | 191100 | C/G | TSC2 | hsa-miR-940, hsa-miR-34b* |
| rs45517232 | 191100 | C/G | TSC2 | hsa-miR-411 |
| rs45517233 | 191100 | C/T | TSC2 | hsa-miR-767-3p |
| rs45517233 | 191100 | C/T | TSC2 | hsa-miR-508-5p |
| rs45517233 | 191100 | C/T | TSC2 | hsa-miR-370 |
| rs45517233 | 191100 | C/T | TSC2 | hsa-miR-146b-3p |
| rs45517233 | 191100 | C/T | TSC2 | hsa-miR-18b* |
| rs45517234 | 191100 | C/T | TSC2 | hsa-miR-664*, hsa-miR-149 |
| rs45517234 | 191100 | C/T | TSC2 | hsa-miR-647 |
| rs45517234 | 191100 | C/T | TSC2 | hsa-miR-892b, hsa-miR-193b, hsa-miR-193a-3p |
| rs45517238 | 191100 | A/C | TSC2 | hsa-miR-1226 |
| rs45517238 | 191100 | A/C | TSC2 | hsa-miR-589* |
| rs45517239 | 191100 | C/T | TSC2 | hsa-miR-1226 |
| rs45517239 | 191100 | C/T | TSC2 | hsa-miR-589* |
| rs45517240 | 191100 | C/T | TSC2 | hsa-miR-873 |
| rs45517240 | 191100 | C/T | TSC2 | hsa-miR-1292 |
| rs45517240 | 191100 | C/T | TSC2 | hsa-miR-184 |
| rs45517248 | 191100 | C/T | TSC2 | hsa-miR-1203 |
| rs45517248 | 191100 | C/T | TSC2 | hsa-miR-588 |
| rs45517249 | 191100 | C/T | TSC2 | hsa-miR-937 |
| rs45517250 | 191100 | C/T | TSC2 | hsa-miR-767-3p |
| rs45517251 | 191100 | C/T | TSC2 | hsa-miR-509-3p |
| rs45517251 | 191100 | C/T | TSC2 | hsa-miR-193b* |
| rs45517251 | 191100 | C/T | TSC2 | hsa-miR-1914*, hsa-miR-423-5p |
| rs45517251 | 191100 | C/T | TSC2 | hsa-miR-92a-1* |
| rs45517253 | 191100 | C/G | TSC2 | hsa-miR-135b, hsa-miR-135a, hsa-miR-135a |
| rs45517254 | 191100 | A/G | TSC2 | hsa-miR-140-3p |
| rs45517254 | 191100 | A/G | TSC2 | hsa-miR-606 |
| rs45517256 | 191100 | G/T | TSC2 | hsa-miR-891b |
| rs45517256 | 191100 | G/T | TSC2 | hsa-miR-593* |
| rs45517256 | 191100 | G/T | TSC2 | hsa-miR-196a* |
| rs45517257 | 191100 | A/C | TSC2 | hsa-miR-593* |
| rs45517258 | 191100 | C/G/T | TSC2 | hsa-miR-525-5p, hsa-miR-520a-5p |
| rs45517258 | 191100 | C/G/T | TSC2 | hsa-miR-1180 |
| rs45517259 | 191100 | A/G | TSC2 | hsa-miR-875-3p |
| rs45517259 | 191100 | A/G | TSC2 | hsa-miR-1180 |
| rs45517259 | 191100 | A/G | TSC2 | hsa-miR-1248, hsa-miR-1237 |
| rs45517259 | 191100 | A/G | TSC2 | hsa-miR-1299, hsa-miR-516b, hsa-miR-516b |
| rs45517267 | 191100 | C/G | — | hsa-miR-629* |
| rs45517268 | 191100 | G/T | TSC2 | hsa-miR-942 |
| rs45517269 | 191100 | G/T | TSC2 | hsa-miR-1207-3p |
| rs45517269 | 191100 | G/T | TSC2 | hsa-miR-1301 |
| rs45517269 | 191100 | G/T | TSC2 | hsa-miR-125a-5p, hsa-miR-125b, hsa-miR-125b |
| rs45517269 | 191100 | G/T | TSC2 | hsa-miR-127-5p |
| rs45517269 | 191100 | G/T | TSC2 | hsa-miR-1205, hsa-miR-1184, hsa-miR-17* |
| rs45517270 | 191100 | G/T | TSC2 | hsa-miR-1251, hsa-miR-517*, hsa-miR-517*, hsa-miR-517* |
| rs45517273 | 191100 | A/T | TSC2 | hsa-miR-615-5p |
| rs45517273 | 191100 | A/T | TSC2 | hsa-miR-365* |
| rs45517273 | 191100 | A/T | TSC2 | hsa-miR-625 |
| rs45517273 | 191100 | A/T | TSC2 | hsa-miR-892b, hsa-miR-193b, hsa-miR-193a-3p |
| rs45517273 | 191100 | A/T | TSC2 | hsa-miR-193a-5p |
| rs45517273 | 191100 | A/T | TSC2 | hsa-miR-1288 |
| rs45517274 | 191100 | A/G | TSC2 | hsa-miR-1978 |
| rs45517274 | 191100 | A/G | TSC2 | hsa-miR-635 |
| rs45517274 | 191100 | A/G | TSC2 | hsa-miR-1915* |
| rs45517275 | 191100 | A/G | TSC2 | hsa-miR-1262 |
| rs45517275 | 191100 | A/G | TSC2 | hsa-miR-1308 |
| rs45517277 | 191100 | A/G | TSC2 | hsa-miR-92b* |
| rs45517277 | 191100 | A/G | TSC2 | hsa-miR-1231, hsa-miR-632 |
| rs45517277 | 191100 | A/G | TSC2 | hsa-miR-654-3p |
| rs45517278 | 191100 | G/T | TSC2 | hsa-miR-602 |
| rs45517278 | 191100 | G/T | TSC2 | hsa-miR-1285, hsa-miR-612 |
| rs45517278 | 191100 | G/T | TSC2 | hsa-miR-1302 |
| rs45517280 | 191100 | A/G | TSC2 | hsa-miR-525-5p, hsa-miR-520a-5p |
| rs45517280 | 191100 | A/G | TSC2 | hsa-miR-198 |

TABLE 2-continued

| SNP | OMIM | MUTATION | GENE | MIR |
|---|---|---|---|---|
| rs45517281 | 191100 | C/T | TSC2 | hsa-miR-1270, hsa-miR-620 |
| rs45517281 | 191100 | C/T | TSC2 | hsa-miR-7 |
| rs45517281 | 191100 | C/T | TSC2 | hsa-miR-2110 |
| rs45517281 | 191100 | C/T | TSC2 | hsa-miR-1253 |
| rs45517284 | 191100 | C/T | TSC2 | hsa-miR-1286 |
| rs45517284 | 191100 | C/T | TSC2 | hsa-miR-220c |
| rs45517285 | 191100 | C/T | TSC2 | hsa-miR-629 |
| rs45517285 | 191100 | C/T | TSC2 | hsa-miR-575 |
| rs45517285 | 191100 | C/T | TSC2 | hsa-miR-125b-1* |
| rs45517286 | 191100 | C/G | TSC2 | hsa-miR-508-5p |
| rs45517286 | 191100 | C/G | TSC2 | hsa-miR-198 |
| rs45517286 | 191100 | C/G | TSC2 | hsa-miR-766 |
| rs45517287 | 191100 | A/C | TSC2 | hsa-miR-554 |
| rs45517288 | 191100 | C/T | TSC2 | hsa-miR-139-5p |
| rs45517288 | 191100 | C/T | TSC2 | hsa-miR-1301 |
| rs45517288 | 191100 | C/T | TSC2 | hsa-miR-1288 |
| rs45517288 | 191100 | C/T | TSC2 | hsa-miR-509-3-5p, hsa-miR-509-5p, hsa-miR-509-5p, hsa-miR-217 |
| rs45517288 | 191100 | C/T | TSC2 | hsa-miR-1205, hsa-miR-1184, hsa-miR-17* |
| rs45517292 | 191100 | C/T | TSC2 | hsa-miR-370 |
| rs45517292 | 191100 | C/T | TSC2 | hsa-miR-93* |
| rs45517294 | 191100 | G/T | TSC2 | hsa-miR-31 |
| rs45517294 | 191100 | G/T | TSC2 | hsa-miR-564 |
| rs45517295 | 191100 | C/T | TSC2 | hsa-miR-132* |
| rs45517296 | 191100 | A/C/G | TSC2 | hsa-miR-1295 |
| rs45517296 | 191100 | A/C/G | TSC2 | hsa-miR-1207-3p |
| rs45517296 | 191100 | A/C/G | TSC2 | hsa-miR-590-5p, hsa-miR-21 |
| rs45517296 | 191100 | A/C/G | TSC2 | hsa-miR-1972 |
| rs45517296 | 191100 | A/C/G | TSC2 | hsa-miR-1266 |
| rs45517297 | 191100 | C/T | TSC2 | hsa-miR-155* |
| rs45517297 | 191100 | C/T | TSC2 | hsa-miR-1976 |
| rs45517298 | 191100 | C/T | TSC2 | hsa-miR-146b-3p |
| rs45517298 | 191100 | C/T | TSC2 | hsa-miR-18b* |
| rs45517305 | 191100 | A/C | TSC2 | hsa-miR-611, hsa-miR-151-5p |
| rs45517306 | 191100 | C/T | TSC2 | hsa-miR-139-5p |
| rs45517306 | 191100 | C/T | TSC2 | hsa-miR-1909 |
| rs45517306 | 191100 | C/T | TSC2 | hsa-miR-155* |
| rs45517306 | 191100 | C/T | TSC2 | hsa-miR-1205, hsa-miR-1184, hsa-miR-17* |
| rs45517306 | 191100 | C/T | TSC2 | hsa-miR-1976 |
| rs45517307 | 191100 | C/T | TSC2 | hsa-miR-558 |
| rs45517308 | 191100 | C/G | TSC2 | hsa-miR-139-5p |
| rs45517308 | 191100 | C/G | TSC2 | hsa-miR-617 |
| rs45517308 | 191100 | C/G | TSC2 | hsa-miR-643 |
| rs45517308 | 191100 | C/G | TSC2 | hsa-miR-493*, hsa-let-7g*, hsa-let-7a-2* |
| rs45517309 | 191100 | C/G | TSC2 | hsa-miR-668 |
| rs45517309 | 191100 | C/G | TSC2 | hsa-miR-134 |
| rs45517310 | 191100 | A/C | TSC2 | hsa-miR-1978 |
| rs45517311 | 191100 | C/T | TSC2 | hsa-miR-1914*, hsa-miR-423-5p |
| rs45517311 | 191100 | C/T | TSC2 | hsa-miR-1253 |
| rs45517314 | 191100 | A/G | TSC2 | hsa-miR-485-5p |
| rs45517314 | 191100 | A/G | TSC2 | hsa-miR-181a-2* |
| rs45517314 | 191100 | A/G | TSC2 | hsa-miR-15a* |
| rs45517319 | 191100 | A/G | TSC2 | hsa-miR-658 |
| rs45517319 | 191100 | A/G | TSC2 | hsa-miR-25* |
| rs45517321 | 191100 | G/T | TSC2 | hsa-miR-221, hsa-miR-222, hsa-miR-187* |
| rs45517323 | 191100 | A/G | TSC2 | hsa-miR-933 |
| rs45517323 | 191100 | A/G | TSC2 | hsa-miR-550 |
| rs45517323 | 191100 | A/G | TSC2 | hsa-miR-1973 |
| rs45517326 | 191100 | A/C | TSC2 | hsa-miR-617 |
| rs45517326 | 191100 | A/C | TSC2 | hsa-miR-610 |
| rs45517326 | 191100 | A/C | TSC2 | hsa-miR-138-1* |
| rs45517327 | 191100 | G/T | TSC2 | hsa-miR-1470 |
| rs45517328 | 191100 | C/T | TSC2 | hsa-miR-449b* |
| rs45517329 | 191100 | C/T | TSC2 | hsa-miR-875-3p |
| rs45517329 | 191100 | C/T | TSC2 | hsa-miR-1287 |
| rs45517330 | 191100 | C/T | TSC2 | hsa-miR-139-5p |
| rs45517330 | 191100 | C/T | TSC2 | hsa-miR-934 |
| rs45517330 | 191100 | C/T | TSC2 | hsa-miR-1301 |
| rs45517330 | 191100 | C/T | TSC2 | hsa-miR-346 |
| rs45517330 | 191100 | C/T | TSC2 | hsa-miR-1205, hsa-miR-1184, hsa-miR-17* |
| rs45517331 | 191100 | C/T | TSC2 | hsa-miR-598 |
| rs45517331 | 191100 | C/T | TSC2 | hsa-miR-1234 |
| rs45517332 | 191100 | C/G | TSC2 | hsa-miR-1915 |
| rs45517332 | 191100 | C/G | TSC2 | hsa-miR-662 |
| rs45517332 | 191100 | C/G | TSC2 | hsa-miR-431* |
| rs45517333 | 191100 | C/T | TSC2 | hsa-miR-575 |
| rs45517334 | 191100 | A/G | TSC2 | hsa-miR-383 |
| rs45517334 | 191100 | A/G | TSC2 | hsa-miR-1911* |

TABLE 2-continued

| SNP | OMIM | MUTATION | GENE | MIR |
|---|---|---|---|---|
| rs45517335 | 191100 | A/C | TSC2 | hsa-miR-1295 |
| rs45517335 | 191100 | A/C | TSC2 | hsa-miR-1249 |
| rs45517335 | 191100 | A/C | TSC2 | hsa-miR-18b* |
| rs45517335 | 191100 | A/C | TSC2 | hsa-miR-645 |
| rs45517336 | 191100 | C/T | TSC2 | hsa-miR-511 |
| rs45517336 | 191100 | C/T | TSC2 | hsa-miR-141* |
| rs45517337 | 191100 | C/T | TSC2 | hsa-miR-621 |
| rs45517337 | 191100 | C/T | TSC2 | hsa-miR-328 |
| rs45517338 | 191100 | C/G | TSC2 | hsa-miR-939 |
| rs45517338 | 191100 | C/G | TSC2 | hsa-miR-1908, hsa-miR-663 |
| rs45517338 | 191100 | C/G | TSC2 | hsa-miR-625 |
| rs45517338 | 191100 | C/G | TSC2 | hsa-miR-744 |
| rs45517339 | 191100 | C/T | TSC2 | hsa-miR-31 |
| rs45517339 | 191100 | C/T | TSC2 | hsa-miR-1228* |
| rs45517340 | 191100 | C/T | TSC2 | hsa-miR-1266 |
| rs45517341 | 191100 | A/C | TSC2 | hsa-miR-554 |
| rs45517343 | 191100 | C/G | TSC2 | hsa-miR-642 |
| rs45517343 | 191100 | C/G | TSC2 | hsa-miR-550 |
| rs45517344 | 191100 | A/C | TSC2 | hsa-miR-193b* |
| rs45517344 | 191100 | A/C | TSC2 | hsa-miR-637 |
| rs45517344 | 191100 | A/C | TSC2 | hsa-miR-563, hsa-miR-380* |
| rs45517344 | 191100 | A/C | TSC2 | hsa-miR-653 |
| rs45517348 | 191100 | C/T | TSC2 | hsa-miR-221, hsa-miR-222, hsa-miR-187* |
| rs45517348 | 191100 | C/T | TSC2 | hsa-miR-139-5p |
| rs45517348 | 191100 | C/T | TSC2 | hsa-miR-1286 |
| rs45517348 | 191100 | C/T | TSC2 | hsa-miR-558 |
| rs45517348 | 191100 | C/T | TSC2 | hsa-miR-22 |
| rs45517348 | 191100 | C/T | TSC2 | hsa-miR-610 |
| rs45517348 | 191100 | C/T | TSC2 | hsa-miR-1205, hsa-miR-1184, hsa-miR-17* |
| rs45517349 | 191100 | G/T | TSC2 | hsa-miR-143 |
| rs45517349 | 191100 | G/T | TSC2 | hsa-miR-558 |
| rs45517349 | 191100 | G/T | TSC2 | hsa-miR-22 |
| rs45517349 | 191100 | G/T | TSC2 | hsa-miR-1205, hsa-miR-1184, hsa-miR-17* |
| rs45517352 | 191100 | C/T | TSC2 | hsa-miR-1288 |
| rs45517352 | 191100 | C/T | TSC2 | hsa-miR-134 |
| rs45517352 | 191100 | C/T | TSC2 | hsa-miR-892a |
| rs45517353 | 191100 | G/T | TSC2 | hsa-miR-379 |
| rs45517353 | 191100 | G/T | TSC2 | hsa-miR-611, hsa-miR-151-5p |
| rs45517353 | 191100 | G/T | TSC2 | hsa-miR-877 |
| rs45517354 | 191100 | C/T | TSC2 | hsa-miR-1197 |
| rs45517354 | 191100 | C/T | TSC2 | hsa-miR-184 |
| rs45517355 | 191100 | A/G | TSC2 | hsa-miR-603, hsa-miR-329, hsa-miR-329, hsa-miR-362-3p |
| rs45517355 | 191100 | A/G | TSC2 | hsa-miR-220c |
| rs45517360 | 191100 | A/G | TSC2 | hsa-miR-639 |
| rs45517360 | 191100 | A/G | TSC2 | hsa-miR-720 |
| rs45517360 | 191100 | A/G | TSC2 | hsa-miR-27b* |
| rs45517361 | 191100 | C/G | TSC2 | hsa-miR-588 |
| rs45517361 | 191100 | C/G | TSC2 | hsa-miR-652 |
| rs45517362 | 191100 | C/T | TSC2 | hsa-miR-184 |
| rs45517362 | 191100 | C/T | TSC2 | hsa-miR-1265 |
| rs45517364 | 191100 | A/G | TSC2 | hsa-miR-1289 |
| rs45517364 | 191100 | A/G | TSC2 | hsa-miR-505* |
| rs45517364 | 191100 | A/G | TSC2 | hsa-miR-708, hsa-miR-28-5p |
| rs45517365 | 191100 | A/T | TSC2 | hsa-miR-20b* |
| rs45517365 | 191100 | A/T | TSC2 | hsa-miR-936, hsa-miR-199a-3p, hsa-miR-199b-3p, hsa-miR-199a-3p |
| rs45517365 | 191100 | A/T | TSC2 | hsa-miR-770-5p |
| rs45517365 | 191100 | A/T | TSC2 | hsa-miR-486-5p |
| rs45517365 | 191100 | A/T | TSC2 | hsa-miR-135b* |
| rs45517366 | 191100 | C/G | TSC2 | hsa-miR-934 |
| rs45517366 | 191100 | C/G | TSC2 | hsa-miR-340* |
| rs45517367 | 191100 | C/T | TSC2 | hsa-miR-1915 |
| rs45517367 | 191100 | C/T | TSC2 | hsa-miR-296-5p |
| rs45517367 | 191100 | C/T | TSC2 | hsa-miR-1538 |
| rs45517367 | 191100 | C/T | TSC2 | hsa-miR-1972 |
| rs45517368 | 191100 | C/G | TSC2 | hsa-miR-221, hsa-miR-222, hsa-miR-187* |
| rs45517368 | 191100 | C/G | TSC2 | hsa-miR-1915 |
| rs45517369 | 191100 | A/G | TSC2 | hsa-miR-1915 |
| rs45517369 | 191100 | A/G | TSC2 | hsa-miR-532-3p, hsa-miR-150 |
| rs45517369 | 191100 | A/G | TSC2 | hsa-miR-1266 |
| rs45517370 | 191100 | C/T | TSC2 | hsa-miR-198 |
| rs45517370 | 191100 | C/T | TSC2 | hsa-miR-1972 |
| rs45517371 | 191100 | A/G | TSC2 | hsa-miR-338-3p |
| rs45517371 | 191100 | A/G | TSC2 | hsa-miR-621 |
| rs45517371 | 191100 | A/G | TSC2 | hsa-miR-1227 |
| rs45517371 | 191100 | A/G | TSC2 | hsa-miR-922, hsa-miR-214 |
| rs45517371 | 191100 | A/G | TSC2 | hsa-miR-1202 |

TABLE 2-continued

| SNP | OMIM | MUTATION | GENE | MIR |
|---|---|---|---|---|
| rs45517372 | 191100 | A/G | TSC2 | hsa-miR-597 |
| rs45517372 | 191100 | A/G | TSC2 | hsa-miR-338-3p |
| rs45517372 | 191100 | A/G | TSC2 | hsa-miR-517c, hsa-miR-517a |
| rs45517372 | 191100 | A/G | TSC2 | hsa-miR-1227 |
| rs45517372 | 191100 | A/G | TSC2 | hsa-miR-187 |
| rs45517372 | 191100 | A/G | TSC2 | hsa-miR-1202 |
| rs45517378 | 191100 | C/T | TSC2 | hsa-miR-7 |
| rs45517378 | 191100 | C/T | TSC2 | hsa-miR-483-5p |
| rs45517378 | 191100 | C/T | TSC2 | hsa-miR-553 |
| rs45517378 | 191100 | C/T | TSC2 | hsa-miR-424* |
| rs45517378 | 191100 | C/T | TSC2 | hsa-miR-337-5p |
| rs45517378 | 191100 | C/T | TSC2 | hsa-miR-570 |
| rs45517379 | 191100 | A/C | TSC2 | hsa-miR-663b |
| rs45517379 | 191100 | A/C | TSC2 | hsa-miR-328 |
| rs45517379 | 191100 | A/C | TSC2 | hsa-miR-1204 |
| rs45517381 | 191100 | C/G | TSC2 | hsa-miR-502-5p |
| rs45517381 | 191100 | C/G | TSC2 | hsa-miR-1915* |
| rs45517382 | 191100 | A/G | TSC2 | hsa-miR-20b* |
| rs45517382 | 191100 | A/G | TSC2 | hsa-miR-1208 |
| rs45517382 | 191100 | A/G | TSC2 | hsa-miR-668 |
| rs45517382 | 191100 | A/G | TSC2 | hsa-miR-616 |
| rs45517382 | 191100 | A/G | TSC2 | hsa-miR-1183 |
| rs45517383 | 191100 | C/T | TSC2 | hsa-miR-224 |
| rs45517383 | 191100 | C/T | TSC2 | hsa-miR-1203 |
| rs45517383 | 191100 | C/T | TSC2 | hsa-miR-1289 |
| rs45517384 | 191100 | A/C/T | TSC2 | hsa-miR-1226 |
| rs45517384 | 191100 | A/C/T | TSC2 | hsa-miR-1203 |
| rs45517384 | 191100 | A/C/T | TSC2 | hsa-miR-1289 |
| rs45517384 | 191100 | A/C/T | TSC2 | hsa-miR-627 |
| rs45517384 | 191100 | A/C/T | TSC2 | hsa-miR-197 |
| rs45517385 | 191100 | C/T | TSC2 | hsa-miR-100* |
| rs45517387 | 191100 | C/T | TSC2 | hsa-miR-486-3p |
| rs45517387 | 191100 | C/T | TSC2 | hsa-miR-593* |
| rs45517387 | 191100 | C/T | TSC2 | hsa-miR-767-5p |
| rs45517388 | 191100 | C/T | TSC2 | hsa-miR-139-5p |
| rs45517388 | 191100 | C/T | TSC2 | hsa-miR-1909 |
| rs45517388 | 191100 | C/T | TSC2 | hsa-miR-509-3-5p, hsa-miR-509-5p, hsa-miR-509-5p, hsa-miR-217 |
| rs45517388 | 191100 | C/T | TSC2 | hsa-miR-1205, hsa-miR-1184, hsa-miR-17* |
| rs45517392 | 191100 | A/G | TSC2 | hsa-miR-1974, hsa-miR-453 |
| rs45517393 | 191100 | C/G/T | TSC2 | hsa-miR-518e |
| rs45517393 | 191100 | C/G/T | TSC2 | hsa-miR-1207-5p |
| rs45517394 | 191100 | A/C | TSC2 | hsa-miR-1908, hsa-miR-663 |
| rs45517395 | 191100 | A/C/G | TSC2 | hsa-miR-1908, hsa-miR-663 |
| rs45517395 | 191100 | A/C/G | TSC2 | hsa-miR-541, hsa-miR-654-5p, hsa-miR-92a-2* |
| rs45517395 | 191100 | A/C/G | TSC2 | hsa-miR-637 |
| rs45517395 | 191100 | A/C/G | TSC2 | hsa-miR-1275 |
| rs45517396 | 191100 | C/T | TSC2 | hsa-miR-1908, hsa-miR-663 |
| rs45517397 | 191100 | C/G | TSC2 | hsa-miR-486-3p |
| rs45517398 | 191100 | C/T | TSC2 | hsa-miR-517b |
| rs45517398 | 191100 | C/T | TSC2 | hsa-miR-143* |
| rs45517398 | 191100 | C/T | TSC2 | hsa-miR-1909 |
| rs45517398 | 191100 | C/T | TSC2 | hsa-miR-744 |
| rs45517407 | 191100 | A/C | TSC2 | hsa-miR-1207-3p |
| rs45517408 | 191100 | C/T | TSC2 | hsa-miR-491-5p |
| rs45517408 | 191100 | C/T | TSC2 | hsa-miR-15a* |
| rs45517408 | 191100 | C/T | TSC2 | hsa-miR-1294 |
| rs45517409 | 191100 | C/T | TSC2 | hsa-miR-646, hsa-miR-503, hsa-miR-497, hsa-miR-424, hsa-miR-195, hsa-miR-15b, hsa-miR-16, hsa-miR-15a, hsa-miR-16 |
| rs45517410 | 191100 | A/C | TSC2 | hsa-miR-296-3p |
| rs45517410 | 191100 | A/C | TSC2 | hsa-miR-1914*, hsa-miR-423-5p |
| rs45517410 | 191100 | A/C | TSC2 | hsa-miR-379 |
| rs45517412 | 191100 | C/G/T | TSC2 | hsa-miR-575 |
| rs45517412 | 191100 | C/G/T | TSC2 | hsa-miR-1225-3p, hsa-miR-1233 |
| rs45517413 | 191100 | C/T | TSC2 | hsa-miR-1908, hsa-miR-663 |
| rs45517413 | 191100 | C/T | TSC2 | hsa-miR-658 |
| rs45517413 | 191100 | C/T | TSC2 | hsa-miR-25* |
| rs45517413 | 191100 | C/T | TSC2 | hsa-miR-505* |
| rs45517413 | 191100 | C/T | TSC2 | hsa-miR-744 |
| rs45517414 | 191100 | C/T | TSC2 | hsa-miR-621 |
| rs45517414 | 191100 | C/T | TSC2 | hsa-miR-25* |
| rs45517418 | 191100 | A/C | TSC2 | hsa-miR-1302 |
| rs45517418 | 191100 | A/C | TSC2 | hsa-miR-31* |
| rs45517419 | 191100 | A/G | TSC2 | hsa-miR-575 |
| rs45517419 | 191100 | A/G | TSC2 | hsa-miR-125a-3p |
| rs45517420 | 191100 | C/G | TSC2 | hsa-miR-376a, hsa-miR-376b |
| rs45517420 | 191100 | C/G | TSC2 | hsa-miR-103-as |

TABLE 2-continued

| SNP | OMIM | MUTATION | GENE | MIR |
|---|---|---|---|---|
| rs45517421 | 191100 | A/G | TSC2 | hsa-miR-664*, hsa-miR-149 |
| rs45517421 | 191100 | A/G | TSC2 | hsa-miR-328 |
| rs45517421 | 191100 | A/G | TSC2 | hsa-miR-24 |
| rs45517421 | 191100 | A/G | TSC2 | hsa-miR-1280, hsa-miR-1224-3p |
| rs45517422 | 191100 | C/G | TSC2 | hsa-miR-1180 |
| rs45517422 | 191100 | C/G | TSC2 | hsa-miR-663b |
| rs45517422 | 191100 | C/G | TSC2 | hsa-miR-572 |
| rs45517423 | 191100 | C/T | TSC2 | hsa-miR-516a-3p, hsa-miR-516b*, hsa-miR-516b* |
| rs45517423 | 191100 | C/T | TSC2 | hsa-miR-1827 |
| rs55870409 | 141800 | C/T | HBA2 | hsa-miR-1978 |
| rs55948437 | 141850 | A/C | HBA1 | hsa-miR-933 |
| rs55948437 | 141850 | A/C | HBA1 | hsa-let-7i* |
| rs55948437 | 141850 | A/C | HBA1 | hsa-miR-675 |
| rs55948437 | 141850 | A/C | HBA1 | hsa-miR-1178 |
| rs55948437 | 141850 | A/C | HBA1 | hsa-miR-513a-5p, hsa-miR-27b, hsa-miR-27a |
| rs55948437 | 141850 | A/C | HBA1 | hsa-miR-342-3p |
| rs56205611 | 142200 | C/G | HBG1 | hsa-miR-483-3p |
| rs56205611 | 142200 | C/G | HBG1 | hsa-miR-508-5p |
| rs56205611 | 142200 | C/G | HBG1 | hsa-miR-145 |
| rs56205611 | 142200 | C/G | HBG1 | hsa-miR-181a-2* |
| rs56205611 | 142200 | C/G | HBG1 | hsa-miR-509-3-5p, hsa-miR-509-5p, hsa-miR-509-5p, hsa-miR-217 |
| rs56205611 | 142200 | C/G | HBG1 | hsa-miR-1205, hsa-miR-1184, hsa-miR-17* |
| rs56205611 | 142200 | C/G | HBG1 | hsa-miR-766 |
| rs56308100 | 141850 | A/C | HBA1 | hsa-miR-1250 |
| rs56308100 | 141850 | A/C | HBA1 | hsa-miR-1178 |
| rs56308100 | 141850 | A/C | HBA1 | hsa-miR-1229 |
| rs56308100 | 141850 | A/C | HBA1 | hsa-miR-182* |
| rs56348461 | 141800 | A/C | HBA2 | hsa-miR-299-3p |
| rs56348461 | 141800 | A/C | HBA2 | hsa-miR-567 |
| rs56673169 | 0 | C/G | LMNA | hsa-miR-634 |
| rs56673169 | 0 | C/G | LMNA | hsa-miR-1911* |
| rs56699480 | 0 | C/T | LMNA | hsa-miR-1913, hsa-miR-324-3p, hsa-miR-18a* |
| rs56699480 | 0 | C/T | LMNA | hsa-miR-1912 |
| rs56707768 | 0 | A/G | KRT9 | hsa-miR-219-2-3p |
| rs56707768 | 0 | A/G | KRT9 | hsa-miR-589, hsa-miR-146b-5p, hsa-miR-146a |
| rs57019720 | 0 | A/G | KRT9 | hsa-miR-20a* |
| rs57019720 | 0 | A/G | KRT9 | hsa-miR-200a*, hsa-miR-200b* |
| rs57019720 | 0 | A/G | KRT9 | hsa-miR-500* |
| rs57052654 | 0 | G/T | KRT6A | hsa-miR-646, hsa-miR-503, hsa-miR-497, hsa-miR-424, hsa-miR-195, hsa-miR-15b, hsa-miR-16, hsa-miR-15a, hsa-miR-16 |
| rs57052654 | 0 | G/T | KRT6A | hsa-miR-338-3p |
| rs57052654 | 0 | G/T | KRT6A | hsa-miR-922, hsa-miR-214 |
| rs57052654 | 0 | G/T | KRT6A | hsa-miR-766 |
| rs57120761 | 0 | C/T | GFAP | hsa-miR-508-5p |
| rs57121345 | 0 | A/C | — | hsa-miR-1202 |
| rs57318642 | 0 | C/T | — | hsa-miR-220c |
| rs57348201 | 0 | A/T | KRT5 | hsa-miR-621 |
| rs57358989 | 0 | A/G | KRT16 | hsa-miR-544 |
| rs57358989 | 0 | A/G | KRT16 | hsa-miR-20a* |
| rs57358989 | 0 | A/G | KRT16 | hsa-miR-584 |
| rs57358989 | 0 | A/G | KRT16 | hsa-miR-297, hsa-miR-675* |
| rs57364972 | 0 | A/T | KRT14 | hsa-miR-338-3p |
| rs57364972 | 0 | A/T | KRT14 | hsa-miR-922, hsa-miR-214 |
| rs57364972 | 0 | A/T | KRT14 | hsa-miR-1205, hsa-miR-1184, hsa-miR-17* |
| rs57364972 | 0 | A/T | KRT14 | hsa-miR-766 |
| rs57364972 | 0 | A/T | KRT14 | hsa-miR-1976 |
| rs57419521 | 0 | A/G | KRT81 | hsa-miR-502-5p |
| rs57419521 | 0 | A/G | KRT81 | hsa-miR-1249 |
| rs57419521 | 0 | A/G | KRT81 | hsa-miR-1915* |
| rs57419521 | 0 | A/G | KRT81 | hsa-miR-874 |
| rs57424749 | 0 | C/G | KRT16 | hsa-miR-615-5p |
| rs57499803 | 264800 | C/T | ABCC6 | hsa-miR-181a* |
| rs57499803 | 264800 | C/T | ABCC6 | hsa-miR-1247 |
| rs57499817 | 0 | C/T | KRT5 | hsa-miR-1324 |
| rs57499817 | 0 | C/T | KRT5 | hsa-miR-483-5p |
| rs57499817 | 0 | C/T | KRT5 | hsa-miR-608, hsa-miR-342-5p |
| rs57520892 | 0 | C/G | LMNA | hsa-miR-1207-5p |
| rs57520892 | 0 | C/G | LMNA | hsa-miR-940, hsa-miR-34b* |
| rs57521499 | 0 | A/G | LMNB2 | hsa-miR-876-3p, hsa-miR-323-5p |
| rs57521499 | 0 | A/G | LMNB2 | hsa-miR-25* |
| rs57536312 | 0 | A/T | KRT9 | hsa-miR-219-2-3p |
| rs57639980 | 0 | C/T | DES | hsa-miR-542-5p |
| rs57758262 | 0 | A/G | KRT9 | hsa-miR-1207-3p |
| rs57758262 | 0 | A/G | KRT9 | hsa-miR-1300, hsa-miR-580 |
| rs57830985 | 0 | A/G | LMNA | hsa-miR-301b, hsa-miR-454, hsa-miR-301a, hsa-miR-130b, hsa-miR-130a |

TABLE 2-continued

| SNP | OMIM | MUTATION | GENE | MIR |
|---|---|---|---|---|
| rs57830985 | 0 | A/G | LMNA | hsa-miR-143* |
| rs57830985 | 0 | A/G | LMNA | hsa-miR-339-3p |
| rs57830985 | 0 | A/G | LMNA | hsa-miR-1909* |
| rs57837128 | 0 | C/T | KRT1 | hsa-miR-216b, hsa-miR-216a |
| rs57837128 | 0 | C/T | KRT1 | hsa-miR-622 |
| rs57837128 | 0 | C/T | KRT1 | hsa-miR-449b, hsa-miR-449a, hsa-miR-34c-5p, hsa-miR-34a |
| rs57872071 | 0 | A/G | KRT3 | hsa-miR-502-5p |
| rs57872071 | 0 | A/G | KRT3 | hsa-miR-1249 |
| rs57872071 | 0 | A/G | KRT3 | hsa-miR-1915* |
| rs57872071 | 0 | A/G | KRT3 | hsa-miR-874 |
| rs57920071 | 0 | C/T | LMNA | hsa-miR-770-5p |
| rs57920071 | 0 | C/T | LMNA | hsa-miR-545* |
| rs57955682 | 0 | C/T | DES | hsa-miR-105* |
| rs57965306 | 0 | C/G | DES | hsa-miR-1180 |
| rs58058996 | 0 | G/T | KRT5 | hsa-miR-664*, hsa-miR-149 |
| rs58058996 | 0 | G/T | KRT5 | hsa-miR-432* |
| rs58058996 | 0 | G/T | KRT5 | hsa-miR-604 |
| rs58058996 | 0 | G/T | KRT5 | hsa-miR-647 |
| rs58058996 | 0 | G/T | KRT5 | hsa-miR-93* |
| rs58058996 | 0 | G/T | KRT5 | hsa-miR-1299, hsa-miR-516b, hsa-miR-516b |
| rs58064122 | 0 | C/T | GFAP | hsa-miR-517b |
| rs58064122 | 0 | C/T | GFAP | hsa-miR-143* |
| rs58064122 | 0 | C/T | GFAP | hsa-miR-127-3p |
| rs58072617 | 0 | C/T | KRT5 | hsa-miR-490-5p |
| rs58072617 | 0 | C/T | KRT5 | hsa-miR-132* |
| rs58073789 | 264800 | A/G | ABCC6 | hsa-miR-629* |
| rs58075662 | 0 | A/G | KRT10 | hsa-miR-876-3p, hsa-miR-323-5p |
| rs58075662 | 0 | A/G | KRT10 | hsa-miR-125a-3p |
| rs58163069 | 0 | C/G | KRT5 | hsa-miR-1182 |
| rs58163069 | 0 | C/G | KRT5 | hsa-miR-193a-5p |
| rs58163069 | 0 | C/G | KRT5 | hsa-miR-431 |
| rs58163069 | 0 | C/G | KRT5 | hsa-miR-653 |
| rs58163069 | 0 | C/G | KRT5 | hsa-miR-526b |
| rs58163069 | 0 | C/G | KRT5 | hsa-miR-609 |
| rs58293603 | 0 | G/T | KRT16 | hsa-miR-377* |
| rs58293603 | 0 | G/T | KRT16 | hsa-miR-1304 |
| rs58330629 | 0 | A/G | KRT14 | hsa-miR-876-3p, hsa-miR-323-5p |
| rs58330629 | 0 | A/G | KRT14 | hsa-miR-125a-3p |
| rs58331765 | 0 | C/T | ABCA4 | hsa-miR-586 |
| rs58343600 | 0 | C/G | KRT12 | hsa-miR-590-5p, hsa-miR-21 |
| rs58380626 | 0 | C/T | KRT14 | hsa-miR-541, hsa-miR-654-5p, hsa-miR-92a-2* |
| rs58380626 | 0 | C/T | KRT14 | hsa-miR-1293, hsa-miR-363* |
| rs58380626 | 0 | C/T | KRT14 | hsa-miR-1262 |
| rs58597584 | 0 | A/G | KRT9 | hsa-miR-1250 |
| rs58597584 | 0 | A/G | KRT9 | hsa-miR-20a* |
| rs58599399 | 0 | G/T | PRPH | hsa-miR-1469 |
| rs58668703 | 264800 | A/G | ABCC6 | hsa-miR-1203 |
| rs58668703 | 264800 | A/G | ABCC6 | hsa-miR-1180 |
| rs58672172 | 0 | C/T | LMNA | hsa-miR-604 |
| rs58672172 | 0 | C/T | LMNA | hsa-miR-1207-3p |
| rs58672172 | 0 | C/T | LMNA | hsa-miR-22 |
| rs58694313 | 264800 | A/G | ABCC6 | hsa-miR-644 |
| rs58694313 | 264800 | A/G | ABCC6 | hsa-miR-1539 |
| rs58694313 | 264800 | A/G | ABCC6 | hsa-miR-1914 |
| rs58694313 | 264800 | A/G | ABCC6 | hsa-miR-147 |
| rs58695352 | 264800 | C/T | ABCC6 | hsa-miR-631 |
| rs58695352 | 264800 | C/T | ABCC6 | hsa-miR-649, hsa-miR-490-3p |
| rs58730926 | 0 | C/T | KRT17 | hsa-miR-449b, hsa-miR-449a, hsa-miR-34c-5p, hsa-miR-34a |
| rs58730926 | 0 | C/T | KRT17 | hsa-miR-940, hsa-miR-34b* |
| rs58732244 | 0 | A/T | GFAP | hsa-miR-376a, hsa-miR-376b |
| rs58732244 | 0 | A/T | GFAP | hsa-miR-616 |
| rs58751565 | 0 | A/C | KRT5 | hsa-miR-943 |
| rs58762773 | 0 | A/G | KRT14 | hsa-miR-502-5p |
| rs58762773 | 0 | A/G | KRT14 | hsa-miR-1249 |
| rs58762773 | 0 | A/G | KRT14 | hsa-miR-1915* |
| rs58762773 | 0 | A/G | KRT14 | hsa-miR-874 |
| rs58901407 | 0 | G/T | KRT10 | hsa-miR-1254, hsa-miR-661 |
| rs58901407 | 0 | G/T | KRT10 | hsa-miR-20a* |
| rs58901407 | 0 | G/T | KRT10 | hsa-miR-29b-1* |
| rs58901407 | 0 | G/T | KRT10 | hsa-miR-218-2* |
| rs58912633 | 0 | C/T | LMNA | hsa-miR-573 |
| rs58912633 | 0 | C/T | LMNA | hsa-miR-148a* |
| rs58912633 | 0 | C/T | LMNA | hsa-miR-432 |
| rs58918655 | 0 | G/T | KRT12 | hsa-miR-196b, hsa-miR-196a, hsa-miR-196a |
| rs58932704 | 0 | C/T | LMNA | hsa-miR-1324 |
| rs58932704 | 0 | C/T | LMNA | hsa-miR-575 |

TABLE 2-continued

| SNP | OMIM | MUTATION | GENE | MIR |
|---|---|---|---|---|
| rs59002125 | 264800 | C/T | ABCC6 | hsa-miR-422a, hsa-miR-378 |
| rs59002125 | 264800 | C/T | ABCC6 | hsa-miR-29c* |
| rs59002125 | 264800 | C/T | ABCC6 | hsa-miR-1243 |
| rs59115483 | 0 | A/G | KRT5 | hsa-miR-767-3p |
| rs59151893 | 0 | A/G | KRT17 | hsa-miR-668 |
| rs59151893 | 0 | A/G | KRT17 | hsa-miR-1304 |
| rs59151893 | 0 | A/G | KRT17 | hsa-miR-616 |
| rs59157279 | 264800 | C/T | ABCC6 | hsa-miR-500 |
| rs59190510 | 0 | A/G | KRT5 | hsa-miR-502-5p |
| rs59190510 | 0 | A/G | KRT5 | hsa-miR-1249 |
| rs59190510 | 0 | A/G | KRT5 | hsa-miR-1238 |
| rs59190510 | 0 | A/G | KRT5 | hsa-miR-1915* |
| rs59190510 | 0 | A/G | KRT5 | hsa-miR-874 |
| rs59285727 | 0 | A/G | GFAP | hsa-miR-518b, hsa-miR-518a-3p, hsa-miR-518f, hsa-miR-518c, hsa-miR-518a-3p, hsa-miR-518d-3p |
| rs59285727 | 0 | A/G | GFAP | hsa-miR-330-3p |
| rs59285727 | 0 | A/G | GFAP | hsa-miR-140-5p |
| rs59285727 | 0 | A/G | GFAP | hsa-miR-519d, hsa-miR-526b*, hsa-miR-20b, hsa-miR-106b, hsa-miR-106a, hsa-miR-93, hsa-miR-17, hsa-miR-20a |
| rs59285727 | 0 | A/G | GFAP | hsa-miR-520h, hsa-miR-520g |
| rs59296273 | 0 | A/T | KRT9 | hsa-miR-219-2-3p |
| rs59296273 | 0 | A/T | KRT9 | hsa-let-7c* |
| rs59328451 | 0 | A/T | KRT16 | hsa-miR-664 |
| rs59328451 | 0 | A/T | KRT16 | hsa-miR-586 |
| rs59328451 | 0 | A/T | KRT16 | hsa-miR-33b, hsa-miR-33a |
| rs59349773 | 0 | A/C | KRT16 | hsa-miR-544 |
| rs59349773 | 0 | A/C | KRT16 | hsa-miR-20a* |
| rs59349773 | 0 | A/C | KRT16 | hsa-miR-182* |
| rs59461468 | 264800 | A/G | ABCC6 | hsa-miR-644 |
| rs59461468 | 264800 | A/G | ABCC6 | hsa-miR-147b, hsa-miR-210 |
| rs59461468 | 264800 | A/G | ABCC6 | hsa-miR-147 |
| rs59510579 | 0 | C/T | KRT9 | hsa-miR-1539 |
| rs59510579 | 0 | C/T | KRT9 | hsa-miR-20a* |
| rs59565950 | 0 | A/G | GFAP | hsa-miR-644 |
| rs59565950 | 0 | A/G | GFAP | hsa-miR-127-3p |
| rs59593133 | 264800 | A/G | ABCC6 | hsa-miR-1269 |
| rs59593133 | 264800 | A/G | ABCC6 | hsa-miR-145* |
| rs59629244 | 0 | C/T | KRT14 | hsa-miR-604 |
| rs59629244 | 0 | C/T | KRT14 | hsa-miR-1207-3p |
| rs59629244 | 0 | C/T | KRT14 | hsa-miR-22 |
| rs59730172 | 0 | A/C | KRT5 | hsa-miR-129-5p |
| rs59730172 | 0 | A/C | KRT5 | hsa-miR-1974, hsa-miR-453 |
| rs59757815 | 264800 | A/T | ABCC6 | hsa-miR-522*, hsa-miR-519a*, hsa-miR-523*, hsa-miR-518f*, hsa-miR-526a, hsa-miR-520c-5p, hsa-miR-526a, hsa-miR-518e*, hsa-miR-518d-5p, hsa-miR-519c-5p, hsa-miR-519b-5p |
| rs59757815 | 264800 | A/T | ABCC6 | hsa-miR-618 |
| rs59757815 | 264800 | A/T | ABCC6 | hsa-miR-628-3p, hsa-miR-325 |
| rs59757815 | 264800 | A/T | ABCC6 | hsa-miR-1278 |
| rs59793293 | 0 | C/T | GFAP | hsa-miR-518b, hsa-miR-518a-3p, hsa-miR-518f, hsa-miR-518c, hsa-miR-518a-3p, hsa-miR-518d-3p |
| rs59878153 | 0 | A/C | KRT9 | hsa-miR-593* |
| rs59878153 | 0 | A/C | KRT9 | hsa-miR-596 |
| rs59878153 | 0 | A/C | KRT9 | hsa-miR-500* |
| rs59885338 | 0 | C/T | LMNA | hsa-miR-105* |
| rs59886214 | 0 | A/G | LMNA | hsa-miR-24-1*, hsa-miR-24-2* |
| rs59886214 | 0 | A/G | LMNA | hsa-miR-1280, hsa-miR-1224-3p |
| rs59962885 | 0 | C/G | DES | hsa-miR-615-5p |
| rs59962885 | 0 | C/G | DES | hsa-miR-1268, hsa-miR-585 |
| rs59977263 | 0 | A/G | KRT17 | hsa-miR-521 |
| rs60171927 | 0 | A/G | KRT14 | hsa-miR-668 |
| rs60171927 | 0 | A/G | KRT14 | hsa-miR-1304 |
| rs60171927 | 0 | A/G | KRT14 | hsa-miR-616 |
| rs60284988 | 605646 | C/T | SLC26A4 | hsa-miR-196b* |
| rs60310264 | 0 | A/G | LMNA | hsa-miR-502-5p |
| rs60310264 | 0 | A/G | LMNA | hsa-miR-1248, hsa-miR-1237 |
| rs60310264 | 0 | A/G | LMNA | hsa-miR-578 |
| rs60399023 | 0 | C/T | KRT14 | hsa-miR-449b, hsa-miR-449a, hsa-miR-34c-5p, hsa-miR-34a |
| rs60399023 | 0 | C/T | KRT14 | hsa-miR-940, hsa-miR-34b* |
| rs60580541 | 0 | C/T | LMNA | hsa-miR-451 |
| rs60580541 | 0 | C/T | LMNA | hsa-miR-589, hsa-miR-146b-5p, hsa-miR-146a |
| rs60580541 | 0 | C/T | LMNA | hsa-miR-1300, hsa-miR-580 |
| rs60586163 | 0 | C/G | KRT5 | hsa-miR-1248, hsa-miR-1237 |
| rs60586163 | 0 | C/G | KRT5 | hsa-miR-375 |

TABLE 2-continued

| SNP | OMIM | MUTATION | GENE | MIR |
|---|---|---|---|---|
| rs60627726 | 0 | A/G | KRT6B | hsa-miR-502-5p |
| rs60627726 | 0 | A/G | KRT6B | hsa-miR-1249 |
| rs60627726 | 0 | A/G | KRT6B | hsa-miR-1915* |
| rs60627726 | 0 | A/G | KRT6B | hsa-miR-874 |
| rs60652225 | 0 | G/T | LMNA | hsa-miR-922, hsa-miR-214 |
| rs60652225 | 0 | G/T | LMNA | hsa-miR-615-3p |
| rs60715293 | 0 | C/T | KRT5 | hsa-miR-650 |
| rs60715293 | 0 | C/T | KRT5 | hsa-miR-486-3p |
| rs60715293 | 0 | C/T | KRT5 | hsa-miR-1827 |
| rs60715293 | 0 | C/T | KRT5 | hsa-miR-1252 |
| rs60725382 | 0 | A/T | KRT14 | hsa-miR-485-3p |
| rs60725382 | 0 | A/T | KRT14 | hsa-miR-593 |
| rs60791294 | 264800 | A/G | ABCC6 | hsa-miR-422a, hsa-miR-378 |
| rs60791294 | 264800 | A/G | ABCC6 | hsa-miR-532-5p |
| rs60791294 | 264800 | A/G | ABCC6 | hsa-miR-1254, hsa-miR-661 |
| rs60831116 | 0 | A/C | KRT14 | hsa-miR-532-5p |
| rs60831116 | 0 | A/C | KRT14 | hsa-miR-1286 |
| rs60831116 | 0 | A/C | KRT14 | hsa-miR-1266 |
| rs60864230 | 0 | C/G | LMNA | hsa-miR-658 |
| rs60864230 | 0 | C/G | LMNA | hsa-miR-615-3p |
| rs60864230 | 0 | C/G | LMNA | hsa-miR-505* |
| rs60890628 | 0 | C/T | LMNA | hsa-miR-558 |
| rs60890628 | 0 | C/T | LMNA | hsa-miR-361-3p |
| rs60890628 | 0 | C/T | LMNA | hsa-miR-615-3p |
| rs60934003 | 0 | C/T | LMNA | hsa-miR-505* |
| rs60934003 | 0 | C/T | LMNA | hsa-miR-920 |
| rs60934003 | 0 | C/T | LMNA | hsa-miR-30c-1*, hsa-miR-30b*, hsa-miR-30c-2* |
| rs60975032 | 264800 | C/T | ABCC6 | hsa-miR-525-3p, hsa-miR-524-3p |
| rs60975032 | 264800 | C/T | ABCC6 | hsa-miR-506, hsa-miR-124, hsa-miR-124, hsa-miR-124 |
| rs61046466 | 0 | C/T | LMNA | hsa-miR-92b* |
| rs61046466 | 0 | C/T | LMNA | hsa-miR-1302 |
| rs61064130 | 0 | A/G | LMNA | hsa-miR-572 |
| rs61064130 | 0 | A/G | LMNA | hsa-miR-1280, hsa-miR-1224-3p |
| rs61214927 | 0 | A/G | LMNA | hsa-miR-569 |
| rs61214927 | 0 | A/G | LMNA | hsa-miR-2053 |
| rs61218439 | 0 | A/T | KRT1 | hsa-miR-508-5p |
| rs61218439 | 0 | A/T | KRT1 | hsa-miR-216b, hsa-miR-216a |
| rs61218439 | 0 | A/T | KRT1 | hsa-miR-515-5p, hsa-miR-519e* |
| rs61282106 | 0 | A/G | LMNA | hsa-miR-302f |
| rs61305583 | 0 | G/T | KRT5 | hsa-miR-891b |
| rs61340537 | 264800 | A/C | ABCC6 | hsa-miR-1914*, hsa-miR-423-5p |
| rs61340537 | 264800 | A/C | ABCC6 | hsa-miR-1275 |
| rs61348633 | 0 | A/G | KRT5 | hsa-miR-361-3p |
| rs61348633 | 0 | A/G | KRT5 | hsa-miR-1470 |
| rs61348633 | 0 | A/G | KRT5 | hsa-miR-1249 |
| rs61348633 | 0 | A/G | KRT5 | hsa-miR-766 |
| rs61371557 | 0 | G/T | KRT14 | hsa-miR-642 |
| rs61434181 | 0 | A/G | KRT10 | hsa-miR-889 |
| rs61434181 | 0 | A/G | KRT10 | hsa-miR-513c |
| rs61434181 | 0 | A/G | KRT10 | hsa-miR-200a*, hsa-miR-200b* |
| rs61434181 | 0 | A/G | KRT10 | hsa-miR-195*, hsa-miR-16-2* |
| rs61491953 | 0 | C/G | NEFL | hsa-miR-624* |
| rs61622935 | 0 | C/T | GFAP | hsa-miR-548p |
| rs61630004 | 0 | A/G | KRT85 | hsa-miR-592 |
| rs61630004 | 0 | A/G | KRT85 | hsa-miR-22 |
| rs61672878 | 0 | A/G | LMNA | hsa-miR-581 |
| rs61726465 | 0 | C/T | DES | hsa-miR-936, hsa-miR-199a-3p, hsa-miR-199b-3p, hsa-miR-199a-3p |
| rs61726465 | 0 | C/T | DES | hsa-miR-1180 |
| rs61726465 | 0 | C/T | DES | hsa-miR-770-5p |
| rs61726465 | 0 | C/T | DES | hsa-miR-145 |
| rs61748392 | 0 | A/G | — | hsa-miR-1975 |
| rs61748392 | 0 | A/G | — | hsa-miR-508-5p |
| rs61748396 | 0 | C/G | MECP2 | hsa-miR-606 |
| rs61748405 | 0 | G/T | — | hsa-miR-377 |
| rs61748405 | 0 | G/T | — | hsa-miR-128 |
| rs61748405 | 0 | G/T | — | hsa-miR-132, hsa-miR-212 |
| rs61748421 | 0 | C/T | MECP2 | hsa-miR-1229 |
| rs61748435 | 0 | C/T | — | hsa-miR-532-3p, hsa-miR-150 |
| rs61748435 | 0 | C/T | — | hsa-miR-1979, hsa-miR-1260, hsa-miR-188-3p |
| rs61748435 | 0 | C/T | — | hsa-miR-1280, hsa-miR-1224-3p |
| rs61748436 | 0 | A/G | — | hsa-miR-1976 |
| rs61748548 | 0 | G/T | — | hsa-miR-485-3p |
| rs61748559 | 0 | A/G | — | hsa-miR-127-3p |
| rs61749387 | 0 | C/T | — | hsa-let-7i* |
| rs61749387 | 0 | C/T | — | hsa-miR-501-3p, hsa-miR-502-3p |
| rs61749665 | 0 | G/T | — | hsa-miR-658 |

TABLE 2-continued

| SNP | OMIM | MUTATION | GENE | MIR |
|---|---|---|---|---|
| rs61749665 | 0 | G/T | — | hsa-miR-765 |
| rs61749665 | 0 | G/T | — | hsa-miR-25* |
| rs61749700 | 0 | A/T | — | hsa-miR-181c* |
| rs61749700 | 0 | A/T | — | hsa-miR-582-3p |
| rs61749721 | 0 | C/T | MECP2 | hsa-miR-516a-3p, hsa-miR-516b*, hsa-miR-516b* |
| rs61749721 | 0 | C/T | MECP2 | hsa-miR-335* |
| rs61749755 | 0 | C/T | — | hsa-miR-2110 |
| rs61749755 | 0 | C/T | — | hsa-miR-637 |
| rs61749755 | 0 | C/T | — | hsa-miR-1290, hsa-miR-876-5p |
| rs61750061 | 0 | A/G | — | hsa-miR-1248, hsa-miR-1237 |
| rs61750061 | 0 | A/G | — | hsa-miR-1976 |
| rs61750126 | 0 | G/T | — | hsa-miR-665 |
| rs61750130 | 0 | C/T | — | hsa-miR-665 |
| rs61750130 | 0 | C/T | — | hsa-miR-575 |
| rs61750130 | 0 | C/T | — | hsa-miR-920 |
| rs61750130 | 0 | C/T | — | hsa-miR-708, hsa-miR-28-5p |
| rs61750172 | 0 | C/T | — | hsa-miR-933 |
| rs61750172 | 0 | C/T | — | hsa-miR-517b |
| rs61750172 | 0 | C/T | — | hsa-miR-483-3p |
| rs61750173 | 0 | A/G | — | hsa-miR-933 |
| rs61750173 | 0 | A/G | — | hsa-miR-1973 |
| rs61750173 | 0 | A/G | — | hsa-miR-218 |
| rs61750200 | 0 | C/T | — | hsa-miR-518e |
| rs61750200 | 0 | C/T | — | hsa-miR-483-3p |
| rs61750200 | 0 | C/T | — | hsa-miR-508-5p |
| rs61750240 | 0 | C/T | MECP2 | hsa-miR-30e*, hsa-miR-30d*, hsa-miR-30a* |
| rs61750420 | 0 | A/G | — | hsa-miR-660 |
| rs61750420 | 0 | A/G | — | hsa-miR-1280, hsa-miR-1224-3p |
| rs61750434 | 0 | C/T | — | hsa-miR-886-5p |
| rs61750595 | 0 | C/T | — | hsa-miR-625 |
| rs61750595 | 0 | C/T | — | hsa-miR-1266 |
| rs61751362 | 0 | C/T | MECP2 | hsa-miR-383 |
| rs61751374 | 0 | C/T | — | hsa-miR-422a, hsa-miR-378 |
| rs61751374 | 0 | C/T | — | hsa-miR-492 |
| rs61751374 | 0 | C/T | — | hsa-miR-1285, hsa-miR-612 |
| rs61751374 | 0 | C/T | — | hsa-miR-1287 |
| rs61751392 | 0 | C/T | — | hsa-miR-1270, hsa-miR-620 |
| rs61751392 | 0 | C/T | — | hsa-miR-1825, hsa-miR-199a-5p, hsa-miR-199b-5p, hsa-miR-199a-5p |
| rs61751392 | 0 | C/T | — | hsa-miR-936, hsa-miR-199a-3p, hsa-miR-199b-3p, hsa-miR-199a-3p |
| rs61751392 | 0 | C/T | — | hsa-miR-770-5p |
| rs61751392 | 0 | C/T | — | hsa-miR-194* |
| rs61751392 | 0 | C/T | — | hsa-miR-185 |
| rs61751392 | 0 | C/T | — | hsa-miR-411 |
| rs61751408 | 0 | C/T | — | hsa-miR-646, hsa-miR-503, hsa-miR-497, hsa-miR-424, hsa-miR-195, hsa-miR-15b, hsa-miR-16, hsa-miR-15a, hsa-miR-16 |
| rs61752063 | 0 | C/T | — | hsa-miR-937 |
| rs61752067 | 0 | C/T | — | hsa-miR-575 |
| rs61752067 | 0 | C/T | — | hsa-miR-1972 |
| rs61752068 | 0 | A/G | — | hsa-miR-1285, hsa-miR-612 |
| rs61752068 | 0 | A/G | — | hsa-miR-558 |
| rs61752095 | 0 | C/G | — | hsa-miR-663b |
| rs61752095 | 0 | C/G | — | hsa-miR-1207-3p |
| rs61752095 | 0 | C/G | — | hsa-miR-125a-3p |
| rs61752095 | 0 | C/G | — | hsa-miR-552 |
| rs61752103 | 0 | C/T | — | hsa-miR-561 |
| rs61752103 | 0 | C/T | — | hsa-miR-520h, hsa-miR-520g |
| rs61752112 | 0 | C/T | — | hsa-miR-31 |
| rs61752112 | 0 | C/T | — | hsa-miR-548b-3p |
| rs61752112 | 0 | C/T | — | hsa-miR-548d-3p |
| rs61752115 | 0 | C/T | — | hsa-miR-125a-3p |
| rs61752116 | 0 | C/T | — | hsa-miR-1976 |
| rs61752117 | 0 | C/T | — | hsa-miR-1228, hsa-miR-220a |
| rs61752117 | 0 | C/T | — | hsa-miR-377 |
| rs61752117 | 0 | C/T | — | hsa-miR-767-5p |
| rs61752119 | 0 | A/G | — | hsa-miR-664*, hsa-miR-149 |
| rs61752119 | 0 | A/G | — | hsa-miR-518c*, hsa-miR-330-5p, hsa-miR-326 |
| rs61752119 | 0 | A/G | — | hsa-miR-9 |
| rs61752132 | 0 | C/T | — | hsa-miR-665 |
| rs61752132 | 0 | C/T | — | hsa-miR-149* |
| rs61752132 | 0 | C/T | — | hsa-miR-1226 |
| rs61752132 | 0 | C/T | — | hsa-miR-1911* |
| rs61752137 | 0 | C/T | — | hsa-miR-376a, hsa-miR-376b |
| rs61752137 | 0 | C/T | — | hsa-miR-135a* |
| rs61752138 | 0 | G/T | — | hsa-miR-590-5p, hsa-miR-21 |
| rs61752138 | 0 | G/T | — | hsa-miR-103-2* |

TABLE 2-continued

| SNP | OMIM | MUTATION | GENE | MIR |
|---|---|---|---|---|
| rs61752878 | 0 | A/G | — | hsa-miR-1256 |
| rs61752895 | 0 | C/T | — | hsa-miR-34a* |
| rs61752895 | 0 | C/T | — | hsa-miR-15b* |
| rs61752909 | 0 | C/T | — | hsa-miR-410 |
| rs61753033 | 0 | C/T | — | hsa-miR-299-3p |
| rs61753033 | 0 | C/T | — | hsa-miR-663b |
| rs61753034 | 0 | G/T | — | hsa-miR-665 |
| rs61753034 | 0 | G/T | — | hsa-miR-1915 |
| rs61753034 | 0 | G/T | — | hsa-miR-1203 |
| rs61753034 | 0 | G/T | — | hsa-miR-532-3p, hsa-miR-150 |
| rs61753178 | 0 | C/T | — | hsa-miR-522*, hsa-miR-519a*, hsa-miR-523*, hsa-miR-518f*, hsa-miR-526a, hsa-miR-520c-5p, hsa-miR-526a, hsa-miR-518e*, hsa-miR-518d-5p, hsa-miR-519c-5p, hsa-miR-519b-5p |
| rs61753178 | 0 | C/T | — | hsa-miR-539 |
| rs61753180 | 0 | A/G | — | hsa-miR-513a-5p, hsa-miR-27b, hsa-miR-27a |
| rs61753180 | 0 | A/G | — | hsa-miR-588 |
| rs61753180 | 0 | A/G | — | hsa-miR-138 |
| rs61753185 | 0 | A/G | — | hsa-miR-1976 |
| rs61753238 | 0 | C/G | — | hsa-miR-142-3p |
| rs61753238 | 0 | C/G | — | hsa-miR-18b* |
| rs61753238 | 0 | C/G | — | hsa-miR-874 |
| rs61753246 | 0 | A/G | — | hsa-miR-1249 |
| rs61753246 | 0 | A/G | — | hsa-miR-146b-3p |
| rs61753965 | 0 | C/T | — | hsa-miR-1296 |
| rs61753965 | 0 | C/T | — | hsa-miR-185* |
| rs61753965 | 0 | C/T | — | hsa-miR-637 |
| rs61753971 | 0 | A/G | — | hsa-miR-1207-3p |
| rs61753971 | 0 | A/G | — | hsa-miR-626 |
| rs61753971 | 0 | A/G | — | hsa-miR-1181 |
| rs61754011 | 0 | A/G | VWF | hsa-miR-573 |
| rs61754011 | 0 | A/G | VWF | hsa-miR-1200, hsa-miR-378* |
| rs61754360 | 0 | A/G | — | hsa-miR-522*, hsa-miR-519a*, hsa-miR-523*, hsa-miR-518f*, hsa-miR-526a, hsa-miR-520c-5p, hsa-miR-526a, hsa-miR-518e*, hsa-miR-518d-5p, hsa-miR-519c-5p, hsa-miR-519b-5p |
| rs61754360 | 0 | A/G | — | hsa-miR-525-5p, hsa-miR-520a-5p |
| rs61754360 | 0 | A/G | — | hsa-miR-1324 |
| rs61754360 | 0 | A/G | — | hsa-miR-324-5p |
| rs61754367 | 0 | A/G | — | hsa-miR-889 |
| rs61754367 | 0 | A/G | — | hsa-miR-195*, hsa-miR-16-2* |
| rs61754375 | 0 | A/G | — | hsa-miR-491-3p |
| rs61754387 | 0 | A/C | — | hsa-miR-664 |
| rs61754387 | 0 | A/C | — | hsa-miR-145 |
| rs61754387 | 0 | A/C | — | hsa-miR-587 |
| rs61755771 | 0 | C/T | — | hsa-miR-30e*, hsa-miR-30d*, hsa-miR-30a* |
| rs61755771 | 0 | C/T | — | hsa-let-7c* |
| rs61755783 | 0 | C/T | — | hsa-miR-936, hsa-miR-199a-3p, hsa-miR-199b-3p, hsa-miR-199a-3p |
| rs61755783 | 0 | C/T | — | hsa-miR-770-5p |
| rs61755783 | 0 | C/T | — | hsa-miR-1244 |
| rs61755789 | 0 | A/G | — | hsa-miR-744* |
| rs61755793 | 0 | A/G | — | hsa-miR-1200, hsa-miR-378* |
| rs61755794 | 0 | A/T | — | hsa-miR-1910, hsa-miR-455-3p |
| rs61755798 | 0 | C/G | — | hsa-miR-92b* |
| rs61755798 | 0 | C/G | — | hsa-miR-191 |
| rs61755798 | 0 | C/G | — | hsa-miR-553 |
| rs61755798 | 0 | C/G | — | hsa-miR-488 |
| rs61755816 | 0 | C/G | — | hsa-miR-220c |
| rs61755816 | 0 | C/G | — | hsa-miR-563, hsa-miR-380* |
| rs61755816 | 0 | C/G | — | hsa-miR-552 |
| rs62507347 | 0 | A/G | — | hsa-miR-660 |
| rs62507347 | 0 | A/G | — | hsa-miR-452* |
| rs62508588 | 0 | A/G | — | hsa-miR-92a-1* |
| rs62508588 | 0 | A/G | — | hsa-miR-431* |
| rs62508646 | 0 | C/T | — | hsa-miR-1207-5p |
| rs62508646 | 0 | C/T | — | hsa-miR-183 |
| rs62508646 | 0 | C/T | — | hsa-miR-1286 |
| rs62508646 | 0 | C/T | — | hsa-miR-425 |
| rs62508646 | 0 | C/T | — | hsa-miR-1255b, hsa-miR-1255a |
| rs62508698 | 0 | C/G | — | hsa-miR-92a-1* |
| rs62508698 | 0 | C/G | — | hsa-miR-1275 |
| rs62514893 | 0 | A/G | — | hsa-miR-190b, hsa-miR-190 |
| rs62514893 | 0 | A/G | — | hsa-miR-1261 |
| rs62514927 | 0 | A/G | — | hsa-miR-376a, hsa-miR-376b |
| rs62514927 | 0 | A/G | — | hsa-miR-103-as |
| rs62514927 | 0 | A/G | — | hsa-miR-513a-5p, hsa-miR-27b, hsa-miR-27a |
| rs62514927 | 0 | A/G | — | hsa-miR-545 |

TABLE 2-continued

| SNP | OMIM | MUTATION | GENE | MIR |
|---|---|---|---|---|
| rs62514927 | 0 | A/G | — | hsa-miR-342-3p |
| rs62514934 | 0 | A/G | — | hsa-miR-136 |
| rs62514934 | 0 | A/G | — | hsa-miR-515-5p, hsa-miR-519e* |
| rs62514934 | 0 | A/G | — | hsa-miR-141* |
| rs62514942 | 0 | C/T | — | hsa-miR-125b-2* |
| rs62514942 | 0 | C/T | — | hsa-miR-220c |
| rs62514942 | 0 | C/T | — | hsa-miR-552 |
| rs62514942 | 0 | C/T | — | hsa-miR-431* |
| rs62514953 | 0 | C/T | — | hsa-miR-432 |
| rs62514958 | 0 | C/G | — | hsa-miR-615-3p |
| rs62514959 | 0 | A/G | — | hsa-miR-497* |
| rs62514959 | 0 | A/G | — | hsa-miR-770-5p |
| rs62514959 | 0 | A/G | — | hsa-miR-545* |
| rs62514959 | 0 | A/G | — | hsa-miR-628-3p, hsa-miR-325 |
| rs62514959 | 0 | A/G | — | hsa-miR-708* |
| rs62516060 | 0 | C/T | — | hsa-miR-298 |
| rs62516060 | 0 | C/T | — | hsa-miR-1225-3p, hsa-miR-1233 |
| rs62516060 | 0 | C/T | — | hsa-miR-589* |
| rs62516095 | 0 | A/C | — | hsa-miR-1179 |
| rs62516095 | 0 | A/C | — | hsa-miR-1278 |
| rs62516101 | 0 | A/G | — | hsa-miR-411*, hsa-miR-379*, hsa-miR-380 |
| rs62516101 | 0 | A/G | — | hsa-miR-2054 |
| rs62516151 | 0 | A/C | — | hsa-miR-1207-5p |
| rs62516151 | 0 | A/C | — | hsa-miR-934 |
| rs62516151 | 0 | A/C | — | hsa-miR-622 |
| rs62516151 | 0 | A/C | — | hsa-miR-449b, hsa-miR-449a, hsa-miR-34c-5p, hsa-miR-34a |
| rs62516151 | 0 | A/C | — | hsa-miR-484 |
| rs62635018 | 0 | A/G | — | hsa-miR-1913, hsa-miR-324-3p, hsa-miR-18a* |
| rs62635018 | 0 | A/G | — | hsa-miR-1915 |
| rs62635018 | 0 | A/G | — | hsa-miR-626 |
| rs62635018 | 0 | A/G | — | hsa-miR-198 |
| rs62635288 | 0 | G/T | — | hsa-miR-145 |
| rs62635288 | 0 | G/T | — | hsa-miR-582-5p |
| rs62635654 | 0 | C/T | — | hsa-miR-602 |
| rs62635655 | 0 | G/T | — | hsa-miR-130b* |
| rs62635655 | 0 | G/T | — | hsa-miR-138-2* |
| rs62635655 | 0 | G/T | — | hsa-miR-760 |
| rs62635656 | 0 | C/T | — | hsa-miR-490-5p |
| rs62636275 | 0 | A/G | — | hsa-miR-29a* |
| rs62636275 | 0 | A/G | — | hsa-miR-146a* |
| rs62636291 | 0 | C/T | — | hsa-miR-518b, hsa-miR-518a-3p, hsa-miR-518f, hsa-miR-518c, hsa-miR-518a-3p, hsa-miR-518d-3p |
| rs62636291 | 0 | C/T | — | hsa-miR-664 |
| rs62636291 | 0 | C/T | — | hsa-miR-1179 |
| rs62636291 | 0 | C/T | — | hsa-miR-1206 |
| rs62636505 | 0 | C/T | — | hsa-miR-604 |
| rs62636505 | 0 | C/T | — | hsa-miR-185* |
| rs62636505 | 0 | C/T | — | hsa-miR-637 |
| rs62636505 | 0 | C/T | — | hsa-miR-558 |
| rs62636505 | 0 | C/T | — | hsa-miR-22 |
| rs62637004 | 0 | G/T | — | hsa-miR-514 |
| rs62637004 | 0 | G/T | — | hsa-miR-489 |
| rs62637004 | 0 | G/T | — | hsa-miR-181d, hsa-miR-181b, hsa-miR-181a, hsa-miR-181a, hsa-miR-181b, hsa-miR-181c |
| rs62637012 | 0 | C/T | — | hsa-miR-892b, hsa-miR-193b, hsa-miR-193a-3p |
| rs62637014 | 0 | A/G | — | hsa-miR-579 |
| rs62637014 | 0 | A/G | — | hsa-miR-377 |
| rs62637014 | 0 | A/G | — | hsa-miR-1298 |
| rs62637014 | 0 | A/G | — | hsa-miR-205* |
| rs62637015 | 0 | G/T | — | hsa-let-7i* |
| rs62637015 | 0 | G/T | — | hsa-miR-1539 |
| rs62637015 | 0 | G/T | — | hsa-miR-29c, hsa-miR-29b, hsa-miR-29b, hsa-miR-29a |
| rs62637015 | 0 | G/T | — | hsa-miR-191* |
| rs62637015 | 0 | G/T | — | hsa-miR-125a-5p, hsa-miR-125b, hsa-miR-125b |
| rs62637021 | 0 | A/C | — | hsa-miR-24 |
| rs62637021 | 0 | A/C | — | hsa-miR-1266 |
| rs62637021 | 0 | A/C | — | hsa-miR-484 |
| rs62637037 | 0 | A/G | — | hsa-miR-1910, hsa-miR-455-3p |
| rs62637037 | 0 | A/G | — | hsa-miR-145 |
| rs62637037 | 0 | A/G | — | hsa-miR-554 |
| rs62638185 | 0 | C/T | — | hsa-miR-149* |
| rs62638185 | 0 | C/T | — | hsa-miR-650 |
| rs62638185 | 0 | C/T | — | hsa-miR-765 |
| rs62638185 | 0 | C/T | — | hsa-miR-1253 |
| rs62638190 | 0 | G/T | — | hsa-miR-1270, hsa-miR-620 |

TABLE 2-continued

| SNP | OMIM | MUTATION | GENE | MIR |
|---|---|---|---|---|
| rs62638190 | 0 | G/T | — | hsa-miR-449b* |
| rs62638190 | 0 | G/T | — | hsa-miR-505* |
| rs62638191 | 0 | G/T | — | hsa-miR-361-3p |
| rs62638191 | 0 | G/T | — | hsa-miR-361-3p |
| rs62638193 | 0 | A/G | — | hsa-miR-142-3p |
| rs62638193 | 0 | A/G | — | hsa-miR-886-3p |
| rs62638193 | 0 | A/G | — | hsa-miR-125b-1* |
| rs62638194 | 0 | C/T | — | hsa-miR-20b* |
| rs62638194 | 0 | C/T | — | hsa-miR-1908, hsa-miR-663 |
| rs62638197 | 0 | C/T | — | hsa-miR-665 |
| rs62638197 | 0 | C/T | — | hsa-miR-1226 |
| rs62638197 | 0 | C/T | — | hsa-miR-873 |
| rs62638197 | 0 | C/T | — | hsa-miR-1292 |
| rs62638197 | 0 | C/T | — | hsa-miR-1911* |
| rs62638197 | 0 | C/T | — | hsa-miR-767-5p |
| rs62638202 | 0 | A/G | — | hsa-miR-662 |
| rs62638202 | 0 | A/G | — | hsa-miR-566 |
| rs62638208 | 0 | A/G | — | hsa-miR-1296 |
| rs62638208 | 0 | A/G | — | hsa-miR-1909 |
| rs62638214 | 0 | C/T | — | hsa-miR-1307 |
| rs62638214 | 0 | C/T | — | hsa-miR-1538 |
| rs62638624 | 0 | C/T | — | hsa-miR-139-5p |
| rs62638624 | 0 | C/T | — | hsa-miR-1909 |
| rs62638624 | 0 | C/T | — | hsa-miR-1205, hsa-miR-1184, hsa-miR-17* |
| rs62638625 | 0 | A/G | — | hsa-miR-653 |
| rs62638634 | 0 | G/T | — | hsa-miR-888* |
| rs62638634 | 0 | G/T | — | hsa-miR-192* |
| rs62638637 | 0 | A/C | — | hsa-miR-644 |
| rs62638637 | 0 | A/C | — | hsa-miR-609 |
| rs62638637 | 0 | A/C | — | hsa-miR-1974, hsa-miR-453 |
| rs62638644 | 0 | G/T | — | hsa-miR-548n |
| rs62638644 | 0 | G/T | — | hsa-miR-519d, hsa-miR-526b*, hsa-miR-20b, hsa-miR-106b, hsa-miR-106a, hsa-miR-93, hsa-miR-17, hsa-miR-20a |
| rs62638644 | 0 | G/T | — | hsa-miR-425 |
| rs62638651 | 0 | C/T | — | hsa-miR-124* |
| rs62638651 | 0 | C/T | — | hsa-miR-637 |
| rs62638651 | 0 | C/T | — | hsa-miR-608, hsa-miR-342-5p |
| rs62638651 | 0 | C/T | — | hsa-miR-450b-3p, hsa-miR-769-3p |
| rs62638651 | 0 | C/T | — | hsa-miR-609 |
| rs62642057 | 0 | A/G | — | hsa-miR-510, hsa-miR-512-5p, hsa-miR-512-5p |
| rs62642057 | 0 | A/G | — | hsa-miR-1912 |
| rs62642926 | 0 | C/G | — | hsa-miR-542-3p |
| rs62642926 | 0 | C/G | — | hsa-miR-1253 |
| rs62642926 | 0 | C/G | — | hsa-miR-1300, hsa-miR-580 |
| rs62642930 | 0 | C/T | — | hsa-miR-539 |
| rs62642933 | 0 | G/T | — | hsa-miR-330-3p |
| rs62642933 | 0 | G/T | — | hsa-miR-1207-3p |
| rs62642933 | 0 | G/T | — | hsa-miR-320d, hsa-miR-320c, hsa-miR-320b, hsa-miR-320c, hsa-miR-320b, hsa-miR-320a |
| rs62642936 | 0 | C/T | — | hsa-miR-1203 |
| rs62642936 | 0 | C/T | — | hsa-miR-941 |
| rs62642936 | 0 | C/T | — | hsa-miR-1912 |
| rs62642936 | 0 | C/T | — | hsa-miR-185 |
| rs62642937 | 0 | C/T | — | hsa-miR-136 |
| rs62642937 | 0 | C/T | — | hsa-miR-508-5p |
| rs62642937 | 0 | C/T | — | hsa-miR-425 |
| rs62642937 | 0 | C/T | — | hsa-miR-542-3p |
| rs62644473 | 0 | C/T | — | hsa-miR-202, hsa-let-7i, hsa-let-7g, hsa-miR-98, hsa-let-7a, hsa-let-7a, hsa-let-7a, hsa-let-7b, hsa-let-7c, hsa-let-7d, hsa-let-7e, hsa-let-7f, hsa-let-7f |
| rs62644499 | 0 | A/G | — | hsa-miR-886-5p |
| rs62644499 | 0 | A/G | — | hsa-miR-1974, hsa-miR-453 |
| rs62654861 | 122470 | A/G | NIPBL | hsa-miR-384 |
| rs62654862 | 122470 | A/G | — | hsa-miR-129-5p |
| rs62654862 | 122470 | A/G | — | hsa-miR-375 |
| rs62654864 | 122470 | C/G | NIPBL | hsa-miR-629* |
| rs63159160 | 0 | C/G/T | — | hsa-miR-140-3p |
| rs63159160 | 0 | C/G/T | — | hsa-miR-220b |
| rs63749796 | 264800 | C/G | — | hsa-miR-512-3p, hsa-miR-520f |
| rs63749797 | 142200 | G/T | HBG1 | hsa-miR-224 |
| rs63749797 | 142200 | G/T | HBG1 | hsa-miR-573 |
| rs63749797 | 142200 | G/T | HBG1 | hsa-miR-509-3-5p, hsa-miR-509-5p, hsa-miR-509-5p, hsa-miR-217 |
| rs63749797 | 142200 | G/T | HBG1 | hsa-miR-1205, hsa-miR-1184, hsa-miR-17* |
| rs63749800 | 264800 | C/G | — | hsa-miR-149* |
| rs63749800 | 264800 | C/G | — | hsa-miR-92b* |
| rs63749800 | 264800 | C/G | — | hsa-miR-939 |

TABLE 2-continued

| SNP | OMIM | MUTATION | GENE | MIR |
|---|---|---|---|---|
| rs63749800 | 264800 | C/G | — | hsa-miR-765 |
| rs63749800 | 264800 | C/G | — | hsa-miR-1265 |
| rs63749800 | 264800 | C/G | — | hsa-miR-1185 |
| rs63749805 | 0 | C/G/T | — | hsa-miR-135a* |
| rs63749807 | 264800 | G/T | — | hsa-miR-1913, hsa-miR-324-3p, hsa-miR-18a* |
| rs63749807 | 264800 | G/T | — | hsa-miR-1243 |
| rs63749807 | 264800 | G/T | — | hsa-miR-146b-3p |
| rs63749807 | 264800 | G/T | — | hsa-miR-874 |
| rs63749808 | 141800 | A/G | HBA2 | hsa-miR-663b |
| rs63749808 | 141800 | A/G | HBA2 | hsa-miR-1228* |
| rs63749808 | 141800 | A/G | HBA2 | hsa-miR-1293, hsa-miR-363* |
| rs63749808 | 141800 | A/G | HBA2 | hsa-miR-588 |
| rs63749808 | 141800 | A/G | HBA2 | hsa-miR-1262 |
| rs63749809 | 141800 | A/T | HBA2 | hsa-miR-423-3p |
| rs63749810 | 0 | A/G | — | hsa-miR-141* |
| rs63749823 | 264800 | A/G | — | hsa-miR-1280, hsa-miR-1224-3p |
| rs63749824 | 0 | C/T | — | hsa-miR-122* |
| rs63749824 | 0 | C/T | — | hsa-miR-566 |
| rs63749851 | 0 | A/C | — | hsa-miR-1908, hsa-miR-663 |
| rs63749851 | 0 | A/C | — | hsa-miR-886-3p |
| rs63749851 | 0 | A/C | — | hsa-miR-379 |
| rs63749856 | 264800 | A/G | — | hsa-miR-146b-3p |
| rs63749856 | 264800 | A/G | — | hsa-miR-874 |
| rs63749865 | 141800 | C/G/T | — | hsa-miR-382 |
| rs63749869 | 117000 | A/G | — | hsa-miR-581 |
| rs63749871 | 609311 | G/T | FGD4 | hsa-miR-200a*, hsa-miR-200b* |
| rs63749871 | 609311 | G/T | FGD4 | hsa-miR-877* |
| rs63749871 | 609311 | G/T | FGD4 | hsa-miR-875-5p |
| rs63749881 | 141800 | C/G | HBA2 | hsa-miR-541, hsa-miR-654-5p, hsa-miR-92a-2* |
| rs63749881 | 141800 | C/G | HBA2 | hsa-miR-1469 |
| rs63749881 | 141800 | C/G | HBA2 | hsa-miR-1228* |
| rs63749881 | 141800 | C/G | HBA2 | hsa-miR-431* |
| rs63749882 | 141800 | A/C/G | HBA1 | hsa-miR-582-3p |
| rs63749882 | 141800 | A/C/G | HBA1 | hsa-miR-1307 |
| rs63749882 | 141800 | A/C/G | HBA1 | hsa-miR-1469 |
| rs63749882 | 141800 | A/C/G | HBA1 | hsa-miR-1228* |
| rs63749882 | 141800 | A/C/G | HBA1 | hsa-miR-1285, hsa-miR-612 |
| rs63749882 | 141800 | A/C/G | HBA1 | hsa-miR-890 |
| rs63749884 | 0 | A/G | — | hsa-miR-31* |
| rs63749885 | 0 | C/T | — | hsa-miR-432* |
| rs63749885 | 0 | C/T | — | hsa-miR-1246 |
| rs63749885 | 0 | C/T | — | hsa-miR-490-5p |
| rs63749885 | 0 | C/T | — | hsa-miR-1255b, hsa-miR-1255a |
| rs63749888 | 604928 | C/G | CISD2 | hsa-miR-758 |
| rs63749891 | 0 | A/C/G/T | — | hsa-miR-629* |
| rs63749923 | 0 | C/T | — | hsa-miR-1270, hsa-miR-620 |
| rs63749923 | 0 | C/T | — | hsa-miR-384 |
| rs63749927 | 141800 | A/C | HBA1 | hsa-miR-1909 |
| rs63749927 | 141800 | A/C | HBA1 | hsa-miR-1266 |
| rs63749934 | 141850 | C/T | HBA2 | hsa-miR-1254, hsa-miR-661 |
| rs63749934 | 141850 | C/T | HBA2 | hsa-miR-596 |
| rs63749934 | 141850 | C/T | HBA2 | hsa-miR-619 |
| rs63749934 | 141850 | C/T | HBA2 | hsa-miR-649, hsa-miR-490-3p |
| rs63749939 | 0 | A/G | — | hsa-miR-640 |
| rs63749948 | 141800 | A/C | HBA2 | hsa-miR-198 |
| rs63749948 | 141800 | A/C | HBA2 | hsa-miR-1268, hsa-miR-585 |
| rs63749997 | 141850 | A/G | HBA2 | hsa-miR-1306 |
| rs63749998 | 264800 | C/T | — | hsa-miR-644 |
| rs63749998 | 264800 | C/T | — | hsa-miR-299-3p |
| rs63750018 | 264800 | C/G | — | hsa-miR-575 |
| rs63750021 | 142250 | A/G | — | hsa-miR-129-5p |
| rs63750021 | 142250 | A/G | — | hsa-miR-590-3p |
| rs63750047 | 0 | C/T | — | hsa-miR-610 |
| rs63750048 | 0 | C/T | — | hsa-miR-483-3p |
| rs63750048 | 0 | C/T | — | hsa-miR-412 |
| rs63750066 | 0 | A/G | — | hsa-miR-31* |
| rs63750067 | 141850 | A/G | HBA2 | hsa-miR-617 |
| rs63750067 | 141850 | A/G | HBA2 | hsa-miR-1298 |
| rs63750073 | 141850 | C/T | HBA2 | hsa-miR-936, hsa-miR-199a-3p, hsa-miR-199b-3p, hsa-miR-199a-3p |
| rs63750073 | 141850 | C/T | HBA2 | hsa-miR-194* |
| rs63750073 | 141850 | C/T | HBA2 | hsa-miR-590-5p, hsa-miR-21 |
| rs63750077 | 0 | C/T | — | hsa-miR-432* |
| rs63750077 | 0 | C/T | — | hsa-miR-1243 |
| rs63750077 | 0 | C/T | — | hsa-miR-28-3p |
| rs63750082 | 0 | A/C/G/T | — | hsa-miR-499-3p |
| rs63750082 | 0 | A/C/G/T | — | hsa-miR-548p |
| rs63750082 | 0 | A/C/G/T | — | hsa-miR-545 |

TABLE 2-continued

| SNP | OMIM | MUTATION | GENE | MIR |
|---|---|---|---|---|
| rs63750082 | 0 | A/C/G/T | — | hsa-miR-1228, hsa-miR-220a |
| rs63750082 | 0 | A/C/G/T | — | hsa-miR-495, hsa-miR-7-1*, hsa-miR-7-2* |
| rs63750083 | 0 | A/C/T | — | hsa-miR-429, hsa-miR-200c, hsa-miR-200b |
| rs63750092 | 0 | A/T | — | hsa-miR-1915* |
| rs63750092 | 0 | A/T | — | hsa-miR-197 |
| rs63750110 | 0 | A/C | — | hsa-miR-663b |
| rs63750110 | 0 | A/C | — | hsa-miR-1293, hsa-miR-363* |
| rs63750110 | 0 | A/C | — | hsa-miR-588 |
| rs63750110 | 0 | A/C | — | hsa-miR-609 |
| rs63750125 | 264800 | A/C | — | hsa-miR-1231, hsa-miR-632 |
| rs63750125 | 264800 | A/C | — | hsa-miR-1251, hsa-miR-517*, hsa-miR-517*, hsa-miR-517* |
| rs63750125 | 264800 | A/C | — | hsa-miR-654-3p |
| rs63750129 | 0 | A/C | — | hsa-miR-514 |
| rs63750129 | 0 | A/C | — | hsa-miR-1269 |
| rs63750129 | 0 | A/C | — | hsa-miR-542-3p |
| rs63750134 | 141800 | A/C/G/T | HBA2 | hsa-miR-101, hsa-miR-144 |
| rs63750134 | 141800 | A/C/G/T | HBA2 | hsa-miR-302c* |
| rs63750134 | 141800 | A/C/G/T | HBA2 | hsa-miR-451 |
| rs63750134 | 141800 | A/C/G/T | HBA2 | hsa-miR-1183 |
| rs63750134 | 141800 | A/C/G/T | HBA2 | hsa-miR-132, hsa-miR-212 |
| rs63750134 | 141800 | A/C/G/T | HBA2 | hsa-miR-16-1* |
| rs63750135 | 264800 | C/T | — | hsa-miR-484 |
| rs63750146 | 264800 | A/G | — | hsa-miR-365 |
| rs63750206 | 0 | A/G/T | — | hsa-miR-1250 |
| rs63750206 | 0 | A/G/T | — | hsa-miR-125a-3p |
| rs63750209 | 264800 | A/G | — | hsa-miR-200a*, hsa-miR-200b* |
| rs63750215 | 0 | A/T | — | hsa-miR-124* |
| rs63750215 | 0 | A/T | — | hsa-miR-383 |
| rs63750215 | 0 | A/T | — | hsa-miR-609 |
| rs63750217 | 0 | A/G | — | hsa-miR-301b, hsa-miR-454, hsa-miR-301a, hsa-miR-130b, hsa-miR-130a |
| rs63750217 | 0 | A/G | — | hsa-miR-33b, hsa-miR-33a |
| rs63750217 | 0 | A/G | — | hsa-miR-103-as |
| rs63750218 | 0 | C/T | — | hsa-miR-589* |
| rs63750231 | 0 | A/C/G | — | hsa-miR-579 |
| rs63750231 | 0 | A/C/G | — | hsa-miR-33b, hsa-miR-33a |
| rs63750231 | 0 | A/C/G | — | hsa-miR-587 |
| rs63750235 | 264800 | A/G | — | hsa-miR-662 |
| rs63750235 | 264800 | A/G | — | hsa-miR-129-3p, hsa-miR-129* |
| rs63750235 | 264800 | A/G | — | hsa-miR-1975 |
| rs63750235 | 264800 | A/G | — | hsa-miR-18b* |
| rs63750264 | 0 | A/C/G/T | — | hsa-miR-1322, hsa-miR-1272 |
| rs63750264 | 0 | A/C/G/T | — | hsa-miR-1224-5p |
| rs63750264 | 0 | A/C/G/T | — | hsa-miR-1185 |
| rs63750265 | 0 | A/C/G/T | — | hsa-miR-1295 |
| rs63750265 | 0 | A/C/G/T | — | hsa-miR-655 |
| rs63750265 | 0 | A/C/G/T | — | hsa-miR-575 |
| rs63750265 | 0 | A/C/G/T | — | hsa-miR-633 |
| rs63750265 | 0 | A/C/G/T | — | hsa-miR-889 |
| rs63750265 | 0 | A/C/G/T | — | hsa-miR-122* |
| rs63750265 | 0 | A/C/G/T | — | hsa-miR-15a* |
| rs63750265 | 0 | A/C/G/T | — | hsa-miR-1202 |
| rs63750290 | 141800 | A/C | HBA1 | hsa-miR-1307 |
| rs63750290 | 141800 | A/C | HBA1 | hsa-miR-1908, hsa-miR-663 |
| rs63750290 | 141800 | A/C | HBA1 | hsa-miR-1469 |
| rs63750290 | 141800 | A/C | HBA1 | hsa-miR-744 |
| rs63750294 | 141800 | C/G | — | hsa-miR-492 |
| rs63750295 | 264800 | C/T | — | hsa-miR-665 |
| rs63750295 | 264800 | C/T | — | hsa-miR-1265 |
| rs63750295 | 264800 | C/T | — | hsa-miR-1255b, hsa-miR-1255a |
| rs63750295 | 264800 | C/T | — | hsa-miR-1294 |
| rs63750306 | 0 | A/C/G/T | — | hsa-miR-1197 |
| rs63750306 | 0 | A/C/G/T | — | hsa-miR-641 |
| rs63750306 | 0 | A/C/G/T | — | hsa-miR-425 |
| rs63750306 | 0 | A/C/G/T | — | hsa-miR-433 |
| rs63750315 | 611067 | C/T | PLEKHG5 | hsa-miR-149* |
| rs63750315 | 611067 | C/T | PLEKHG5 | hsa-miR-1321 |
| rs63750315 | 611067 | C/T | PLEKHG5 | hsa-miR-765 |
| rs63750315 | 611067 | C/T | PLEKHG5 | hsa-miR-765 |
| rs63750315 | 611067 | C/T | PLEKHG5 | hsa-miR-1252 |
| rs63750331 | 0 | A/G | — | hsa-miR-584 |
| rs63750349 | 0 | C/G | — | hsa-miR-412 |
| rs63750349 | 0 | C/G | — | hsa-miR-182* |
| rs63750363 | 0 | C/G | — | hsa-miR-576-3p |
| rs63750363 | 0 | C/G | — | hsa-miR-143 |
| rs63750376 | 0 | G/T | — | hsa-miR-1281 |
| rs63750388 | 141800 | C/G/T | HBA1 | hsa-miR-149* |

TABLE 2-continued

| SNP | OMIM | MUTATION | GENE | MIR |
|---|---|---|---|---|
| rs63750388 | 141800 | C/G/T | HBA1 | hsa-miR-939 |
| rs63750388 | 141800 | C/G/T | HBA1 | hsa-miR-1908, hsa-miR-663 |
| rs63750388 | 141800 | C/G/T | HBA1 | hsa-miR-658 |
| rs63750388 | 141800 | C/G/T | HBA1 | hsa-miR-611, hsa-miR-151-5p |
| rs63750388 | 141800 | C/G/T | HBA1 | hsa-miR-744 |
| rs63750388 | 141800 | C/G/T | HBA1 | hsa-miR-542-5p |
| rs63750391 | 0 | A/C/G/T | — | hsa-miR-101* |
| rs63750391 | 0 | A/C/G/T | — | hsa-miR-433 |
| rs63750391 | 0 | A/C/G/T | — | hsa-miR-1245 |
| rs63750391 | 0 | A/C/G/T | — | hsa-miR-921 |
| rs63750399 | 0 | A/G | — | hsa-miR-181a-2* |
| rs63750399 | 0 | A/G | — | hsa-miR-34c-3p |
| rs63750402 | 264800 | C/T | — | hsa-miR-483-3p |
| rs63750402 | 264800 | C/T | — | hsa-miR-508-5p |
| rs63750402 | 264800 | C/T | — | hsa-miR-572 |
| rs63750410 | 264800 | C/G | — | hsa-miR-1913, hsa-miR-324-3p, hsa-miR-18a* |
| rs63750410 | 264800 | C/G | — | hsa-miR-1538 |
| rs63750410 | 264800 | C/G | — | hsa-miR-221* |
| rs63750410 | 264800 | C/G | — | hsa-miR-328 |
| rs63750414 | 264800 | A/C/T | — | hsa-miR-1913, hsa-miR-324-3p, hsa-miR-18a* |
| rs63750414 | 264800 | A/C/T | — | hsa-miR-147b, hsa-miR-210 |
| rs63750414 | 264800 | A/C/T | — | hsa-miR-143* |
| rs63750414 | 264800 | A/C/T | — | hsa-miR-1301 |
| rs63750414 | 264800 | A/C/T | — | hsa-miR-218 |
| rs63750416 | 0 | A/C | — | hsa-miR-190b, hsa-miR-190 |
| rs63750416 | 0 | A/C | — | hsa-miR-656 |
| rs63750416 | 0 | A/C | — | hsa-miR-640 |
| rs63750424 | 0 | C/T | — | hsa-miR-490-5p |
| rs63750424 | 0 | C/T | — | hsa-miR-132* |
| rs63750425 | 0 | C/T | — | hsa-miR-582-3p |
| rs63750427 | 264800 | A/C/G | — | hsa-miR-1182 |
| rs63750427 | 264800 | A/C/G | — | hsa-miR-193a-5p |
| rs63750427 | 264800 | A/C/G | — | hsa-miR-595 |
| rs63750445 | 0 | G/T | — | hsa-miR-412 |
| rs63750445 | 0 | G/T | — | hsa-miR-1279 |
| rs63750445 | 0 | G/T | — | hsa-miR-141* |
| rs63750446 | 264800 | A/G | — | hsa-miR-370 |
| rs63750446 | 264800 | A/G | — | hsa-miR-192* |
| rs63750451 | 0 | C/T | — | hsa-miR-664 |
| rs63750451 | 0 | C/T | — | hsa-miR-579 |
| rs63750467 | 141800 | A/G/T | HBA1 | hsa-miR-1915 |
| rs63750467 | 141800 | A/G/T | HBA1 | hsa-miR-198 |
| rs63750467 | 141800 | A/G/T | HBA1 | hsa-miR-1911* |
| rs63750473 | 264800 | C/G | — | hsa-miR-1913, hsa-miR-324-3p, hsa-miR-18a* |
| rs63750473 | 264800 | C/G | — | hsa-miR-1254, hsa-miR-661 |
| rs63750473 | 264800 | C/G | — | hsa-miR-146b-3p |
| rs63750473 | 264800 | C/G | — | hsa-miR-874 |
| rs63750512 | 0 | A/C/G | — | hsa-miR-876-3p, hsa-miR-323-5p |
| rs63750512 | 0 | A/C/G | — | hsa-miR-1274b, hsa-miR-339-5p |
| rs63750512 | 0 | A/C/G | — | hsa-miR-1914 |
| rs63750512 | 0 | A/C/G | — | hsa-miR-1249 |
| rs63750512 | 0 | A/C/G | — | hsa-miR-146b-3p |
| rs63750512 | 0 | A/C/G | — | hsa-miR-132* |
| rs63750526 | 0 | A/C | — | hsa-miR-510, hsa-miR-512-5p, hsa-miR-512-5p |
| rs63750546 | 141800 | A/G | HBA2 | hsa-miR-650 |
| rs63750546 | 141800 | A/G | HBA2 | hsa-miR-1908, hsa-miR-663 |
| rs63750546 | 141800 | A/G | HBA2 | hsa-miR-541, hsa-miR-654-5p, hsa-miR-92a-2* |
| rs63750546 | 141800 | A/G | HBA2 | hsa-miR-1228* |
| rs63750550 | 0 | C/T | — | hsa-miR-202, hsa-let-7i, hsa-let-7g, hsa-miR-98, hsa-let-7a, hsa-let-7a, hsa-let-7a, hsa-let-7b, hsa-let-7c, hsa-let-7d, hsa-let-7e, hsa-let-7f, hsa-let-7f |
| rs63750567 | 105250 | C/T | — | hsa-miR-2052, hsa-miR-19a*, hsa-miR-19b-1*, hsa-miR-19b-2* |
| rs63750567 | 105250 | C/T | — | hsa-miR-223 |
| rs63750567 | 105250 | C/T | — | hsa-miR-590-3p |
| rs63750570 | 0 | A/G | — | hsa-miR-221* |
| rs63750570 | 0 | A/G | — | hsa-miR-587 |
| rs63750570 | 0 | A/G | — | hsa-miR-619 |
| rs63750577 | 0 | C/T | — | hsa-miR-143 |
| rs63750579 | 0 | A/C/G | — | hsa-miR-581 |
| rs63750579 | 0 | A/C/G | — | hsa-miR-544 |
| rs63750579 | 0 | A/C/G | — | hsa-miR-19a, hsa-miR-19b, hsa-miR-19b |
| rs63750579 | 0 | A/C/G | — | hsa-miR-450b-5p, hsa-miR-557, hsa-miR-507 |
| rs63750579 | 0 | A/C/G | — | hsa-miR-141* |
| rs63750585 | 141800 | G/T | HBA2 | hsa-miR-29c, hsa-miR-29b, hsa-miR-29b, hsa-miR-29a |
| rs63750585 | 141800 | G/T | HBA2 | hsa-miR-769-5p |
| rs63750590 | 0 | A/G | — | hsa-miR-432* |

TABLE 2-continued

| SNP | OMIM | MUTATION | GENE | MIR |
|---|---|---|---|---|
| rs63750590 | 0 | A/G | — | hsa-miR-1246 |
| rs63750590 | 0 | A/G | — | hsa-miR-564 |
| rs63750590 | 0 | A/G | — | hsa-miR-490-5p |
| rs63750590 | 0 | A/G | — | hsa-miR-105* |
| rs63750599 | 0 | C/T | — | hsa-miR-1276, hsa-miR-583 |
| rs63750606 | 141800 | A/C | HBA1 | hsa-miR-1307 |
| rs63750606 | 141800 | A/C | HBA1 | hsa-miR-1469 |
| rs63750606 | 141800 | A/C | HBA1 | hsa-miR-887 |
| rs63750606 | 141800 | A/C | HBA1 | hsa-miR-523 |
| rs63750607 | 264800 | A/G | — | hsa-miR-662 |
| rs63750608 | 264800 | C/T | — | hsa-miR-628-5p |
| rs63750608 | 264800 | C/T | — | hsa-miR-138 |
| rs63750608 | 264800 | C/T | — | hsa-miR-640 |
| rs63750609 | 141850 | A/C/G/T | HBA2 | hsa-miR-136 |
| rs63750609 | 141850 | A/C/G/T | HBA2 | hsa-miR-29c, hsa-miR-29b, hsa-miR-29b, hsa-miR-29a |
| rs63750609 | 141850 | A/C/G/T | HBA2 | hsa-miR-767-5p |
| rs63750622 | 264800 | A/G/T | — | hsa-miR-1270, hsa-miR-620 |
| rs63750622 | 264800 | A/G/T | — | hsa-miR-301b, hsa-miR-454, hsa-miR-301a, hsa-miR-130b, hsa-miR-130a |
| rs63750622 | 264800 | A/G/T | — | hsa-miR-143* |
| rs63750622 | 264800 | A/G/T | — | hsa-miR-122 |
| rs63750622 | 264800 | A/G/T | — | hsa-miR-339-3p |
| rs63750622 | 264800 | A/G/T | — | hsa-miR-1909* |
| rs63750622 | 264800 | A/G/T | — | hsa-miR-185 |
| rs63750625 | 264800 | A/G | — | hsa-miR-942 |
| rs63750625 | 264800 | A/G | — | hsa-miR-1976 |
| rs63750635 | 0 | C/T | — | hsa-miR-493 |
| rs63750635 | 0 | C/T | — | hsa-miR-432 |
| rs63750635 | 0 | C/T | — | hsa-miR-890 |
| rs63750643 | 0 | A/G | — | hsa-miR-1208 |
| rs63750653 | 0 | G/T | — | hsa-miR-411*, hsa-miR-379*, hsa-miR-380 |
| rs63750653 | 0 | G/T | — | hsa-miR-2054 |
| rs63750666 | 0 | C/T | — | hsa-miR-490-5p |
| rs63750666 | 0 | C/T | — | hsa-miR-132* |
| rs63750670 | 201475 | C/T | — | hsa-miR-1207-3p |
| rs63750670 | 201475 | C/T | — | hsa-miR-22 |
| rs63750671 | 0 | C/G | — | hsa-miR-942 |
| rs63750671 | 0 | C/G | — | hsa-miR-544 |
| rs63750671 | 0 | C/G | — | hsa-miR-629* |
| rs63750671 | 0 | C/G | — | hsa-miR-518a-5p, hsa-miR-527 |
| rs63750671 | 0 | C/G | — | hsa-miR-515-5p, hsa-miR-519e* |
| rs63750691 | 0 | C/G | — | hsa-miR-382 |
| rs63750691 | 0 | C/G | — | hsa-miR-148a* |
| rs63750691 | 0 | C/G | — | hsa-miR-1298 |
| rs63750691 | 0 | C/G | — | hsa-miR-1206 |
| rs63750700 | 264800 | A/C | — | hsa-miR-662 |
| rs63750700 | 264800 | A/C | — | hsa-miR-518c*, hsa-miR-330-5p, hsa-miR-326 |
| rs63750708 | 141800 | G/T | HBA2 | hsa-miR-532-3p, hsa-miR-150 |
| rs63750708 | 141800 | G/T | HBA2 | hsa-miR-1178 |
| rs63750708 | 141800 | G/T | HBA2 | hsa-miR-513a-5p, hsa-miR-27b, hsa-miR-27a |
| rs63750708 | 141800 | G/T | HBA2 | hsa-miR-342-3p |
| rs63750710 | 0 | A/C | — | hsa-miR-604 |
| rs63750710 | 0 | A/C | — | hsa-miR-455-5p |
| rs63750710 | 0 | A/C | — | hsa-miR-218 |
| rs63750711 | 0 | A/T | — | hsa-miR-942 |
| rs63750711 | 0 | A/T | — | hsa-miR-412 |
| rs63750711 | 0 | A/T | — | hsa-miR-513a-5p, hsa-miR-27b, hsa-miR-27a |
| rs63750711 | 0 | A/T | — | hsa-miR-103-2* |
| rs63750734 | 0 | A/G | — | hsa-miR-1208 |
| rs63750734 | 0 | A/G | — | hsa-miR-34c-3p |
| rs63750743 | 604400 | C/T | — | hsa-miR-545 |
| rs63750743 | 604400 | C/T | — | hsa-miR-18b, hsa-miR-18a |
| rs63750752 | 141800 | A/G/T | HBA2 | hsa-miR-885-3p |
| rs63750752 | 141800 | A/G/T | HBA2 | hsa-miR-194* |
| rs63750752 | 141800 | A/G/T | HBA2 | hsa-miR-485-5p |
| rs63750752 | 141800 | A/G/T | HBA2 | hsa-miR-449b, hsa-miR-449a, hsa-miR-34c-5p, hsa-miR-34a |
| rs63750758 | 264800 | A/G | — | hsa-miR-31* |
| rs63750759 | 264800 | C/T | — | hsa-miR-449b* |
| rs63750759 | 264800 | C/T | — | hsa-miR-103, hsa-miR-107 |
| rs63750763 | 264800 | C/T | — | hsa-miR-483-5p |
| rs63750781 | 0 | C/G/T | — | hsa-miR-502-5p |
| rs63750781 | 0 | C/G/T | — | hsa-miR-335* |
| rs63750781 | 0 | C/G/T | — | hsa-miR-643 |
| rs63750783 | 141900 | A/G | HBB | hsa-miR-1975 |
| rs63750783 | 141900 | A/G | HBB | hsa-miR-139-5p |
| rs63750783 | 141900 | A/G | HBB | hsa-miR-220c |

TABLE 2-continued

| SNP | OMIM | MUTATION | GENE | MIR |
|---|---|---|---|---|
| rs63750783 | 141900 | A/G | HBB | hsa-miR-18b* |
| rs63750783 | 141900 | A/G | HBB | hsa-miR-874 |
| rs63750798 | 264800 | G/T | — | hsa-miR-643 |
| rs63750801 | 141800 | C/T | HBA2 | hsa-miR-615-5p |
| rs63750801 | 141800 | C/T | HBA2 | hsa-miR-1275 |
| rs63750815 | 0 | G/T | — | hsa-miR-513a-5p, hsa-miR-27b, hsa-miR-27a |
| rs63750815 | 0 | G/T | — | hsa-miR-220c |
| rs63750818 | 0 | A/G | — | hsa-miR-29a* |
| rs63750818 | 0 | A/G | — | hsa-miR-345 |
| rs63750818 | 0 | A/G | — | hsa-miR-625* |
| rs63750840 | 141900 | A/C/G | HBB | hsa-miR-412 |
| rs63750840 | 141900 | A/C/G | HBB | hsa-miR-205 |
| rs63750871 | 0 | C/T | — | hsa-miR-1297, hsa-miR-26a, hsa-miR-26a, hsa-miR-26b |
| rs63750871 | 0 | C/T | — | hsa-miR-148a* |
| rs63750874 | 264800 | A/G | — | hsa-miR-345 |
| rs63750874 | 264800 | A/G | — | hsa-miR-1972 |
| rs63750874 | 264800 | A/G | — | hsa-miR-1201 |
| rs63750874 | 264800 | A/G | — | hsa-miR-484 |
| rs63750875 | 0 | C/G | — | hsa-miR-218-2* |
| rs63750875 | 0 | C/G | — | hsa-miR-29b-2* |
| rs63750886 | 0 | C/G | — | hsa-miR-634 |
| rs63750886 | 0 | C/G | — | hsa-miR-338-3p |
| rs63750899 | 0 | C/T | — | hsa-miR-486-3p |
| rs63750912 | 0 | C/T | — | hsa-miR-656 |
| rs63750921 | 0 | C/G | — | hsa-miR-508-5p |
| rs63750921 | 0 | C/G | — | hsa-miR-627 |
| rs63750950 | 141850 | A/C/G/T | HBA1 | hsa-miR-581 |
| rs63750950 | 141850 | A/C/G/T | HBA1 | hsa-miR-143* |
| rs63750950 | 141850 | A/C/G/T | HBA1 | hsa-miR-198 |
| rs63750950 | 141850 | A/C/G/T | HBA1 | hsa-miR-643 |
| rs63750950 | 141850 | A/C/G/T | HBA1 | hsa-miR-1909 |
| rs63750950 | 141850 | A/C/G/T | HBA1 | hsa-miR-493*, hsa-let-7g*, hsa-let-7a-2* |
| rs63750950 | 141850 | A/C/G/T | HBA1 | hsa-miR-375 |
| rs63750958 | 141800 | A/G/T | HBA2 | hsa-miR-196b, hsa-miR-196a, hsa-miR-196a |
| rs63750958 | 141800 | A/G/T | HBA2 | hsa-miR-1178 |
| rs63750958 | 141800 | A/G/T | HBA2 | hsa-miR-431* |
| rs63750959 | 0 | A/G/T | — | hsa-miR-1908, hsa-miR-663 |
| rs63750959 | 0 | A/G/T | — | hsa-miR-491-5p |
| rs63750959 | 0 | A/G/T | — | hsa-miR-541, hsa-miR-654-5p, hsa-miR-92a-2* |
| rs63750959 | 0 | A/G/T | — | hsa-miR-1914*, hsa-miR-423-5p |
| rs63750959 | 0 | A/G/T | — | hsa-miR-221* |
| rs63750959 | 0 | A/G/T | — | hsa-miR-744 |
| rs63750973 | 0 | C/T | — | hsa-miR-1208 |
| rs63750987 | 264800 | C/G/T | — | hsa-miR-1324 |
| rs63750987 | 264800 | C/G/T | — | hsa-miR-936, hsa-miR-199a-3p, hsa-miR-199b-3p, hsa-miR-199a-3p |
| rs63750987 | 264800 | C/G/T | — | hsa-miR-770-5p |
| rs63750987 | 264800 | C/G/T | — | hsa-miR-562 |
| rs63750992 | 264800 | A/G | — | hsa-miR-181a-2* |
| rs63751001 | 264800 | A/G | — | hsa-miR-758 |
| rs63751008 | 141800 | A/G | HBA1 | hsa-miR-500* |
| rs63751037 | 0 | A/G | — | hsa-miR-96* |
| rs63751037 | 0 | A/G | — | hsa-miR-1322, hsa-miR-1272 |
| rs63751037 | 0 | A/G | — | hsa-miR-433 |
| rs63751039 | 0 | A/G | — | hsa-miR-544 |
| rs63751039 | 0 | A/G | — | hsa-miR-141* |
| rs63751039 | 0 | A/G | — | hsa-miR-1976 |
| rs63751048 | 0 | C/T | — | hsa-miR-498 |
| rs63751068 | 0 | G/T | — | hsa-miR-600 |
| rs63751086 | 264800 | A/G | — | hsa-miR-558 |
| rs63751086 | 264800 | A/G | — | hsa-miR-1301 |
| rs63751086 | 264800 | A/G | — | hsa-miR-22 |
| rs63751086 | 264800 | A/G | — | hsa-miR-505* |
| rs63751086 | 264800 | A/G | — | hsa-miR-1205, hsa-miR-1184, hsa-miR-17* |
| rs63751108 | 0 | A/C/T | — | hsa-miR-223 |
| rs63751108 | 0 | A/C/T | — | hsa-miR-222* |
| rs63751108 | 0 | A/C/T | — | hsa-miR-802 |
| rs63751108 | 0 | A/C/T | — | hsa-miR-545* |
| rs63751108 | 0 | A/C/T | — | hsa-miR-924 |
| rs63751109 | 0 | C/T | — | hsa-miR-1257 |
| rs63751109 | 0 | C/T | — | hsa-miR-183* |
| rs63751109 | 0 | C/T | — | hsa-miR-758 |
| rs63751109 | 0 | C/T | — | hsa-miR-590-3p |
| rs63751109 | 0 | C/T | — | hsa-miR-1290, hsa-miR-876-5p |
| rs63751112 | 264800 | C/T | — | hsa-miR-143 |
| rs63751112 | 264800 | C/T | — | hsa-miR-625 |
| rs63751112 | 264800 | C/T | — | hsa-miR-637 |

TABLE 2-continued

| SNP | OMIM | MUTATION | GENE | MIR |
|---|---|---|---|---|
| rs63751112 | 264800 | C/T | — | hsa-miR-1275 |
| rs63751112 | 264800 | C/T | — | hsa-miR-1255b, hsa-miR-1255a |
| rs63751112 | 264800 | C/T | — | hsa-miR-30c-1*, hsa-miR-30b*, hsa-miR-30c-2* |
| rs63751114 | 141800 | C/T | HBA2 | hsa-miR-149* |
| rs63751114 | 141800 | C/T | HBA2 | hsa-miR-939 |
| rs63751114 | 141800 | C/T | HBA2 | hsa-miR-1908, hsa-miR-663 |
| rs63751114 | 141800 | C/T | HBA2 | hsa-miR-658 |
| rs63751114 | 141800 | C/T | HBA2 | hsa-miR-25* |
| rs63751114 | 141800 | C/T | HBA2 | hsa-miR-744 |
| rs63751114 | 141800 | C/T | HBA2 | hsa-miR-542-5p |
| rs63751114 | 141800 | C/T | HBA2 | hsa-miR-185 |
| rs63751116 | 141800 | A/T | HBA2 | hsa-miR-149* |
| rs63751116 | 141800 | A/T | HBA2 | hsa-miR-939 |
| rs63751116 | 141800 | A/T | HBA2 | hsa-miR-876-3p, hsa-miR-323-5p |
| rs63751116 | 141800 | A/T | HBA2 | hsa-miR-1293, hsa-miR-363* |
| rs63751116 | 141800 | A/T | HBA2 | hsa-miR-608, hsa-miR-342-5p |
| rs63751116 | 141800 | A/T | HBA2 | hsa-miR-542-5p |
| rs63751126 | 0 | A/C | — | hsa-miR-571, hsa-miR-219-1-3p |
| rs63751126 | 0 | A/C | — | hsa-miR-1304 |
| rs63751128 | 141900 | A/G | HBB | hsa-miR-335* |
| rs63751141 | 0 | C/G | — | hsa-miR-1270, hsa-miR-620 |
| rs63751141 | 0 | C/G | — | hsa-miR-490-5p |
| rs63751141 | 0 | C/G | — | hsa-miR-185 |
| rs63751144 | 0 | A/C | — | hsa-miR-499-3p |
| rs63751144 | 0 | A/C | — | hsa-miR-421 |
| rs63751144 | 0 | A/C | — | hsa-miR-545 |
| rs63751148 | 142250 | A/G | — | hsa-miR-136* |
| rs63751163 | 0 | C/T | — | hsa-miR-143 |
| rs63751165 | 0 | A/G | — | hsa-miR-377 |
| rs63751165 | 0 | A/G | — | hsa-miR-23b, hsa-miR-130a*, hsa-miR-23a |
| rs63751207 | 0 | C/G | — | hsa-miR-873 |
| rs63751215 | 264800 | C/T | — | hsa-miR-518a-5p, hsa-miR-527 |
| rs63751220 | 148900 | C/T | — | hsa-miR-552 |
| rs63751220 | 148900 | C/T | — | hsa-miR-125b-1* |
| rs63751220 | 148900 | C/T | — | hsa-miR-23b*, hsa-miR-23a* |
| rs63751223 | 0 | C/G | — | hsa-miR-31 |
| rs63751223 | 0 | C/G | — | hsa-miR-183 |
| rs63751223 | 0 | C/G | — | hsa-miR-1252 |
| rs63751229 | 0 | C/T | — | hsa-miR-492 |
| rs63751235 | 0 | C/G | — | hsa-miR-1207-3p |
| rs63751235 | 0 | C/G | — | hsa-miR-558 |
| rs63751235 | 0 | C/G | — | hsa-miR-425 |
| rs63751237 | 0 | A/G | HBA1 | hsa-miR-1250 |
| rs63751241 | 264800 | A/G | — | hsa-miR-502-5p |
| rs63751241 | 264800 | A/G | — | hsa-miR-1281 |
| rs63751241 | 264800 | A/G | — | hsa-miR-1915* |
| rs63751243 | 0 | A/C | — | hsa-miR-15a* |
| rs63751262 | 264800 | A/G | — | hsa-miR-1270, hsa-miR-620 |
| rs63751262 | 264800 | A/G | — | hsa-miR-1203 |
| rs63751262 | 264800 | A/G | — | hsa-miR-1180 |
| rs63751262 | 264800 | A/G | — | hsa-miR-1299, hsa-miR-516b, hsa-miR-516b |
| rs63751263 | 0 | A/C | — | hsa-miR-141* |
| rs63751272 | 0 | A/C/T | — | hsa-miR-136* |
| rs63751272 | 0 | A/C/T | — | hsa-miR-452* |
| rs63751272 | 0 | A/C/T | — | hsa-miR-141* |
| rs63751273 | 0 | C/T | — | hsa-miR-665 |
| rs63751273 | 0 | C/T | — | hsa-miR-1915 |
| rs63751273 | 0 | C/T | — | hsa-miR-92b* |
| rs63751273 | 0 | C/T | — | hsa-miR-532-3p, hsa-miR-150 |
| rs63751279 | 264800 | A/G | — | hsa-miR-767-3p |
| rs63751279 | 264800 | A/G | — | hsa-miR-93* |
| rs63751282 | 141800 | A/C/G/T | HBA2 | hsa-miR-302a* |
| rs63751282 | 141800 | A/C/G/T | HBA2 | hsa-miR-548m |
| rs63751285 | 141900 | C/G | HBB | hsa-miR-1975 |
| rs63751287 | 0 | A/C/G/T | — | hsa-miR-665 |
| rs63751287 | 0 | A/C/G/T | — | hsa-miR-335 |
| rs63751287 | 0 | A/C/G/T | — | hsa-miR-1226* |
| rs63751294 | 0 | C/T | — | hsa-miR-369-5p |
| rs63751308 | 141800 | A/C | — | hsa-miR-187 |
| rs63751318 | 264800 | C/T | — | hsa-miR-149* |
| rs63751318 | 264800 | C/T | — | hsa-miR-365* |
| rs63751318 | 264800 | C/T | — | hsa-miR-1321 |
| rs63751318 | 264800 | C/T | — | hsa-miR-625 |
| rs63751318 | 264800 | C/T | — | hsa-miR-765 |
| rs63751320 | 0 | A/C | — | hsa-miR-488* |
| rs63751391 | 0 | G/T | — | hsa-miR-1281 |
| rs63751399 | 0 | A/C/T | — | hsa-miR-604 |
| rs63751399 | 0 | A/C/T | — | hsa-miR-1207-3p |

TABLE 2-continued

| SNP | OMIM | MUTATION | GENE | MIR |
|---|---|---|---|---|
| rs63751399 | 0 | A/C/T | — | hsa-miR-93* |
| rs63751399 | 0 | A/C/T | — | hsa-miR-22 |
| rs63751417 | 141800 | C/T | HBA2 | hsa-miR-220c |
| rs63751417 | 141800 | C/T | HBA2 | hsa-miR-505* |
| rs63751417 | 141800 | C/T | HBA2 | hsa-miR-708, hsa-miR-28-5p |
| rs63751438 | 0 | A/C/T | — | hsa-miR-92b* |
| rs63751438 | 0 | A/C/T | — | hsa-miR-139-3p |
| rs63751612 | 0 | A/G | — | hsa-miR-664*, hsa-miR-149 |
| rs63751612 | 0 | A/G | — | hsa-miR-328 |
| rs63751615 | 0 | C/T | — | hsa-miR-513c |
| rs63751615 | 0 | C/T | — | hsa-miR-516a-5p |
| rs66469337 | 300461 | C/G/T | — | hsa-miR-627 |
| rs66469337 | 300461 | C/G/T | — | hsa-miR-1245 |
| rs66469337 | 300461 | C/G/T | — | hsa-miR-452* |
| rs66492417 | 264800 | G/T | — | hsa-miR-186 |
| rs66492417 | 264800 | G/T | — | hsa-miR-142-5p |
| rs66492417 | 264800 | G/T | — | hsa-let-7a*, hsa-let-7b*, hsa-let-7f-1*, hsa-let-7f-2* |
| rs66492417 | 264800 | G/T | — | hsa-miR-340 |
| rs66521141 | 300461 | A/G/T | — | hsa-miR-942 |
| rs66521141 | 300461 | A/G/T | — | hsa-miR-32* |
| rs66521141 | 300461 | A/G/T | — | hsa-miR-590-3p |
| rs66539573 | 300461 | A/G/T | — | hsa-miR-186 |
| rs66539573 | 300461 | A/G/T | — | hsa-miR-105 |
| rs66550389 | 300461 | G/T | — | hsa-miR-1303 |
| rs66550389 | 300461 | G/T | — | hsa-miR-375 |
| rs66564822 | 300461 | A/C | — | hsa-miR-1263, hsa-miR-150* |
| rs66616071 | 264800 | C/T | — | hsa-miR-767-3p |
| rs66616071 | 264800 | C/T | — | hsa-miR-370 |
| rs66724222 | 300461 | A/G | — | hsa-miR-558 |
| rs66724222 | 300461 | A/G | — | hsa-miR-22 |
| rs66724222 | 300461 | A/G | — | hsa-miR-505* |
| rs66864705 | 264800 | C/T | — | hsa-miR-513b |
| rs66864705 | 264800 | C/T | — | hsa-miR-513a-5p, hsa-miR-27b, hsa-miR-27a |
| rs66864705 | 264800 | C/T | — | hsa-miR-485-5p |
| rs66867430 | 300461 | A/G | — | hsa-miR-184 |
| rs66867430 | 300461 | A/G | — | hsa-miR-1263, hsa-miR-150* |
| rs66867430 | 300461 | A/G | — | hsa-miR-1265 |
| rs67120076 | 300461 | C/T | — | hsa-miR-24 |
| rs67156896 | 300461 | A/C | — | hsa-miR-595 |
| rs67283833 | 300461 | A/T | — | hsa-miR-130b* |
| rs67283833 | 300461 | A/T | — | hsa-miR-877* |
| rs67283833 | 300461 | A/T | — | hsa-miR-875-5p |
| rs67284661 | 300461 | C/T | — | hsa-miR-1207-3p |
| rs67294955 | 300461 | A/G | — | hsa-miR-1274a |
| rs67294955 | 300461 | A/G | — | hsa-miR-188-5p |
| rs67294955 | 300461 | A/G | — | hsa-miR-640 |
| rs67294955 | 300461 | A/G | — | hsa-miR-125a-5p, hsa-miR-125b, hsa-miR-125b |
| rs67330615 | 300461 | C/G | — | hsa-miR-218-1* |
| rs67330615 | 300461 | C/G | — | hsa-miR-516a-3p, hsa-miR-516b*, hsa-miR-516b* |
| rs67330615 | 300461 | C/G | — | hsa-miR-138 |
| rs67330615 | 300461 | C/G | — | hsa-miR-29b-1* |
| rs67333670 | 300461 | A/C | — | hsa-miR-1231, hsa-miR-632 |
| rs67333670 | 300461 | A/C | — | hsa-miR-511 |
| rs67333670 | 300461 | A/C | — | hsa-miR-2054 |
| rs67333670 | 300461 | A/C | — | hsa-miR-302d*, hsa-miR-302b* |
| rs67414444 | 300461 | G/T | — | hsa-miR-617 |
| rs67414444 | 300461 | G/T | — | hsa-miR-205 |
| rs67418243 | 300461 | C/G | — | hsa-miR-770-5p |
| rs67418243 | 300461 | C/G | — | hsa-miR-1911 |
| rs67418243 | 300461 | C/G | — | hsa-miR-145 |
| rs67470843 | 264800 | C/T | — | hsa-miR-1207-5p |
| rs67470843 | 264800 | C/T | — | hsa-miR-184 |
| rs67470843 | 264800 | C/T | — | hsa-miR-922, hsa-miR-214 |
| rs67486158 | 300461 | G/T | — | hsa-miR-629* |
| rs67486158 | 300461 | G/T | — | hsa-miR-1266 |
| rs67501347 | 300461 | A/C | — | hsa-miR-31 |
| rs67501347 | 300461 | A/C | — | hsa-miR-1285, hsa-miR-612 |
| rs67501347 | 300461 | A/C | — | hsa-miR-19a, hsa-miR-19b, hsa-miR-19b |
| rs67561842 | 264800 | A/G | — | hsa-miR-1254, hsa-miR-661 |
| rs67561842 | 264800 | A/G | — | hsa-miR-1285, hsa-miR-612 |
| rs67561842 | 264800 | A/G | — | hsa-miR-596 |
| rs67752076 | 300461 | A/G | — | hsa-miR-1248, hsa-miR-1237 |
| rs67752076 | 300461 | A/G | — | hsa-miR-29c, hsa-miR-29b, hsa-miR-29b, hsa-miR-29a |
| rs67752076 | 300461 | A/G | — | hsa-miR-141* |
| rs67870244 | 300461 | C/G | — | hsa-miR-1208 |
| rs67870244 | 300461 | C/G | — | hsa-miR-1183 |
| rs67890094 | 300461 | C/G | — | hsa-miR-218-1* |

TABLE 2-continued

| SNP | OMIM | MUTATION | GENE | MIR |
|---|---|---|---|---|
| rs67890094 | 300461 | C/G | — | hsa-miR-22* |
| rs67890094 | 300461 | C/G | — | hsa-miR-182* |
| rs67890094 | 300461 | C/G | — | hsa-miR-218-2* |
| rs67890094 | 300461 | C/G | — | hsa-miR-103-2* |
| rs67939655 | 300461 | A/T | — | hsa-miR-561 |
| rs67960011 | 300461 | C/G | — | hsa-miR-483-3p |
| rs67960011 | 300461 | C/G | — | hsa-miR-508-5p |
| rs67960011 | 300461 | C/G | — | hsa-miR-766 |
| rs67993095 | 300461 | A/G | — | hsa-miR-646, hsa-miR-503, hsa-miR-497, hsa-miR-424, hsa-miR-195, hsa-miR-15b, hsa-miR-16, hsa-miR-15a, hsa-miR-16 |
| rs67996820 | 264800 | C/G | — | hsa-miR-183 |
| rs67996820 | 264800 | C/G | — | hsa-miR-122 |
| rs67996820 | 264800 | C/G | — | hsa-miR-449b, hsa-miR-449a, hsa-miR-34c-5p, hsa-miR-34a |
| rs67996820 | 264800 | C/G | — | hsa-miR-30c-1*, hsa-miR-30b*, hsa-miR-30c-2* |
| rs68033093 | 300461 | A/T | — | hsa-miR-34a* |
| rs68033093 | 300461 | A/T | — | hsa-miR-30c, hsa-miR-30e, hsa-miR-30b, hsa-miR-30d, hsa-miR-30a |
| rs72549407 | 610532 | C/T | — | hsa-miR-196a* |
| rs72552292 | 611777 | A/G | — | hsa-miR-720 |
| rs72552292 | 611777 | A/G | — | hsa-miR-1915* |
| rs72552293 | 611777 | A/G | — | hsa-miR-934 |
| rs72552293 | 611777 | A/G | — | hsa-miR-1249 |
| rs72552293 | 611777 | A/G | — | hsa-miR-874 |
| rs72552294 | 611777 | C/T | — | hsa-miR-1539 |
| rs72552294 | 611777 | C/T | — | hsa-miR-1205, hsa-miR-1184, hsa-miR-17* |
| rs72552295 | 300461 | C/T | — | hsa-miR-141* |
| rs72552296 | 300461 | A/G | — | hsa-miR-101, hsa-miR-144 |
| rs72552296 | 300461 | A/G | — | hsa-miR-132, hsa-miR-212 |
| rs72552296 | 300461 | A/G | — | hsa-miR-16-1* |
| rs72552300 | 300461 | C/T | — | hsa-miR-497* |
| rs72552300 | 300461 | C/T | — | hsa-miR-205* |
| rs72552300 | 300461 | C/T | — | hsa-miR-1305 |
| rs72552300 | 300461 | C/T | — | hsa-miR-607 |
| rs72554304 | 300461 | C/T | — | hsa-miR-142-3p |
| rs72554305 | 300461 | C/T | — | hsa-miR-221, hsa-miR-222, hsa-miR-187* |
| rs72554305 | 300461 | C/T | — | hsa-miR-1207-3p |
| rs72554305 | 300461 | C/T | — | hsa-miR-22 |
| rs72554306 | 300461 | G/T | — | hsa-miR-938 |
| rs72554306 | 300461 | G/T | — | hsa-miR-1291 |
| rs72554306 | 300461 | G/T | — | hsa-miR-205 |
| rs72554307 | 300461 | C/T | — | hsa-miR-1291 |
| rs72554307 | 300461 | C/T | — | hsa-miR-129-3p, hsa-miR-129* |
| rs72554307 | 300461 | C/T | — | hsa-miR-513a-5p, hsa-miR-27b, hsa-miR-27a |
| rs72554308 | 300461 | A/G | — | hsa-miR-328 |
| rs72554309 | 300461 | C/T | — | hsa-miR-493 |
| rs72554309 | 300461 | C/T | — | hsa-miR-1253 |
| rs72554309 | 300461 | C/T | — | hsa-miR-548m |
| rs72554309 | 300461 | C/T | — | hsa-miR-1300, hsa-miR-580 |
| rs72554310 | 300461 | C/T | — | hsa-miR-1303 |
| rs72554311 | 300461 | C/G | — | hsa-miR-1303 |
| rs72554311 | 300461 | C/G | — | hsa-miR-582-5p |
| rs72554312 | 300461 | C/T | — | hsa-miR-122 |
| rs72554312 | 300461 | C/T | — | hsa-miR-129-5p |
| rs72554312 | 300461 | C/T | — | hsa-miR-1303 |
| rs72554315 | 300461 | C/T | — | hsa-miR-561 |
| rs72554315 | 300461 | C/T | — | hsa-miR-379 |
| rs72554315 | 300461 | C/T | — | hsa-let-7c* |
| rs72554317 | 300461 | A/G | — | hsa-miR-1248, hsa-miR-1237 |
| rs72554318 | 300461 | A/T | — | hsa-miR-889 |
| rs72554318 | 300461 | A/T | — | hsa-miR-141* |
| rs72554319 | 300461 | G/T | — | hsa-miR-302d*, hsa-miR-302b* |
| rs72554321 | 300461 | A/T | — | hsa-miR-103-as |
| rs72554321 | 300461 | A/T | — | hsa-miR-92b, hsa-miR-367, hsa-miR-363, hsa-miR-25, hsa-miR-32, hsa-miR-92a, hsa-miR-92a |
| rs72554321 | 300461 | A/T | — | hsa-miR-448, hsa-miR-153, hsa-miR-153 |
| rs72554322 | 300461 | A/G | — | hsa-miR-376a, hsa-miR-376b |
| rs72554323 | 300461 | C/T | — | hsa-miR-628-5p |
| rs72554323 | 300461 | C/T | — | hsa-miR-633 |
| rs72554323 | 300461 | C/T | — | hsa-miR-93* |
| rs72554324 | 300461 | C/T | — | hsa-miR-30e*, hsa-miR-30d*, hsa-miR-30a* |
| rs72554324 | 300461 | C/T | — | hsa-miR-127-3p |
| rs72554324 | 300461 | C/T | — | hsa-miR-205* |
| rs72554325 | 300461 | G/T | — | hsa-miR-629* |
| rs72554326 | 300461 | C/T | — | hsa-miR-138-2* |
| rs72554328 | 300461 | C/T | — | hsa-miR-142-5p |
| rs72554329 | 300461 | G/T | — | hsa-miR-203 |

TABLE 2-continued

| SNP | OMIM | MUTATION | GENE | MIR |
|---|---|---|---|---|
| rs72554329 | 300461 | G/T | — | hsa-miR-106a* |
| rs72554329 | 300461 | G/T | — | hsa-miR-1915* |
| rs72554330 | 300461 | C/T | — | hsa-miR-338-5p |
| rs72554330 | 300461 | C/T | — | hsa-miR-106a* |
| rs72554330 | 300461 | C/T | — | hsa-miR-1915* |
| rs72554330 | 300461 | C/T | — | hsa-miR-600 |
| rs72554331 | 300461 | A/G | — | hsa-miR-942 |
| rs72554331 | 300461 | A/G | — | hsa-miR-1915* |
| rs72554331 | 300461 | A/G | — | hsa-miR-623, hsa-miR-204, hsa-miR-211 |
| rs72554332 | 300461 | A/G | — | hsa-miR-617 |
| rs72554332 | 300461 | A/G | — | hsa-miR-623, hsa-miR-204, hsa-miR-211 |
| rs72554333 | 300461 | G/T | — | hsa-miR-617 |
| rs72554335 | 300461 | G/T | — | hsa-miR-1266 |
| rs72554336 | 300461 | C/G | — | hsa-miR-532-5p |
| rs72554337 | 300461 | A/G | — | hsa-miR-532-5p |
| rs72554337 | 300461 | A/G | — | hsa-miR-654-3p |
| rs72554338 | 300461 | A/G | — | hsa-miR-302a* |
| rs72554338 | 300461 | A/G | — | hsa-miR-513c |
| rs72554338 | 300461 | A/G | — | hsa-miR-616*, hsa-miR-371-5p, hsa-miR-373* |
| rs72554339 | 300461 | A/T | — | hsa-miR-26a-2*, hsa-miR-26a-1* |
| rs72554340 | 300461 | A/G | — | hsa-miR-130b* |
| rs72554340 | 300461 | A/G | — | hsa-miR-624* |
| rs72554340 | 300461 | A/G | — | hsa-miR-877* |
| rs72554340 | 300461 | A/G | — | hsa-miR-1278 |
| rs72554341 | 300461 | A/G | — | hsa-miR-1911 |
| rs72554341 | 300461 | A/G | — | hsa-miR-496 |
| rs72554341 | 300461 | A/G | — | hsa-miR-1278 |
| rs72554342 | 300461 | G/T | — | hsa-miR-1911 |
| rs72554342 | 300461 | G/T | — | hsa-miR-1248, hsa-miR-1237 |
| rs72554342 | 300461 | G/T | — | hsa-miR-1278 |
| rs72554344 | 300461 | A/G | — | hsa-miR-375 |
| rs72554345 | 300461 | C/G | — | hsa-miR-409-3p, hsa-miR-33a* |
| rs72554347 | 300461 | A/G | — | hsa-miR-20b* |
| rs72554347 | 300461 | A/G | — | hsa-miR-129-5p |
| rs72554349 | 300461 | A/G | — | hsa-miR-330-3p |
| rs72554349 | 300461 | A/G | — | hsa-miR-24-1*, hsa-miR-24-2* |
| rs72554349 | 300461 | A/G | — | hsa-miR-934 |
| rs72554349 | 300461 | A/G | — | hsa-miR-1264 |
| rs72554349 | 300461 | A/G | — | hsa-miR-520h, hsa-miR-520g |
| rs72554350 | 300461 | A/C | — | hsa-miR-301b, hsa-miR-454, hsa-miR-301a, hsa-miR-130b, hsa-miR-130a |
| rs72554350 | 300461 | A/C | — | hsa-miR-148a* |
| rs72554350 | 300461 | A/C | — | hsa-miR-520b, hsa-miR-302e, hsa-miR-519a, hsa-miR-519a, hsa-miR-520c-3p, hsa-miR-520d-3p, hsa-miR-520e, hsa-miR-519c-3p, hsa-miR-520a-3p, hsa-miR-519b-3p, hsa-miR-302c, hsa-miR-302d, hsa-miR-372, hsa-miR-373, hsa-miR-302b, hsa-miR-302a |
| rs72554350 | 300461 | A/C | — | hsa-miR-518a-5p, hsa-miR-527 |
| rs72554350 | 300461 | A/C | — | hsa-miR-607 |
| rs72554350 | 300461 | A/C | — | hsa-miR-19a, hsa-miR-19b, hsa-miR-19b |
| rs72554351 | 300461 | G/T | — | hsa-miR-532-3p, hsa-miR-150 |
| rs72554351 | 300461 | G/T | — | hsa-miR-155* |
| rs72554352 | 300461 | A/G | — | hsa-miR-532-3p, hsa-miR-150 |
| rs72554352 | 300461 | A/G | — | hsa-miR-511 |
| rs72554352 | 300461 | A/G | — | hsa-miR-654-3p |
| rs72554358 | 300461 | A/G | — | hsa-miR-187 |
| rs72554358 | 300461 | A/G | — | hsa-miR-1973 |
| rs72555358 | 230500 | C/T | — | hsa-miR-548p |
| rs72555359 | 230500 | C/T | — | hsa-miR-888 |
| rs72555360 | 230500 | C/T | — | hsa-miR-518e |
| rs72555360 | 230500 | C/T | — | hsa-miR-220c |
| rs72555360 | 230500 | C/T | — | hsa-miR-657 |
| rs72555360 | 230500 | C/T | — | hsa-miR-552 |
| rs72555362 | 230500 | G/T | — | hsa-miR-575 |
| rs72555363 | 230500 | G/T | — | hsa-miR-198 |
| rs72555363 | 230500 | G/T | — | hsa-miR-487b |
| rs72555363 | 230500 | G/T | — | hsa-miR-145 |
| rs72555363 | 230500 | G/T | — | hsa-miR-582-5p |
| rs72555364 | 230500 | C/T | — | hsa-miR-532-5p |
| rs72555364 | 230500 | C/T | — | hsa-miR-875-5p |
| rs72555367 | 230500 | A/G | — | hsa-miR-136 |
| rs72555367 | 230500 | A/G | — | hsa-miR-508-5p |
| rs72555367 | 230500 | A/G | — | hsa-miR-617 |
| rs72555368 | 230500 | A/G | — | hsa-miR-575 |
| rs72555369 | 230500 | A/C | — | hsa-miR-619 |
| rs72555369 | 230500 | A/C | — | hsa-miR-1261 |
| rs72555370 | 230500 | C/T | — | hsa-miR-575 |

TABLE 2-continued

| SNP | OMIM | MUTATION | GENE | MIR |
|---|---|---|---|---|
| rs72555370 | 230500 | C/T | — | hsa-miR-1910, hsa-miR-455-3p |
| rs72555372 | 230500 | C/T | — | hsa-miR-513a-5p, hsa-miR-27b, hsa-miR-27a |
| rs72555373 | 230500 | A/T | — | hsa-miR-302f |
| rs72555390 | 230500 | C/T | — | hsa-miR-576-3p |
| rs72555390 | 230500 | C/T | — | hsa-miR-143 |
| rs72555391 | 230500 | A/G | — | hsa-miR-377 |
| rs72555391 | 230500 | A/G | — | hsa-miR-23b, hsa-miR-130a*, hsa-miR-23a |
| rs72555392 | 230500 | A/G | — | hsa-miR-602 |
| rs72555392 | 230500 | A/G | — | hsa-miR-1308 |
| rs72555392 | 230500 | A/G | — | hsa-miR-30c-1*, hsa-miR-30b*, hsa-miR-30c-2* |
| rs72556252 | 300461 | C/T | — | hsa-miR-338-5p |
| rs72556253 | 300461 | C/T | — | hsa-miR-338-5p |
| rs72556253 | 300461 | C/T | — | hsa-miR-645 |
| rs72556256 | 300461 | A/C | — | hsa-miR-587 |
| rs72556256 | 300461 | A/C | — | hsa-miR-141* |
| rs72556257 | 300461 | A/T | — | hsa-miR-891b |
| rs72556257 | 300461 | A/T | — | hsa-miR-20a* |
| rs72556258 | 300461 | A/G | — | hsa-miR-20a* |
| rs72556258 | 300461 | A/G | — | hsa-miR-509-3-5p, hsa-miR-509-5p, hsa-miR-509-5p, hsa-miR-217 |
| rs72556258 | 300461 | A/G | — | hsa-miR-1183 |
| rs72556259 | 300461 | C/T | — | hsa-miR-429, hsa-miR-200c, hsa-miR-200b |
| rs72556260 | 300461 | C/G | — | hsa-miR-1827 |
| rs72556261 | 300461 | A/T | — | hsa-let-7a*, hsa-let-7b*, hsa-let-7f-1*, hsa-let-7f-2* |
| rs72556261 | 300461 | A/T | — | hsa-miR-516a-5p |
| rs72556262 | 300461 | A/T | — | hsa-miR-655 |
| rs72556262 | 300461 | A/T | — | hsa-let-7a*, hsa-let-7b*, hsa-let-7f-1*, hsa-let-7f-2* |
| rs72556262 | 300461 | A/T | — | hsa-miR-569 |
| rs72556262 | 300461 | A/T | — | hsa-miR-2053 |
| rs72556263 | 300461 | C/G | — | hsa-miR-29a* |
| rs72556263 | 300461 | C/G | — | hsa-miR-216b, hsa-miR-216a |
| rs72556263 | 300461 | C/G | — | hsa-miR-508-3p, hsa-miR-219-5p, hsa-miR-219-5p |
| rs72556265 | 300461 | G/T | — | hsa-miR-575 |
| rs72556266 | 300461 | C/T | — | hsa-miR-575 |
| rs72556266 | 300461 | C/T | — | hsa-miR-302d*, hsa-miR-302b* |
| rs72556266 | 300461 | C/T | — | hsa-miR-1911* |
| rs72556267 | 300461 | G/T | — | hsa-miR-103-2* |
| rs72556268 | 300461 | A/C | — | hsa-miR-432* |
| rs72556268 | 300461 | A/C | — | hsa-miR-103-2* |
| rs72556270 | 300461 | A/G | — | hsa-miR-181a* |
| rs72556271 | 300461 | A/G | — | hsa-miR-181a-2* |
| rs72556273 | 300461 | C/T | — | hsa-miR-885-3p |
| rs72556274 | 300461 | C/G | — | hsa-miR-216b, hsa-miR-216a |
| rs72556274 | 300461 | C/G | — | hsa-miR-1229 |
| rs72556274 | 300461 | C/G | — | hsa-miR-513a-5p, hsa-miR-27b, hsa-miR-27a |
| rs72556274 | 300461 | C/G | — | hsa-miR-342-3p |
| rs72556275 | 300461 | G/T | — | hsa-miR-425 |
| rs72556276 | 300461 | A/T | — | hsa-miR-92a-1* |
| rs72556276 | 300461 | A/T | — | hsa-miR-1265 |
| rs72556277 | 300461 | C/G | — | hsa-miR-1265 |
| rs72556278 | 300461 | C/T | — | hsa-miR-1265 |
| rs72556279 | 300461 | A/T | — | hsa-miR-582-3p |
| rs72556279 | 300461 | A/T | — | hsa-miR-873 |
| rs72556279 | 300461 | A/T | — | hsa-miR-1243 |
| rs72556279 | 300461 | A/T | — | hsa-miR-1299, hsa-miR-516b, hsa-miR-516b |
| rs72556280 | 300461 | C/G | — | hsa-miR-665 |
| rs72556280 | 300461 | C/G | — | hsa-miR-338-3p |
| rs72556281 | 300461 | C/G | — | hsa-miR-665 |
| rs72556281 | 300461 | C/G | — | hsa-miR-1207-5p |
| rs72556281 | 300461 | C/G | — | hsa-miR-575 |
| rs72556281 | 300461 | C/G | — | hsa-miR-1286 |
| rs72556281 | 300461 | C/G | — | hsa-miR-940, hsa-miR-34b* |
| rs72556282 | 300461 | C/T | — | hsa-miR-34a* |
| rs72556282 | 300461 | C/T | — | hsa-miR-202, hsa-let-7i, hsa-let-7g, hsa-miR-98, hsa-let-7a, hsa-let-7a, hsa-let-7a, hsa-let-7b, hsa-let-7c, hsa-let-7d, hsa-let-7e, hsa-let-7f, hsa-let-7f |
| rs72556282 | 300461 | C/T | — | hsa-miR-383 |
| rs72556283 | 300461 | A/G | — | hsa-miR-202, hsa-let-7i, hsa-let-7g, hsa-miR-98, hsa-let-7a, hsa-let-7a, hsa-let-7a, hsa-let-7b, hsa-let-7c, hsa-let-7d, hsa-let-7e, hsa-let-7f, hsa-let-7f |
| rs72556283 | 300461 | A/G | — | hsa-miR-1827 |
| rs72556284 | 300461 | C/T | — | hsa-miR-1294 |
| rs72556286 | 300461 | C/T | — | hsa-miR-637 |
| rs72556286 | 300461 | C/T | — | hsa-miR-1268, hsa-miR-585 |
| rs72556290 | 300461 | A/G | — | hsa-miR-124* |
| rs72556290 | 300461 | A/G | — | hsa-miR-384 |
| rs72556291 | 300461 | A/T | — | hsa-miR-124* |
| rs72556291 | 300461 | A/T | — | hsa-let-7c* |

TABLE 2-continued

| SNP | OMIM | MUTATION | GENE | MIR |
|---|---|---|---|---|
| rs72556293 | 300461 | A/G | — | hsa-miR-221, hsa-miR-222, hsa-miR-187* |
| rs72556293 | 300461 | A/G | — | hsa-miR-139-5p |
| rs72556293 | 300461 | A/G | — | hsa-miR-582-5p |
| rs72556295 | 300461 | G/T | — | hsa-miR-208b, hsa-miR-499-5p, hsa-miR-208a |
| rs72556295 | 300461 | G/T | — | hsa-miR-548b-3p |
| rs72556296 | 300461 | C/T | — | hsa-miR-493 |
| rs72556296 | 300461 | C/T | — | hsa-miR-555 |
| rs72556296 | 300461 | C/T | — | hsa-miR-1226* |
| rs72556297 | 300461 | G/T | — | hsa-miR-886-3p |
| rs72556297 | 300461 | G/T | — | hsa-miR-22 |
| rs72556297 | 300461 | G/T | — | hsa-miR-1226* |
| rs72556298 | 300461 | C/G | — | hsa-miR-1207-3p |
| rs72556299 | 300461 | A/G | — | hsa-miR-1207-3p |
| rs72556301 | 300461 | A/G | — | hsa-miR-384 |
| rs72556301 | 300461 | A/G | — | hsa-miR-202*, hsa-miR-337-3p |
| rs72558403 | 300461 | A/T | — | hsa-miR-1826 |
| rs72558403 | 300461 | A/T | — | hsa-miR-640 |
| rs72558403 | 300461 | A/T | — | hsa-miR-375 |
| rs72558404 | 300461 | A/C | — | hsa-miR-375 |
| rs72558405 | 300461 | A/G | — | hsa-miR-144* |
| rs72558405 | 300461 | A/G | — | hsa-miR-375 |
| rs72558406 | 300461 | A/G | — | hsa-miR-452 |
| rs72558406 | 300461 | A/G | — | hsa-miR-375 |
| rs72558406 | 300461 | A/G | — | hsa-miR-26b* |
| rs72558407 | 300461 | C/T | — | hsa-miR-301b, hsa-miR-454, hsa-miR-301a, hsa-miR-130b, hsa-miR-130a |
| rs72558407 | 300461 | C/T | — | hsa-miR-143* |
| rs72558407 | 300461 | C/T | — | hsa-miR-1286 |
| rs72558408 | 300461 | C/T | — | hsa-miR-301b, hsa-miR-454, hsa-miR-301a, hsa-miR-130b, hsa-miR-130a |
| rs72558408 | 300461 | C/T | — | hsa-miR-1911 |
| rs72558408 | 300461 | C/T | — | hsa-miR-143* |
| rs72558408 | 300461 | C/T | — | hsa-miR-122 |
| rs72558408 | 300461 | C/T | — | hsa-miR-1286 |
| rs72558408 | 300461 | C/T | — | hsa-miR-1909* |
| rs72558409 | 300461 | A/C | — | hsa-miR-1207-5p |
| rs72558409 | 300461 | A/C | — | hsa-miR-301b, hsa-miR-454, hsa-miR-301a, hsa-miR-130b, hsa-miR-130a |
| rs72558409 | 300461 | A/C | — | hsa-miR-143* |
| rs72558409 | 300461 | A/C | — | hsa-miR-122 |
| rs72558409 | 300461 | A/C | — | hsa-miR-1909* |
| rs72558410 | 300461 | C/G | — | hsa-miR-148b, hsa-miR-152, hsa-miR-148a |
| rs72558410 | 300461 | C/G | — | hsa-miR-122 |
| rs72558410 | 300461 | C/G | — | hsa-miR-1909* |
| rs72558411 | 300461 | A/G | — | hsa-miR-96* |
| rs72558411 | 300461 | A/G | — | hsa-miR-1322, hsa-miR-1272 |
| rs72558411 | 300461 | A/G | — | hsa-miR-433 |
| rs72558412 | 300461 | G/T | — | hsa-miR-96* |
| rs72558414 | 300461 | A/G | — | hsa-miR-191* |
| rs72558414 | 300461 | A/G | — | hsa-miR-1206 |
| rs72558415 | 300461 | A/C | — | hsa-miR-767-3p |
| rs72558415 | 300461 | A/C | — | hsa-miR-191* |
| rs72558416 | 300461 | A/G | — | hsa-miR-1178 |
| rs72558416 | 300461 | A/G | — | hsa-miR-191* |
| rs72558416 | 300461 | A/G | — | hsa-miR-218 |
| rs72558417 | 300461 | C/T | — | hsa-miR-639 |
| rs72558417 | 300461 | C/T | — | hsa-miR-205* |
| rs72558418 | 300461 | A/C | — | hsa-miR-639 |
| rs72558418 | 300461 | A/C | — | hsa-miR-219-2-3p |
| rs72558418 | 300461 | A/C | — | hsa-miR-302f |
| rs72558419 | 300461 | A/T | — | hsa-miR-33b, hsa-miR-33a |
| rs72558419 | 300461 | A/T | — | hsa-miR-106a* |
| rs72558419 | 300461 | A/T | — | hsa-miR-19a, hsa-miR-19b, hsa-miR-19b |
| rs72558420 | 300461 | C/T | — | hsa-miR-33b, hsa-miR-33a |
| rs72558420 | 300461 | C/T | — | hsa-miR-181d, hsa-miR-181b, hsa-miR-181a, hsa-miR-181a, hsa-miR-181b, hsa-miR-181c |
| rs72558420 | 300461 | C/T | — | hsa-miR-18b, hsa-miR-18a |
| rs72558421 | 300461 | C/T | — | hsa-miR-301b, hsa-miR-454, hsa-miR-301a, hsa-miR-130b, hsa-miR-130a |
| rs72558421 | 300461 | C/T | — | hsa-miR-493 |
| rs72558421 | 300461 | C/T | — | hsa-miR-520b, hsa-miR-302e, hsa-miR-519a, hsa-miR-519a, hsa-miR-520c-3p, hsa-miR-520d-3p, hsa-miR-520e, hsa-miR-519c-3p, hsa-miR-520a-3p, hsa-miR-519b-3p, hsa-miR-302c, hsa-miR-302d, hsa-miR-372, hsa-miR-373, hsa-miR-302b, hsa-miR-302a |

TABLE 2-continued

| SNP | OMIM | MUTATION | GENE | MIR |
|---|---|---|---|---|
| rs72558421 | 300461 | C/T | — | hsa-miR-519d, hsa-miR-526b*, hsa-miR-20b, hsa-miR-106b, hsa-miR-106a, hsa-miR-93, hsa-miR-17, hsa-miR-20a |
| rs72558421 | 300461 | C/T | — | hsa-miR-18b, hsa-miR-18a |
| rs72558421 | 300461 | C/T | — | hsa-miR-488 |
| rs72558423 | 300461 | C/G | — | hsa-miR-493 |
| rs72558423 | 300461 | C/G | — | hsa-miR-1201 |
| rs72558424 | 300461 | A/C | — | hsa-miR-516a-3p, hsa-miR-516b*, hsa-miR-516b* |
| rs72558424 | 300461 | A/C | — | hsa-miR-22 |
| rs72558424 | 300461 | A/C | — | hsa-miR-1201 |
| rs72558424 | 300461 | A/C | — | hsa-miR-1200, hsa-miR-378* |
| rs72558425 | 300461 | C/G | — | hsa-miR-936, hsa-miR-199a-3p, hsa-miR-199b-3p, hsa-miR-199a-3p |
| rs72558425 | 300461 | C/G | — | hsa-miR-9 |
| rs72558425 | 300461 | C/G | — | hsa-miR-450b-5p, hsa-miR-557, hsa-miR-507 |
| rs72558426 | 300461 | C/T | — | hsa-miR-1303 |
| rs72558426 | 300461 | C/T | — | hsa-miR-9 |
| rs72558428 | 300461 | A/C | — | hsa-miR-24 |
| rs72558428 | 300461 | A/C | — | hsa-miR-340* |
| rs72558429 | 300461 | C/T | — | hsa-miR-192* |
| rs72558430 | 300461 | G/T | — | hsa-miR-767-3p |
| rs72558430 | 300461 | G/T | — | hsa-miR-31* |
| rs72558435 | 300461 | C/T | — | hsa-miR-1263, hsa-miR-150* |
| rs72558436 | 300461 | A/T | — | hsa-miR-891b |
| rs72558437 | 300461 | A/C | — | hsa-miR-335* |
| rs72558437 | 300461 | A/C | — | hsa-miR-30e*, hsa-miR-30d*, hsa-miR-30a* |
| rs72558440 | 300461 | A/C | — | hsa-miR-136 |
| rs72558440 | 300461 | A/C | — | hsa-miR-766 |
| rs72558441 | 300461 | C/T | — | hsa-miR-655 |
| rs72558442 | 300461 | A/G | — | hsa-miR-1231, hsa-miR-632 |
| rs72558443 | 300461 | A/G | — | hsa-miR-486-5p |
| rs72558443 | 300461 | A/G | — | hsa-miR-214* |
| rs72558443 | 300461 | A/G | — | hsa-miR-1231, hsa-miR-632 |
| rs72558443 | 300461 | A/G | — | hsa-miR-520b, hsa-miR-302e, hsa-miR-519a, hsa-miR-519a, hsa-miR-520c-3p, hsa-miR-520d-3p, hsa-miR-520e, hsa-miR-519c-3p, hsa-miR-520a-3p, hsa-miR-519b-3p, hsa-miR-302c, hsa-miR-302d, hsa-miR-372, hsa-miR-373, hsa-miR-302b, hsa-miR-302a |
| rs72558443 | 300461 | A/G | — | hsa-miR-33b*, hsa-miR-515-3p, hsa-miR-519e, hsa-miR-515-3p, hsa-miR-371-3p |
| rs72558443 | 300461 | A/G | — | hsa-miR-550 |
| rs72558443 | 300461 | A/G | — | hsa-miR-595 |
| rs72558444 | 300461 | A/G | — | hsa-miR-1231, hsa-miR-632 |
| rs72558444 | 300461 | A/G | — | hsa-miR-595 |
| rs72558445 | 300461 | C/T | — | hsa-miR-595 |
| rs72558445 | 300461 | C/T | — | hsa-miR-574-5p |
| rs72558446 | 300461 | G/T | — | hsa-miR-374a* |
| rs72558446 | 300461 | G/T | — | hsa-miR-519d, hsa-miR-526b*, hsa-miR-20b, hsa-miR-106b, hsa-miR-106a, hsa-miR-93, hsa-miR-17, hsa-miR-20a |
| rs72558446 | 300461 | G/T | — | hsa-miR-520h, hsa-miR-520g |
| rs72558447 | 300461 | A/G | — | hsa-miR-1297, hsa-miR-26a, hsa-miR-26a, hsa-miR-26b |
| rs72558447 | 300461 | A/G | — | hsa-miR-498 |
| rs72558449 | 300461 | C/T | — | hsa-miR-636 |
| rs72558449 | 300461 | C/T | — | hsa-miR-1973 |
| rs72558450 | 300461 | A/G | — | hsa-miR-375 |
| rs72558450 | 300461 | A/G | — | hsa-miR-587 |
| rs72558451 | 300461 | C/T | — | hsa-miR-578 |
| rs72558454 | 300461 | C/T | — | hsa-miR-449b* |
| rs72558455 | 300461 | C/T | — | hsa-miR-1254, hsa-miR-661 |
| rs72558455 | 300461 | C/T | — | hsa-miR-596 |
| rs72558455 | 300461 | C/T | — | hsa-miR-505* |
| rs72558461 | 300461 | C/G | — | hsa-miR-198 |
| rs72558461 | 300461 | C/G | — | hsa-miR-145 |
| rs72558463 | 300461 | C/T | — | hsa-miR-340 |
| rs72558463 | 300461 | C/T | — | hsa-miR-16-1* |
| rs72558464 | 300461 | A/G | — | hsa-miR-142-3p |
| rs72558464 | 300461 | A/G | — | hsa-miR-562 |
| rs72558464 | 300461 | A/G | — | hsa-miR-1244 |
| rs72558465 | 300461 | G/T | — | hsa-miR-31 |
| rs72558465 | 300461 | G/T | — | hsa-miR-1285, hsa-miR-612 |
| rs72558467 | 300461 | A/G | — | hsa-miR-483-3p |
| rs72558467 | 300461 | A/G | — | hsa-miR-1248, hsa-miR-1237 |
| rs72558470 | 300461 | G/T | — | hsa-miR-186 |
| rs72558470 | 300461 | G/T | — | hsa-miR-664 |
| rs72558470 | 300461 | G/T | — | hsa-miR-617 |

TABLE 2-continued

| SNP | OMIM | MUTATION | GENE | MIR |
|---|---|---|---|---|
| rs72558473 | 300461 | C/T | — | hsa-miR-369-5p |
| rs72558473 | 300461 | C/T | — | hsa-miR-611, hsa-miR-151-5p |
| rs72558474 | 300461 | G/T | — | hsa-miR-369-5p |
| rs72558474 | 300461 | G/T | — | hsa-miR-611, hsa-miR-151-5p |
| rs72558474 | 300461 | G/T | — | hsa-miR-877 |
| rs72558475 | 300461 | A/C | — | hsa-miR-101* |
| rs72558475 | 300461 | A/C | — | hsa-miR-1245 |
| rs72558475 | 300461 | A/C | — | hsa-miR-369-5p |
| rs72558475 | 300461 | A/C | — | hsa-miR-921 |
| rs72558476 | 300461 | A/G | — | hsa-miR-518c*, hsa-miR-330-5p, hsa-miR-326 |
| rs72558476 | 300461 | A/G | — | hsa-miR-9 |
| rs72558477 | 300461 | G/T | — | hsa-miR-491-3p |
| rs72558477 | 300461 | G/T | — | hsa-miR-532-5p |
| rs72558477 | 300461 | G/T | — | hsa-miR-544 |
| rs72558478 | 300461 | A/G | — | hsa-miR-1468 |
| rs72558480 | 300461 | A/T | — | hsa-miR-130b* |
| rs72558480 | 300461 | A/T | — | hsa-miR-877* |
| rs72558481 | 300461 | A/G | — | hsa-miR-934 |
| rs72558481 | 300461 | A/G | — | hsa-miR-138-1* |
| rs72558482 | 300461 | A/G | — | hsa-miR-375 |
| rs72558486 | 300461 | G/T | — | hsa-miR-596 |
| rs72558486 | 300461 | G/T | — | hsa-miR-1201 |
| rs72558487 | 300461 | C/G | — | hsa-miR-425 |
| rs72558489 | 300461 | C/T | — | hsa-miR-486-3p |
| rs72558489 | 300461 | C/T | — | hsa-miR-593* |
| rs72558489 | 300461 | C/T | — | hsa-miR-767-5p |
| rs72558490 | 300461 | C/T | — | hsa-miR-922, hsa-miR-214 |
| rs72558490 | 300461 | C/T | — | hsa-miR-1909 |
| rs72558490 | 300461 | C/T | — | hsa-miR-744 |
| rs72558490 | 300461 | C/T | — | hsa-miR-542-5p |
| rs72558491 | 300461 | A/C | — | hsa-miR-30e*, hsa-miR-30d*, hsa-miR-30a* |
| rs72558493 | 300461 | A/C | — | hsa-miR-571, hsa-miR-219-1-3p |
| rs72558494 | 300461 | C/T | — | hsa-miR-558 |
| rs72558494 | 300461 | C/T | — | hsa-miR-610 |
| rs72558494 | 300461 | C/T | — | hsa-miR-18b, hsa-miR-18a |
| rs72558495 | 300461 | G/T | — | hsa-miR-513a-3p |
| rs72558495 | 300461 | G/T | — | hsa-miR-421 |
| rs72558495 | 300461 | G/T | — | hsa-miR-543 |
| rs72558495 | 300461 | G/T | — | hsa-miR-32* |
| rs72558497 | 300461 | A/G | — | hsa-miR-938 |
| rs72558497 | 300461 | A/G | — | hsa-miR-129-3p, hsa-miR-129* |
| rs72631815 | 610529 | A/C | — | hsa-miR-129-3p, hsa-miR-129* |
| rs72631815 | 610529 | A/C | — | hsa-miR-518c*, hsa-miR-330-5p, hsa-miR-326 |
| rs72650698 | 264800 | C/T | — | hsa-miR-1282 |
| rs72650698 | 264800 | C/T | — | hsa-miR-450b-5p, hsa-miR-557, hsa-miR-507 |
| rs72650699 | 264800 | C/T | — | hsa-miR-139-5p |
| rs72650699 | 264800 | C/T | — | hsa-miR-1301 |
| rs72650699 | 264800 | C/T | — | hsa-miR-1205, hsa-miR-1184, hsa-miR-17* |
| rs72650699 | 264800 | C/T | — | hsa-miR-103, hsa-miR-107 |
| rs72650700 | 264800 | C/T | — | hsa-miR-105* |
| rs72650701 | 264800 | A/G | — | hsa-miR-575 |
| rs72650702 | 264800 | A/C | — | hsa-miR-1258 |
| rs72650702 | 264800 | A/C | — | hsa-miR-651 |
| rs72653703 | 264800 | C/T | — | hsa-miR-298 |
| rs72653703 | 264800 | C/T | — | hsa-miR-139-5p |
| rs72653703 | 264800 | C/T | — | hsa-miR-1205, hsa-miR-1184, hsa-miR-17* |
| rs72653704 | 264800 | C/G | — | hsa-miR-196b, hsa-miR-196a, hsa-miR-196a |
| rs72653704 | 264800 | C/G | — | hsa-miR-657 |
| rs72653704 | 264800 | C/G | — | hsa-miR-645 |
| rs72653705 | 264800 | C/T | — | hsa-miR-1228, hsa-miR-220a |
| rs72653705 | 264800 | C/T | — | hsa-miR-377 |
| rs72653705 | 264800 | C/T | — | hsa-miR-767-5p |
| rs72653706 | 264800 | C/T | — | hsa-miR-613, hsa-miR-1, hsa-miR-206, hsa-miR-1 |
| rs72653743 | 264800 | C/T | — | hsa-miR-1254, hsa-miR-661 |
| rs72653743 | 264800 | C/T | — | hsa-miR-23b*, hsa-miR-23a* |
| rs72653745 | 264800 | A/G | — | hsa-miR-198 |
| rs72653745 | 264800 | A/G | — | hsa-miR-145 |
| rs72653746 | 264800 | C/T | — | hsa-miR-20a* |
| rs72653746 | 264800 | C/T | — | hsa-miR-155* |
| rs72653746 | 264800 | C/T | — | hsa-miR-324-5p |
| rs72653747 | 264800 | G/T | — | hsa-miR-1972 |
| rs72653747 | 264800 | G/T | — | hsa-miR-554 |
| rs72653748 | 264800 | A/G | — | hsa-miR-198 |
| rs72653748 | 264800 | A/G | — | hsa-miR-645 |
| rs72653749 | 264800 | C/T | — | hsa-miR-223 |
| rs72653749 | 264800 | C/T | — | hsa-miR-222* |
| rs72653749 | 264800 | C/T | — | hsa-miR-431* |
| rs72653749 | 264800 | C/T | — | hsa-miR-16-1* |

TABLE 2-continued

| SNP | OMIM | MUTATION | GENE | MIR |
|---|---|---|---|---|
| rs72653750 | 264800 | A/G | — | hsa-miR-522*, hsa-miR-519a*, hsa-miR-523*, hsa-miR-518r, hsa-miR-526a, hsa-miR-520c-5p, hsa-miR-526a, hsa-miR-518e*, hsa-miR-518d-5p, hsa-miR-519c-5p, hsa-miR-519b-5p |
| rs72653750 | 264800 | A/G | — | hsa-miR-525-5p, hsa-miR-520a-5p |
| rs72653750 | 264800 | A/G | — | hsa-miR-488* |
| rs72653751 | 264800 | A/T | — | hsa-miR-554 |
| rs72653755 | 264800 | A/G | — | hsa-miR-1470 |
| rs72653756 | 264800 | C/T | — | hsa-miR-22* |
| rs72653756 | 264800 | C/T | — | hsa-miR-148a* |
| rs72653756 | 264800 | C/T | — | hsa-miR-148b* |
| rs72653756 | 264800 | C/T | — | hsa-miR-10a* |
| rs72653756 | 264800 | C/T | — | hsa-miR-495, hsa-miR-7-1*, hsa-miR-7-2* |
| rs72653757 | 264800 | C/T | — | hsa-miR-1537 |
| rs72653757 | 264800 | C/T | — | hsa-miR-607 |
| rs72653757 | 264800 | C/T | — | hsa-miR-498 |
| rs72653758 | 264800 | G/T | — | hsa-miR-499-3p |
| rs72653759 | 264800 | C/G | — | hsa-miR-1282 |
| rs72653760 | 264800 | A/G | — | hsa-miR-544 |
| rs72653760 | 264800 | A/G | — | hsa-miR-370 |
| rs72653761 | 264800 | C/T | — | hsa-miR-140-3p |
| rs72653762 | 264800 | A/G | — | hsa-miR-493*, hsa-let-7g*, hsa-let-7a-2* |
| rs72653764 | 264800 | A/G | — | hsa-miR-422a, hsa-miR-378 |
| rs72653764 | 264800 | A/G | — | hsa-miR-1287 |
| rs72653765 | 264800 | C/T | — | hsa-miR-937 |
| rs72653767 | 264800 | A/T | — | hsa-miR-149* |
| rs72653767 | 264800 | A/T | — | hsa-miR-1321 |
| rs72653767 | 264800 | A/T | — | hsa-miR-1293, hsa-miR-363* |
| rs72653767 | 264800 | A/T | — | hsa-miR-765 |
| rs72653768 | 264800 | A/G | — | hsa-miR-214* |
| rs72653768 | 264800 | A/G | — | hsa-miR-1914 |
| rs72653768 | 264800 | A/G | — | hsa-miR-550 |
| rs72653769 | 264800 | A/T | — | hsa-miR-1914 |
| rs72653769 | 264800 | A/T | — | hsa-miR-1224-5p |
| rs72653769 | 264800 | A/T | — | hsa-miR-1261 |
| rs72653769 | 264800 | A/T | — | hsa-miR-1200, hsa-miR-378* |
| rs72653769 | 264800 | A/T | — | hsa-miR-1185 |
| rs72653771 | 264800 | A/T | — | hsa-miR-1322, hsa-miR-1272 |
| rs72653772 | 264800 | A/G | — | hsa-miR-432* |
| rs72653772 | 264800 | A/G | — | hsa-miR-105* |
| rs72653772 | 264800 | A/G | — | hsa-miR-432 |
| rs72653774 | 264800 | C/T | — | hsa-miR-1324 |
| rs72653774 | 264800 | C/T | — | hsa-miR-21* |
| rs72653774 | 264800 | C/T | — | hsa-miR-548p |
| rs72653774 | 264800 | C/T | — | hsa-miR-545 |
| rs72653774 | 264800 | C/T | — | hsa-miR-922, hsa-miR-214 |
| rs72653775 | 264800 | C/T | — | hsa-miR-664 |
| rs72653775 | 264800 | C/T | — | hsa-miR-376a, hsa-miR-376b |
| rs72653775 | 264800 | C/T | — | hsa-miR-103-as |
| rs72653776 | 264800 | C/T | — | hsa-miR-492 |
| rs72653777 | 264800 | C/T | — | hsa-miR-1324 |
| rs72653777 | 264800 | C/T | — | hsa-miR-483-5p |
| rs72653778 | 264800 | G/T | — | hsa-miR-1226 |
| rs72653778 | 264800 | G/T | — | hsa-miR-549 |
| rs72653778 | 264800 | G/T | — | hsa-miR-1911* |
| rs72653779 | 264800 | A/G | — | hsa-miR-129-3p, hsa-miR-129* |
| rs72653779 | 264800 | A/G | — | hsa-miR-637 |
| rs72653779 | 264800 | A/G | — | hsa-miR-146b-3p |
| rs72653780 | 264800 | G/T | — | hsa-miR-1324 |
| rs72653780 | 264800 | G/T | — | hsa-miR-29c* |
| rs72653781 | 264800 | G/T | — | hsa-miR-1975 |
| rs72653781 | 264800 | G/T | — | hsa-miR-361-3p |
| rs72653781 | 264800 | G/T | — | hsa-miR-181a-2* |
| rs72653782 | 264800 | C/T | — | hsa-miR-149* |
| rs72653782 | 264800 | C/T | — | hsa-miR-1915 |
| rs72653782 | 264800 | C/T | — | hsa-miR-1321 |
| rs72653783 | 264800 | A/C | — | hsa-miR-637 |
| rs72653783 | 264800 | A/C | — | hsa-miR-1976 |
| rs72653784 | 264800 | G/T | — | hsa-miR-1972 |
| rs72653784 | 264800 | G/T | — | hsa-miR-324-5p |
| rs72653784 | 264800 | G/T | — | hsa-miR-1976 |
| rs72653785 | 264800 | C/T | — | hsa-miR-628-3p, hsa-miR-325 |
| rs72653785 | 264800 | C/T | — | hsa-miR-1263, hsa-miR-150* |
| rs72653785 | 264800 | C/T | — | hsa-miR-1278 |
| rs72653786 | 264800 | A/T | — | hsa-miR-664 |
| rs72653786 | 264800 | A/T | — | hsa-miR-578 |
| rs72653787 | 264800 | A/G | — | hsa-miR-1270, hsa-miR-620 |
| rs72653787 | 264800 | A/G | — | hsa-miR-1203 |

TABLE 2-continued

| SNP | OMIM | MUTATION | GENE | MIR |
|---|---|---|---|---|
| rs72653787 | 264800 | A/G | — | hsa-miR-1299, hsa-miR-516b, hsa-miR-516b |
| rs72653787 | 264800 | A/G | — | hsa-miR-518c*, hsa-miR-330-5p, hsa-miR-326 |
| rs72653788 | 264800 | C/T | — | hsa-miR-449b* |
| rs72653788 | 264800 | C/T | — | hsa-miR-181a-2* |
| rs72653790 | 264800 | A/G | — | hsa-miR-338-3p |
| rs72653790 | 264800 | A/G | — | hsa-miR-616 |
| rs72653790 | 264800 | A/G | — | hsa-miR-1298 |
| rs72653791 | 264800 | C/T | — | hsa-miR-1226 |
| rs72653791 | 264800 | C/T | — | hsa-miR-1911* |
| rs72653792 | 264800 | G/T | — | hsa-miR-519d, hsa-miR-526b*, hsa-miR-20b, hsa-miR-106b, hsa-miR-106a, hsa-miR-93, hsa-miR-17, hsa-miR-20a |
| rs72653792 | 264800 | G/T | — | hsa-miR-520h, hsa-miR-520g |
| rs72653793 | 264800 | C/T | — | hsa-miR-187 |
| rs72653793 | 264800 | C/T | — | hsa-miR-654-3p |
| rs72653794 | 264800 | A/G | — | hsa-miR-592 |
| rs72653794 | 264800 | A/G | — | hsa-miR-187 |
| rs72653795 | 264800 | A/G | — | hsa-miR-433 |
| rs72653795 | 264800 | A/G | — | hsa-miR-1300, hsa-miR-580 |
| rs72653796 | 264800 | C/T | — | hsa-miR-517b |
| rs72653797 | 264800 | C/G | — | hsa-miR-1254, hsa-miR-661 |
| rs72653797 | 264800 | C/G | — | hsa-miR-596 |
| rs72653797 | 264800 | C/G | — | hsa-miR-484 |
| rs72653798 | 264800 | C/T | — | hsa-miR-338-3p |
| rs72653798 | 264800 | C/T | — | hsa-miR-1202 |
| rs72653799 | 264800 | C/T | — | hsa-miR-7 |
| rs72653799 | 264800 | C/T | — | hsa-miR-525-5p, hsa-miR-520a-5p |
| rs72653800 | 264800 | G/T | — | hsa-miR-24-1*, hsa-miR-24-2* |
| rs72653800 | 264800 | G/T | — | hsa-miR-1976 |
| rs72653801 | 264800 | C/T | — | hsa-miR-625 |
| rs72653801 | 264800 | C/T | — | hsa-miR-608, hsa-miR-342-5p |
| rs72657689 | 264800 | A/G | — | hsa-miR-648 |
| rs72657689 | 264800 | A/G | — | hsa-miR-1909* |
| rs72657689 | 264800 | A/G | — | hsa-miR-574-5p |
| rs72657690 | 264800 | G/T | — | hsa-miR-7 |
| rs72657690 | 264800 | G/T | — | hsa-miR-1827 |
| rs72657690 | 264800 | G/T | — | hsa-miR-940, hsa-miR-34b* |
| rs72657692 | 264800 | C/G | — | hsa-miR-7 |
| rs72657692 | 264800 | C/G | — | hsa-miR-1225-3p, hsa-miR-1233 |
| rs72657693 | 264800 | G/T | — | hsa-miR-1270, hsa-miR-620 |
| rs72657693 | 264800 | G/T | — | hsa-miR-432 |
| rs72657693 | 264800 | G/T | — | hsa-miR-1253 |
| rs72657694 | 264800 | A/C | — | hsa-miR-505 |
| rs72657694 | 264800 | A/C | — | hsa-miR-598 |
| rs72657695 | 264800 | G/T | — | hsa-miR-1203 |
| rs72657695 | 264800 | G/T | — | hsa-miR-1282 |
| rs72657699 | 264800 | A/G | — | hsa-miR-1322, hsa-miR-1272 |
| rs72657700 | 264800 | A/T | — | hsa-miR-7 |
| rs72657701 | 264800 | C/G | — | hsa-miR-517b |
| rs72657701 | 264800 | C/G | — | hsa-miR-143* |
| rs72657701 | 264800 | C/G | — | hsa-miR-198 |
| rs72658152 | 0 | A/G | — | hsa-miR-769-5p |
| rs72658152 | 0 | A/G | — | hsa-miR-1911* |
| rs72658176 | 0 | A/G | — | hsa-miR-1208 |
| rs72658176 | 0 | A/G | — | hsa-miR-21* |
| rs72658176 | 0 | A/G | — | hsa-miR-452 |
| rs72658176 | 0 | A/G | — | hsa-miR-200a, hsa-miR-141 |
| rs72658200 | 0 | A/G | — | hsa-miR-665 |
| rs72658200 | 0 | A/G | — | hsa-miR-1227 |
| rs72658200 | 0 | A/G | — | hsa-miR-33b*, hsa-miR-515-3p, hsa-miR-519e, hsa-miR-515-3p, hsa-miR-371-3p |
| rs72658200 | 0 | A/G | — | hsa-miR-512-3p, hsa-miR-520f |
| rs72658200 | 0 | A/G | — | hsa-miR-1202 |
| rs72659343 | 0 | G/T | — | hsa-miR-299-5p |
| rs72659343 | 0 | G/T | — | hsa-miR-575 |
| rs72659355 | 0 | A/C | — | hsa-miR-1977 |
| rs72659355 | 0 | A/C | — | hsa-miR-562 |
| rs72659355 | 0 | A/C | — | hsa-miR-651 |
| rs72659357 | 0 | A/G | — | hsa-miR-136 |
| rs72659357 | 0 | A/G | — | hsa-miR-181a* |
| rs72659357 | 0 | A/G | — | hsa-miR-760 |
| rs72659361 | 0 | C/T | — | hsa-miR-625* |
| rs72659361 | 0 | C/T | — | hsa-miR-1208 |
| rs72659361 | 0 | C/T | — | hsa-miR-1183 |
| rs72664281 | 264800 | A/G | — | hsa-miR-1197 |
| rs72664283 | 264800 | A/G | — | hsa-miR-1972 |
| rs72664283 | 264800 | A/G | — | hsa-miR-484 |
| rs72664285 | 264800 | A/C | — | hsa-miR-576-3p |

TABLE 2-continued

| SNP | OMIM | MUTATION | GENE | MIR |
|---|---|---|---|---|
| rs72664285 | 264800 | A/C | — | hsa-miR-455-5p |
| rs72664286 | 264800 | G/T | — | hsa-miR-564 |
| rs72664286 | 264800 | G/T | — | hsa-miR-1538 |
| rs72664287 | 264800 | A/G | — | hsa-miR-24 |
| rs72664288 | 264800 | A/C | — | hsa-miR-1914*, hsa-miR-423-5p |
| rs72664288 | 264800 | A/C | — | hsa-miR-1265 |
| rs72664289 | 264800 | C/T | — | hsa-miR-1227 |
| rs72664289 | 264800 | C/T | — | hsa-miR-126 |
| rs72664289 | 264800 | C/T | — | hsa-miR-1911* |
| rs72664289 | 264800 | C/T | — | hsa-miR-1973 |
| rs72664289 | 264800 | C/T | — | hsa-miR-1202 |
| rs73625096 | 601771 | C/T | — | hsa-miR-15a* |

REFERENCES

Throughout this application, various references describe the state of the art to which this invention pertains. The disclosures of these references are hereby incorporated by reference into the present disclosure.

1. McCarroll, S. A. et al. Deletion polymorphism upstream of IRGM associated with altered IRGM expression and Crohn's disease. Nat. Genet. 40, 1107-1112 (2008).
2. Prescott, N. J. et al. Independent and population-specific association of risk variants at the IRGM locus with Crohn's disease. Hum. Mol. Genet. 19, 1828-1839 (2010).
3. Bekpen, C. et al. Death and resurrection of the human IRGM gene. PLoS Genet. 5, e1000403 (2009).
4. Parkes, M. et al. Sequence variants in the autophagy gene IRGM and multiple other replicating loci contribute to Crohn's disease susceptibility. Nat. Genet. 39, 830-832 (2007).
5. Brest, P. et al. Autophagy and Crohn's disease: at the crossroads of infection, inflammation, immunity, and cancer. Curr. Mol. Med. 10, 486-502 (2010).
6. Abelson, J. F. et al. Sequence variants in SLITRK1 are associated with Tourette's syndrome. Science. 310, 317-320 (2005).
7. Yu, Z. et al. Aberrant allele frequencies of the SNPs located in microRNA target sites are potentially associated with human cancers. Nucleic. Acids Res. 35, 4535-4541 (2007).
8. Norme, N., Ameyar-Zazoua, M., Souidi, M. & Harel-Bellan, A. Tandem affinity purification of miRNA target mRNAs (TAP-Tar). Nucleic. Acids Res. 38, e20 (2010).
9. O'Connell, R. M., Taganov, K. D., Boldin, M. P., Cheng, G. & Baltimore, D. MicroRNA-155 is induced during the macrophage inflammatory response. Proc. Natl. Acad. Sci. USA 104, 1604-1609 (2007).
10. Zhou, R. et al. NF-kappaB p65-dependent transactivation of miRNA genes following Cryptosporidium parvum infection stimulates epithelial cell immune responses. PLoS Pathog. 5, e1000681 (2009).
11. Moschos, S. A. et al. Expression profiling in vivo demonstrates rapid changes in lung microRNA levels following lipopolysaccharide-induced inflammation but not in the anti-inflammatory action of glucocorticoids. BMC Genomics. 8, 240 (2007).
12. Pedersen, I. M. et al. Interferon modulation of cellular microRNAs as an antiviral mechanism. Nature. 449, 919-922 (2007).
13. Cadwell, K. et al. A key role for autophagy and the autophagy gene Atg16l1 in mouse and human intestinal Paneth cells. Nature. 456, 259-63 (2008).
14. Singh, S. B., Davis, A. S., Taylor, G. A. & Deretic, V. Human IRGM induces autophagy to eliminate intracellular mycobacteria. Science. 313, 1438-1441 (2006).
15. Lapaquette, P., Glasser, A. L., Huett, A., Xavier, R. J. & Darfeuille-Michaud, A. Crohn's disease-associated adherent-invasive E. coli are selectively favoured by impaired autophagy to replicate intracellularly. Cell. Microbiol. 12, 99-113 (2010).
16. Bekpen, C. et al. The interferon-inducible p47 (IRG) GTPases in vertebrates: loss of the cell autonomous resistance mechanism in the human lineage. Genome Biol. 6, R92 (2005).
17. MacMicking, J. D., Taylor, G. A. & McKinney, J. D. Immune control of tuberculosis by IFN-gamma-inducible LRG-47. Science. 302, 654-659 (2003).
18. D'Haens, G. R. et al. Early lesions of recurrent Crohn's disease caused by infusion of intestinal contents in excluded ileum. Gastroenterology. 114, 262-267 (1998).
19. Kuballa, P., Huett, A., Rioux, J. D., Daly, M. J. & Xavier, R. J. Impaired autophagy of an intracellular pathogen induced by a Crohn's disease associated ATG16L1 variant. PLoS One. 3, e3391 (2008).
20. Cesaro, A. et al. Differential expression and regulation of ADAM17 and TIMP3 in acute inflamed intestinal epithelia. Am. J. Physiol. Gastrointest. Liver Physiol. 296, 61332-1343 (2009).
21. Cesaro, A. et al. Amplification loop of the inflammatory process is induced by P2X7R activation in intestinal epithelial cells in response to neutrophil transepithelial migration. Am. J. Physiol. Gastrointest. Liver Physiol. 299, G32-42 (2009).
22. Ogura, Y. et al. Expression of NOD2 in Paneth cells: a possible link to Crohn's ileitis. Gut. 52, 1591-1597 (2003).
23. Boudeau, J., Glasser, A. L., Masseret, E., Joly, B. & Darfeuille-Michaud, A. Invasive ability of an Escherichia coli strain isolated from the ileal mucosa of a patient with Crohn's disease. Infect. Immun. 67, 4499-4509 (1999).
24. Rafnar T, Sulem P, Stacey S N, Geller F, Gudmundsson J, Sigurdsson A, Jakobsdottir M, Helgadottir H, Thorlacius S, Aben K K, Blöndal T, Thorgeirsson T E, Thorleifsson G, Kristjansson K, Thorisdottir K, Ragnarsson R, Sigurgeirsson B, Skuladottir H, Gudbjartsson T, Isaksson H J, Einarsson G V, Benediktsdottir K R, Agnarsson B A, Olafsson K, Salvarsdottir A, Bjarnason H, Asgeirsdottir M, Kristinsson K T, Matthiasdottir S, Sveinsdottir S G, Polidoro S, Höiom V, Botella-Estrada R, Hemminki K, Rudnai P, Bishop D T, Campagna M, Kellen E, Zeegers M P, de Verdier P, Ferrer A, Isla D, Vidal M J, Andres R, Saez B, Juberias P, Banzo J, Navarrete S, Tres A, Kan D, Lindblom A, Gurzau E, Koppova K, de Vegt F, Schalken J A, van der Heijden H F, Smit H J, Termeer R A, Oosterwijk E, van Hooij O, Nagore E, Porru S, Steineck G, Hansson J, Buntinx F, Catalona W J, Matullo G, Vineis P, Kiltie A E, Mayordomo J I, Kumar R, Kiemeney L A, Frigge M L, Jonsson T, Saemundsson H, Barkardottir R B, Jonsson E, Jonsson S, Olafsson J H, Gulcher J R, Masson G, Gudbjartsson D F, Kong A, Thorsteinsdottir U, Stefansson K; "Sequence variants at the TERT-CLPTM1L locus associate with many cancer types"; Nat. Genet. 2009 February; 41(2):221-7.

25. Kim J, Bartel D P; "Allelic imbalance sequencing reveals that single-nucleotide polymorphisms frequently alter microRNA-directed repression"; Nat. Biotechnol. 2009 May; 27(5):472-7.

26. Bartel D P; "MicroRNAs: target recognition and regulatory functions"; Cell. 2009 Jan. 23; 136(2):215-33.

27. Norme N, Ameyar-Zazoua M, Souidi M, Harel-Bellan A; Tandem affinity purification of miRNA target mRNAs (TAP-Tar); Nucleic Acids Res. 2010 March; 38(4):e20.

The invention claimed is:

1. An in vitro method for diagnosing and/or prognosing a pathology associated with a synonymous mutation occurring within a gene of interest in a subject, said method comprising the following steps of:
   detecting said synonymous mutation in a biological sample from said subject,
   measuring a level of expression of a miR which binds to a wild-type (WT) sequence of said gene of interest in said biological sample,
   comparing a level of expression of said miR to a predetermined value, and
   when said level of expression is higher than the predetermined value, concluding that said subject is affected with said pathology or
   when said level of expression is lower than the predetermined value, concluding that said subject is not affected with said pathology.

2. The method according to claim 1, wherein said synonymous mutation is in a coding region of the immunity-related GTPase family, M (IRGM) gene.

3. The method according to claim 2, wherein said synonymous mutation in said IRGM gene is a 313C>T substitution.

4. The method according to claim 3, wherein said miR is miR-196.

5. The method according to claim 1, wherein said pathology is an inflammatory disease.

6. The method according to claim 5, wherein said inflammatory disease is an inflammatory bowel disease such as Crohn disease and Ulcerative colitis.

* * * * *

SEQUENCE LISTING

```
<160> NUMBER OF SEQ ID NOS: 10

<210> SEQ ID NO 1
<211> LENGTH: 22
<212> TYPE: RNA
<213> ORGANISM: Artificial Sequence
<220> FEATURE:
<223> OTHER INFORMATION: Synthetic modified miR-196a

<400> SEQUENCE: 1
uaaguaguuu cauguuguug gg                                              22

<210> SEQ ID NO 2
<211> LENGTH: 22
<212> TYPE: RNA
<213> ORGANISM: Artificial Sequence
<220> FEATURE:
<223> OTHER INFORMATION: Synthetic modified miR-196b

<400> SEQUENCE: 2
uaaguaguuu ccuguuguug gg                                              22

<210> SEQ ID NO 3
<211> LENGTH: 22
<212> TYPE: RNA
<213> ORGANISM: Artificial Sequence
<220> FEATURE:
<223> OTHER INFORMATION: Synthetic IRGM 313C RNA 5' to 3'

<400> SEQUENCE: 3
cacaacccug gagaacuacc ug                                              22

<210> SEQ ID NO 4
<211> LENGTH: 22
<212> TYPE: RNA
<213> ORGANISM: Artificial Sequence
<220> FEATURE:
<223> OTHER INFORMATION: Synthetic miR-196A RNA 3' to 5'

<400> SEQUENCE: 4
ggguuguugu acuuugaugg au                                              22

<210> SEQ ID NO 5
<211> LENGTH: 22
<212> TYPE: RNA
<213> ORGANISM: Artificial Sequence
<220> FEATURE:
<223> OTHER INFORMATION: Synthetic IRGM RNA 313T 5' to 3'

<400> SEQUENCE: 5
cacaacccug gagaacuacu ug                                              22

<210> SEQ ID NO 6
<211> LENGTH: 22
<212> TYPE: RNA
<213> ORGANISM: Artificial Sequence
<220> FEATURE:
```

```
<223> OTHER INFORMATION: Synthetic miR-196A RNA 3' to 5'

<400> SEQUENCE: 6
ggguuguugu acuuugaugg au                                              22

<210> SEQ ID NO 7
<211> LENGTH: 22
<212> TYPE: RNA
<213> ORGANISM: Artificial Sequence
<220> FEATURE:
<223> OTHER INFORMATION: Synthetic IRGM 313C RNA 5' to 3'

<400> SEQUENCE: 7
cacaacccug gagaacuacc ug                                              22

<210> SEQ ID NO 8
<211> LENGTH: 22
<212> TYPE: RNA
<213> ORGANISM: Artificial Sequence
<220> FEATURE:
<223> OTHER INFORMATION: Synthyetic miR-196B RNA 5' to 3'

<400> SEQUENCE: 8
ggguuguugu ccuuugaugg au                                              22

<210> SEQ ID NO 9
<211> LENGTH: 22
<212> TYPE: RNA
<213> ORGANISM: Artificial Sequence
<220> FEATURE:
<223> OTHER INFORMATION: Synthetic IRGM 313T RNA 5' to 3'

<400> SEQUENCE: 9
cacaacccug gagaacuacu ug                                              22

<210> SEQ ID NO 10
<211> LENGTH: 22
<212> TYPE: RNA
<213> ORGANISM: Artificial Sequence
<220> FEATURE:
<223> OTHER INFORMATION: Synthetic miR-196B RNA 3' to 5'

<400> SEQUENCE: 10
ggguuguugu ccuuugaugg au                                              22
```